US010925889B2

(12) United States Patent
Peyman

(10) Patent No.: US 10,925,889 B2
(45) Date of Patent: Feb. 23, 2021

(54) METHOD OF TREATING, REDUCING, OR ALLEVIATING A MEDICAL CONDITION IN A PATIENT

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 16/861,128

(22) Filed: Apr. 28, 2020

(65) Prior Publication Data
US 2020/0289534 A1   Sep. 17, 2020

Related U.S. Application Data

(63) Continuation-in-part of application No. 16/246,618, filed on Jan. 14, 2019, and a continuation-in-part of application No. 15/816,140, filed on Nov. 17, 2017, now Pat. No. 10,278,920, and a continuation-in-part of application No. 15/653,053, filed on Jul. 18, 2017, now Pat. No. 10,206,569, and a continuation-in-part of application No. 15/631,219, filed on Jun. 23, 2017, now Pat. No. 10,195,081, and a continuation-in-part of application No. 15/285,375, filed on Oct. 4, 2016, now Pat. No. 9,744,029, and a continuation-in-part of application No. 15/230,445, filed on Aug. 7, 2016, now Pat. No. 9,937,033, and a continuation-in-part of
(Continued)

(51) Int. Cl.
| | |
|---|---|
| *A61K 31/706* | (2006.01) |
| *A61K 9/00* | (2006.01) |
| *A61K 31/727* | (2006.01) |
| *A61K 31/352* | (2006.01) |
| *A61K 31/13* | (2006.01) |
| *A61K 31/7072* | (2006.01) |
| *A61K 31/522* | (2006.01) |
| *A61K 31/7064* | (2006.01) |
| *A61K 31/513* | (2006.01) |
| *A61K 31/4045* | (2006.01) |
| *A61K 31/7056* | (2006.01) |
| *A61P 31/14* | (2006.01) |
| *A61K 47/06* | (2006.01) |
| *A61M 1/34* | (2006.01) |
| *A61M 1/16* | (2006.01) |

(52) U.S. Cl.
CPC .......... *A61K 31/706* (2013.01); *A61K 9/0019* (2013.01); *A61K 9/0053* (2013.01); *A61K 9/0073* (2013.01); *A61K 31/13* (2013.01); *A61K 31/352* (2013.01); *A61K 31/4045* (2013.01); *A61K 31/513* (2013.01); *A61K 31/522* (2013.01); *A61K 31/7056* (2013.01); *A61K 31/7064* (2013.01); *A61K 31/7072* (2013.01); *A61K 31/727* (2013.01); *A61K 47/06* (2013.01); *A61P 31/14* (2018.01); *A61M 1/16* (2013.01); *A61M 1/3496* (2013.01); *A61M 2202/0208* (2013.01); *A61M 2205/05* (2013.01)

(58) Field of Classification Search
CPC .. A61K 31/706; A61K 9/0019; A61K 9/0073; A61K 31/727; A61K 31/352; A61K 31/13; A61K 31/7072; A61K 31/522; A61K 31/7064; A61K 31/513; A61K 31/4045; A61K 31/7056; A61K 47/06; A61K 9/0053; A61K 31/365; A61K 31/551; A61K 45/06; A61P 31/14; A61M 2205/05; A61M 1/3496; A61M 1/16; A61M 2202/0208; A61M 1/1698; A61F 9/00
See application file for complete search history.

(56) References Cited

U.S. PATENT DOCUMENTS

| | | | |
|---|---|---|---|
| 3,760,807 | A | 9/1973 | Neefe |
| 4,563,779 | A | 1/1986 | Kelman |
| 4,665,913 | A | 5/1987 | L'Esperance, Jr. |

(Continued)

FOREIGN PATENT DOCUMENTS

| | | | | |
|---|---|---|---|---|
| CA | 2662943 A1 | * | 10/2009 | ........... A61K 31/137 |
| EP | 1616568 A2 | | 1/2016 | |

(Continued)

OTHER PUBLICATIONS

Wang et al., Lancet 2020;295:1569-78. (Year: 2020).*
Laporte et al., Virology 2017, 24:16-24. (Year: 2017).*
Ma et al., Clinical Immunology 214 (2020) 108408 (available online Apr. 1, 2020). (Year: 2020).*
Sedger, https://theconversation.com/in-the-fight-against-coronavirus-antivirals-are-as-important-as-a-vaccine-heres-where-the-science-is-up-to-133926 (last accessed Oct. 24, 2020). (Year: 2020)*
Farkas, Internet Book of Critical Care (IBCC), https://emcrit.org/ibcc/covid19/ (last accessed Oct. 24, 2020). (Year: 2020).*

(Continued)

*Primary Examiner* — Robert S Cabral
(74) *Attorney, Agent, or Firm* — The Law Office of Patrick F. O'Reilly III, LLC

(57) ABSTRACT

A method of treating, reducing, or alleviating a medical condition in a patient is disclosed herein. The method includes administering to a patient in need thereof a biocompatible drug comprising one or more antiviral medications together with one or more cell pathway inhibitors dissolved in a non-toxic semifluorinated alkane, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to leave the biocompatible drug at a desired treatment location. The administration of the biocompatible drug to the patient treats the one or more respiratory tract inflammatory diseases, reduces the symptoms associated with the one or more respiratory tract inflammatory diseases, and/or alleviates one or more respiratory tract inflammatory diseases.

24 Claims, 34 Drawing Sheets

Related U.S. Application Data application No. 14/709,801, filed on May 12, 2015, now Pat. No. 9,427,355.

(60) Provisional application No. 62/839,738, filed on Apr. 28, 2019, provisional application No. 63/016,258, filed on Apr. 27, 2020, provisional application No. 62/617,251, filed on Jan. 14, 2018, provisional application No. 62/423,734, filed on Nov. 17, 2016, provisional application No. 62/363,382, filed on Jul. 18, 2016, provisional application No. 62/353,632, filed on Jun. 23, 2016, provisional application No. 62/360,439, filed on Jul. 10, 2016, provisional application No. 62/360,281, filed on Jul. 8, 2016, provisional application No. 61/991,785, filed on May 12, 2014, provisional application No. 62/065,714, filed on Oct. 19, 2014.

(56) References Cited

U.S. PATENT DOCUMENTS

| | | |
|---|---|---|
| 4,718,418 A | 1/1988 | L'Esperance, Jr. |
| 4,793,344 A | 12/1988 | Cumming et al. |
| 4,799,931 A | 1/1989 | Lindstrom |
| 4,840,175 A | 6/1989 | Peyman |
| 4,842,599 A | 6/1989 | Bronstein |
| 4,903,695 A | 2/1990 | Warner et al. |
| 4,994,058 A | 2/1991 | Raven et al. |
| 5,171,318 A | 12/1992 | Gibson et al. |
| 5,336,261 A | 8/1994 | Barrett et al. |
| 5,552,452 A | 9/1996 | Khadem |
| 5,702,441 A | 12/1997 | Zhou |
| 5,964,748 A | 10/1999 | Peyman |
| 6,102,946 A | 8/2000 | Nigam |
| 6,110,166 A | 8/2000 | Juhasz |
| 6,180,687 B1 | 1/2001 | Hammer |
| 6,197,019 B1 | 3/2001 | Peyman |
| 6,537,545 B1 | 3/2003 | Karageozian et al. |
| 6,551,307 B2 | 4/2003 | Peyman |
| 7,001,374 B2 | 2/2006 | Peyman |
| 7,004,902 B2 | 2/2006 | Luce |
| 7,044,945 B2 | 5/2006 | Sand |
| 7,083,802 B2 | 8/2006 | Peyman |
| 7,598,288 B2 | 10/2009 | Hellberg et al. |
| 8,632,489 B1 | 1/2014 | Ahmed |
| 8,911,768 B2 | 12/2014 | Whitcup et al. |
| 9,249,424 B2 | 2/2016 | Wolf et al. |
| 9,301,925 B2 | 4/2016 | Xu et al. |
| 9,370,446 B2 | 6/2016 | Peyman |
| 9,427,355 B1 | 8/2016 | Peyman |
| 9,486,357 B2 | 11/2016 | Peyman |
| 9,814,567 B2 | 11/2017 | Peyman |
| 9,861,521 B2 | 1/2018 | de Juan, Jr. et al. |
| 9,931,171 B1 | 4/2018 | Peyman |
| 2001/0027314 A1 | 10/2001 | Peyman |
| 2002/0006394 A1 | 1/2002 | Redmond et al. |
| 2002/0071856 A1 | 6/2002 | Dillingham |
| 2002/0123744 A1 | 9/2002 | Reynard |
| 2003/0035843 A1 | 2/2003 | Livesey et al. |
| 2004/0029855 A1 | 2/2004 | Klaveness et al. |
| 2004/0049174 A1 | 3/2004 | Peyman |
| 2005/0070942 A1 | 3/2005 | Perez |
| 2005/0246018 A1 | 11/2005 | Grubbs |
| 2006/0110428 A1 | 5/2006 | deJuan et al. |
| 2006/0135477 A1 | 6/2006 | Haitjema |
| 2006/0166919 A1 | 7/2006 | Shepard et al. |
| 2007/0135754 A1 | 6/2007 | Akiyama et al. |
| 2007/0142908 A1 | 6/2007 | Xu |
| 2007/0255404 A1 | 11/2007 | Pinchuk |
| 2009/0171305 A1 | 7/2009 | El Hage |
| 2009/0177139 A1 | 7/2009 | Boyden et al. |
| 2009/0196903 A1 | 8/2009 | Kliman |
| 2009/0208577 A1 | 8/2009 | Xu et al. |
| 2009/0253661 A1 | 10/2009 | Peyman |
| 2009/0263899 A1 | 10/2009 | Steinfeld et al. |
| 2009/0287005 A1 | 11/2009 | Baker, Jr. et al. |
| 2010/0087920 A1 | 4/2010 | Marmo |
| 2010/0198348 A1 | 8/2010 | Hiles et al. |
| 2010/0210996 A1 | 8/2010 | Peyman |
| 2010/0215717 A1 | 8/2010 | Soker et al. |
| 2011/0076734 A1 | 3/2011 | Zhou et al. |
| 2011/0152219 A1 | 6/2011 | Stagni et al. |
| 2011/0166650 A1 | 7/2011 | Busin |
| 2011/0208300 A1 | 8/2011 | de Juan, Jr. et al. |
| 2011/0250688 A1 | 10/2011 | Hasan |
| 2012/0203161 A1 | 8/2012 | Herekar |
| 2012/0226139 A1 | 9/2012 | Peyman |
| 2012/0226351 A1 | 9/2012 | Peyman |
| 2012/0245683 A1 | 9/2012 | Christie et al. |
| 2013/0218167 A1 | 8/2013 | Coffey et al. |
| 2015/0134049 A1 | 5/2015 | Austen, Jr. et al. |
| 2015/0223930 A1 | 8/2015 | Shiuey |
| 2015/0342875 A1 | 12/2015 | Haffner |
| 2015/0366706 A1 | 12/2015 | Belkin et al. |
| 2016/0022495 A1 | 1/2016 | Feingold |
| 2016/0081852 A1 | 3/2016 | Peyman |
| 2016/0081920 A1 | 3/2016 | Csaky |
| 2016/0117443 A1 | 4/2016 | Van Ooijen et al. |
| 2016/0331868 A1 | 11/2016 | Grubbs et al. |
| 2016/0346389 A1 | 12/2016 | Friedman et al. |
| 2017/0007395 A1 | 1/2017 | Peyman |
| 2019/0054183 A1 | 2/2019 | Yang et al. |
| 2019/0083518 A1* | 3/2019 | Borody ............... A61K 9/5153 |
| 2020/0222557 A1* | 7/2020 | Berlin ............... A61K 47/6923 |

FOREIGN PATENT DOCUMENTS

| | | |
|---|---|---|
| WO | 89/04153 A1 | 5/1989 |
| WO | 92/16172 A1 | 10/1992 |
| WO | 01/58495 A2 | 8/2001 |
| WO | 2004/108064 A2 | 12/2004 |
| WO | 2008/055118 A2 | 5/2008 |

OTHER PUBLICATIONS

Singh et al., Ther Adv Infectious Dis 2017, vol. 4(4) 105-131 (Year: 2017).*

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).

Wollensak et al., "Riboflavin/Ultraviolet-A—induced Collagen Crosslinking for the Treatment of Keratoconus", American Journal of Ophthalmology, vol. 135, pp. 620-627 (2003).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.

Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).

First office action on the merits (Non-Final Rejection) in U.S. Appl. No. 14/709,801, dated Jan. 11, 2016.

Second office action on the merits (Final Rejection) in U.S. Appl. No. 14/709,801, dated May 4, 2016.

Notice of Allowance in U.S. Appl. No. 14/709,801, dated Jul. 19, 2016.

First office action on the merits (Non-Final Rejection) in U.S. Appl. No. 15/230,445, dated Jul. 11, 2017.

Notice of Allowance in U.S. Appl. No. 15/230,445, dated Dec. 4, 2017.

First office action on the merits (Non-Final Rejection) in U.S. Appl. No. 15/816,140, dated Oct. 22, 2018.

Notice of Allowance in U.S. Appl. No. 15/816,140, dated Feb. 19, 2019.

PCT Form 210, International Search Report for PCT/US2019/030931, dated Jul. 17, 2019.

(56) References Cited

OTHER PUBLICATIONS

PCT Form 237, Written Opinion of the International Searching Authority for PCT/US2019/030931, dated Jul. 17, 2019.
Darwish et al. "Subbasal Nerve Fiber Regeneration after LASIK and LASEK Assessed by Noncontact Esthesiometry and in Vivo Confocal Microscopy: Prospective Study." Journal of Cataract & Refractive Surgery, vol. 33, No. 9, Sep. 2007, pp. 1515-1521, doi:https://doi.org/10.1016/j.jcrs.2007.05.023.
Townes-Anderson et al. "Fasudil, a Clinically Used ROCK Inhibitor, Stabilizes Rod Photoreceptor Synapses after Retinal Detachment." Translational Vision Science & Technology, vol. 6, No. 3, ser. 22, Jun. 2017. 22, doi:10.1167/tvst.6.3.22.
Abegunde et al. "Doxycycline plus Ivermectin versus Ivermectin Alone for Treatment of Patients with Onchocerciasis." The Cochrane Database of Systematic Reviews, U.S. National Library of Medicine, Jan. 15, 2016, www.ncbi.nlm.nih.gov/pmc/articles/PMC5029467/.
Hegde et al. "A Skin-Depth Analysis of Integrins: Role of the Integrin Network in Health and Disease." Cell Communication & Adhesion, vol. 20, No. 6, Nov. 2013, pp. 155-169, doi:https:1/doi.org/10.3109/15419061.2013.854334.
Todorich et al. "Simultaneous Dexamethasone Intravitreal Implant and Anti-VEGF Therapy for Neovascular Age-Related Macular Degeneration Resistant to Anti-VEGF Monotherapy." Journal of Vitreoretinal Diseases, vol. 1, No. 1, Jan. 26, 2017, pp. 65-74, doi:10.1177/2474126416683299.
Tao et al. "Treatment of Burn Scars in Fitzpatrick Phototype III Patients with a Combination of Pulsed Dye Laser and Von-Ablative Fractional Resurfacing 1550 Nm Erbium:Glass/1927 Nm Thulium Laser Devices." Scars, Burns & Healing, SAGE Publications, Feb. 23, 2018, www.ncbi.nlm.nih.gov/pmc/articles/PMC5965338/.
Stepp et al. "Wounding the Cornea to Learn How It Heals." Experimental Eye Research, U.S. National Library of Medicine, Apr. 2014, www.ncbi.nlm.nih.gov/pmc/articles/PMC4072315/.
Loewen. Ocular Surgery News. "How Many Medications Should Be Tried to Lower IOP before Moving on to SLT or Glaucoma Filtering Surgery?" Healio Ocular Surgery News, Healio, Oct. 25, 2010, www.healio.com/ophthalmology/glaucoma/news/print/ocular-surgery-news/%7Bd9857d89-570c-4b52-af40-26bfd5273ddc%7D/how-many-medications-should-be-tried-to-lower-iop-before-moving-on-to-slt-or-glaucoma-filtering-surgery.
Li et al. "Intranasal Delivery of FSD-C10, a Novel Rho Kinase Inhibitor, Exhibits Therapeutic Potential in Experimental Autoimmune Encephalomyelitis." Immunology, Blackwell Science Inc, Oct. 2014, www.ncbi.nlm.nih.gov/pmc/articles/PMC4172138/.
First office action on the merits (Non-Final Rejection) in U.S. Appl. No. 15/941,641, dated Sep. 27, 2018.
Notice of Allowance in U.S. Appl. No. 15/941,641, dated Mar. 21, 2019.
"KY02111", MedChemExpress Website, Web page <https://www.medchemexpress.com/KY02111.html?src=google-product&gclid=EAIaIQobChMl0OP38Ony5wIVFvbjBx3joQOGEAAYASAAEgJOkfD_BwE>, 3 pages, dated at least as early as Feb. 27, 2020, retrieved from MedChemExpress website on Feb. 27, 2020.
"WAY 316606", APExBIO Website, Web page <http://www.apexbt.com/way-316606.html?gclid=EAIaIQobChMIlsj51Ory5wIVxMDACh3qogIdEAAYASAAEglSkfD_BwE>, 4 pages, dated at least as early as Feb. 27, 2020, retrieved from APExBIO website on Feb. 27, 2020.
"IWP-2", MedChemExpress Website, Web page <https://www.medchemexpress.com/IWP-2.html>, 3 pages, dated at least as early as Feb. 27, 2020, retrieved from MedChemExpress website on Feb. 27, 2020.
"LGK974", MedChemExpress Website, Web page <https://www.medchemexpress.com/LGK974.html?src=google-product&gclid=EAIaIQobChMIyIH14_zy5wIV0YZbCh15nws7EAAYASAAEgKTTPD_BwE>, 3 pages, dated at least as early as Feb. 27, 2020, retrieved from MedChemExpress website on Feb. 27, 2020.
"C59", Abcam Website, Web page <https://www.abcam.com/c59-wnt-antagonist-wnt-signaling-pathway-inhibitor-ab142216.html>, 3 pages, dated at least as early as Feb. 27, 2020, retrieved from Abcam website on Feb. 27, 2020.
First office action on the merits (Non-Final Rejection) in U.S. Appl. No. 16/246,618, dated Nov. 27, 2019.
Second office action on the merits (Final Rejection) in U.S. Appl. No. 16/246,618, dated Mar. 5, 2020.
Third office action on the merits (Non-Final Rejection) in U.S. Appl. No. 16/246,618, dated Jul. 1, 2020.

* cited by examiner

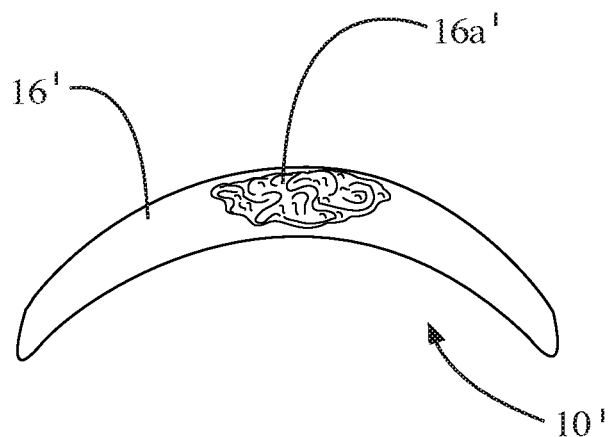
FIG. 2A
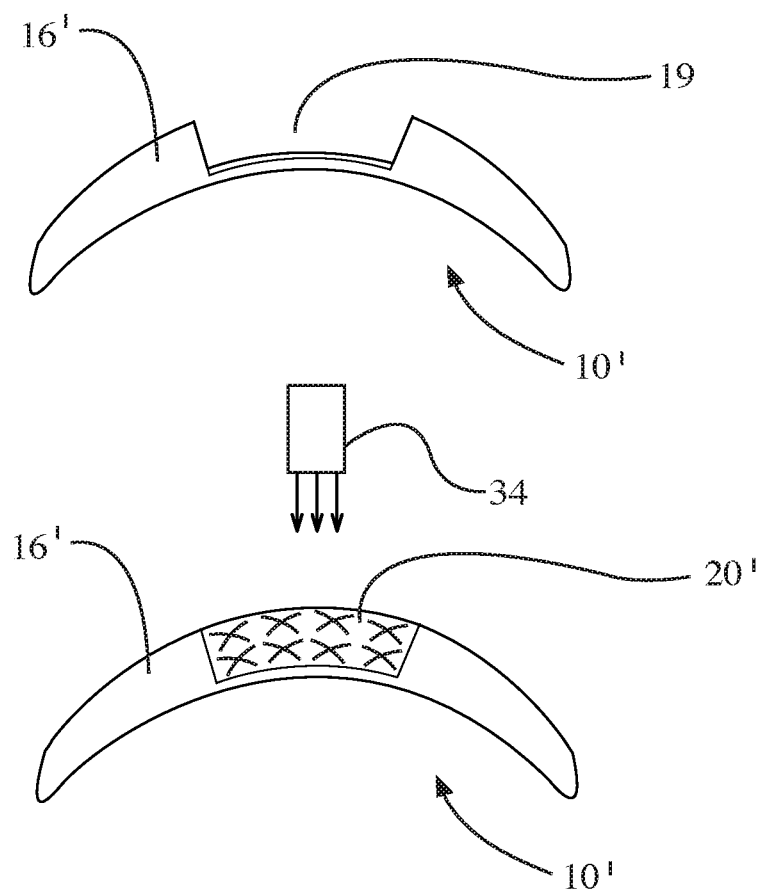
FIG. 2B
FIG. 2C

Detail "A"

Detail "B"

Detail "C"

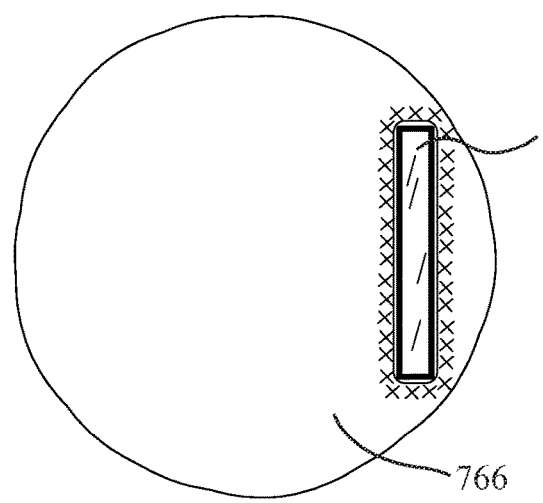
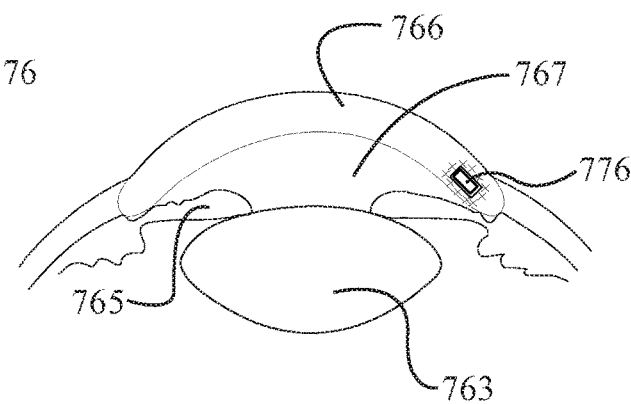
FIG. 69A          FIG. 69B
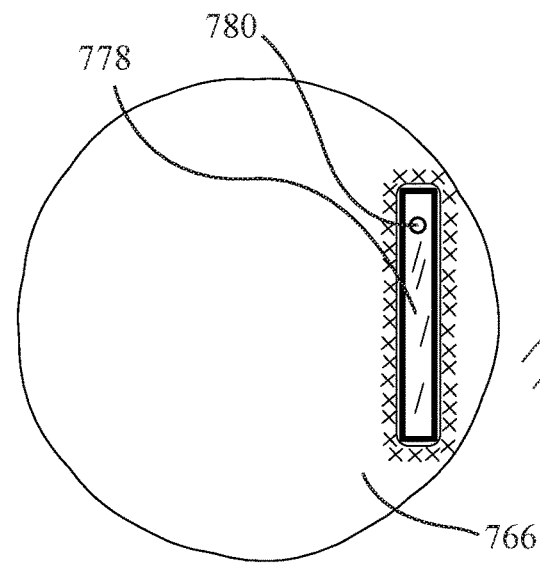
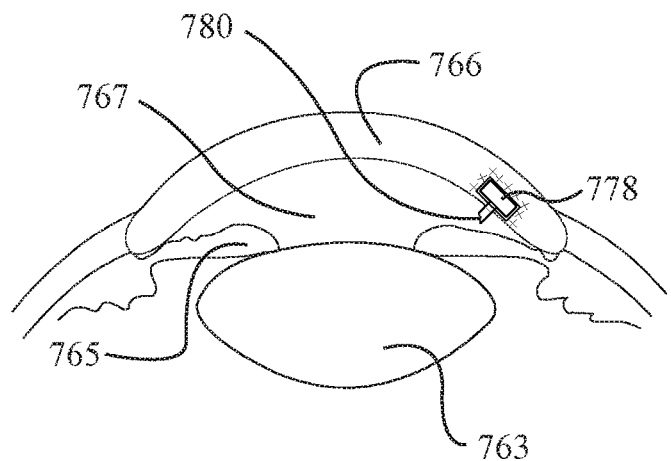
FIG. 70A          FIG. 70B

METHOD OF TREATING, REDUCING, OR ALLEVIATING A MEDICAL CONDITION IN A PATIENT

CROSS-REFERENCE TO RELATED APPLICATIONS

This patent application claims priority to U.S. Provisional Patent Application No. 62/839,738, entitled "Method Of Treating, Reducing, Or Alleviating A Medical Condition In A Patient", filed on Apr. 28, 2019, and to U.S. Provisional Patent Application No. 63/016,258, entitled "Treatment Methods For Respiratory Infections", filed on Apr. 27, 2020, and is a continuation-in-part of application Ser. No. 16/246,618, entitled "Methods For Treatment Of Dry Eye And Other Acute Or Chronic Inflammatory Processes", filed Jan. 14, 2019, which claims priority to U.S. Provisional Patent Application No. 62/617,251, entitled "Methods For Treatment Of Dry Eye And Other Acute Or Chronic Inflammatory Processes", filed on Jan. 14, 2018, and is a continuation-in-part of application Ser. No. 15/816,140, entitled "Drug Delivery Implant And A Method Using The Same", filed Nov. 17, 2017, which claims priority to U.S. Provisional Patent Application No. 62/423,734, entitled "Drug Delivery Implant And A Method Using The Same", filed on Nov. 17, 2016, and Ser. No. 15/816,140 is a continuation-in-part of application Ser. No. 15/653,053, entitled "Corneal Intraocular Pressure Sensor And A Surgical Method Using The Same", filed Jul. 18, 2017, which claims priority to U.S. Provisional Patent Application No. 62/363,382, entitled "Corneal Intraocular Pressure Sensor And A Surgical Method Using The Same", filed on Jul. 18, 2016, and Ser. No. 15/653,053 is a continuation-in-part of application Ser. No. 15/631,219, entitled "Method of Prevention of Capsular Opacification and Fibrosis After Cataract Extraction and/or Prevention of Fibrosis Around a Shunt or Stent After Glaucoma Surgery", filed Jun. 23, 2017, which claims priority to U.S. Provisional Patent Application No. 62/353,632, entitled "Method of Prevention of Capsular Opacification and Fibrosis After Cataract Extraction and/or Prevention of Fibrosis Around a Shunt or Stent After Glaucoma Surgery", filed on Jun. 23, 2016, and Ser. No. 15/631,219 is a continuation-in-part of application Ser. No. 15/285,375, entitled "Method of Preventing Capsular Opacification and Fibrosis Utilizing an Accommodative Intraocular Lens Implant", filed Oct. 4, 2016, now U.S. Pat. No. 9,744,029, which claims priority to U.S. Provisional Patent Application No. 62/360,439, entitled "Method of Preventing Capsular Opacification and Fibrosis with the Creation of an Accommodative Intraocular Lens", filed on Jul. 10, 2016, and Ser. No. 15/285,375 is a continuation-in-part of application Ser. No. 15/230,445, entitled "Corneal Lenslet Implantation With A Cross-Linked Cornea", filed Aug. 7, 2016, now U.S. Pat. No. 9,937,033, which claims priority to U.S. Provisional Patent Application No. 62/360,281, entitled "Method of Altering the Refractive Properties of an Eye", filed on Jul. 8, 2016, and Ser. No. 15/230,445 is a continuation-in-part of application Ser. No. 14/709,801, entitled "Corneal Transplantation With A Cross-Linked Cornea", filed May 12, 2015, now U.S. Pat. No. 9,427,355, which claims priority to U.S. Provisional Patent Application No. 61/991,785, entitled "Corneal Transplantation With A Cross-Linked Cornea", filed on May 12, 2014, and to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to methods of treating, reducing, or alleviating a medical condition in a patient. More particularly, the invention relates to combination therapy for the treatment of various medical conditions, which include respiratory infections.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, and other corneal dystrophies. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea converting an image of the point of light to a line. Therefore, an astigmatic eye is incapable of sharply focusing images on the retina.

While laser surgical techniques, such as laser-assisted in situ keratomileusis (LASIK) and photorefractive keratectomy (PRK) are known for correcting refractive errors of the eye, these laser surgical techniques have complications, such as post-operative pain and dry eye. Also, these laser surgical techniques cannot be safely used on patients with corneas having certain biomechanical properties. For example, corneal ectasia may occur if these laser surgical techniques are applied to patients having thin corneas (e.g., corneas with thicknesses that are less than 500 microns).

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells. Also, what is needed is a method for corneal lenslet implantation for modifying the cornea to better correct ametropic conditions. In addition, a method is needed for corneal lenslet implantation that prevents a lens implant from moving around inside the cornea once implanted so that the lens implant remains centered about the visual axis of the eye.

Moreover, many cataract patients experience complications following their cataract surgery. For example, opacification of the lens capsule affects about 80-90% of the eyes after cataract surgery because of proliferation of the remaining cells in the lens capsule. This post-surgery opacification requires a laser disruption of the posterior capsule for the patient to see. Also, conventional monofocal intraocular lenses do not permit accommodation. As such, patients with monofocal intraocular lenses typically require reading glasses after cataract surgery.

Therefore, it is apparent that a need also exists for treatment of cell proliferation of the lens capsule after cataract extraction, and for an accommodative intraocular lens implant that enables the cataract patient to see both far and near objects without the need for supplemental lenses, such as reading glasses.

Furthermore, cataract patients who additionally have glaucoma pose difficult challenges for the treating ophthalmologist. When glaucoma is associated with a cataract in the same patient, the two surgeries must often be performed at the same time. However, unfortunately, both conditions can have their own complications. For example, as mentioned above, opacification of the lens capsule affects about 80-90% of the eyes after cataract surgery because of proliferation of the remaining cells in the lens capsule. This post-surgery opacification requires a laser disruption of the posterior capsule for the patient to see. Similarly, after glaucoma surgery, the connecting hole from the eye to the subconjunctival space may become plugged by fibrous proliferation occurring after surgery in an attempt to reject the shunt after the surgery or even a shunt in place, as a response of the surgical procedure creating a hole in the eye wall to drain the intraocular fluid.

Therefore, it is apparent that a need further exists for treatment of cell proliferation of the lens capsule after cataract extraction, and for treatment of fibrous cell proliferation after glaucoma surgery with or without a drainage tube.

Glaucoma is a disease that affects the eye and is considered one of the major causes of blindness in the world. There are many forms of glaucoma, having different pathogenesis. Among these are open angle glaucoma (OAG) where the anterior chamber located between the cornea and the iris is open, closed angle glaucoma where the anterior chamber angle is closed, and secondary glaucoma caused by different etiologies, but often an inflammatory process proceeds its occurrence. The glaucoma can be congenital or acquired, and some have genetic predisposition. Regardless of its pathogenesis, the hallmark of the disease is mostly an increased intraocular pressure (IOP), except for in the low tension glaucoma where the IOP appears to be normal, but the patient has the other symptoms of glaucoma. The other characteristic findings in glaucoma eyes are the cupping of the optic nerve head, and the loss of the nerve fiber layer of the retina and ganglion cells of the retina. These can lead to, or can also be considered a consequence of a degenerative process affecting potentially the retinal ganglion cells and an imbalance of the IOP and intracranial pressure leading to gradual loss of the visual field that can be constricted with time or completely lost resulting in blindness.

There are many treatment modalities in managing the disease processes. Since the IOP is, in most cases, elevated beyond a normal level of 10-20 mmHg, routine checking of the IOP including potentially a 24-hour or more measuring of these values during the day and night is needed to find out if there are any pressure variations during the course of the day, especially during sleep where the IOP generally is raised. These pressure variations can obviously compromise the retinal nerves and circulation, even if the pressure is within a normal range of 10-20 mmHg, such as in patients with low tension glaucoma. Thus far, the measurement of the IOP has been sporadic because it is limited by a patient's visit to the doctor's office.

The treatment for glaucoma has been mostly medicinal, that is by applying antiglaucoma medication(s) as eye drops to reduce the intraocular pressure. If the IOP cannot be controlled, either by laser surgery of the angle or ciliary body processes where the fluid is produced, then alternatively, one tries to drain the intraocular fluid to outside of the eye through a stent or shunt opening with one end in the anterior chamber and the other end located in the subconjunctival space or connecting the intraocular fluid via a shunt tube from the inside the eye to the choroidal space. In some situations, the surgeon makes a small hole in the eye wall connecting the anterior chamber fluid or aqueous directly to the subconjunctival space. There are a number of variations of this surgery having the same goal of reducing the IOP to a normal level. The glaucoma can also be associated with a cataract and not seldom requires doing the two surgeries at the same time. However, unfortunately both conditions can have their own complications (e.g., opacification of the lens capsule after cataract surgery affecting about 80-90% percent of the eyes because of proliferation of the remaining cells in the lens capsule, and requiring a laser disruption of the posterior capsule for the patient to see). Similarly, after glaucoma surgery, the connecting hole from the eye to the subconjunctival space can become plugged by fibrous proliferation occurring after surgery with or without a shunt tubing.

Recently, efforts have been made experimentally to measure the intraocular pressure via a contact lens positioned on the surface of the cornea for a duration of 24 hours with a pressure sensor and transmit the information wirelessly to a receiver mounted on an eye glass frame. The disadvantage of this contact lens system is that the system provides the measurement of the IOP indirectly from the eye cavity and depends on how the corneal curvature is deformed in response to the IOP. Also, the contact lens can be worn only for a short time because, otherwise it can interfere with the corneal oxygenation that happens mostly from the outside air and nutrition of the cornea that is, in part, supplied by the tear film that is compromised by placement of a static contact lens on the cornea. The chances of a corneal abrasion is increased by the described shortcomings, and for the patient, the placement and removal of the contact lens is particularly difficult in elderly patients.

Another recent effort has implanted such a system inside the lens capsule of the eye, by removing the natural crystalline lens, but leaving the lens capsule intact so that the device can be positioned inside the lens capsule and measure the IOP, and then transmit it outside the eye to a receiver. Because the system disposed in the lens capsule requires a battery to operate, the eventual need to replace the battery necessitates another surgical procedure to be performed later. Also, the initial surgical procedure has its own serious complications, and often is not justified when one is dealing with young patients or children. In addition, this process creates capsular opacification, it deprives the patient from the use of his or her natural lens, and can have the lifelong potential complication of inflammation that aggravates the existing glaucoma itself.

Therefore, it is apparent that a need further exists for an intraocular pressure measurement device and a method using the same that eliminates the shortcomings of the aforedescribed procedures.

Further, conventional ocular drug delivery systems include medication dissolved or suspended in a physiological solutions applied as drops to the cornea and conjunctiva bathing the superficial structure of the eye. The drops can have also particulate matter for faster tissue penetration or slow release of medication potentially lasting 1-2 days or months, etc. The medication, when applied as drops, partially penetrates the barrier of the corneal epithelium and reaches in sufficient concentration in the aqueous fluid of the anterior chamber. The aqueous is constantly produced in the eye from the ciliary body epithelium in the back or the iris in the posterior chamber and moves through the pupil in the anterior chamber, and is removed from the eye through the trabecular meshwork located in the angle of the eye between the iris and the cornea. A part of the aqueous mixes with the vitreous. In general, topically-applied medication reaches the back of the eye in lower concentrations and slower than when injected in the vitreous cavity.

The injection of medication in the eye cavity, in the form of solution or micro-particulates, can bypass the ocular barrier and effectively treat the retinal and choroidal diseases, for months. Therefore, they have to be reinjected frequently in chronic disease of the eye.

The polymeric slow release systems release the medication inside the eye and have been implanted in the vitreous cavity, over or under the retina, providing medication only to the back of the eye for a period of 3 months to a year.

In general, a drug delivery device has been implanted in most places of the eye, except in the cornea. A non-biodegradable device can be injected in the vitreous cavity if they are very small otherwise, they can move around scratching the retina or move to the anterior chamber damaging the corneal endothelial cells. However, they can be sutured in the sclera with their anchoring section, while the drug delivery section is located inside the eye, i.e., in the vitreous cavity to release the medication.

These devices, in general, initiate a foreign body response associated with fibroblast cell migration around the device, and the device becomes encapsulated, making the amount of drug release unpredictable through the thick fibrotic scar tissue.

Similarly, stem cellular drug delivery devices, such as ciliary body neurotrophic factors that produce needed factors for the retinal survival in certain degenerative diseases can be only be implanted inside the vitreous cavity where it is considered an immune-privileged space. Otherwise, it becomes encapsulated by the scar tissue and become less effective. The vitreous cavity is considered an immune privileged space meaning that blood vessels have no access to it to produce a cellular immune response that would attack and destroy the stem cells or surround a device with a fibrous membrane which would make the system useless.

To date, in general, the cornea has not been considered a suitable location to implant a slow release drug delivery device because of concern that it becomes vascularized affecting the transparency of cornea, which is vital for passing the light through it to reach the photoreceptors of the retina creating sensation of vision.

Therefore, it is apparent that a need exists for a drug delivery implant and a method using the same that is capable of effectively delivering medications to the cornea of the eye and to parts of the body other than the cornea of the eye.

Further, it is known that on the cell surface membrane, Wnt proteins bind to receptors of the Frizzled and LRP protein families causing accumulation of beta-catenin in the cytoplasm and its translocation in the nucleus that forms a complex with transcriptional cofactor (TCF) to activate the transcription of Wnt targeted genes.

The Wnt pathway is considered canonical when it is dependent on beta-catenin, or non-canonical when it is independent. The canonical Wnt/β-catenin plays an important role in the expression of several inflammatory molecules during acute or chronic inflammatory diseases affecting mucosal surfaces of the body.

It is known that innate immunity protects the host cells from invasion and infection and development of an adaptive immune response. However, uncontrolled inflammation causes damage to the tissue.

Conventional oral medication or topical medications used for the mucosa have contained steroids, systemic medication, such as hormonal therapy and or omega-3 oil along with systemic medications, have unwanted side effects and are not tolerated by many patients.

As such, an improved treatment method is needed for an inflammatory process that involves the conjunctiva, sclera, optic nerve, nasal, oral and throat including dry eye syndrome, mucosal form of lichen planus, psoriasis, and inflammatory bowel diseases, plantar fasciitis, skin form of lichen planus or chronic pain caused by inflammatory disease affecting the nerves such as in diabetes or after surgery or trauma, etc.

Respiratory infections also involve inflammatory processes. Respiratory infections are mostly manifested as bacterial or viral infections affecting the nose, throat, epiglottis, trachea, and the lungs. Often these infections in the end stage can cause serious damage to the lungs as pneumonia and superinfection and serious consequences.

In an upper respiratory Infection (URI), the bacterial culprit is group A streptococcal bacteria producing sinusitis and or bronchitis. The common symptoms are redness of the throat and tonsils and moderately elevated temperature of about 38 degrees C. and enlarged cervical nodes. One of the symptoms of laryngotracheitis is roughness of the voice, etc. and positive culture of the organism.

The viral infection is caused often by influenza virus, Epstein Barr virus, Herpes virus, etc. and can be diagnosed by available rapid tests for antibody or polymerase chain reaction (PCR) viral proteins (e.g., enzyme assays for reverse transcriptase in retroviruses), or virus particles (e.g., by electron microscopy or Raman surface enhance spectroscopy, QuantiFERON-virus Gold test (QFV-G) and Surface-enhanced Raman scattering (SERS) detection of multiple viral antigens using magnetic capture of SERS-active nanoparticles as known in the art). In a hospitalized patient, a blood culture might be taken to verify the extent of the systemic involvement. Management of these cases is done in general by oral and systemic antibiotics, penicillin, fluoroquinolones (e.g., levofloxacin, moxifloxacin etc.). Hospitalization might be required in advanced cases affecting the lung with the symptom of dyspnea. The viral infection of the upper respiratory tract is caused by a variety of viruses, among them, the most common are Rhinoviruses, Coxsackie viruses, Adenoviruses and Coronaviruses and Respiratory syncytial virus (RSV) and Epstein Barr Virus (EBV) causing a variety disease manifestations, such as infectious mononucleosis, or Cytomegalovirus. Rhinoviruses cause a number of common cold infections in adults and are seasonal, appearing in fall and winter. These cause approximately 30-50% of colds in adults. The Adenovirus causes conjunctivitis and laryngitis. *H. influenzae* type b (Hib) often causes epiglottitis in children, whereas influenza, Human parainfluenza viruses (HPIVs) viruses and RSV cause laryngitis and some cause pelvic inflammatory diseases of various types. Most of the viral infections are initiated by close contact, travel, or in patients with immune suppression. In general vaccination can reduce a number of these infections. Some viruses are seen more often in male patients than females, or during menstrual cycles etc. and some with preference in children, yet others in the elderly. Some of the viruses produce epidemic diseases such as Middle East respiratory syndrome, pandemic H1N1, and H7N9, thus affecting a large number of the population and can be diagnosed by diagnosed by polymerase chain reaction (PCR) panels, etc. Therapy with antibiotics are useless in majorities of viral infections unless it is accompanied by a bacterial superinfection. The antiviral therapies are effective, such as administration of ribavirin in lung transplant patients; however, they are not affordable for common viral infections or Motavizumab, a second-generation anti-RSV antibody, or intravenous immunoglobin (RI-002).

Although influenza and parainfluenza viruses are often self-limited, unfortunately they can be associated with life threatening consequences in patients after lung transplantation or immunosuppressed patients, and may have a high mortality rate similar to RSV disease, and 20% of patients with COVID-19 have multi-organ failure due to cytokine storm.

Among viruses that cause epidemic or pandemic disease are severe acute respiratory syndrome coronavirus (2SARS-CoV-2) and COVID-19 an RNA virus involving bird and mammals which was found initially in the Wuhan Seafood Wholesale market. By now COVID-19 has affected every country in every continent. It is a highly contagious virus and survives 3-7 hours, and sometimes more hours on surfaces.

The COVID-19 coronavirus affects the bronchoalveolar cell linings as seen with other Coronaviruses. The viruses utilize certain protease proteins of these cells membrane to enter in the cell cytoplasm and utilize the genetic machinery of the cell to multiply. The incubation time varies between 3-7 days or more, while the patient remains relatively asymptomatic. The transmission occurs by contact or aerosolized droplet sputum by sneezing or being close (less than 6 feet) from an infected person. Thus, one person can transmit the virus to many others. In addition, many patients who have recovered can still transmit the virus to others. At present, at least six or more different coronal viruses have been recognized. Among these are SARS-CoV coronavirus causing severe acute respiratory syndrome or MERS-CoV Middle Eastern respiratory syndrome and some that live in bats.

The mechanism of cell entry of the virus into the cell involves using the receptor binding domain (RBD) of the S protein of the virus to attach to the human receptor ACE2 of the alveoli cell where serine protease cleaves the S protein of the virus and causes the binding of the virus to the cell membrane and facilitates entry in the cell. Among the symptoms of coronavirus, a high fever of 100 Fahrenheit or more, is a common finding in addition to cough, shortness of breath, chills, headache, sore throat, muscle pain and gastrointestinal symptoms, loss of smell or taste, urticaria or discoloration of the foot or toes, etc., followed by laboratory finding of leukopenia, lymphocytopenia and thrombocytopenia, coagulopathy, increase in antiphospholipid antibodies, multiple infarcts, increased C-reactive protein greater than >10 mg/L, elevated lactate dehydrogenase (LDH), elevated creatinine, specifically in patients with cytokine storm, similarly increased IFNγ and increased pro-inflammatory ferritin, D-dimer. Cytokine storm induces damage to many organs, such as heart, kidney, etc. A cytokine storm is often associated with macrophage activation syndrome (MAS) and hemophagocytic lymphohistiocytosis (sHLH), increase in cytokines, such as tumor necrosis factor (TNF)-α, interferon (IFN)-γ, interleukin (IL)-1β, IL-2, IL-6, IL-7, IL-12, IL-18, and granulocyte colony-stimulating factor (GCSF). Interestingly, one finds also the anti-inflammatory stimuli, such as regulatory T cells, cytokines IL-10, transforming growth factor (TGF)-β. The latter can lead to pulmonary fibrosis when the patient has recovered, whereas the presence of IL-2, IL-6, IL-7, TNFα, IFNγ, and GCSF, indicates significant lung injury. Comorbidity conditions are old age, male sex, asthma, heart disease, diabetes, kidney disease, etc.

At present, there is no definite therapy for the COVID-19 coronavirus. In general, the early stages are treated palliative. Since fever is a relatively an early symptom, aspirin and Tylenol are useful, but do not affect the replication of the virus. Protection against infection includes self-isolation quarantine, the use of a mask and gloves, and prevention of the virus spreads by sanitizing drops and handwashing. At present, patients with dyspnea, are treated with inhalation of oxygen through the nose or by ventilator, increasing the tissue oxygenation to a level of 92-96%. If a higher level is required, one has recommended the use of nonrebreather mask, with a flow rate up to 6-10 L while providing 100% $FiO_2$ (fraction of inspired oxygen (FiO20).

BRIEF SUMMARY OF EMBODIMENTS OF THE INVENTION

Accordingly, the present invention is directed to a method of treating, reducing, or alleviating a medical condition in a patient that substantially obviates one or more problems resulting from the limitations and deficiencies of the related art.

In accordance with one or more embodiments of the present invention, there is provided a method of treating, reducing, or alleviating a medical condition in a patient. The method includes administering to a patient in need thereof a biocompatible drug comprising one or more antiviral medications together with one or more cell pathway inhibitors dissolved in a non-toxic semifluorinated alkane, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to leave the biocompatible drug at a desired treatment location. The administration of the biocompatible drug to the patient treats the one or more respiratory tract inflammatory diseases, reduces the symptoms associated with the one or more respiratory tract inflammatory diseases, and/or alleviates one or more respiratory tract inflammatory diseases.

In a further embodiment of the present invention, the one or more respiratory tract inflammatory diseases are selected from the group consisting of influenza, parainfluenza, severe acute respiratory syndrome, a coronavirus disease, an Epstein-bar virus disease, a herpes virus disease, a bacterial infection, and combinations thereof.

In yet a further embodiment, the one or more respiratory tract inflammatory diseases comprise a coronavirus disease, the coronavirus disease selected from the group consisting of COVID-2, COVID-19, and combinations thereof.

In still a further embodiment, the biocompatible drug further comprises nanoparticles or microparticles used as a carrier of the biocompatible drug; and the biocompatible drug with the semifluorinated alkane and the nanoparticles or microparticles is administered by inhalation to the patient to treat one or more respiratory tract inflammatory diseases.

In yet a further embodiment, the nanoparticle or microparticle carriers comprise slow release polymeric nanoparticles or microparticles; and the semifluorinated alkane is used to transport the biocompatible drug with the slow release polymeric nanoparticles or microparticles.

In still a further embodiment, the one or more antiviral medications are selected from the group consisting of amantadine, Lopinavir, linebacker and equivir, Arbidol, a nanoviricide, remdesivir, oseltamivir ribavirin, and combinations thereof.

In yet a further embodiment, the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

In still a further embodiment, the biocompatible drug further comprises one or more protease inhibitors in combination with the one or more antiviral medications and the one or more cell pathway inhibitors.

In yet a further embodiment, the method further comprises the step of, after treatment with the biocompatible drug, removing cytokines, enzymes, dead cells, from the circulation of the patient by plasmapheresis so to prevent a cytokine storm.

In still a further embodiment, the biocompatible drug is administered to the patient by inhalation, orally, intravenously, or combinations thereof.

In accordance with one or more embodiments of the present invention, there is provided a method of treating, reducing, or alleviating a medical condition in a patient. The method includes administering to a patient in need thereof a biocompatible drug comprising one or more antiviral medications together with one or more cell pathway inhibitors dissolved in a non-toxic aerosolized compound and/or conjugated with slow release polymeric nanoparticles or microparticles, the patient having one or more respiratory tract inflammatory diseases, the one or more antiviral medications preventing an attachment of viruses to cell walls, blocking a penetration of the viruses into cells, and/or inhibiting virus replication by damaging nucleic acids of the viruses, and the one or more cell pathway inhibitors blocking an inflammatory response of inflamed tissue without inhibiting an immune response of the patient. The administration of the biocompatible drug to the patient treats the one or more respiratory tract inflammatory diseases, reduces the symptoms associated with the one or more respiratory tract inflammatory diseases, and/or alleviates one or more respiratory tract inflammatory diseases.

In a further embodiment of the present invention, the one or more respiratory tract inflammatory diseases are selected from the group consisting of influenza, parainfluenza, severe acute respiratory syndrome, a coronavirus disease, an Epstein-bar virus disease, a herpes virus disease, a bacterial infection, and combinations thereof.

In yet a further embodiment, the one or more respiratory tract inflammatory diseases comprise a coronavirus disease, the coronavirus disease selected from the group consisting of COVID-2, COVID-19, and combinations thereof.

In still a further embodiment, the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

In yet a further embodiment, the biocompatible drug further comprises one or more protease inhibitors in combination with the one or more antiviral medications and the one or more cell pathway inhibitors.

In still a further embodiment, the one or more antiviral medications are selected from the group consisting of amantadine, azidothymidine, aciclovir, ganciclovir, vidarabine, and combinations thereof.

In yet a further embodiment, the method further comprises the step of administering one or more immunosuppressants and at least one of heparin, low molecular weight heparin, and Coumadin to prevent an overactive immune response and blood clot formation so as to prevent vascular infarct, the one or more immunosuppressants being selected from the group consisting of a macrolide, cyclosporine, mycophenolic acid, and combinations thereof.

In still a further embodiment, after treatment with the biocompatible drug, the method further comprises the steps of removing cytokines, enzymes, dead cells, from the circulation of the patient by plasmapheresis and kidney dialysis so to prevent a cytokine storm; and/or delivery of oxygen to the patient by extracorporeal membrane oxygenation when the blood oxygenation level of the patient is low.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 2A is a partial side cross-sectional view of an eye having internal corneal scar tissue;

FIG. 2B is a partial side cross-sectional view of the eye of FIG. 2A, wherein the scarred corneal tissue has been externally removed from the eye;

FIG. 2C is a partial side cross-sectional view of the eye of FIG. 2A, wherein a cross-linked donor cornea is shown being implanted in the location previously occupied by the scarred corneal tissue;

FIG. 69A is a front view of a cornea of an eye illustrating a generally linear drug delivery implant disposed in a cross-linked pocket in the peripheral portion of the cornea;

FIG. 69B is a partial side cross-sectional view of the eye of FIG. 69A illustrating the generally linear drug delivery implant disposed in the cross-linked pocket in the peripheral portion of the cornea;

FIG. 70A is a front view of a cornea of an eye illustrating a drug delivery implant disposed in a cross-linked pocket in the peripheral portion of the cornea, wherein the implant comprises a needle fluidly coupling the implant to the anterior chamber of the eye; and FIG. 70B is a partial side cross-sectional view of the eye of FIG. 70A illustrating the tubular drug delivery implant with the needle extending into the anterior chamber of the eye with the aqueous fluid of the eye.

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
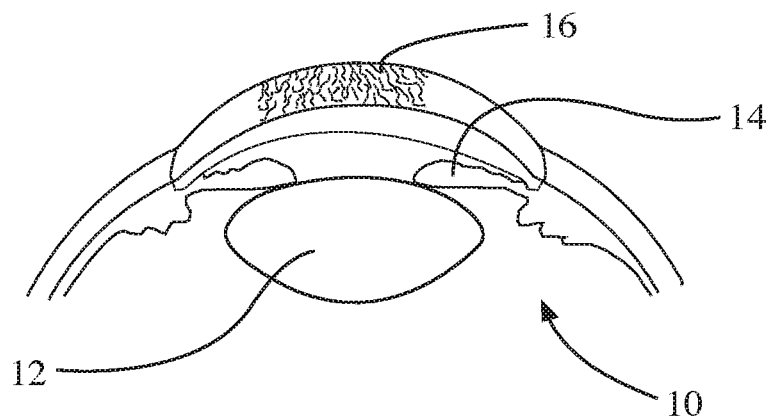
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
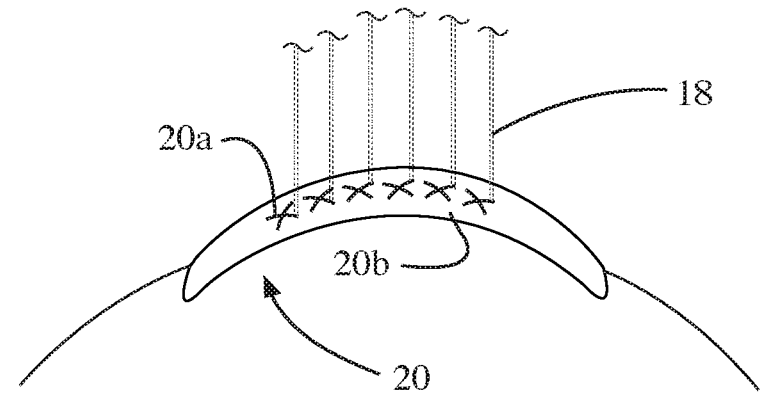
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front portion 20a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the cross-linking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The cross-linker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
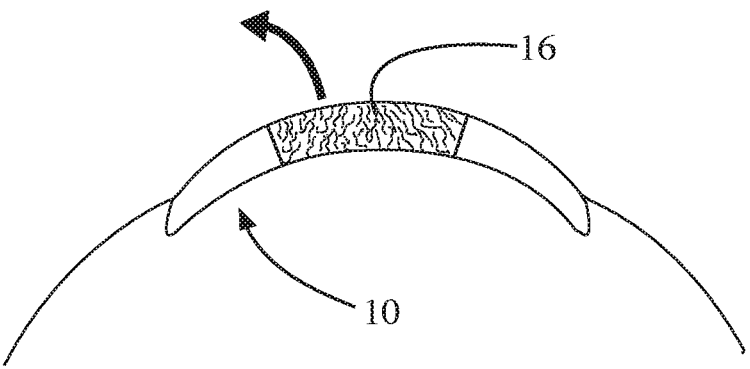
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
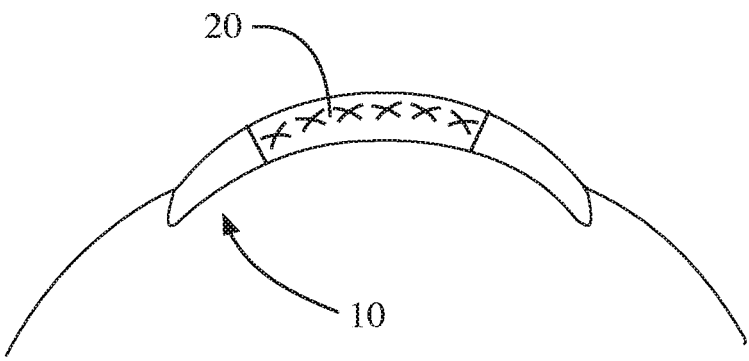
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a non-cross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone)), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In addition, other suitable biodegradable adhesives or glues, which may need an external source of energy, that are able to be used in conjunction with the transplant include combinations of riboflavin, lactoflavin, gallic acid, gallic tannic acid, Chitosan, gelatin, polyphenyl compound, Tannic Acid (N-isopropylacrylamide (PNIPAM), dopamine, and/or Poly(N-vinylpyrrolidone) with polyethylene glycol (PEG). That is, polyethylene glycol (PEG) may be mixed with any one or plurality of riboflavin, lactoflavin, tannic acid, dopamine, gallic tannic acid, Chitosan, gelatin, polyphenyl compound, Tannic Acid (N-isopropylacrylamide (PNIPAM), and Poly(N-vinylpyrrolidone)), so as to form a molecular glue. These adhesives are also suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
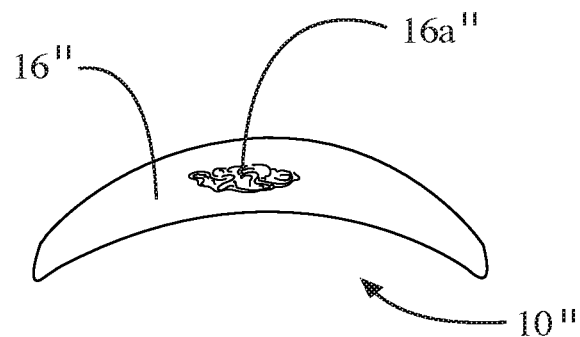
FIG. 3A is a partial side cross-sectional view of an eye having internal corneal scar tissue.
Figure 3B:
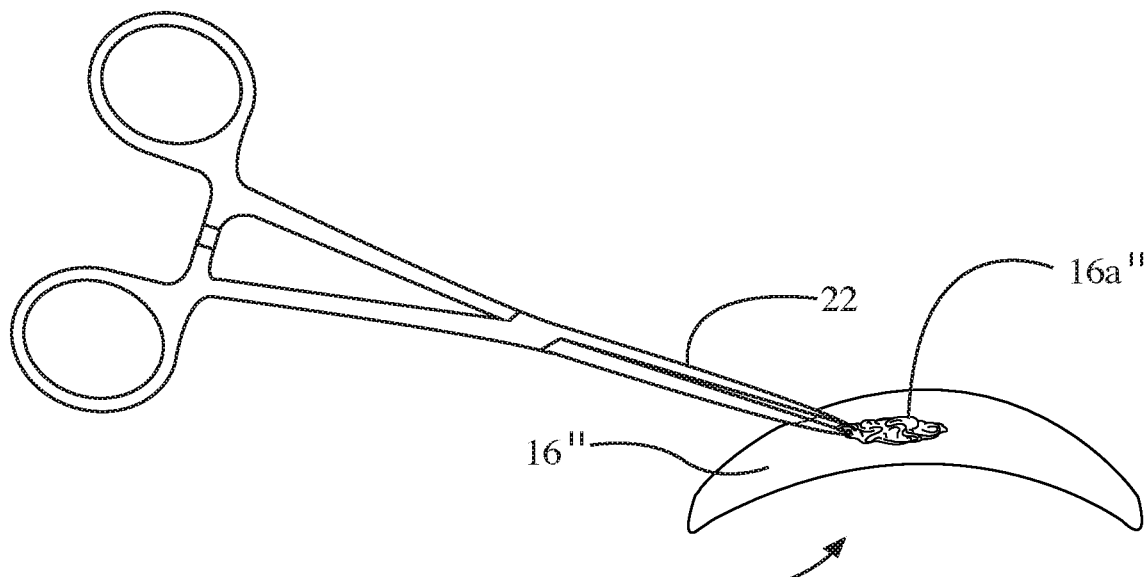
FIG. 3B is a partial side cross-sectional view of the eye of FIG. 3A, wherein the scarred corneal tissue is shown being internally removed from the eye.
Figure 3C:
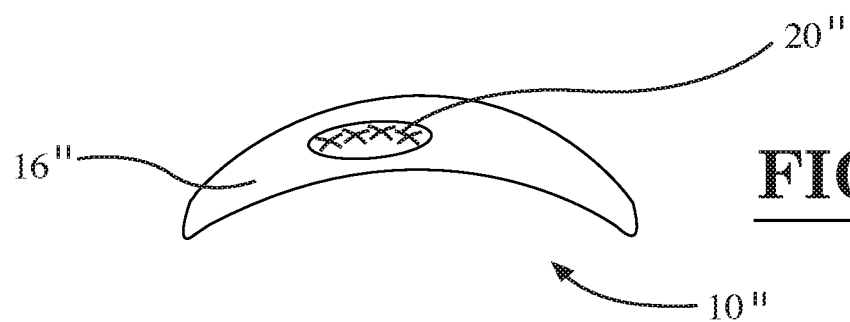
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a''' of the cornea 16''' with a donor corneal portion. Thus, similar to the second and third embodiments explained above, FIGS. 4A-4E illustrate a lamellar keratoplasty procedure wherein only a portion of the cornea 16''' of the eye 10''' contains scarred and/or diseased tissue (i.e., a full-thickness corneal section is not removed). Although, in the procedure of FIGS. 4A-4E, a different-shaped scarred and/or diseased portion 16a''' of the cornea 16''' is removed.

Figure 4A:
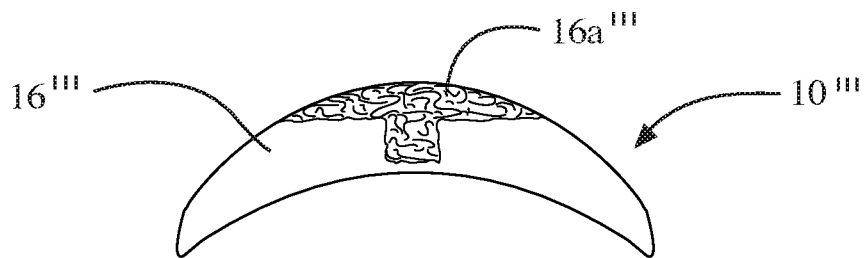
FIG. 4A is a partial side cross-sectional view of an eye having a T-shaped corneal scar and/or diseased tissue portion.

Referring initially to FIG. 4A, it can be seen that only a portion 16a''' of the cornea 16''' having a T-shape or "top hut" shape is scarred and/or diseased. As such, in this embodiment, it is not necessary to replace the entire thickness of the cornea 16''' with a donor cornea as was described above in conjunction with FIGS. 1A-1D, but rather just a portion 16a''' of the cornea 16". In this illustrative embodiment, the back side of the cornea 16''' is maintained (see e.g., FIG. 4D).

Figure 4B:
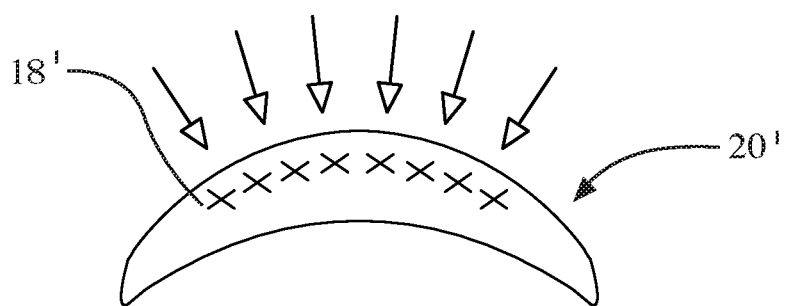
FIG. 4B is another partial side cross-sectional view of a donor cornea undergoing cross-linking.
Figure 4C:
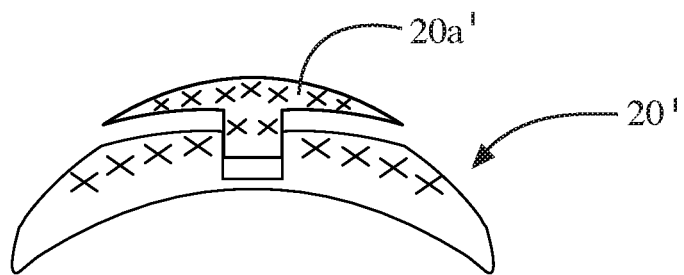
FIG. 4C is a partial side cross-sectional view illustrating a T-shaped portion of the cross-linked donor cornea being cut out from a remainder of the donor cornea.
Figure 5A:
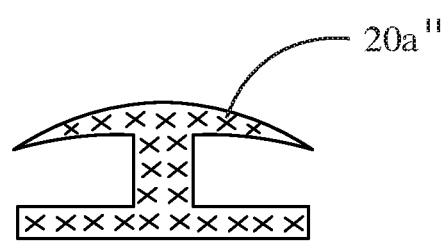
FIG. 5A illustrates an alternative configuration for the cross-linked donor cornea implant, wherein the donor cornea implant has a dumbbell shape.
Figure 5B:
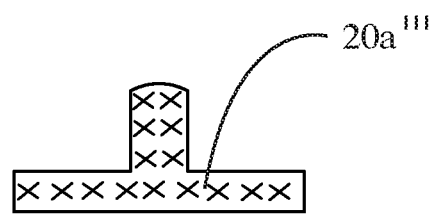
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a''' of the cornea 16''', is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a" (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
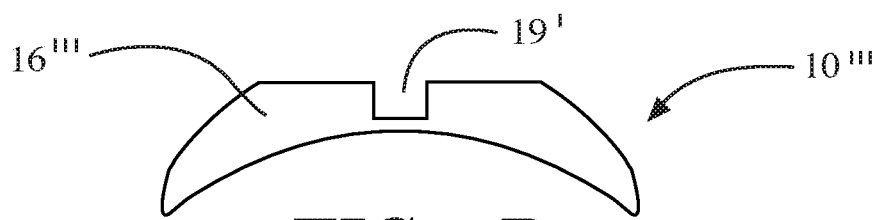
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16*a*''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16*a*''' may be removed from the remainder of the cornea 16''' using various suitable means, such as mechanical means or the laser cutting means (e.g., femtosecond laser) described above.

Figure 4E:
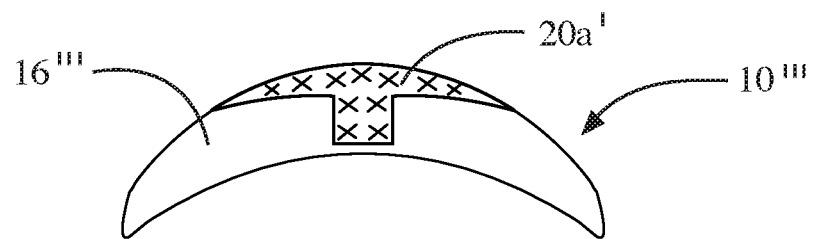
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16*a*''' has been removed from the remainder of the cornea 16''' of the eye 10''', the cross-linked donor corneal portion 20*a'* is implanted into the eye 10''' of the patient in the location previously occupied by the scarred and/or diseased corneal portion 16*a*'''. Because the shape of the transplant corresponds to that of the removed portion 16*a*''' of the cornea 16''', the transplant sits comfortably in its position in the host cornea. As described above, after implantation of the cross-linked donor corneal portion 20*a'* into the eye 10''', sutures or a suitable adhesive (e.g., the biocompatible and biodegradable adhesive described above) may be utilized to secure the cross-linked donor corneal portion 20*a'* in place on the host cornea 16''' of the eye 10''. For example, if a biocompatible and biodegradable adhesive is used to secure the cross-linked donor corneal portion 20*a'* in place in the cornea 16''' of the eye 10''', the edges of the donor corneal portion 20*a'* are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

An illustrative embodiment of a corneal lenslet implantation procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16'''' of the host eye 10'''' is removed during the procedure (i.e., a full-thickness corneal section is not removed). Although, the procedure of FIGS. 6A-6C and 7A-7C differs in several important respects from the abovedescribed procedures. In this embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16'''' of the host eye 10''''. After making an internal pocket 28 in the recipient cornea 16'''' of the host eye 10'''' with a femtosecond laser, the cross-linked transplant is folded and implanted in a predetermined fashion inside the host's corneal pocket 28 to provide stability to the eye 10'''' having keratoconus, keratoglobus, a thin cornea or abnormal corneal curvature, thereby preventing future corneal ectasia in this eye 10'''' and correcting its refractive errors. Advantageously, the procedure of this embodiment comprises a lamellar cross-linked corneal transplantation, which additionally results in simultaneous correction of the refractive error of the eye 10'''' of the patient. As used herein, the term "lenslet" refers to a lens implant configured to be implanted in a cornea of an eye. The lens implant may be formed from an organic material, a synthetic material, or a combination of organic and synthetic materials.

Figure 6A:
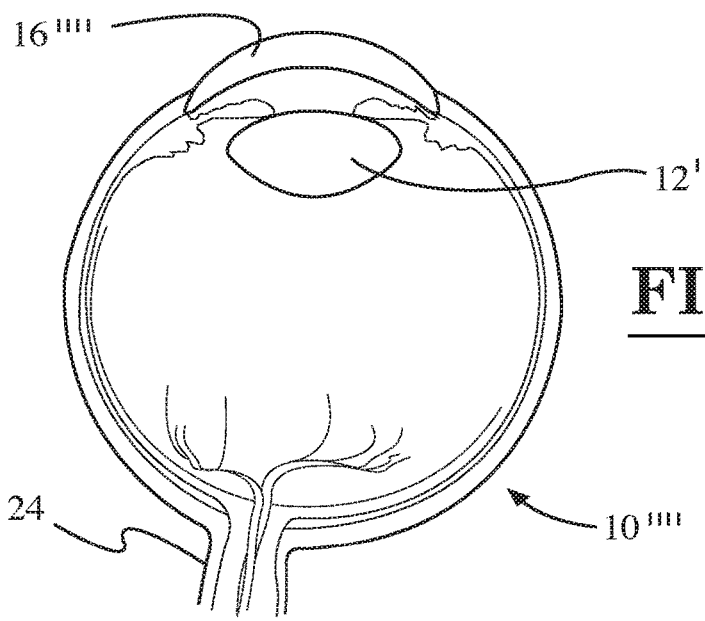
FIG. 6A is a side cross-sectional view of a host eye prior to an transplant procedure.
Figure 6B:
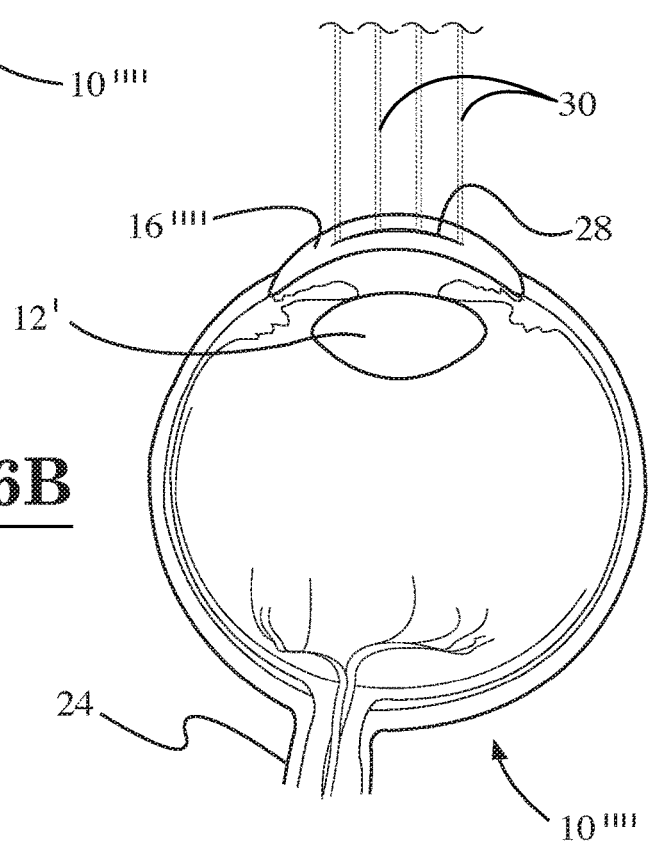
FIG. 6B is another side cross-sectional view of the host eye of FIG. 6A, which illustrates a creation of a corneal pocket therein.

Now, with reference to FIGS. 6A-6C and 7A-7C, the illustrative embodiment will be described in further detail. The host eye 10'''' with lens 12', cornea 16'''', and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16'''' of the host eye 10'''' (e.g., by using a suitable laser, which is indicated diagrammatically in FIG. 6B by lines 30).

Figure 7A:
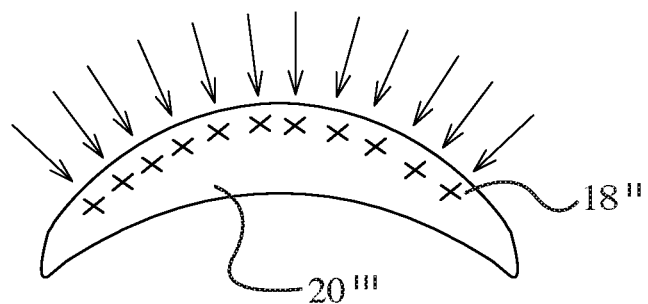
FIG. 7A is a partial side cross-sectional view of a donor cornea being cross-linked prior to being shaped for use in a transplant procedure.
Figure 7B:
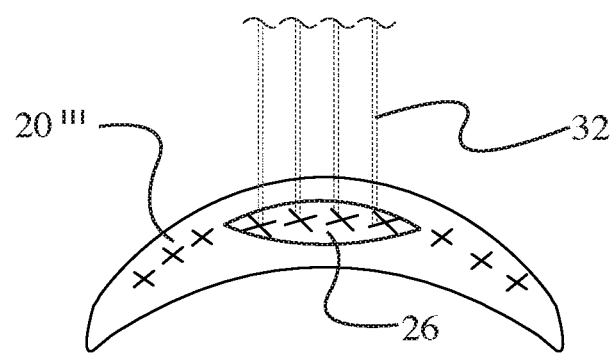
FIG. 7B is another partial side cross-sectional view of the donor cornea of FIG. 7A, which illustrates the cutting of a cross-linked lamellar lenslet from a remainder of the cross-lined donor cornea.
Figure 7C:
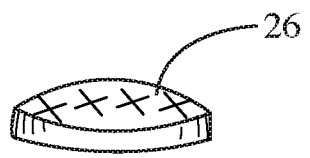
FIG. 7C is a side cross-sectional view of the cross-linked lamellar lenslet after it has been appropriately shaped and removed from the donor cornea of FIGS. 7A and 7B.

In FIG. 7A, the cross-linking 18'' of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked (e.g., by using a photosensitizer in the form of riboflavin and UV radiation as described above), it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10''''. As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20'''.

Figure 6C:
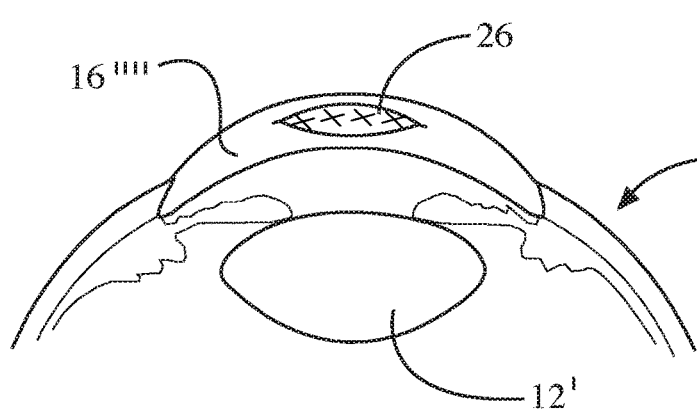
FIG. 6C is another side cross-sectional view of the host eye of FIG. 6A, which illustrates an implantation of the cross-linked lamellar lenslet into the host eye.

Finally, as shown in FIG. 6C, the cross-linked lamellar lenslet 26 is implanted into the cornea 16'''' of the host eye 10'''' of the patient in the location where the pocket 28 was previously formed. Because the shape of the transplant corresponds to that of the pocket 28 formed in the eye 10'''', the transplant sits comfortably in its position in the host cornea 16''''. As described above, after implantation of the cross-linked lamellar lenslet 26 into the eye 10'''', the refractive errors of the eye 10'''' have been corrected because the cross-linked lamellar lenslet 26 has been appropriately shaped to compensate for the specific refractive errors of the host eye 10'''' prior to its implantation into the eye 10''''. In addition, as explained above, the implantation of the cross-linked lamellar lenslet 26 provides additional stability to an eye having keratoconus, keratoglobus, a thin cornea, or abnormal corneal curvature.

Another illustrative embodiment of a corneal lenslet implantation procedure with a cross-linked cornea is shown in FIGS. 8-14. In general, the procedure illustrated in these figures involves forming a two-dimensional cut into a cornea of an eye; creating a three-dimensional pocket in the cornea of the eye, cross-linking the interior stroma, and inserting a lenslet or lens implant into the three-dimensional pocket after the internal stromal tissue has been cross-linked.

Figure 8:
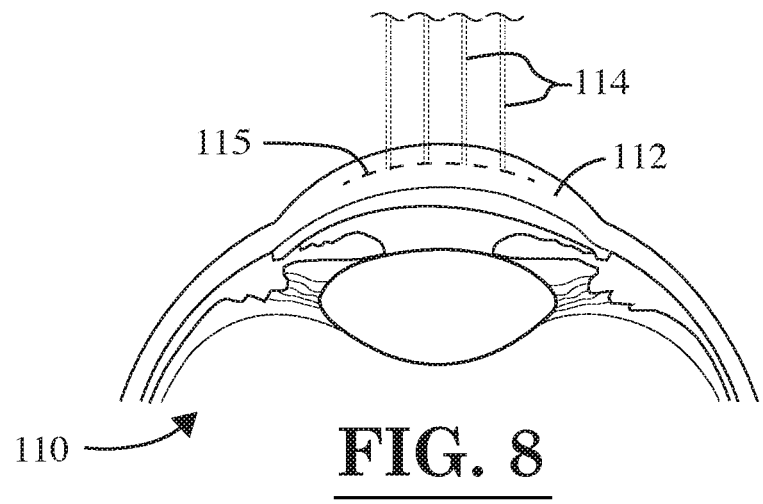
FIG. 8 is a partial side cross-sectional view illustrating the formation of a two-dimensional cut into a cornea of an eye, according to another embodiment of the invention.

Initially, in FIG. 8, the forming of a two-dimensional cut 115 into the cornea 112 of the eye 110 is diagrammatically illustrated. In particular, as shown in the illustrative embodiment of FIG. 8, the two-dimensional cut 115 is formed by making an intrastromal incision in the cornea 112 of the eye 110 using a femtosecond laser (i.e., the incision is cut in the cornea 112 using the laser beam(s) 114 emitted from the femtosecond laser). Alternatively, the two-dimensional cut 115 may be formed in the cornea 112 of the eye 110 using a knife.

Figure 9:
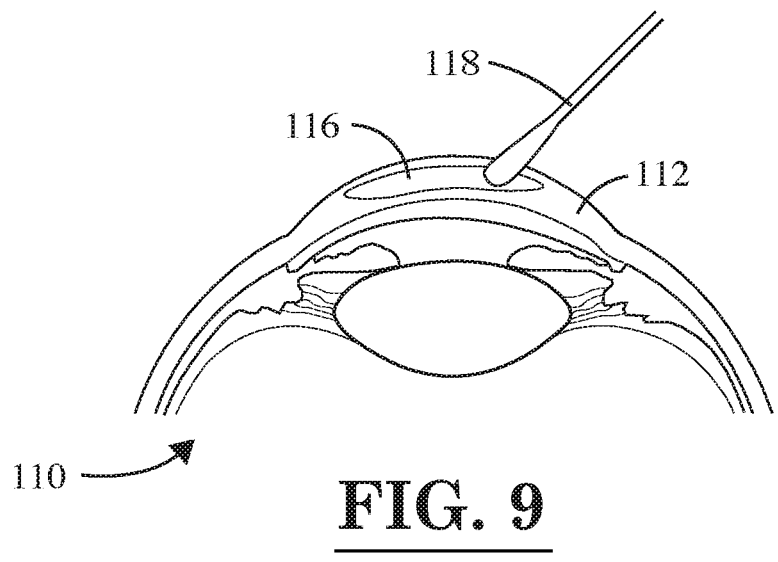
FIG. 9 is another partial side cross-sectional view of the eye of FIG. 8, which illustrates the creation of a three-dimensional pocket in the cornea of the eye.

Then, in FIG. 9, the forming of a three-dimensional corneal pocket 116 in the cornea 112 of the eye 110 is diagrammatically illustrated. In particular, as shown in the illustrative embodiment of FIG. 9, the three-dimensional corneal pocket 116 is formed by using a spatula 118. The formation of the intracorneal pocket 116 in the cornea 112 of the eye 110 allows one to gain access to the tissue surrounding the pocket 116 (i.e., the interior stromal tissue surrounding the pocket 116).

Turning again to FIGS. 8 and 9, in the illustrative embodiment, the corneal pocket 116 formed in the cornea 112 of the eye 110 may be in the form of an intrastromal corneal pocket cut into the corneal stroma. A femtosecond laser may be used to form a 2-dimensional cut into the cornea 112, which is then opened with a spatula 118 to create a 3-dimensional pocket 116. In one embodiment, a piece of the cornea 112 or a cornea which has a scar tissue is first cut with the femtosecond laser. Then, the cavity is cross-linked before filling it with an implant or inlay 128 to replace the lost tissue with a clear flexible inlay or implant 128 (see FIG. 12).

In one embodiment, a three-dimensional (3D) uniform circular, oval, or squared-shaped corneal pocket 116 is cut with a femtosecond laser and the tissue inside the pocket is removed to produce a three-dimensional (3D) pocket 116 to be cross-linked with riboflavin and implanted with a prepared implant.

Figure 10:
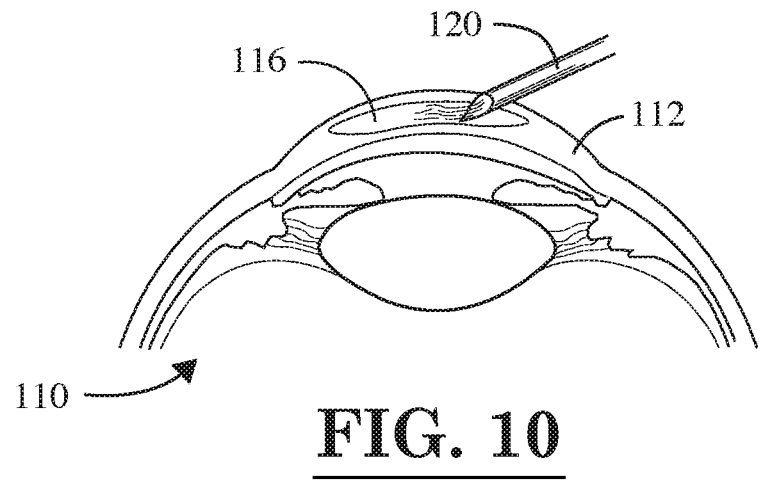
FIG. 10 is yet another partial side cross-sectional view of the eye of FIG. 8, which illustrates the injection of a photosensitizer into the three-dimensional pocket in the cornea of the eye.

After the pocket 116 is formed using the spatula 118, a photosensitizer is applied inside the three-dimensional pocket 116 so that the photosensitizer permeates the tissue surrounding the pocket 116 (see FIG. 10). The photosensitizer facilitates the cross-linking of the tissue surrounding the pocket 116. In the illustrative embodiment, the photosensitizer is injected with a needle 120 inside the stromal pocket 116 without lifting the anterior corneal stroma so as to cover the internal surface of the corneal pocket 116. In one or more embodiments, the photosensitizer or cross-linker that is injected through the needle 120 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 116 may be aspirated through the needle 120 until all, or substantially all, of the excess portion of the photosensitizer is removed from the pocket 116 (i.e., the excess cross-linker may be aspirated through the same needle so that the pocket 116 may be completely emptied or substantially emptied).

Figure 11A:
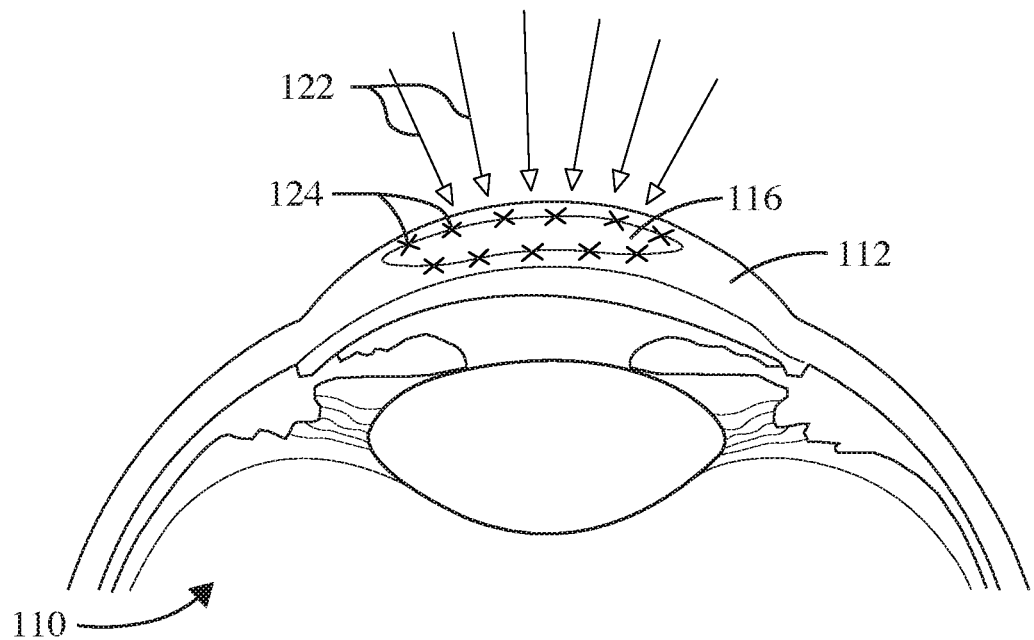
FIG. 11A is still another partial side cross-sectional view of the eye of FIG. 8, which illustrates the irradiation of the stromal tissue surrounding the three-dimensional pocket of the eye using ultraviolet radiation delivered from outside of the cornea.

Next, turning to the illustrative embodiment of FIG. 11A, shortly after the photosensitizer is applied inside the pocket 116, the cornea 112 of the eye 110 is irradiated from the outside using ultraviolet (UV) radiation 122 so as to activate cross-linkers in the portion of the tissue surrounding the three-dimensional pocket 116, and thereby stiffen the cornea 112, prevent corneal ectasia of the cornea 112, and kill cells in the portion of the tissue surrounding the pocket 116. In the illustrative embodiment, the ultraviolet light used to irradiate the cornea 112 may have a wavelength between about 370 nanometers and about 380 nanometers (or between 370 nanometers and 380 nanometers). Also, in the illustrative embodiment, only a predetermined anterior stromal portion 124 of the cornea 112 to which the photosensitizer was applied is cross-linked (i.e., the surrounding wall of the corneal pocket 116), thereby leaving an anterior portion of the cornea 112 and a posterior stromal portion of the cornea 112 uncross-linked. That is, in the illustrative embodiment, the entire corneal area inside the cornea 112 exposed to the cross-linker is selectively cross-linked, thereby leaving the anterior part of the cornea 112 and the posterior part of the stroma uncross-linked. The portion of the cornea 112 without the cross-linker is not cross-linked when exposed to the UV radiation. In an alternative embodiment, the cornea 112 may be irradiated using wavelengths of light other than UV light as an alternative to, or in addition to being irradiated using the ultraviolet (UV) radiation 122 depicted in FIG. 11A. Also, microwave radiation may be used synergistically or additively to correct non-invasively the remaining refractive error(s) of the cornea.

Figure 11B:
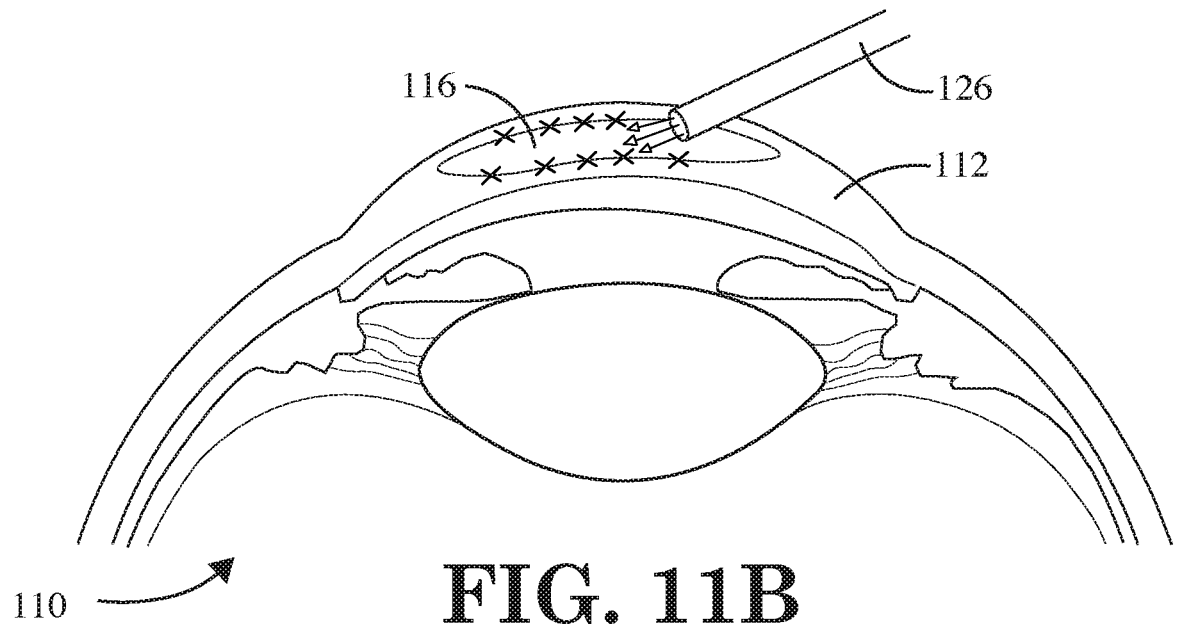
FIG. 11B is yet another partial side cross-sectional view of the eye of FIG. 8, which illustrates the irradiation of the stromal tissue surrounding the three-dimensional pocket of the eye using a fiber optic delivering ultraviolet radiation inside the three-dimensional pocket, according to an alternative embodiment of the invention.

Alternatively, as shown in FIG. 11B, a fiber optic 126 may be inserted into the corneal pocket 116 so as to apply the ultraviolet radiation and activate the photosensitizer in the wall of the corneal pocket 116. When the fiber optic 126 is used to irradiate the wall of the pocket 116, the ultraviolet radiation is applied internally, rather than externally as depicted in FIG. 11A.

Figure 12:
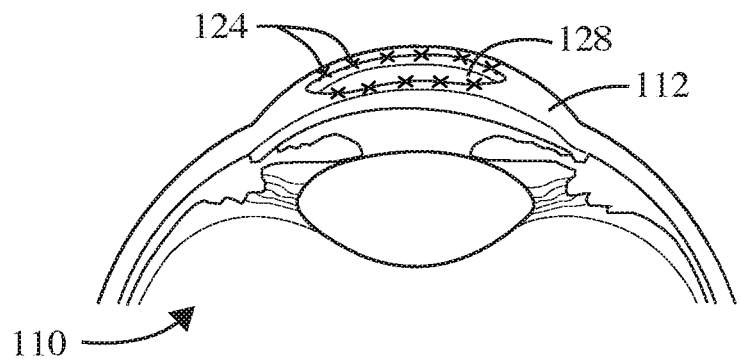
FIG. 12 is still another partial side cross-sectional view of the eye of FIG. 8, which illustrates a lens implant inserted into the pocket so as to change the refractive properties of the eye.

Now, with reference to FIG. 12, it can be seen that, after the wall of the corneal pocket 116 has been stiffened and is devoid of cellular elements by the activation of the cross-linkers, a lens implant 128 is inserted into the corneal pocket 116 in order to change the refractive properties of the eye. In particular, in the illustrated embodiment, the lens implant 128 is inserted through a small incision, and into the corneal pocket 116, using forceps or microforceps. In one or more embodiments, the lens implant 128 that is inserted inside the pocket 116 in the cornea 112 is flexible and porous. Also, in one or more embodiments, the lens implant 128 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof. The surface of the lens implant 128 may have the appropriate shape to reshape the cornea 112 or the dioptric power to nullify the remaining spheric or astigmatic error of the eye. More particularly, in one or more embodiments, the lens implant 128 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In the illustrative embodiment, the irradiation of the cornea 112 using the ultraviolet (UV) radiation 122 only activates cross-linkers in the portion of the stromal tissue surrounding the three-dimensional pocket 116, and only kills the cells in the portion of the tissue surrounding the pocket 116, so as to leave only a thin layer of cross-linked collagen to prevent an immune response and rejection of the lens implant 128 and/or encapsulation by fibrocytes, while preventing post-operative dry eye formation. In addition to preventing encapsulation of the lens implant 128 by fibrocytes, the cross-linking of the stromal tissue surrounding the pocket 116 also advantageously prevents corneal haze formation around the lens implant 128. That is, the cross-linking of the stromal tissue surrounding the lens implant 128 prevents formation of myofibroblast from surrounding keratocytes, which then convert gradually to fibrocytes that appear as a haze, and then white encapsulation inside the cornea, thereby causing light scattering in front of the patient's eye.

Figure 13:
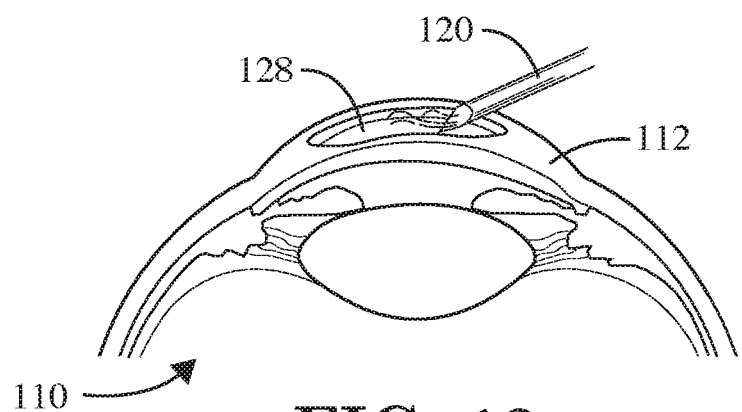
FIG. 13 is yet another partial side cross-sectional view of the eye of FIG. 8, which illustrates the reinjection of a photosensitizer into the three-dimensional pocket with the lens implant disposed therein so that the cross-linking procedure may be repeated.
Figure 14:
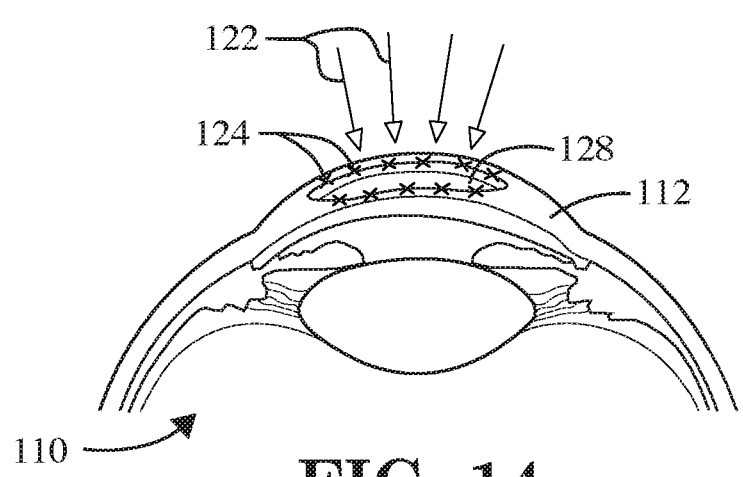
FIG. 14 is still another partial side cross-sectional view of the eye of FIG. 8, which illustrates the re-irradiation of the stromal tissue surrounding the three-dimensional pocket of the eye during the repetition of the cross-linking procedure.

As shown in FIGS. 13 and 14, the crosslinking procedure described above may be repeated after the lens implant 128 is implanted so as to prevent any cellular invasion in the area surrounding the implant 128. Initially, with reference to FIG. 13, the photosensitizer is reinjected inside the space between the lens implant 128 and the surrounding corneal tissue using a needle 120. In one or more embodiments, the needle 120 for injecting the photosensitizer may comprise a 30-32 gauge needle. Then, after the reinjection of the cross-linker, the cornea 112 is re-irradiated with ultraviolet radiation 122 to cross-link the tissue surrounding the lens implant 128 so as to prevent cellular migration towards the lens implant 128 (see FIG. 14).

In one or more embodiments, the lens implant or inlay 128 may be prepared ahead of time with known techniques, wherein the inlay 128 may be coated with a biocompatible material, such as collagen, elastin, polyethylene glycol, biotin, streptavidin, etc., or a combination thereof. The inlay 128 and the coating may be cross-linked with a photosensitizer or cross-linker, such as riboflavin, prior to being implanted into the pocket 116 in the cornea 112 of the eye.

In another embodiment, the lens implant or inlay 128 may be silicone, methacrylate, hydroxyethylmethacrylate (HEMA), or any other biocompatible transparent material, or a mixture thereof. The lens implant or inlay 128 also may be coated with materials, such as collagen or elastin, and may have a desired thickness of from 2 microns to 70 microns or more.

In yet another embodiment, the lens implant or inlay 128 is formed from an eye bank cornea, or a cross-linked eye bank cornea, etc. In general, there is a tremendous paucity of normal cadaver corneas for total or partial implants, such as for a corneal transplant of a corneal inlay. Because all the cellular elements are killed during the crosslinking of the corneal inlay, and because the corneal collagen is cross-linked and denatured, the remaining collagenous elements are not immunogenic when implanted inside the body or in the cornea of a patient. Advantageously, the prior cross-linking of the organic material, such as in the cadaver cornea, permits transplantation of the corneal inlay from an animal or human cornea or any species of animal to another animal or human for the first time without inciting a cellular or humoral response by the body, which rejects the inlay. Thus, cross-linking transparent cadaveric tissue for corneal transplantation, or as an inlay to modify of the refractive power of the eye, is highly beneficial to many patients who are on the waiting list for a corneal surgery. In addition, the surgery may be planned ahead of time without necessitating the urgency of the surgery when a fresh cadaver eye becomes available. In one or more embodiments, the collagens may be driven from the animal cornea, and cross-linked. Also, in one or more embodiments, the implant or inlay 128 may be made of cross-linked animal cornea or human cornea that is cut using a femtosecond laser to any desired shape and size, and then ablated with an excimer laser or cut with a femtosecond laser to a have a desired refractive power.

Figure 15:
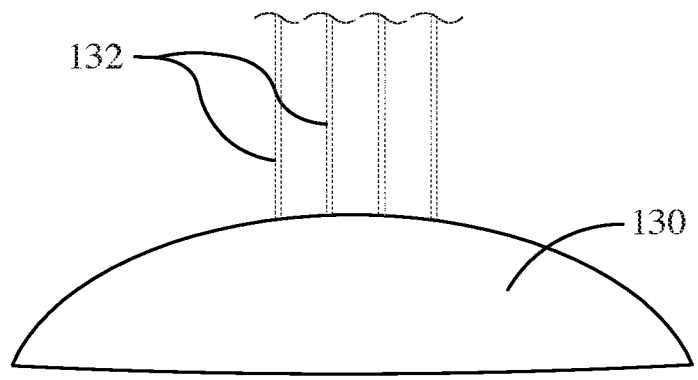
FIG. 15 is a side cross-sectional view illustrating the creation of a lens implant from an organic block of polymer using a excimer laser.
Figure 16:
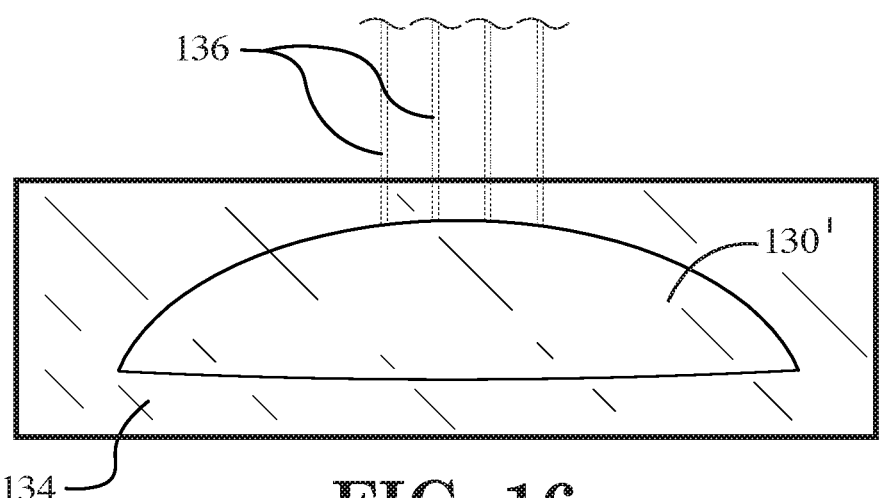
FIG. 16 is a side cross-sectional view illustrating the cutting of a lens implant from an organic block of polymer using a femtosecond laser.

For example, as shown in FIG. 15, the lens implant or inlay 130 may be formed from an organic block of a polymer (e.g., donor cornea) by cutting the lens implant 130 using an excimer laser (e.g., by using the laser beam(s) 132 emitted from the excimer laser). Alternatively, referring to FIG. 16, the lens implant or inlay 130' may be formed from an organic block 134 of a polymer (e.g., donor cornea) by cutting the lens implant 130' from the block 134 using a femtosecond laser or a computerized femto-system (e.g., by using the laser beam(s) 136 emitted from the femtosecond laser).

Figure 17:
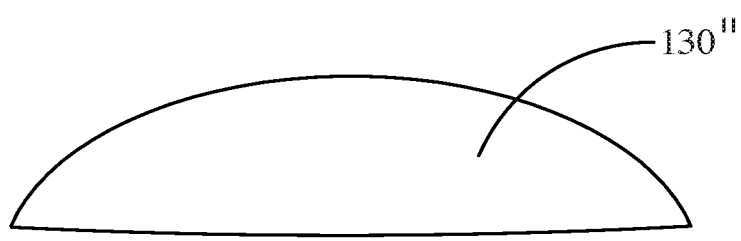
FIG. 17 is a side cross-sectional view illustrating a lens implant that has been formed using a three-dimensional printing technique or a molding technique.

In still another embodiment, as depicted in FIG. 17, the lens implant or inlay 130" is made using three-dimensional (3D) printing technology or a molding technique in order to form the lens implant or inlay 130" into the desired shape, size or thickness. The transparent material of the 3D-printed implant or inlay 130" may be coated with one or more biocompatible polymers and cross-linked prior to the implantation.

In yet another embodiment, after the implantation of an intraocular lens, the remaining refractive error of the eye may be corrected by the implantation of a lens implant or inlay 128 in the cross-linked pocket 116 of the cornea 112, thereby eliminating the need for entering the eye cavity to replace the original intraocular lens.

In still another embodiment, the remaining refractive error of the eye is corrected after an intraocular lens implantation by placing an inlay 128 on the surface of the cornea 112 of the patient while the shape of the cornea 112 is corrected with an excimer laser and wavefront optimized technology so that the patient is provided instant input on its effect on his or her vision. In this embodiment, an inlay similar to a contact lens is placed on the cornea 112 that, after correction, matches the desired refractive correction of the eye, and then, subsequently, the inlay 128 is implanted inside the cross-linked corneal pocket 116.

In yet another embodiment, the implant or inlay 128 may be ablated with an excimer laser for implantation in the cross-linked pocket 116, or after cross-linking the exposed corneal stroma in LASIK surgery.

In still another embodiment, a small amount of hyaluronic acid or a viscous fluid is injected into the pocket 116 prior to the implantation of the implant or inlay 128 so as to simplify the insertion of the implant or inlay 128 in the corneal pocket 116.

In yet another embodiment, the implant or inlay 128 is prepared having four marking holes of 0.1-2 millimeter (mm) in diameter in the inlay periphery at an equally sized distances so that the implant 128 may be rotated with a hook, if desired, after the implantation as needed to match the axis of an astigmatic error of the eye during the surgery as measured simultaneously with a wavefront technology system, such as an Optiwave Refractive Analysis (ORA) system or Holos® system, which are commercially available for measurement of astigmatism or its axis.

In still another embodiment, the implant or inlay 128 is located on the visual axis and may provide 1 to 3 times magnification for patients whose macula is affected by a disease process needing magnifying glasses for reading, such as in age-related macular degeneration, macular edema, degenerative diseases of the retina, etc. Because these eyes cannot be used normally for reading without external magnifier glasses, providing magnification by a corneal implant to one eye assists the patients in being able to read with one eye and navigate the familiar environment with their other eye.

In yet another embodiment, a part of the corneal stroma is removed from the eye of the patient, and its surface is corrected with an excimer laser to a desired refraction. Then, the removed part of the corneal stroma is cross-linked, and implanted back into the corneal pocket so as to correct the refractive power of the cornea.

In still another embodiment, the surface of the cornea 112 is treated after surgery in all cases daily with an anti-inflammatory agent, such as steroids, nonsteriodal anti-inflammatory drugs (NSAIDs), immune-suppressants, such as cyclosporine A or mycophenolic acid, anti-proliferative agents, antimetabolite agents, or anti-inflammatory agents (e.g., steroids, NSAIDS, or antibiotics etc.) to prevent inflammatory processes after the corneal surgery, inlay implantation or crosslinking, while stabilizing the integrity of the implant 128 and preventing future cell growth in the organic implant or the adjacent acellular corneal tissue. In this embodiment, the medication is injected in the corneal pocket 116 along with the implantation or the implant 128 is dipped in the medication first, and then implanted in the cross-linked corneal pocket 116.

In yet another embodiment, a cross-linked corneal inlay is placed over the cross-linked corneal stroma after a LASIK incision, and is abated to the desired size with an excimer laser using a topography guided ablation. By means of this procedure, the refractive power of the eye is corrected, while simultaneously providing stability to an eye prone to conceal ectasia postoperatively after a LASIK surgery. Then, the LASIK flap is placed back over the implant.

Figure 18:
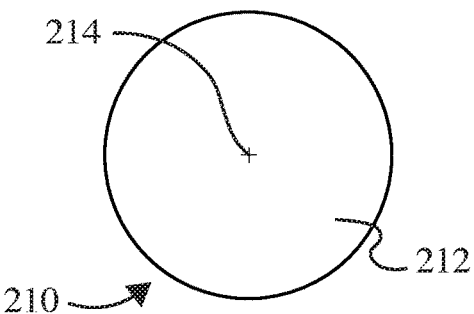
FIG. 18 is a front view of a cornea of an eye, according to yet another embodiment of the invention.

Yet another illustrative embodiment of a corneal lenslet implantation procedure with a cross-linked cornea is shown in FIGS. 18-23. In general, the procedure illustrated in these figures involves initially making an intrastromal square pocket surrounding the visual axis of the eye, and then, after forming the initial square pocket, a three-dimensional circular portion of diseased or weak stromal tissue is cut, removed, and replaced with a circular implant which fits into the circle that borders the four sides of the square. A front view of the cornea 212 of the eye 210 with the centrally-located visual axis 214 is illustrated in FIG. 18. Advantageously, in the illustrative embodiment of FIGS. 18-23, corneal tissue removal around the visual axis is greatly facilitated, and nearly perfect centration of the lens implant or inlay 220 about the visual axis is possible because the lens implant 220 fits within a depressed circular recess at the bottom of the pocket 216. As such, the undesirable decentering of the lens implant is prevented.

Figure 19:
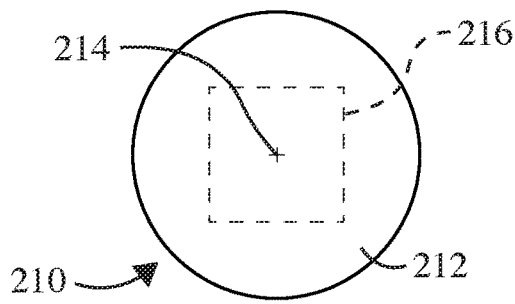
FIG. 19 is another front view of the cornea of the eye of FIG. 18, wherein a square-shaped intrastromal pocket has been formed in the cornea of the eye.

Initially, in FIG. 19, the forming of an intrastromal square-shaped pocket 216 surrounding the visual axis 214 (represented by a plus sign) in the cornea 212 of the eye 210 is diagrammatically illustrated. In particular, as shown in the illustrative embodiment of FIG. 19, the square-shaped pocket 216 is formed by making a two-dimensional intrastromal incision in the cornea 212 of the eye 210 using a femtosecond laser (i.e., the incision is cut in the cornea 212 using the laser beam(s) emitted from the femtosecond laser).

Figure 20:
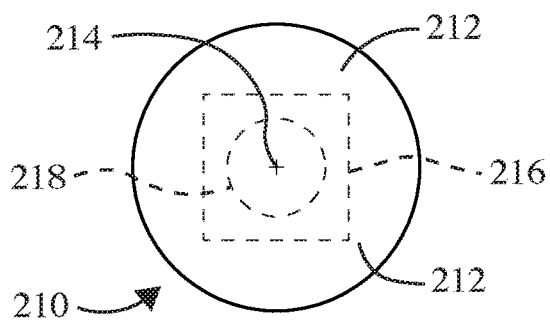
FIG. 20 is yet another front view of the cornea of the eye of FIG. 18, wherein a circular three-dimensional portion of tissue having a first diameter has been removed from the area within the square-shaped intrastromal pocket.
Figure 21:
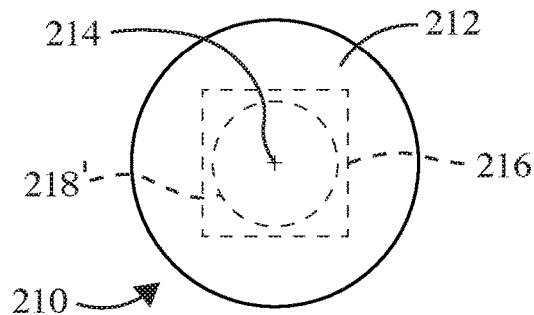
FIG. 21 is still another front view of the cornea of the eye of FIG. 18, wherein a circular three-dimensional portion of tissue having second diameter has been removed from the area within the square-shaped intrastromal pocket, the second diameter of the circular three-dimensional portion of tissue in FIG. 21 being larger than the first diameter of the circular three-dimensional portion of tissue in FIG. 20.

Then, in FIG. 20, the removal of a three-dimensional circular portion 218 of diseased or weak stromal tissue in the cornea 212 of the eye 210 is diagrammatically illustrated. In particular, as shown in the illustrative embodiment of FIG. 20, the three-dimensional circular stromal tissue portion 218 has a first diameter, which is less than a width of the square-shaped pocket 216 so that the three-dimensional circular stromal tissue portion 218 is disposed within the boundaries of the square-shaped pocket 216. The three-dimensional circular stromal tissue portion 218' depicted in FIG. 21 is generally similar to that illustrated in FIG. 20, except that the three-dimensional circular stromal tissue portion 218' depicted in FIG. 21 has a second diameter that is slightly larger than the first diameter of the three-dimensional circular stromal tissue portion 218 in FIG. 20. As such, the periphery of the three-dimensional circular stromal tissue portion 218' depicted in FIG. 21 is disposed closer to the square-shaped pocket 216, but still within the confines of the square-shaped pocket 216. In the illustrative embodiment, the three-dimensional circular stromal tissue portion 218, 218' may be removed using forceps or micro-forceps. In an exemplary embodiment, the diameter of the circular stromal tissue portion 218, 218' that is removed from the cornea 212 is between approximately 5 millimeters and approximately 8 millimeters, inclusive (or between 5 millimeters and 8 millimeters, inclusive).

In an alternative embodiment of the corneal lenslet implantation procedure, three (3) sequential cuts may be made in the stromal portion of the cornea 212 of the eye 210 using a femtosecond laser in order to form the pocket. First, a lower circular cut or incision centered about the visual axis (i.e., a lower incision with the patient in a supine position) is made using the femtosecond laser. Then, a second vertical cut is made above the lower incision using the femtosecond laser to form the side(s) of a circular cutout portion. Finally, a third square or circular cut (i.e., an upper incision) is made above the vertical cut using the femtosecond laser. In the illustrative embodiment, the lower incision is parallel to the upper incision, and the vertical cut extends between lower incision and the upper incision. In this alternative embodiment, the three-dimensional circular stromal tissue cutout portion bounded by the lower incision on the bottom thereof, the vertical cut on the side(s) thereof, and the upper incision on the top thereof is removed from the cornea 212 of the eye 210 using a pair of forceps. A cavity formed by the upper incision facilitates the removal of the three-dimensional circular stromal tissue cutout portion. As described above, the third cut or incision formed using the femtosecond laser may be an upper circular cut that is larger than the lower circular cut, rather than an upper square cut that is larger than the lower circular cut.

Figure 22:
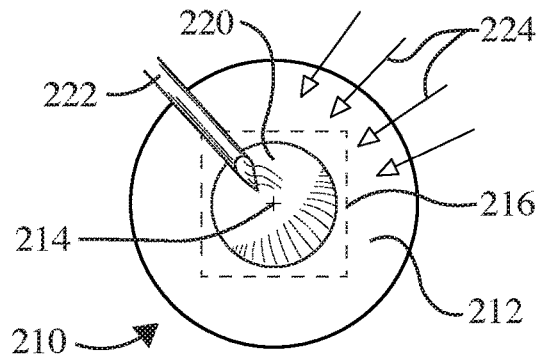
FIG. 22 is yet another front view of the cornea of the eye of FIG. 18, wherein a circular lens implant has been implanted in the area where the circular three-dimensional portion of tissue has been removed, and wherein a photosensitizer is being injected into the pocket in the cornea of the eye.

Turning to FIG. 22, after the three-dimensional circular stromal tissue portion 218, 218' is removed, a photosensitizer is applied inside the pocket 216 so that the photosensitizer permeates the tissue surrounding the pocket 216. The photosensitizer facilitates the cross-linking of the tissue surrounding the pocket 216. In the illustrative embodiment, the photosensitizer is injected with a needle 222 inside the stromal pocket 216. In one or more embodiments, the photosensitizer or cross-linker that is injected through the needle 222 inside the stromal pocket 216 comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 216 may be aspirated through the needle 222 until all, or substantially all, of the excess portion of the photosensitizer is removed from the pocket 216 (i.e., the excess cross-linker may be aspirated through the same needle 222 so that the pocket 216 may be completely emptied or substantially emptied).

Next, turning again to the illustrative embodiment of FIG. 22, shortly after the photosensitizer is applied inside the pocket 216, the cornea 212 of the eye 210 is irradiated from the outside using ultraviolet (UV) radiation 224 so as to activate cross-linkers in the portion of the tissue surrounding the three-dimensional pocket 216, and thereby stiffen the cornea 212, prevent corneal ectasia of the cornea 212, and kill cells in the portion of the tissue surrounding the pocket 216. In the illustrative embodiment, the ultraviolet light used to irradiate the cornea 212 may have a wavelength between about 370 nanometers and about 380 nanometers (or between 370 nanometers and 380 nanometers). Also, in the illustrative embodiment, only a predetermined anterior stromal portion of the cornea 212 to which the photosensitizer was applied is cross-linked (i.e., the surrounding wall of the corneal pocket 216), thereby leaving an anterior portion of the cornea 212 and a posterior stromal portion of the cornea 212 uncross-linked. That is, in the illustrative embodiment, the entire corneal area inside the cornea 212 exposed to the cross-linker is selectively cross-linked, thereby leaving the anterior part of the cornea 212 and the posterior part of the stroma uncross-linked. The portion of the cornea 212 without the cross-linker is not cross-linked when exposed to the UV radiation. In an alternative embodiment, the cornea 212 may be irradiated using wavelengths of light other than UV light as an alternative to, or in addition to being irradiated using the ultraviolet (UV) radiation 224 depicted in FIG. 22. Also, microwave radiation may be used synergistically or additively to correct non-invasively the remaining refractive error(s) of the cornea. In addition, in an alternative embodiment, the ultraviolet (UV) radiation may be applied after the implantation of the lens implant 220 to perform the crosslinking, rather than before the implantation of the lens implant 220 as described above. Further, rather than applying the ultraviolet (UV) radiation from outside the cornea 212, the stromal tissue of the pocket 216 may be irradiated from inside by means of a fiber optic, before or after the implantation of the lens implant 220.

Figure 23:
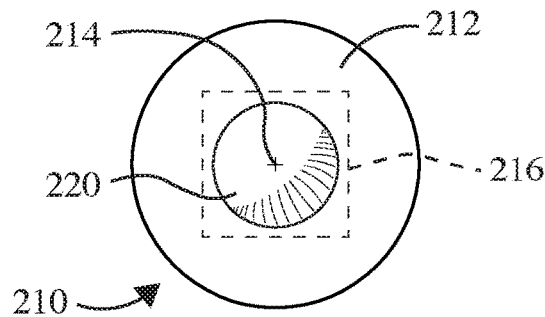
FIG. 23 is still another front view of the cornea of the eye of FIG. 18, wherein the circular lens implant is shown in the area where the circular three-dimensional portion of tissue was removed.

Now, with combined reference to FIGS. 22 and 23, it can be seen that, before or after the wall of the corneal pocket 216 has been stiffened and is devoid of cellular elements by the activation of the cross-linkers, a circular lens implant 220 is inserted into the circular recess at the bottom of the pocket 216 formed by the three-dimensional circular stromal tissue cutout portion 218, 218' that was removed. That is, the circular lens implant 220 fits within the periphery of the circular recess that borders the four sides of the squared-shaped pocket 216. In particular, in the illustrated embodiment, the circular lens implant 220 is inserted through a small incision, and into the circular recess at the bottom of the pocket 216 using forceps or microforceps. In the illustrative embodiment, the flexible lens implant 220 may be folded, inserted through the small incision, placed inside the circular recess at the bottom of the pocket 216, and finally unfolded through then small incision. In one or more embodiments, the lens implant 220 that is inserted inside the pocket 216 in the cornea 212 is flexible and porous. Also, in one or more embodiments, the lens implant 220 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof.

Advantageously, the lens implant 220 of the aforedescribed illustrative embodiment always remains perfectly centered around the visual axis 214 of the eye 210, and will not move because it is disposed within the circular recess at the bottom of the pocket 216. As explained above, the lens implant 220 may be formed from an organic material, synthetic material, polymeric material, and combinations thereof. The lens implant 220 may replace either a diseased tissue or create a new refractive power for the eye 210, as explained hereinafter.

In the illustrative embodiment, the lens implant 220 may correct the refractive errors of the eye 210. The refractive error correction may be done by the lens implant 220 having a curvature that changes the corneal surface of the cornea 212. Alternatively, the lens implant 220 may have a different index of refraction that corrects the refractive power of the cornea 212. In the illustrative embodiment, the lens implant 220 may have the appropriate shape to reshape the cornea 212 or the dioptric power to nullify the remaining spheric or astigmatic error of the eye. More particularly, in one or more embodiments, the lens implant 220 may have one of: (i) a concave anterior surface to correct myopic refractive errors (i.e., a minus lens for correcting nearsightedness), (ii) a convex anterior surface to correct hyperopic refractive errors (i.e., a plus lens for correcting farsightedness), or (iii) a toric shape to correct astigmatic refractive errors.

In the illustrative embodiment, the irradiation of the cornea 212 using the ultraviolet (UV) radiation 224 only activates cross-linkers in the portion of the stromal tissue surrounding the three-dimensional pocket 216, and only kills the cells in the portion of the tissue surrounding the pocket 216, so as to leave only a thin layer of cross-linked collagen to prevent an immune response and rejection of the lens implant 220 and/or encapsulation by fibrocytes, while preventing post-operative dry eye formation. In addition to preventing encapsulation of the lens implant 220 by fibrocytes, the cross-linking of the stromal tissue surrounding the pocket 216 also advantageously prevents corneal haze formation around the lens implant 220. That is, the cross-linking of the stromal tissue surrounding the lens implant 220 prevents formation of myofibroblast from surrounding keratocytes, which then convert gradually to fibrocytes that appear as a haze, and then white encapsulation inside the cornea, thereby causing light scattering in front of the patient's eye.

It is readily apparent that the aforedescribed corneal transplant procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of abovedescribed tissue adhesives reduces the surgical procedure significantly. Moreover, the aforedescribed corneal lenslet implantation procedures modify the cornea so as to better correct ametropic conditions. Furthermore, the corneal lenslet implantation procedures described above prevent the lens implant from moving around inside the cornea once implanted, thereby ensuring that the lens implant remains centered about the visual axis of the eye.

With reference to the illustrative embodiment of FIGS. 24-29, an exemplary method of preventing capsular opacification and fibrosis utilizing an accommodative intraocular lens implant will be explained. In general, the procedure illustrated in FIGS. 24-29 involves treating patients in need of cataract surgery and a replacement intraocular lens.

Figure 24:
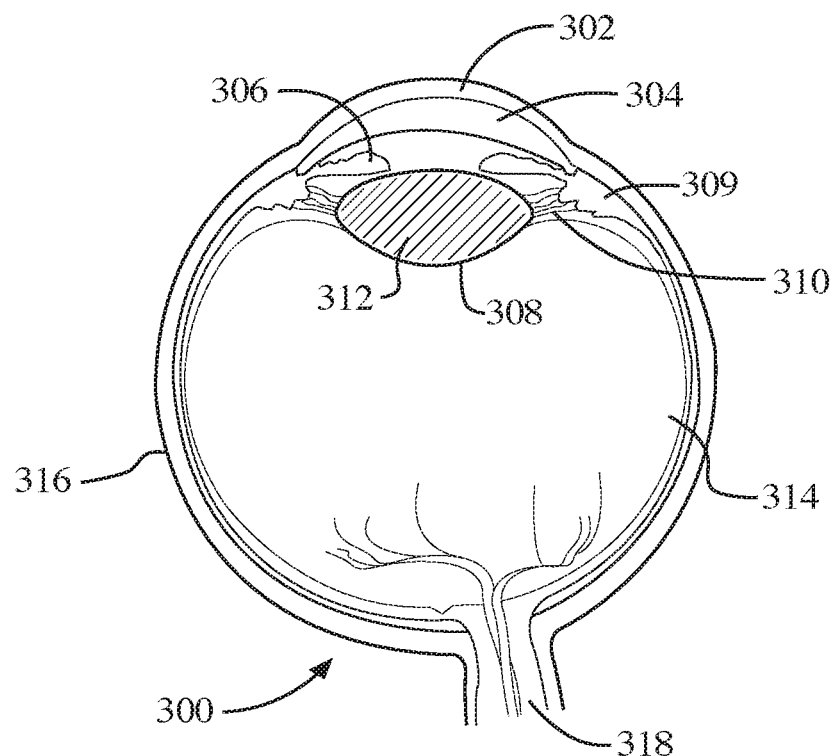
FIG. 24 is a side cross-sectional view illustrating an eye with a cataract, according to still another embodiment of the invention.

Initially, referring to FIG. 24, it can be seen that the eye 300 undergoing cataract surgery generally includes a cornea 302, an anterior chamber 304, an iris 306, a lens capsule or capsular bag 308, ciliary body 309, lens zonules 310, a vitreous cavity 314, a sclera 316, and an optic nerve 318. As shown in FIG. 24, the eye 300 has a cataract 312 (i.e., a cloudy lens), thereby requiring that cataract surgery be performed on the eye 300 of the patient.

Figure 25:
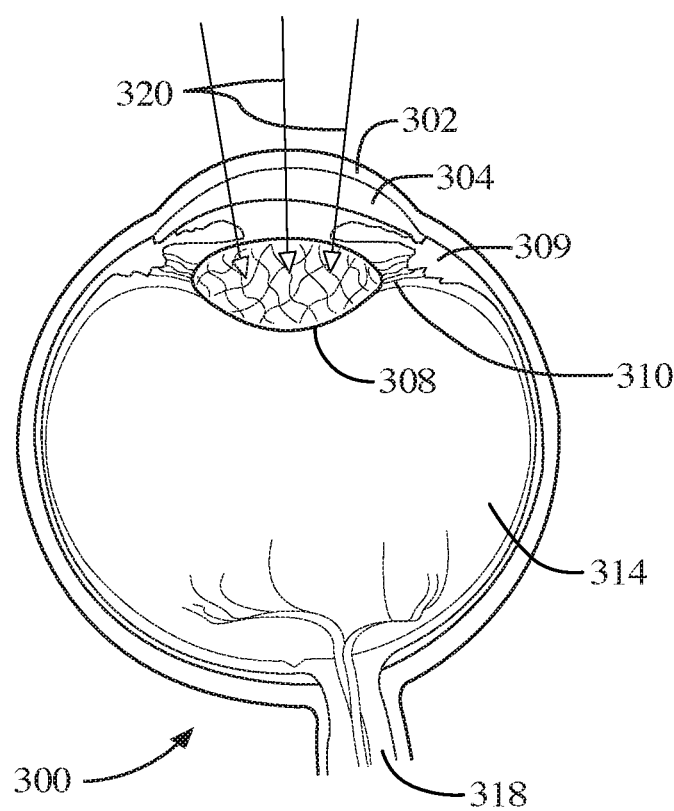
FIG. 25 is another side cross-sectional view of the eye of FIG. 24, which illustrates the breaking apart of the natural lens into lens fragments using a laser.

In FIG. 25, the first stage of the removal of the cortex and nucleus of the natural lens of the eye 300 containing the cataract 312 is diagrammatically illustrated. Specifically, in FIG. 25, the cloudy natural lens of the eye 300 is shown being broken apart into lens fragments by utilizing a femtosecond laser (i.e., the natural lens is broken apart by using the laser beam(s) 320 emitted from the femtosecond laser). The natural lens is initially broken apart into fragments so that it is capable of being more easily removed from the lens capsule 308 of the eye 300.

Figure 26:
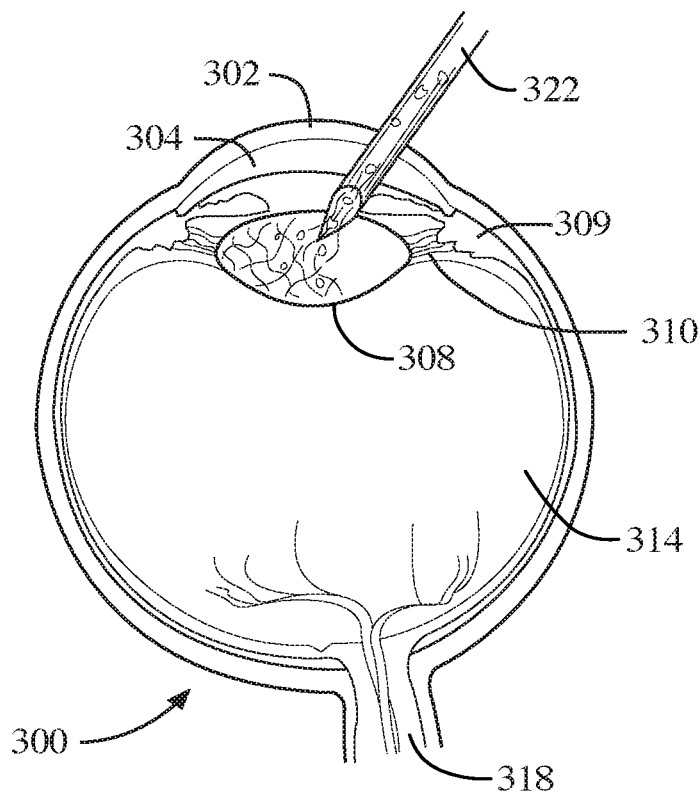
FIG. 26 is yet another side cross-sectional view of the eye of FIG. 24, which illustrates the irrigation and aspiration of the lens fragments of the natural lens using a probe.

Then, referring to FIG. 26, the second stage of the removal of the cortex and nucleus of the natural lens of the eye 300 containing the cataract 312 is diagrammatically shown. In particular, as depicted in FIG. 26, the lens fragments of the natural lens are being removed from the lens capsule 308 of the eye 300 using an ultrasonic probe 322. More particularly, the ultrasonic probe 322 irrigates and aspirates the lens fragments of the natural lens. In addition, the ultrasonic probe 322 may also be used to aspirate a substantial portion of the lens epithelium from the lens capsule 308 through an additional hole made in the lens capsule 308 and used as a bimanual system. That is, in the illustrative embodiment, the ultrasonic probe 322 may be used to aspirate as much of the lens epithelium as possible from the lens capsule 308 to prevent the undesirable propagation of lens epithelium cells following the cataract surgery.

Figure 27:
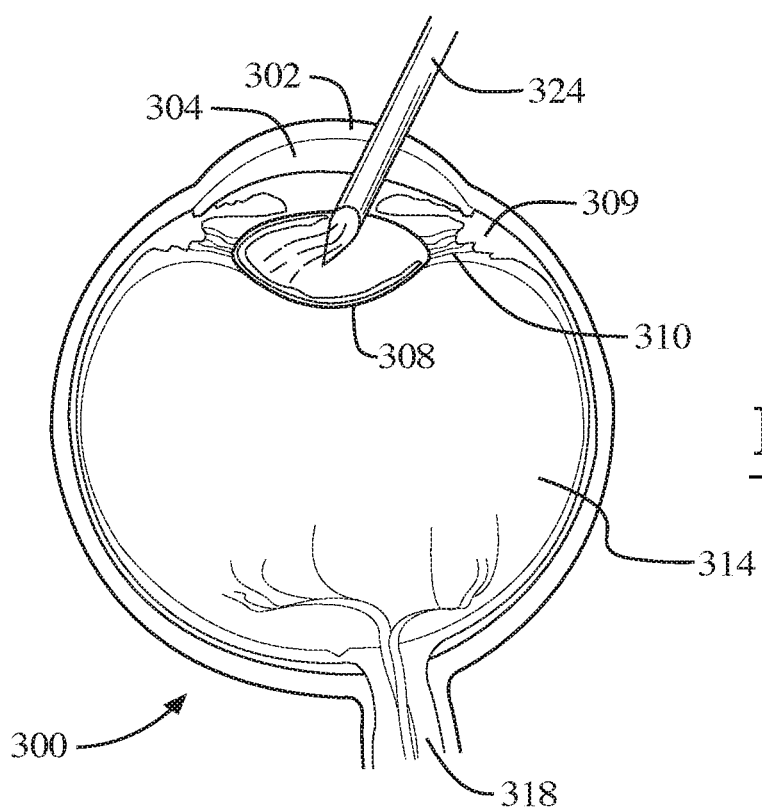
FIG. 27 is still another side cross-sectional view of the eye of FIG. 24, which illustrates the application of a photosensitizer to the capsular bag of the eye after the cataract has been removed.

Next, in FIG. 27, the injection of a cross-linker or photosensitizer (e.g., riboflavin) into the capsular bag 308 of the eye 300 is diagrammatically illustrated. In particular, as shown in the illustrative embodiment of FIG. 27, the cataract 312 has been removed from the capsular bag 308, which leaves the vast majority of the capsular bag 308 intact. Then, as shown in FIG. 27, a photosensitizer is applied inside the capsular bag 308 so that the photosensitizer permeates the tissue in both the anterior and posterior portions of the capsular bag 308. The photosensitizer facilitates the cross-linking of the tissue in the anterior and posterior portions of the capsular bag 308. In the illustrated embodiment of FIG. 27, the photosensitizer is injected with a needle 324 into the capsular bag 308 of the eye 300 by inserting the needle 324 through the anterior chamber 304 of the eye 300, and into the capsular bag 308 through the anterior wall of the capsular bag 308. In one or more embodiments, the photosensitizer or cross-linker that is injected through the needle 324 into the capsular bag 308 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 308 may be aspirated through the needle 324 until all, or substantially all, of the excess portion of the photosensitizer is removed from the capsular bag 308 (i.e., the excess cross-linker may be aspirated through the same needle 324 so that the capsular bag 308 may be completely emptied or substantially emptied). Also, in one or more embodiments, in order to kill the remaining lens epithelial cells that are generally attached to the rear side of the anterior portion of the lens capsule 308, the riboflavin may be in a relatively hypotonic solution that permits the lens cells to swell and makes them easier to remove or kill during the irradiation step described hereinafter.

Figure 28:
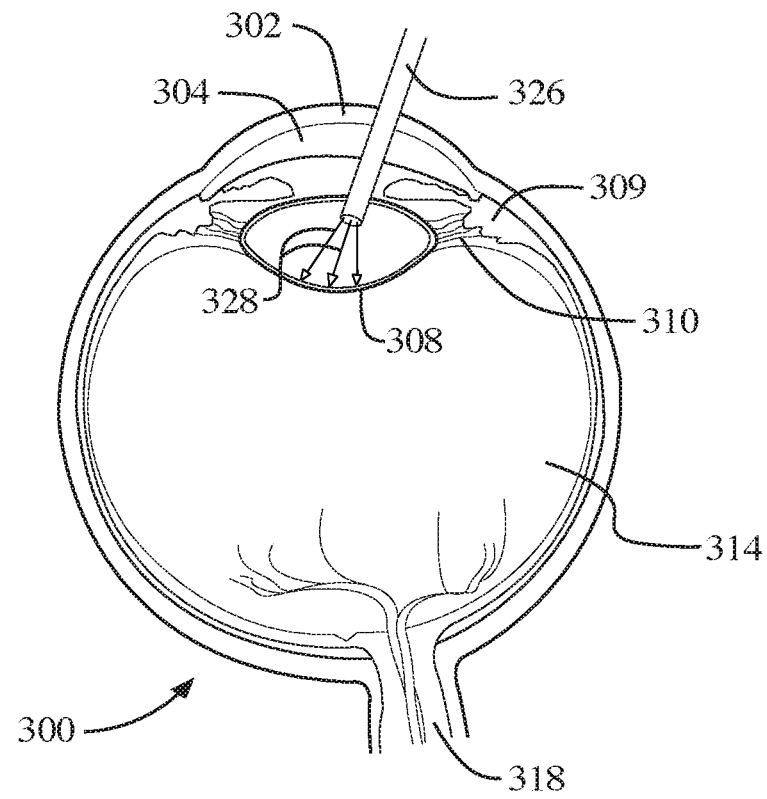
FIG. 28 is yet another side cross-sectional view of the eye of FIG. 24, which illustrates the irradiation of the capsular bag of the eye using a fiber optic so as to activate cross-linkers in the capsular bag.

Next, turning to FIG. 28, shortly after the photosensitizer is applied inside the capsular bag 308, the entire capsular bag 308 of the eye 300 (i.e., both the anterior portion and posterior portion of the lens capsule 308) is irradiated using a fiber optic 326 delivering ultraviolet (UV) radiation 328 so as to damage the remaining lens epithelial cells with UV laser light, thereby preventing capsular opacification and fibrosis. In the illustrative embodiment, the irradiation of the lens capsule 308 includes the anterior portion of the lens capsule 308 in order to prevent growth of the damaged lens epithelial cells and prevent cell migration and opacification because, in some cases, epithelial cells are still left in the lens capsule 308 after irrigation and aspiration of the lens fragments. Advantageously, the killing of the epithelial cells by irradiation prevents the further growth of the lens epithelial cells, and prevents their migration toward the posterior portion of the lens capsule 308 where they later become opaque. Also, in the illustrative embodiment, a painting technique may be utilized to deliver the ultraviolet light 328 to the capsular bag 308 of the eye 300 (i.e., the fiber optic 326 may be manipulated in such a manner by the surgeon so as to "paint" the ultraviolet light 328 on the capsular bag 308). Also, in the illustrative embodiment, ultraviolet (UV) radiation 328 may have a wavelength between about 370 nanometers and about 380 nanometers (or between 370 nanometers and 380 nanometers). In an alternative embodiment, the capsular bag 308 of the eye 300 may be irradiated using another wavelength of light as an alternative to, or in addition to being irradiated using ultraviolet (UV) radiation.

In an alternative embodiment, the anterior portion of the capsular bag 308 may be irradiated from outside the capsular bag 308 rather than from inside the capsular bag 308 as depicted in FIG. 28. In this embodiment, the fiber optic 326 may be disposed in the anterior chamber 304 of the eye 300 so that the ultraviolet (UV) light may be directed towards the anterior portion of the capsular bag 308. For example, the fiber optic 326 may be disposed at an acute angle relative to the capsular bag 308, but not perpendicular to the capsular bag 308 (so that the macula is protected and not damaged by the UV light emitted from the fiber optic 326).

Figure 29:
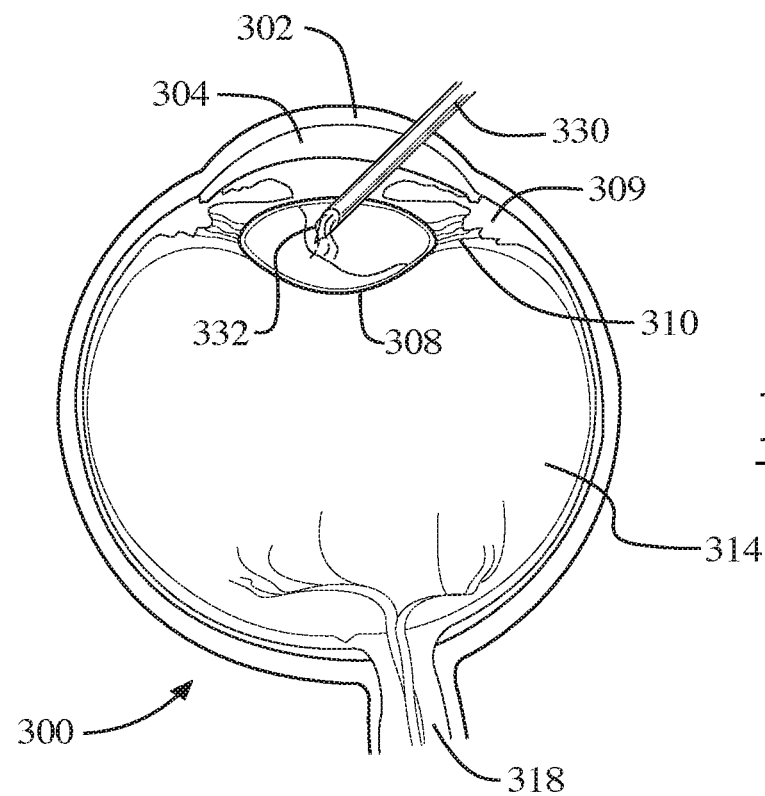
FIG. 29 is still another side cross-sectional view of the eye of FIG. 24, which illustrates the injection a transparent polymer into the lens capsule of the eye in order to form an accommodative intraocular lens for replacing the cortex and nucleus of the natural lens that was removed from the eye.

Finally, referring to FIG. 29, it can be seen that, after the tissue of the capsular bag 308 has been irradiated, a transparent polymer 332 is injected into the capsular bag 308 of the eye 300 using a needle 330 in order to form an accommodative intraocular lens implant for replacing the cortex and nucleus of the cloudy natural lens that was removed from the eye 300. In particular, in the illustrative embodiment, the needle 330 for injecting the transparent polymer 332 forming the accommodative intraocular lens is inserted into the capsular bag 308 of the eye 300 through an anterior hole or holes in the lens capsule 308. The hole or holes in the anterior chamber are plugged after the transparent polymer forming the accommodative intraocular lens hardens. In the illustrative embodiment, the transparent polymer that forms the accommodative intraocular lens remains flexible after the transparent polymer hardens or solidifies. Also, in the illustrative embodiment, after the transparent polymer that forms the accommodative intraocular lens is injected into the capsular bag 308 of the eye using the needle 330, the refractive power of the accommodative intraocular lens is adjusted using a wavefront technology unit intraoperatively so that the intraocular lens is able to be focused for a far distance without accommodation, and additionally is able to be focused for a near distance during accommodation by increasing the refractive power of the intraocular lens using the natural accommodative mechanism of the eye 300. Advantageously, intraoperative units utilizing wavefront technology are capable of indicating perfect refraction. During the injection process, both overfilling or under filling of the capsular bag 308 is not desirable because it does not provide proper refractive power for the lens and the eye 300.

In a further embodiment, the transparent polymer 332 that forms the accommodative intraocular lens implant is partially polymerized when injected into the capsular bag 308, and the transparent polymer becomes completely polymerized within a predetermined time period (e.g., within 5 to 20 minutes) after being injected into the capsular bag 308. In general, the polymerization time of the accommodative intraocular lens implant depends on the polymerization initiator that is used.

In one or more further embodiments, cataract surgery and glaucoma surgery with or without stent implantation may be done in a single session, wherein the photosensitizer is initially injected in the lens capsule after removal of the lens cortex and the nucleus. Then, a fiber optic is used to apply ultraviolet (UV) radiation so as to damage the lens epithelial cells and prevent their cellular proliferation. Immediately thereafter, the tissue around the surgical opening made in the eye wall during the glaucoma surgery with or without the shunt placement to drain the aqueous fluid outside the eye, is stained with the photosensitizer that was injected in the lens capsule. The photosensitizer migrates outside the eye through the surgical hole in the eye wall. The tissue, which is bathed by the photosensitizer (e.g., riboflavin), is then cross-linked with UV radiation applied through a fiber optic from the inside the eye or outside through the conjunctiva over the surgical hole or the shunt, regardless of the presence of a stent. The procedure achieves two goals simultaneously by preventing lens epithelial proliferation in the lens capsule, and by preventing fibroblast proliferation around the surgical hole of the tube.

Now, referring to the illustrative embodiment of FIGS. 30-41, an exemplary method for prevention of capsular opacification and fibrosis after cataract extraction, and for the prevention of fibrosis around a shunt or stent after glaucoma surgery will be explained. In general, the procedure illustrated in FIGS. 30-41 involves treating patients in need of both cataract surgery and glaucoma surgery. In the illustrative embodiment of FIGS. 30-41, the cataract and glaucoma surgeries are performed sequentially. However, as described hereinafter, the cataract and glaucoma surgeries may also be performed as two separate procedures. In these embodiments, the intraocular pressure (IOP) measurement is independent for a patient in need of cataract surgery and/or a glaucoma surgery.

Figure 30:
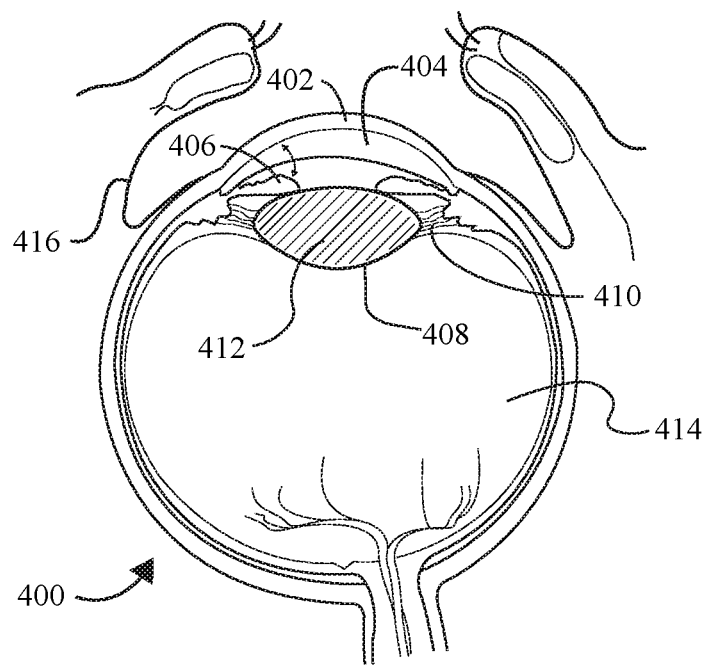
FIG. 30 is a side cross-sectional view illustrating an eye with a cataract, according to yet another embodiment of the invention.

Initially, referring to FIG. 30, it can be seen that the eye 400 undergoing cataract surgery generally includes a cornea 402, an anterior chamber 404, an iris 406, a lens capsule or capsular bag 408, lens zonules 410, a vitreous cavity 414, and a conjunctiva 416. As shown in FIG. 30, the eye 400 has a cataract 412 (i.e., a cloudy lens), thereby requiring that cataract surgery be performed on the eye 400 of the patient.

Figure 31:
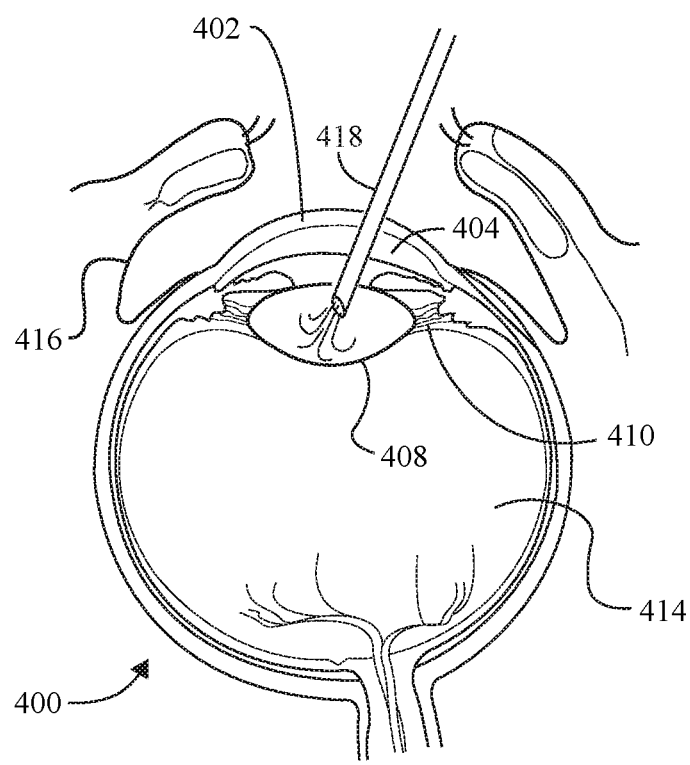
FIG. 31 is another side cross-sectional view of the eye of FIG. 30, which illustrates the application of a photosensitizer to a posterior portion of the capsular bag of the eye after the cataract has been removed.

In FIG. 31, the injection of a photosensitizer (e.g., riboflavin) into the posterior portion of the capsular bag 408 of the eye 400 is diagrammatically illustrated. In particular, as shown in the illustrative embodiment of FIG. 31, the cataract 412 has been removed from the capsular bag 408, which leaves the posterior portion of the capsular bag 408 intact. Then, as shown in FIG. 31, a photosensitizer is applied inside the capsular bag 408 so that the photosensitizer permeates the tissue in the posterior portion of the capsular bag 408. The photosensitizer facilitates the cross-linking of the tissue in the posterior portion of the capsular bag 408. In the illustrated embodiment of FIG. 31, the photosensitizer is injected with a needle 418 into the capsular bag 408 of the eye 400 by inserting the needle 418 through the anterior chamber 404 of the eye 400, and into the capsular bag 408. In one or more embodiments, the photosensitizer or cross-linker that is injected through the needle 418 into the capsular bag 408 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 408 may be aspirated through the needle 418 until all, or substantially all, of the excess portion of the photosensitizer is removed from the capsular bag 408 (i.e., the excess cross-linker may be aspirated through the same needle 418 so that the capsular bag 408 may be completely emptied or substantially emptied).

Figure 32:
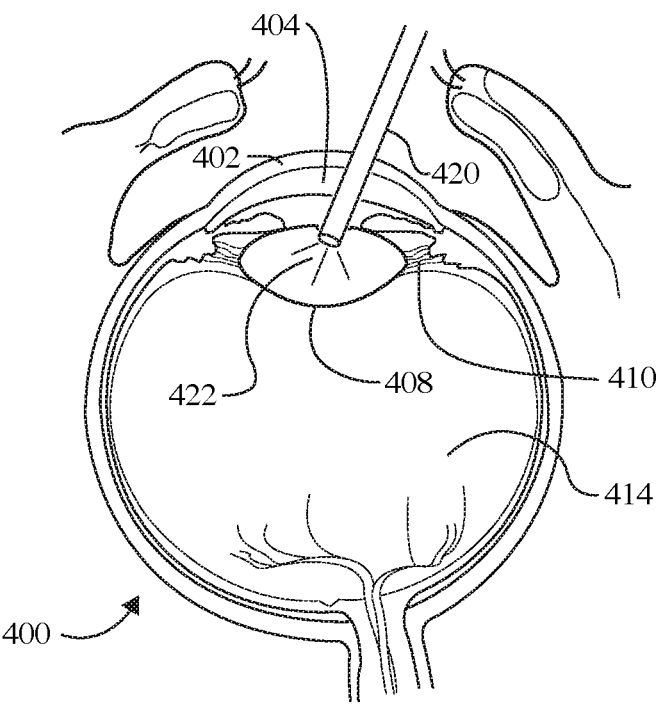
FIG. 32 is yet another side cross-sectional view of the eye of FIG. 30, which illustrates the irradiation of the posterior portion of the capsular bag of the eye so as to activate cross-linkers in the posterior portion of the capsular bag.

Next, turning to FIG. 32, shortly after the photosensitizer is applied inside the capsular bag 408, the remaining posterior portion of the capsular bag 408 of the eye 400 is irradiated using a fiber optic 420 delivering ultraviolet (UV) radiation 422 so as to damage the remaining lens epithelial cells with UV laser light, thereby preventing capsular opacification and fibrosis. In the illustrative embodiment, a painting technique may be utilized to deliver the ultraviolet light 422 to the posterior portion of the capsular bag 408 of the eye 400 (i.e., the fiber optic 420 may be manipulated in such a manner by the surgeon so as to "paint" the ultraviolet light 422 on the posterior portion of the capsular bag 408). Also, in the illustrative embodiment, ultraviolet (UV) radiation 422 may have a wavelength between about 370 nanometers and about 380 nanometers (or between 370 nanometers and 380 nanometers). In an alternative embodiment, the posterior portion of the capsular bag 408 of the eye 400 may be irradiated using another wavelength of light as an alternative to, or in addition to being irradiated using ultraviolet (UV) radiation.

Figure 33:
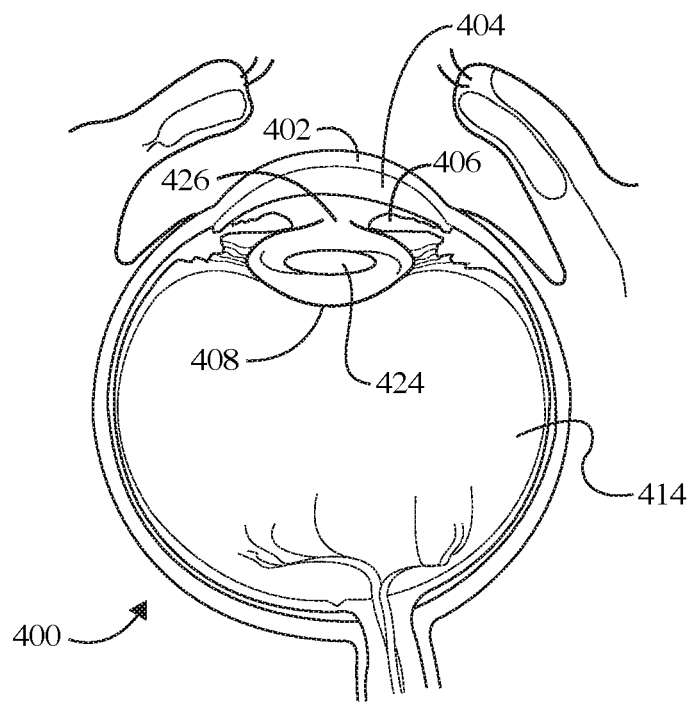
FIG. 33 is still another side cross-sectional view of the eye of FIG. 30, which illustrates the capsular bag of the eye after the removal of the cataract and the placement of an intraocular lens in the capsular bag.

Now, with reference to FIG. 33, it can be seen that, after the cataract 412 has been removed and the posterior portion of the capsular bag 408 has been irradiated, an intraocular lens 424 is implanted into the capsular bag 408 of the eye 400 in order to replace the cloudy natural lens that was removed. In particular, in the illustrative embodiment, the intraocular lens 424 is inserted into the capsular bag 408 of the eye 400 through the anterior opening 426 in the lens capsule 408.

Figure 34:
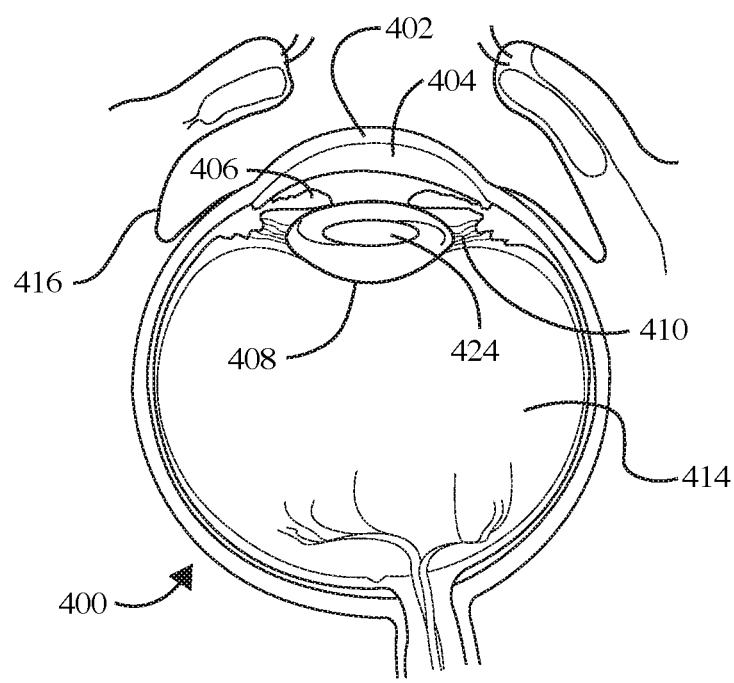
FIG. 34 is a yet another side cross-sectional view of the eye of FIG. 30, which illustrates the intraocular lens in the capsular bag of the eye prior to glaucoma surgery being performed on the eye.

Next, turning to FIGS. 34-38, the stent implantation and fibrosis prevention steps of the combined cataract extraction and glaucoma surgical procedure will be explained. Initially, the eye 400 with the implanted intraocular lens 424 therein is shown in FIG. 34.

Figure 35:
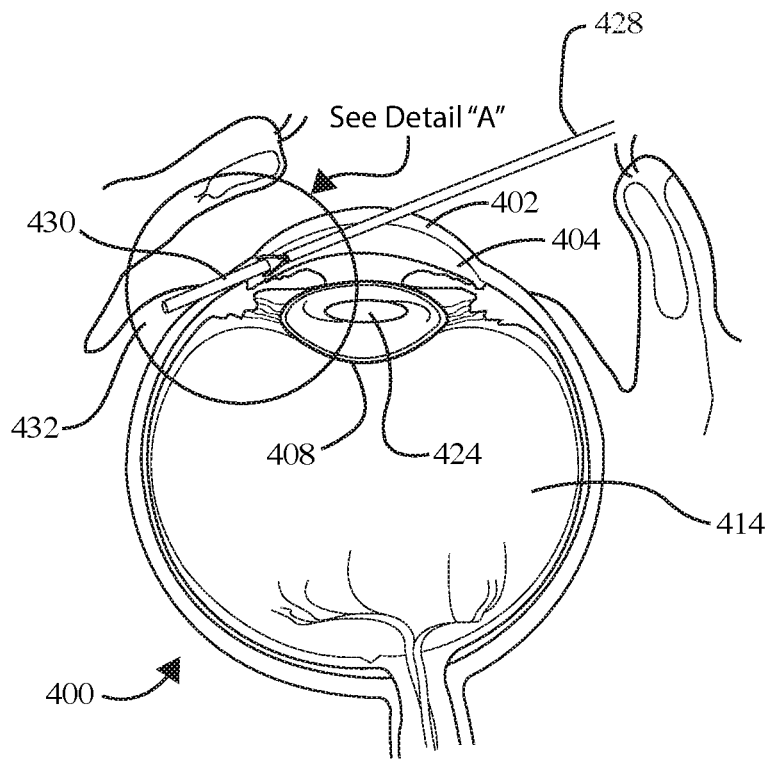
FIG. 35 is still another side cross-sectional view of the eye of FIG. 30, which illustrates the insertion of a stent through an anterior chamber of the eye and into the subconjunctival space.
Figure 36:
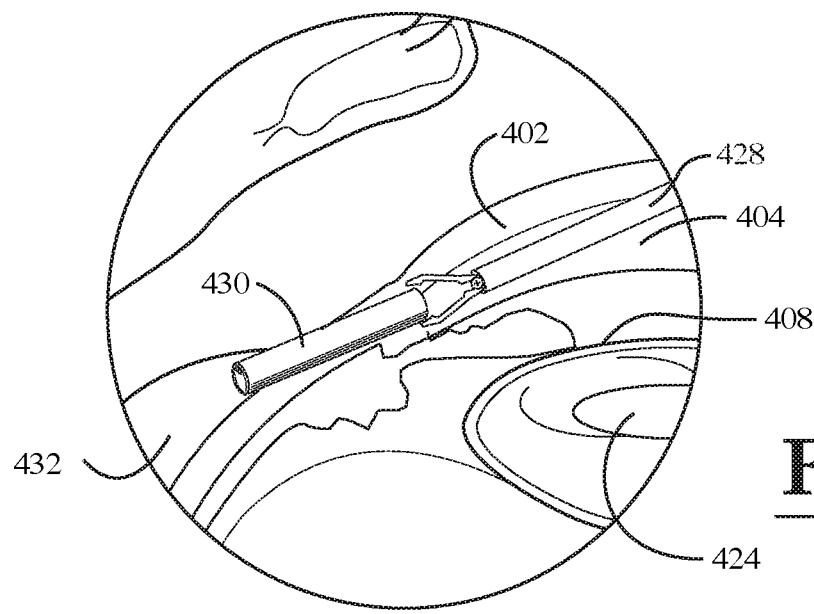
FIG. 36 is a partial, enlarged view illustrating the insertion of the stent in FIG. 35 (Detail "A")

In FIG. 35, the insertion of a glaucoma stent 430 through the anterior chamber 404, and into the subconjunctival space 432 of the eye 400 is diagrammatically illustrated. In particular, in the illustrated embodiment, the glaucoma stent 430 may be inserted into the subconjunctival space 432 of the eye 400 using a pair of forceps or microforceps 428. A detail view of the insertion of the glaucoma stent 430 is shown in FIG. 36. Once inserted, the glaucoma stent 430 extends from the anterior chamber 404 to the subconjunctival space 432.

Figure 37:
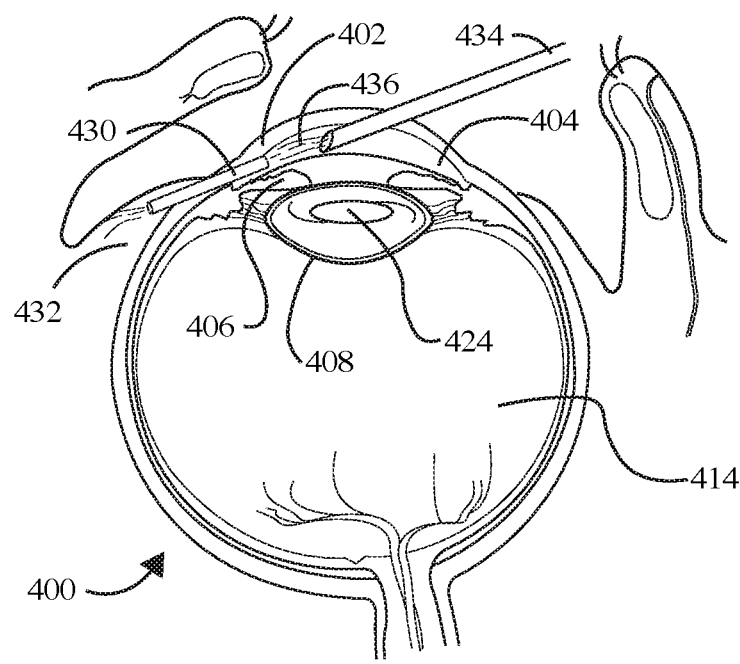
FIG. 37 is yet another side cross-sectional view of the eye of FIG. 30, which illustrates the application of a photo sensitizer to an anterior chamber of the eye so that the photosensitizer is capable of diffusing out of the stent and into the subconjunctival space.

Then, as shown in FIG. 37, the injection of a photosensitizer (e.g., riboflavin) into the anterior chamber 404 so that the photosensitizer diffuses into the tissue surrounding the glaucoma stent 430 is diagrammatically illustrated. In particular, as shown in the illustrative embodiment of FIG. 37, a photosensitizer is applied inside the anterior chamber 404 of the eye 400 and then a diffused stream 436 of the photo sensitizer travels through the central opening of the glaucoma stent 430, and into the subconjunctival space 432 so that the photosensitizer permeates the tissue surrounding the glaucoma stent 430. The photosensitizer facilitates the cross-linking of the tissue surrounding the glaucoma stent 430. In the illustrated embodiment of FIG. 37, the photosensitizer is injected with a needle 434 into the anterior chamber 404 of the eye 400 by inserting the needle 434 into the anterior chamber 404 of the eye 400, and letting the photosensitizer diffuse through the central opening in the glaucoma stent 430. In one or more embodiments, the photosensitizer or cross-linker that is injected through the needle 434 into the anterior chamber 404 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein).

Figure 38:
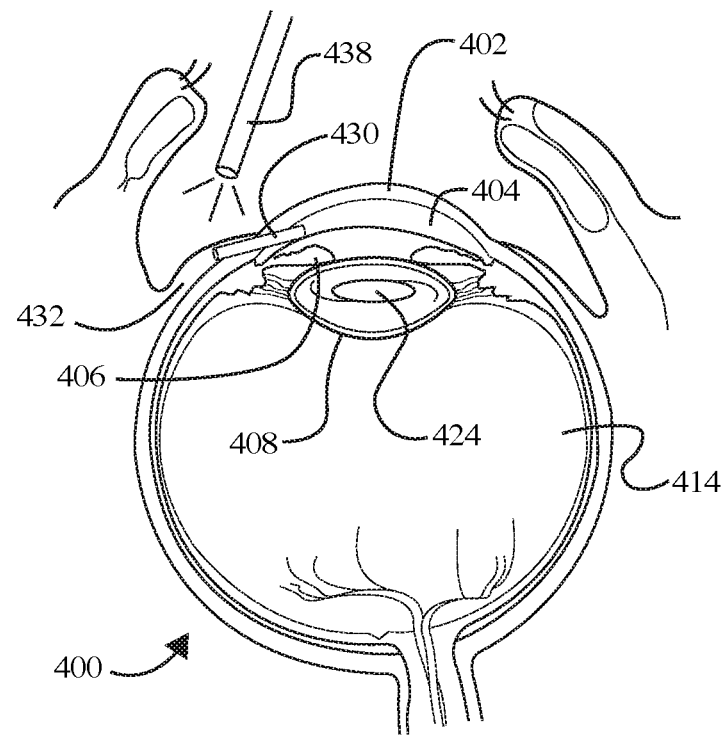
FIG. 38 is still another side cross-sectional view of the eye of FIG. 30, which illustrates the irradiation of the subconjunctival space so as to activate cross-linkers and prevent fibrosis around the stent outflow.

Next, turning to FIG. 38, shortly after the photosensitizer is applied inside the anterior chamber 404, the subconjunctival space 432 of the eye 400 is irradiated using a fiber optic 438 carrying ultraviolet (UV) light so as to cross-link the tissue surrounding the glaucoma stent 430, thereby preventing fibrosis around the stent 430 outflow. In the illustrative embodiment, a painting technique may be utilized to deliver the ultraviolet light to the subconjunctival space 432 of the eye 400 (i.e., the fiber optic 438 may be manipulated in such a manner by the surgeon so as to "paint" the subconjunctival space 432 with the ultraviolet light). Also, in the illustrative embodiment, ultraviolet (UV) radiation may have a wavelength between about 370 nanometers and about 380 nanometers (or between 370 nanometers and 380 nanometers). In an alternative embodiment, the subconjunctival space 432 of the eye 400 may be irradiated using another wavelength of light as an alternative to, or in addition to being irradiated using ultraviolet (UV) radiation.

Figure 39:
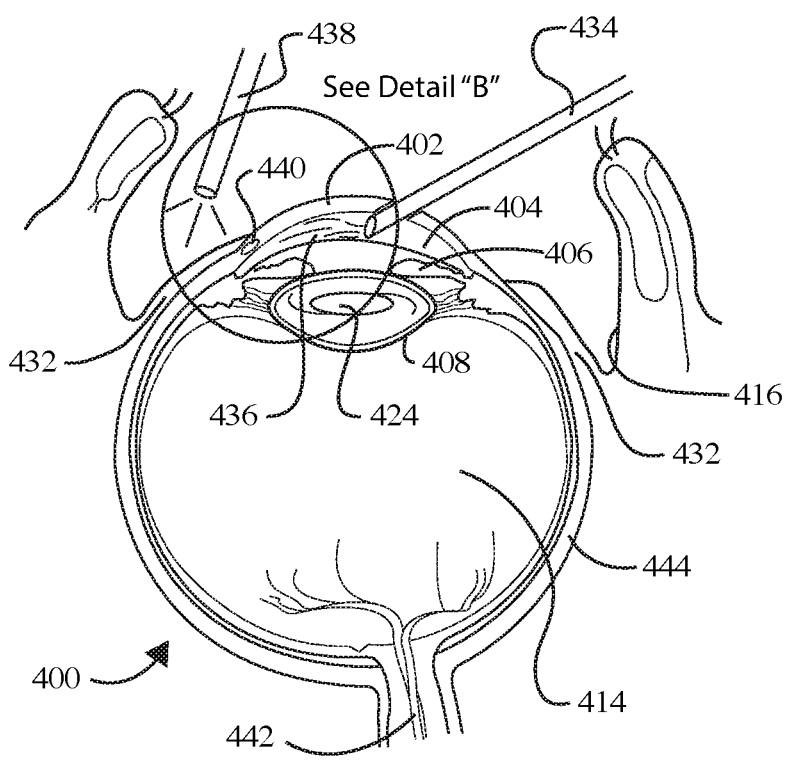
FIG. 39 is yet another side cross-sectional view of the eye of FIG. 30, which illustrates the application of a photo sensitizer to the anterior chamber of the eye and the irradiation of the subconjunctival space so as to activate cross-linkers and prevent fibrosis around a shunt or opening in the eye wall.
Figure 40:
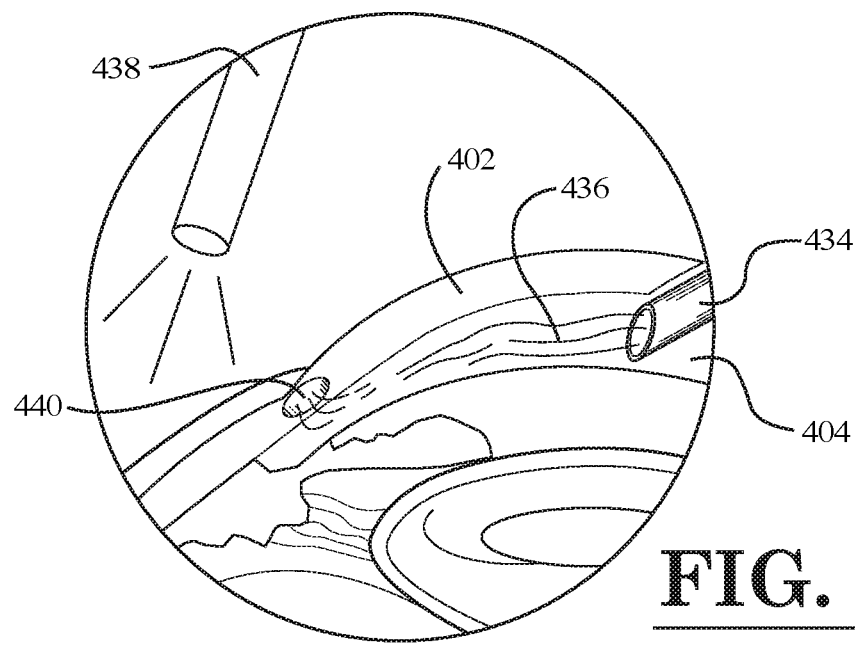
FIG. 40 is a partial, enlarged view illustrating the application of the photosensitizer and the irradiation of the space around the shunt or opening in the eye wall of FIG. 39 (Detail "B")

An alternative embodiment of the invention is depicted in FIG. 39. In particular, glaucoma drainage surgery is illustrated in FIG. 39. As shown in FIG. 39, the eye 400 undergoing glaucoma drainage surgery generally includes a cornea 402, an anterior chamber 404, an iris 406, a lens capsule or capsular bag 408 with an intraocular lens 424 disposed therein, a vitreous cavity 414, a conjunctiva 416, an optic nerve 442, and a sclera 444. Similar to the application of the photosensitizer described above with regard to FIG. 37, in the FIG. 39 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the opening or shunt 440 in the eye wall, and into the subconjunctival space 432 so that the photosensitizer permeates the tissue surrounding the opening or shunt 440. After which, with reference again to FIG. 39, the subconjunctival space 432 of the eye 400 is irradiated using a fiber optic 438 carrying ultraviolet (UV) light so as to cross-link the tissue surrounding the opening or shunt 440, thereby preventing fibrosis around the opening or shunt 440 outflow. A detail view of the application of the photosensitizer to the opening or shunt 440 is shown in FIG. 40. The opening or shunt 440 illustrated in FIGS. 39 and 40 is located in the angle of the eye between the iris 406 and the cornea 402. The opening or shunt 440 connects the anterior chamber 404 of the eye 400 to the subconjunctival space 432.

Figure 41:
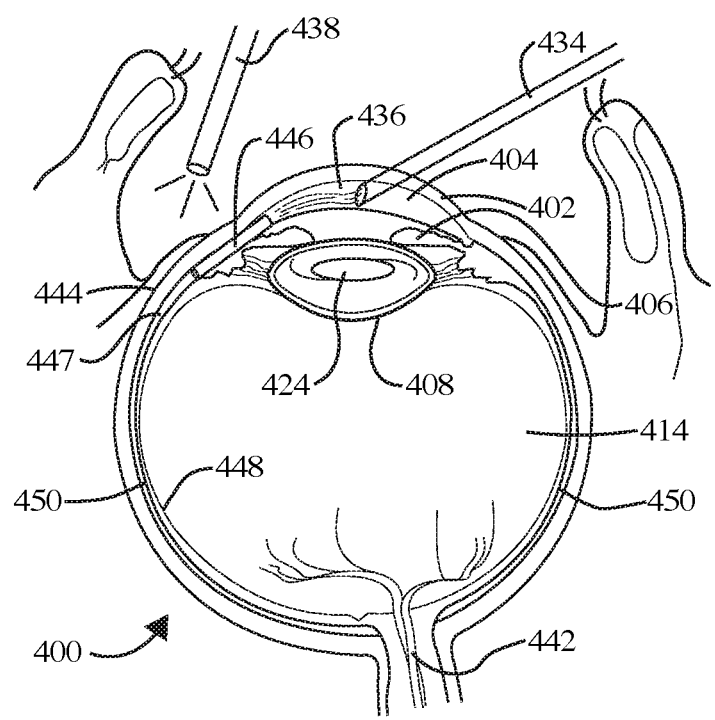
FIG. 41 is still another side cross-sectional view of the eye of FIG. 30, which illustrates the application of a photo sensitizer to the anterior chamber of the eye and the irradiation of the suprachoroidal space so as to activate cross-linkers and prevent fibrosis around a stent in the suprachoroidal space.
Figure 42:
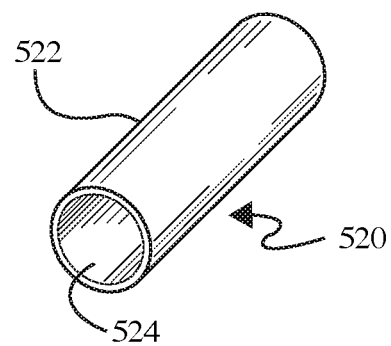
FIG. 42 is a perspective view illustrating a glaucoma stent having a coating provided thereon, according to an embodiment of the invention.

Another alternative embodiment of the invention is depicted in FIG. 41. In particular, a stent 446 positioned in the suprachoroidal space 447 of the eye 400 is illustrated in FIG. 41. More particularly, the glaucoma stent 446 in FIG. 41 extends from the angle of the anterior chamber 404 of the eye 400 to the suprachoroidal space 447. As shown in FIG. 41, the eye 400 undergoing glaucoma surgery generally includes a cornea 402, an anterior chamber 404, an iris 406, a lens capsule or capsular bag 408 with an intraocular lens 424 disposed therein, a vitreous cavity 414, an optic nerve 442, a sclera 444, a retina 448, and a choroid 450. Similar to the application of the photosensitizer described above with regard to FIG. 39, in the FIG. 41 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the glaucoma stent 446 in the suprachoroidal space 447 of the eye 400, and into the suprachoroidal space 447 so that the photosensitizer permeates the tissue surrounding the glaucoma stent 446. After which, with reference again to FIG. 41, the suprachoroidal space 447 of the eye 400 is irradiated using a fiber optic 438 carrying ultraviolet (UV) laser light so as to cross-link the tissue surrounding the glaucoma stent 446, thereby preventing fibrosis around the glaucoma stent 446 outflow.

In another embodiment, the application of the photosensitizer and the irradiation of the tissue surrounding the glaucoma stent 446 is repeated one or more additional times to cross-link the tissue surrounding the stent 446 again so as to prevent any cellular invasion in the area surrounding the stent 446.

In still another embodiment, the cataract surgery and the glaucoma surgery with or without stent implantation is done in two sessions. Initially, the photosensitizer is used to kill the lens epithelial cells using a fiber optic applying ultraviolet (UV) radiation, while in a subsequent glaucoma surgery with or without a stent, a photosensitizer (e.g., riboflavin) is injected in the anterior chamber after the glaucoma surgery with or without a stent and the wall of the outflow hole and the tissue in the subconjunctival space is then irradiated with ultraviolet (UV) light from the external side with a fiber optic in a painting fashion with the desired power to cross-link the collagenous tissue around the eye wall opening or around the stent to kill the cells, thereby preventing the cells from migrating in the surgical area and closing the outflow channel.

In yet another embodiment, in a previous glaucoma surgery involving a shunt or drainage tube, a minimal amount (e.g., 0.02 to 0.1 milliliters or less) of the photosensitizer (e.g., riboflavin) is injected in the anterior chamber of the eye so as to diffuse out of the surgically created hole or a shunt. Then, immediately thereafter, ultraviolet (UV) radiation is applied in an oscillatory painting fashion over the end of the drainage tube or stent, or over the surgically produced opening, at the desired power and duration in order to cross-link the tissue that comes into contact with the photosensitizer, etc.

In still another embodiment, the radiation is done shortly after injection of the photosensitizer (e.g., 5 to 60 seconds thereafter) or slightly longer after injection of the photosensitizer to prevent crosslinking or damage to the conjunctival superficial vessels or the conjunctival epithelial surface, so as to only crosslink the deeper laying tissue of the subtenon space or choroidal tissue immediately in contact with the photosensitizer over the pars plana. This process may be repeated to stabilize the tissue and further prevent tissue adhesion and encapsulation of the drainage shunt.

In one embodiment, the implant has a collagenous coating. The device may be in the form of a stent or a glaucoma drainage device connecting the fluid produced inside the eye to outside, either in the choroid or under the conjunctiva. The collagen coating can be conjugated with a photosensitizer that can be cross-linked after implantation with ultraviolet (UV) radiation or another wavelength of light that is applied to cross-link the collagen surrounding the implant, and to prevent cell growth or migration over the implant and encapsulation of the implant. Advantageously, by preventing cell growth or migration over the implant and the encapsulation of the implant, the aqueous fluid has unimpeded access to the subconjunctival space or the choroidal space.

In another embodiment, a collagen conjugated with a photosensitizer is injected surrounding the body of the implant after the stent or shunt implantation, and then the polymeric collagen and the surrounding tissue is cross-linked so as to provide an area for diffusion of fluid, and to kill the surrounding cells and prevent encapsulation of the implant or a part of it.

In yet another embodiment, the photosensitizer may be injected in the lens capsule after removal of the lens nucleus and the lens cortex so as to cross-link the remaining lens epithelial cells with ultraviolet (UV) light applied through a fiber optic in a painting fashion with an appropriate power to damage the epithelial cells prior to implantation of an intraocular lens (IOL), thereby preventing encapsulation and cell proliferation of the remaining epithelial lens cells in the lens capsule that create a fibrous-like encapsulation closing the space between the anterior and posterior leaflet of the remaining lens capsule or around an implanted intraocular lens. This cell proliferation causes a significant posterior capsular opacification about 3 to 12 months after cataract surgery in over 80% of the patients, or the implant may be tilted as a result of force applied to it, thus requiring laser surgery to cut the capsule open for the patient to have a clear view to the outside for uninterrupted light to reach the retina.

Now, referring to FIGS. 42-46, another embodiment of a glaucoma stent 520 and a surgical procedure using the stent 520 will be described. Initially, referring to the perspective view of the stent 520 in FIG. 42, it can be seen that the glaucoma stent 520 comprises a flexible tube with an external coating 522 disposed on the outside of the stent 520 and an internal coating 524 disposed on the inside of the stent 520. The external and internal stent coating 522, 524 is very important for the surgical procedure. Unless the external and internal stent coating 522, 524 is done with a substance, such as collagen, elastin, and/or polyethylene glycol (PEG), the stent 520 can irritate the surrounding tissue and excite cell migration and encapsulation. The coating may be applied to the stent 520 before or after the implantation of the stent 520. Preferably, the glaucoma stent 520 is formed from a solid, flexible, or semi-flexible material. For example, the stent material may be silicone-based or a mixture of polymers (e.g. acrylic and Hydroxyethyl methacrylate (HEMA), or HEMA alone, etc.) that preferably create a soft stent 520 for its placement under the conjunctiva of the eye. However, the stent 520 may also be implanted under the sclera of the eye. The glaucoma stent 520 may have a diameter between approximately 50 microns and approximately 700 microns (or between 50 microns and 700 microns), and the stent 520 may have a length between approximately 5 millimeters (mm) and approximately 15 millimeters (or between 5 millimeters and 15 millimeters). The diameter and the length of the stent 520 ultimately determine how much fluid is drained at a certain, desired intraocular pressure. This may also be decided by the doctor by him or her choosing a stent 520 that provides the desired pressure inside the patient's eye. In one embodiment, the glaucoma stent 520 may be three-dimensionally (3D) printed, and then coated as known in the art.

In one embodiment, the glaucoma stent 520 may be coated with a photosensitizer (e.g., riboflavin) before being implanted into the eye. Then, after the glaucoma stent 520 is implanted in the eye, the photosensitizer (e.g., riboflavin) may be released by the glaucoma stent 520 into the tissue surrounding the stent 520.

Figure 43:
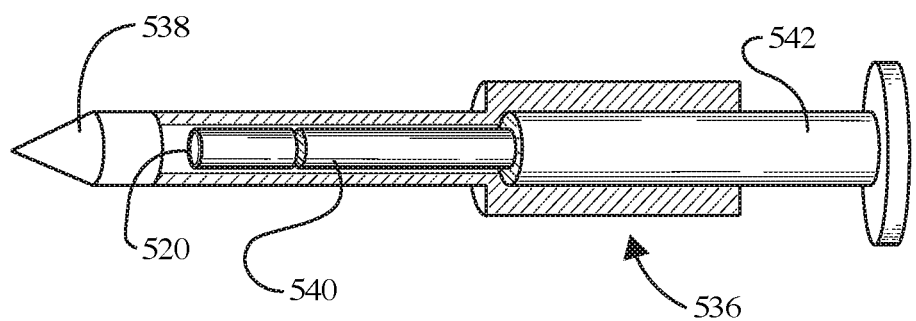
FIG. 43 is a side cross-sectional view illustrating a syringe used for the implantation of the stent of FIG. 42, according to an embodiment of the invention.

Next, turning to FIG. 43, a syringe 536 for implantation of the glaucoma stent 520 will be briefly described. As shown in FIG. 43, the syringe 536 comprises a sharp needle portion 538 for penetrating the tissue, a piston portion 540 for implanting the stent 520 into its desired location, and a plunger 542 for driving the piston 540, which in turn, drives the stent 520 into the tissue of the patient.

Now, referring to the illustrative embodiment of FIGS. 44-46, an exemplary surgical procedure using the stent 520 will be explained. Initially, referring to FIGS. 44-46, it can be seen that the eye 500 undergoing surgery generally includes a cornea 502, an anterior chamber 504, an iris 506, a lens capsule or capsular bag 508 with an intraocular lens 530 disposed therein, lens zonules 510, a vitreous cavity 512, a conjunctiva 514, a sclera 518, a retina 526, and an optic nerve 528.

Figure 44:
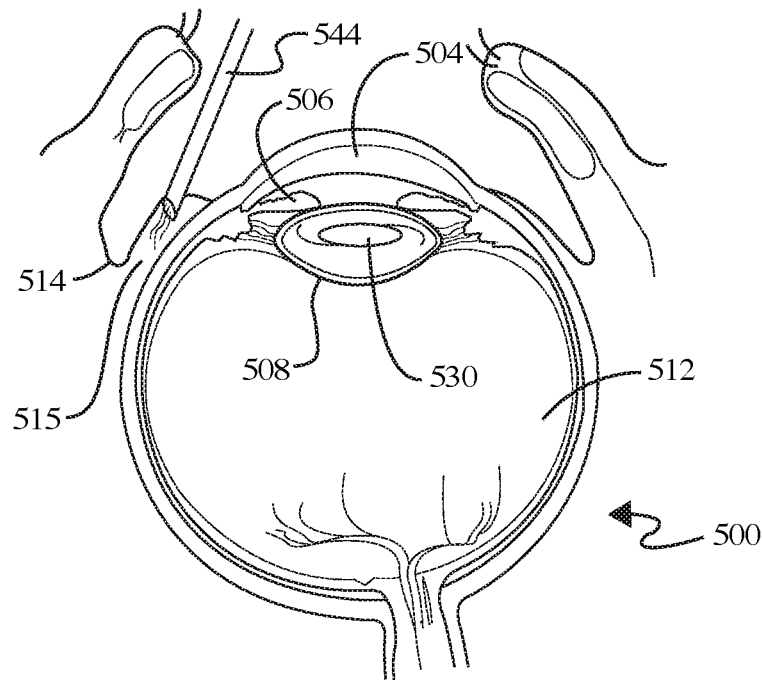
FIG. 44 is a side cross-sectional view of an eye, which illustrates the application of liquid collagen to the subconjunctival space, according to another embodiment of the invention.

In FIG. 44, liquid collagen and hyaluronic acid with or without a photosensitizer is initially injected in the subconjunctival space using a needle 544 so as to create a space (i.e., a bleb) for the stent 520. When the solution comprising the liquid collagen and the hyaluronic acid is subsequently cross-linked with ultraviolet light or another wavelength of light, a honeycomb structure is formed in the subconjunctival space around the stent outflow, thereby facilitating the draining of aqueous fluid from the stent. As such, when the stent 520 is subsequently positioned in liquid collagen that is cross-linked at the end of the surgery, the scar forming cells in the Tenon's capsule under the conjunctiva are killed, and the aqueous fluid is capable of diffusing through the stent 520.

Next, the glaucoma stent 520 is implanted into the conjunctiva 514 of the eye 500 using the syringe 536 described above. The syringe 536 is essentially loaded with the stent 520, and then the sharp needle portion 538 of the syringe 536 is used to penetrate the eye wall before the stent 520 is unloaded by the syringe 536. After the stent 520 is delivered into the tissue, the syringe 536 is withdrawn from the eye 500. Once inserted, the glaucoma stent 520 extends from the anterior chamber 504 to the subconjunctival space 515.

The cross-linked subconjunctival space or bleb may be created immediately before the implantation of the stent 520 during a single surgical procedure so as to prepare the space first so that the end of the stent 520 enters the cross-linked subconjunctival space during the surgery. Alternatively, the cross-linked subconjunctival space or bleb may be created during a first surgical procedure, and then the stent 520 may be implanted thereafter during a second, separate surgical procedure. In this alternative embodiment, the second surgical procedure may be performed a significant time after the first surgical procedure. The cross-linked subconjunctival space or bleb may be irradiated using either an external ultraviolet light or a handheld fiber optic connected to a laser that is placed close to the space or bleb and the tissue that will surround the stent 520 (i.e., the corneoscleral tissue). This tissue may be irradiated for 5 to 20 minutes so as to cross-link the tissue.

Figure 45:
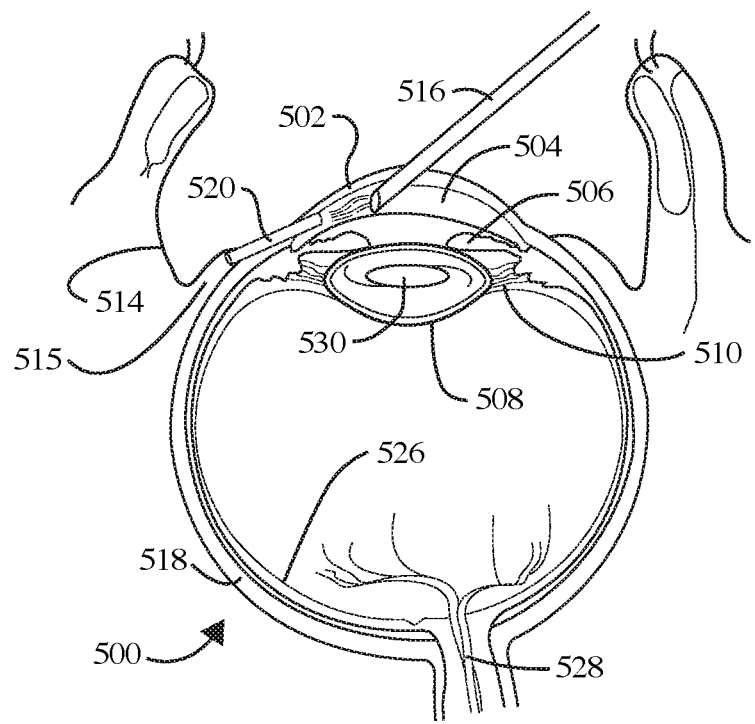
FIG. 45 is another side cross-sectional view of the eye of FIG. 44, which illustrates the application of a photosensitizer after the implantation of the glaucoma stent of FIG. 42 in the eye.
Figure 46:
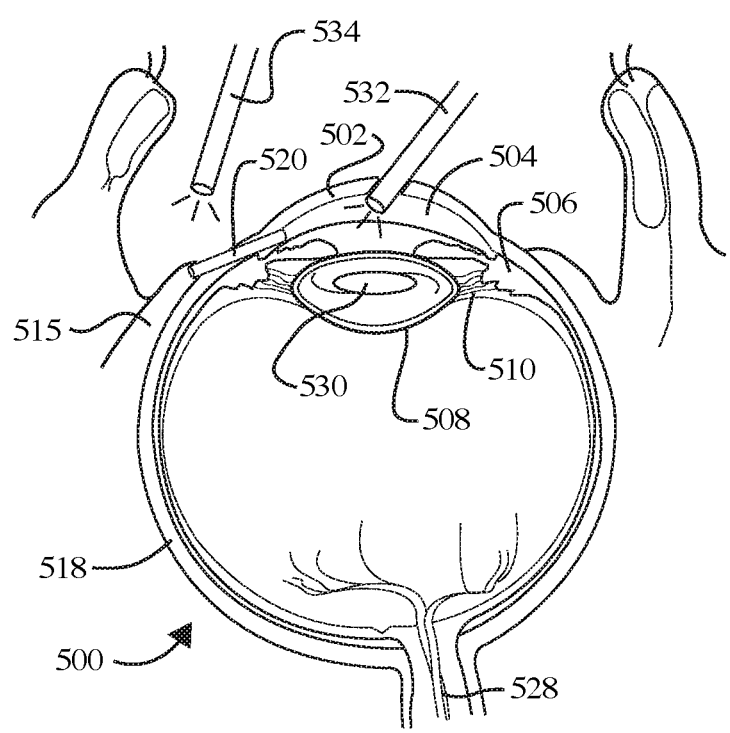
FIG. 46 is yet another side cross-sectional view of the eye of FIG. 44, which illustrates the irradiation of the glaucoma stent and the surrounding areas in the eye so as to activate cross-linkers and prevent fibrosis.
Figure 47:
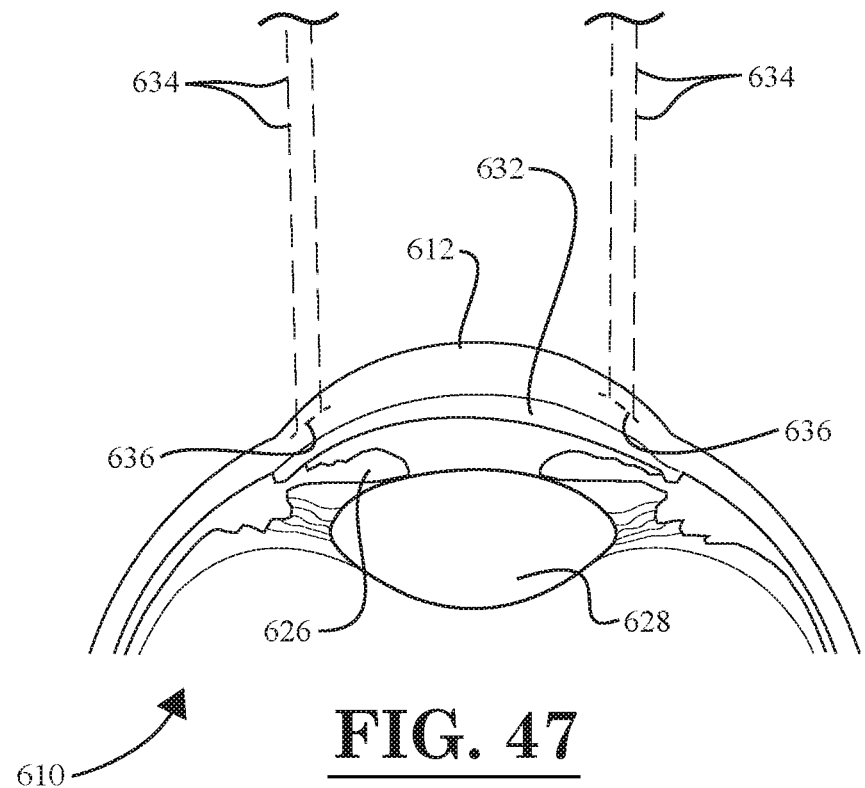
FIG. 47 is a partial side cross-sectional view illustrating the formation of an incision into a peripheral portion of a cornea of an eye so as to create a pocket for receiving a corneal intraocular pressure sensor, according to another embodiment of the invention.

Then, after the implantation of the stent 520 in the conjunctiva 514 of the eye, the photosensitizer (e.g., riboflavin in a biocompatible fluid) is injected into the eye 500 using a needle 516 (see FIG. 45). That is, similar to that described above, the photosensitizer or cross-linker is injected using the needle 516 into the anterior chamber 504 of the eye 500 after the implantation of the stent 520. The photosensitizer injected from the needle 516 travels through the glaucoma stent 520, and into the subconjunctival space 515 of the eye 500 so that the photosensitizer permeates the tissue surrounding the glaucoma stent 520. After which, at the end of the surgical procedure, the stent 520 and the areas surrounding the stent 520, both inside and outside, are cross-linked. In particular, with reference to FIG. 46, an inflow end of the glaucoma stent 520 proximate to the anterior chamber 504 of the eye 500 is irradiated using a fiber optic 532 carrying ultraviolet (UV) laser light so as to cross-link the tissue surrounding the glaucoma stent 520, thereby preventing fibrosis around the glaucoma stent 520. Also, as shown in FIG. 46, an outflow end of the glaucoma stent 520 in the subconjunctival space 515 of the eye 500 is irradiated using a fiber optic 534 carrying ultraviolet (UV) laser light so as to cross-link the tissue surrounding the glaucoma stent 520, thereby preventing fibrosis around the glaucoma stent 520 outflow.

Next, an illustrative embodiment of a method of implanting a corneal intraocular pressure sensor in an eye of a patient will be described below with reference to FIGS. 47-53. In general, the procedure involves the steps of forming a pocket in a cornea of an eye so as to gain access to tissue surrounding the pocket, applying a photosensitizer inside the pocket so that the photosensitizer permeates at least a portion of the tissue surrounding the pocket, irradiating the cornea so as to activate cross-linkers in the portion of the tissue surrounding the pocket, and inserting an intracorneal implant comprising a pressure sensor into the pocket after the tissue has been cross-linked. The pressure sensor of the intracorneal implant is configured to measure the intraocular pressure of the eye of the patient. As shown in FIGS. 47-53, the eye 610 undergoing the implantation of the pressure sensor generally includes a cornea 612, an iris 626, a lens 628, and an anterior chamber 632.

Initially, a pocket is formed in the cornea of the eye so as to gain access to tissue surrounding the pocket. In the illustrative embodiment, referring to FIG. 47, a two or three-dimensional portion of stromal tissue is first cut out from the cornea of the eye using a femtosecond laser (i.e., an incision 636 is first cut in the cornea 612 of the eye 610 using the laser beam(s) 634 emitted from the femtosecond laser). Then, the three-dimensional cut portion of the cornea 612 is removed using forceps so as to create a three-dimensional pocket for receiving the intracorneal implant. The formation of the three-dimensional pocket creates a cavity so that, when the intracorneal implant is placed in it, the implant will not exert any pressure on the stromal tissue of the cornea.

In one or more embodiments, an intrastromal corneal pocket is created in the peripheral part of the cornea involving 1 to 4 millimeter (mm) areas in width located between the cornea and the anterior sclera using a femtosecond laser. Prior to the laser application, if needed, the peripheral conjunctival capillaries are bleached out with a low dose of vasoconstrictive medication, such as 0.5% to 1% phenylephrine applied locally with a cotton swab applicator, and/or a low dose (0.1 to 2%) hyaluronic acid in a fluid is applied to make the corneal limbus area transparent.

In one or more embodiments, the three-dimensional pocket 624 formed in the peripheral portion of the cornea extends between 1 degree and 360 degrees around the corneal periphery (refer to the front view of FIG. 51), and the three-dimensional pocket is located at a predetermined distance from the Bowman's membrane in the corneal periphery of the eye.

In one or more embodiments, one or two incisions are used depending on the size of the pocket to access the intrastromal incision. Then, a curved probe is used to separate the remaining corneal adhesion between the walls of the incision, so as to create a pocket for the injection of a photosensitizer (i.e., a cross-linker).

Figure 48:
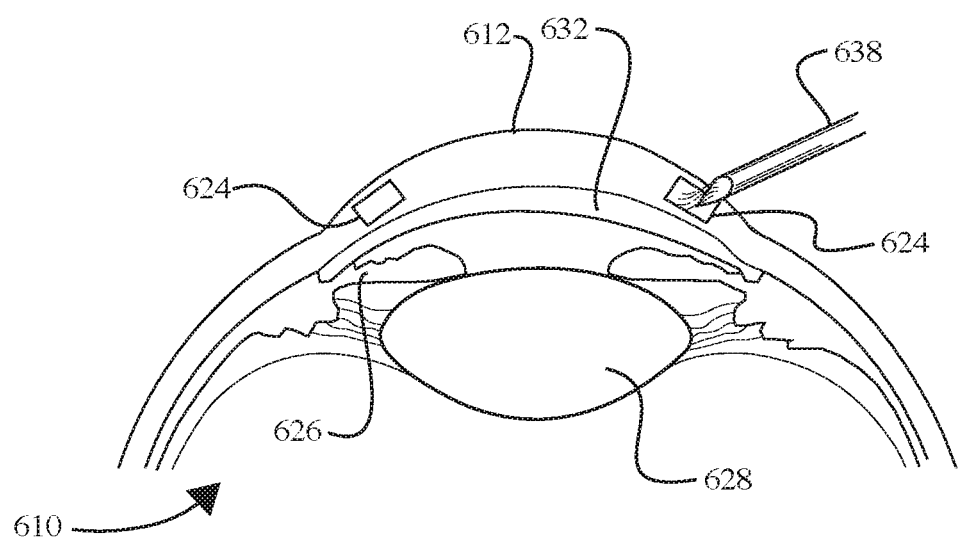
FIG. 48 is another partial side cross-sectional view of the eye of FIG. 47, which illustrates the injection of a photosensitizer into the pocket in the peripheral portion of the cornea of the eye.
Figure 49:
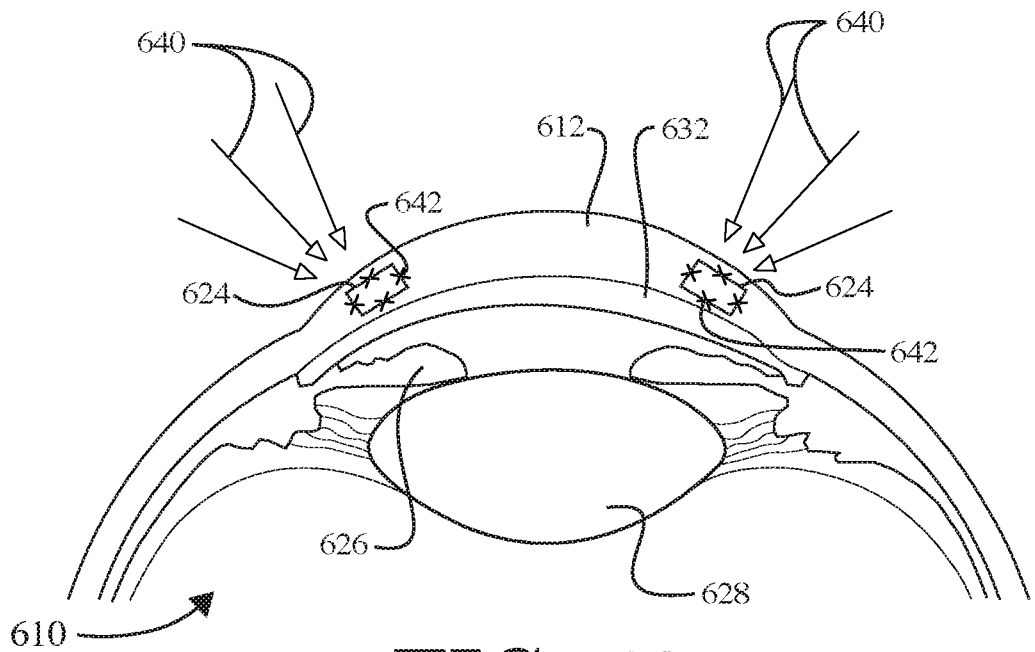
FIG. 49 is yet another partial side cross-sectional view of the eye of FIG. 47, which illustrates the irradiation of the stromal tissue surrounding the pocket in the peripheral portion of the cornea of the eye using ultraviolet radiation delivered from outside of the cornea.
Figure 50:
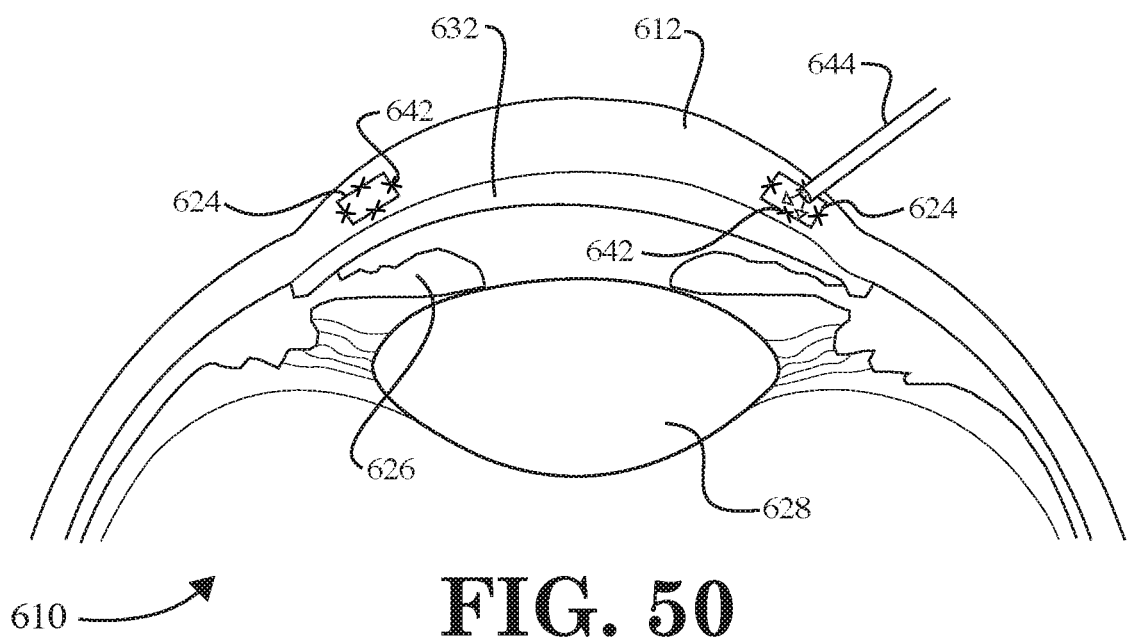
FIG. 50 is still another partial side cross-sectional view of the eye of FIG. 47, which illustrates the irradiation of the stromal tissue surrounding the pocket in the peripheral portion of the cornea of the eye using a fiber optic delivering ultraviolet radiation inside the pocket, according to an alternative embodiment of the invention.

After the three-dimensional pocket 624 is formed, a photosensitizer is applied inside the three-dimensional pocket 624 so that the photosensitizer permeates the tissue surrounding the pocket (refer to FIG. 48). The photosensitizer facilitates the cross-linking of the tissue surrounding the pocket 624. In the illustrative embodiment, a photosensitizer (i.e., a cross-linker), such as riboflavin, is injected with a needle 638 (see FIG. 48) at a concentration of about 0.5% to 4% in a biocompatible fluid, such as a physiological saline solution, etc., in a volume of 0.01 milliliters (ml) to 1 milliliters (ml) as needed for the extent of the pocket 624 to cover the internal walls of the corneal pocket 624 for a desired duration for the photo sensitizer to penetrate at least 20 microns beyond the corneal pocket 624 in the corneal stroma. This will take about a few seconds to about 30 seconds, while avoiding the crosslinking of the entire remaining wall of the cornea 612. In the illustrative embodiment, an effort is made to limit the corneal staining with the photosensitizer to the wall of the pocket 624 so that the photosensitizer never reaches the anterior or posterior full thickness of the cornea 612.

In one or more embodiments, 0.01 milliliters (ml) to 0.1 milliliters (ml) of 0.02 to 2% concentration lidocaine or bupivacaine solution may be injected alone or along with the photosensitizer in the corneal pocket 624 to anesthetize the cornea for a duration of 10 to 15 hours, thereby eliminating pain sensation or discomfort of the surgery.

In one or more embodiments, the width of the corneal pocket 624 may be 1 to 3 millimeters (mm), as needed. The pocket may be circular, semi-circular, C-shaped, doughnut-shaped, rectangular, or any other suitable shape.

Next, in the illustrative embodiment, shortly after the photosensitizer is applied inside the pocket 624, the cornea 612 of the eye 610 is irradiated from the outside using ultraviolet (UV) radiation 640 so as to activate cross-linkers in the portion of the tissue surrounding the three-dimensional pocket 624, and thereby stiffen a wall of the pocket and kill cells in the portion of the tissue surrounding the pocket.

In the illustrative embodiment, ultraviolet (UV) radiation 640 at a desired power of 0.5 to 50 mW/cm2 and a duration 1 to 15 minutes is applied to the cornea 612 of the eye 610 from outside in a stationary manner (see FIG. 49), or using a continuous painting or oscillatory technique with a focused small-sized spots of 1 to 4 millimeters (mm) and high energy to cover the width of the pocket, and to activate the photosensitizer in the corneal pocket 624, and thereby crosslink the collagen of the corneal stroma 642 surrounding the corneal pocket 624, kill all cells located within the cross-linked corneal area while providing a physical stability to the wall of the corneal pocket and preventing the wall from adhering to itself or to a future implant. In other embodiments, if a photosensitizer other than riboflavin is used, radiation with another wavelength of light may be applied to the cornea 612 of the eye 610 to cross-link the collagen of the corneal stroma 642 surrounding the corneal pocket 642.

In one or more embodiments, ultraviolet (UV) radiation at the desired power in a form of stationary or focused light for a duration of 1 to 5 minutes is applied, as needed, depending on the size of the pocket 624, and when using the painting method, the ultraviolet radiation is applied for 1 to 20 minutes depending on the size of the pocket 624. The power used for the UV radiation and the focal spot size of the laser that is used depends on the power of the radiation and the length of the pocket 624. The radiation may be applied externally, or via a fiber optic 644 inserted inside the pocket 624 in a painting fashion (see FIG. 50), so as to activate the photosensitizer and cross-link the collagen of the corneal stroma 642 surrounding the corneal pocket 624, thereby killing all cells located within the cross-linked cornea 642 while preventing encapsulation, cell migration, or rejection of the implant, and also providing an amorphous wall between the implant and the rest of the corneal stroma creating a vascular free zone only to the extent that the cross-linker has penetrated in the cornea surrounding the implant. The radiation is applied a short time after the cross-linker is injected in the pocket 624.

In one or alternative embodiments, the cornea is cross-linked from outside by dropping a cross-linker, such as riboflavin, at concentration of 1-2% in a physiological solution having dextran or hyaluronic acid or chondroitin sulfate over the corneal epithelium or denuded corneal epithelium for a period of time of 15 to 30 minutes. After which, the cornea 612 is cross-linked with the UV laser light for 10 to 50 minutes depending on the power of the UV laser applied, then waiting after cross-linking for a period of 3-4 weeks to implant the intraocular pressure sensor in the cross-linked cornea as described above.

Figure 51:
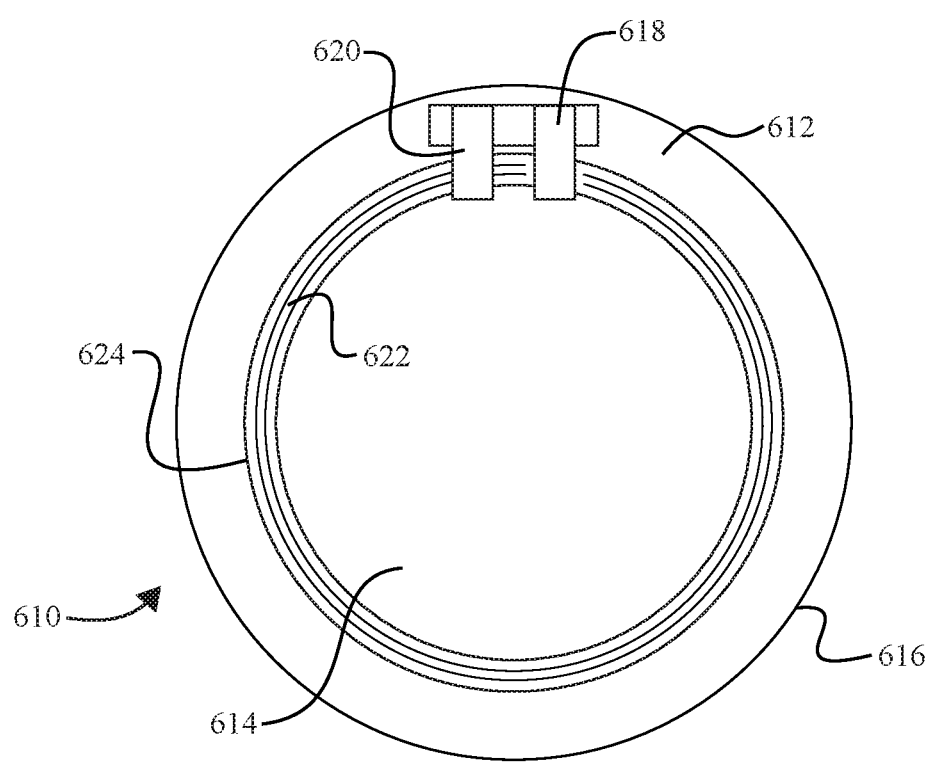
FIG. 51 is a front view of the eye of FIG. 47, which illustrates the components of a corneal intraocular pressure sensor disposed in the pocket in the peripheral portion of the cornea of the eye.
Figure 52:
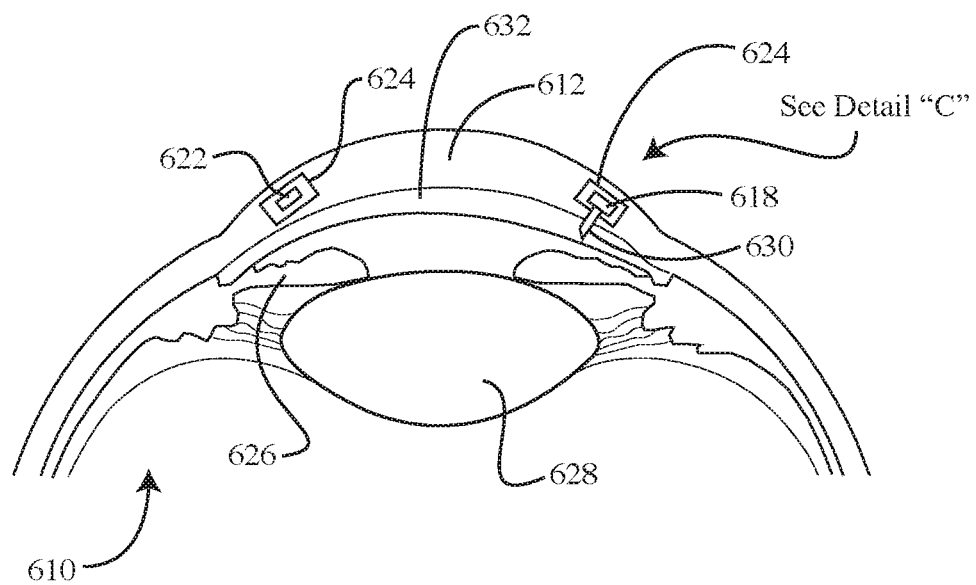
FIG. 52 is still another partial side cross-sectional view of the eye of FIG. 47, which illustrates the peripheral cross-linked corneal pocket with the components of the corneal intraocular pressure sensor disposed therein.
Figure 53:
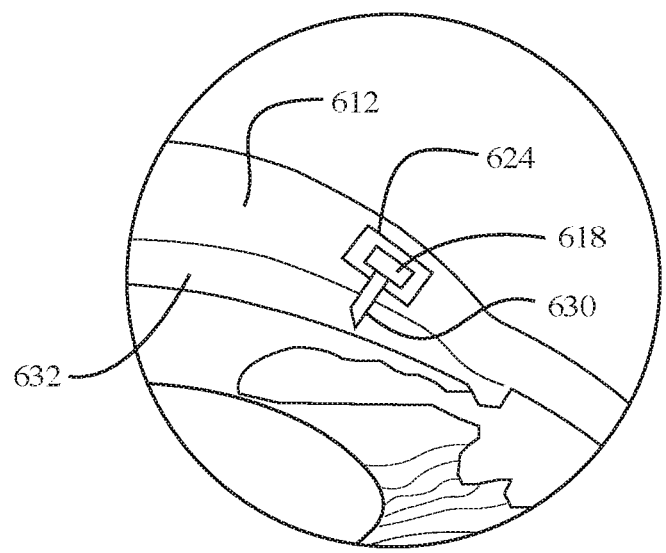
FIG. 53 is a partial, enlarged side cross-sectional view of the eye of FIG. 52 (Detail "C"), which illustrates the needle of the corneal intraocular pressure sensor extending into the anterior chamber of the eye.
Figure 54A:
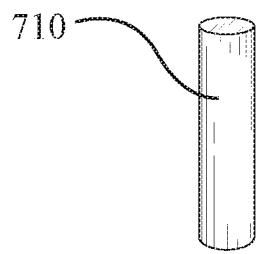
FIG. 54A illustrates a first exemplary shape for the drug delivery implant described herein, which is in the form of a rod-shaped implant.
Figure 54B:
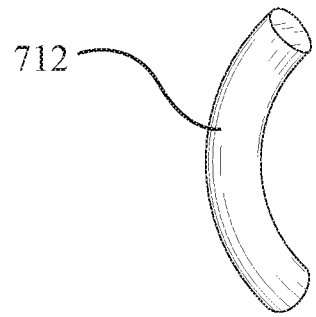
FIG. 54B illustrates a second exemplary shape for the drug delivery implant described herein, which is in the form of a curved implant.
Figure 54C:
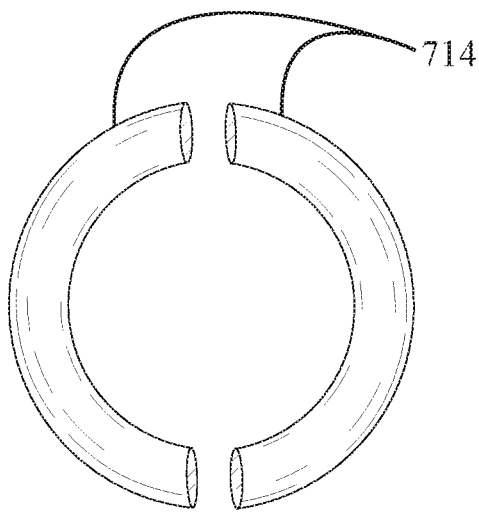
FIG. 54C illustrates a third exemplary shape for the drug delivery implant described herein, which is in the form of a two-part semi-circular implant.
Figure 54D:
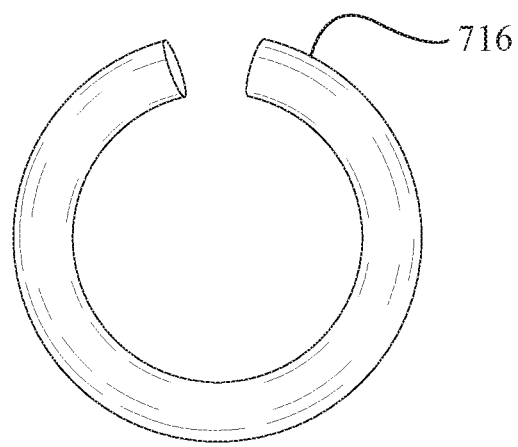
FIG. 54D illustrates a fourth exemplary shape for the drug delivery implant described herein, which is in the form of a one-part semi-circular implant.

Now, with reference to FIGS. 51-53, it can be seen that, after the portion of the tissue surrounding the pocket 624 has been stiffened and is devoid of cellular elements by the activation of the cross-linkers, an intracorneal implant comprising a pressure sensor 618 is inserted into the three-dimensional pocket 624 formed in the cornea 612 of the eye 610, which is in a location anteriorly disposed relative to the iris 626 and the lens 628. As shown in these figures, in the illustrative embodiment, the intracorneal implant is equipped with a pressure sensor 618, such as a capacitor, located in the corneal periphery of the eye 610. Also, as best shown in the sectional view of FIG. 53, the pressure sensor 618 of the intracorneal implant is equipped with a needle 630 that penetrates the rest of the cornea 612 and opens in the anterior chamber 632 of the eye 610 to measure the intraocular pressure directly by a portion of the sensor 618 being disposed inside the needle 630 without obstructing the central vision through the central cornea 614 (e.g., refer to FIG. 51). Turning to FIGS. 51 and 52, it can be seen that the sensor 618 is equipped with an antenna 622 that can transmit the information about the intraocular pressure for a duration of 24 hours and beyond while a receiver located outside of the eye 610 (e.g, a receiver on a regular eyeglass frame) receives the information and records and/or transmits the information to another remote device. The information is transmitted to a processor that transmits the information on the intraocular pressure uninterruptedly for years after implantation over a substantial distance to a doctor's computer or the patient's computer. The capabilities of the present invention are in stark contrast to the aforedescribed conventional contact lenses that can be carried only for 24 hours on the cornea to measure the intraocular pressure (IOP). If the conventional contact lenses are left on the cornea for a long time (i.e., greater than 24 hours), they can affect the integrity of the cornea, interfere with the oxygen and nutrition of the cornea, and ultimately lead to corneal abrasion or an infection.

In one or more embodiments, two-dimensional or three-dimensional stromal tissue is cut and/or removed with a femtosecond laser depending on the thickness of the sensor 618 and the antenna 622 and the location where the implant will be placed. As such, a pocket space 624 is created for the intracorneal implant to stay in place without exerting pressure on the remaining cornea 612 (see FIG. 52). As described above, after the pocket 624 is formed, it is followed by the cross-linking of the wall of the pocket so that the corneal pocket is cross-linked.

In one or more embodiments, the surface of the intraocular implant is coated with albumin or collagen, or another organic polymer, etc. that can absorb the photosensitizer after the implant is dipped in the photosensitizer and implanted in the corneal pocket. The photosensitizer leaks out of the polymeric coating of the implant into the corneal stroma, and then ultraviolet (UV) radiation at the desired power and duration is applied externally to activate the photosensitizer in the corneal pocket 624 and the implant coating to cross-link the collagen surrounding the implant, while killing all cells located within the cross-linked cornea, providing physical stability to the cornea, preventing the adhesion or gluing of the implant to the surrounding tissue, and preventing fibrous ingrowth or encapsulation, which can lead to an implant rejection. Also, advantageously, the cross-linking of the corneal pocket 624 makes it possible to exchange the implant when needed without the occurrence of much trauma to the cornea 612, because the prior cross-linking eliminates the cells that cause adhesion between the cornea 612 and the implant.

In one or more embodiments, if needed in the postoperative period, the cross-linking of the wall of the intraocular implant can be repeated by injection of riboflavin with a 33 gauge needle in the space between the implant and the wall of the cavity in which the implant resides, and then the cornea 612 with the implant may be subsequently cross-linked with ultraviolet (UV) radiation to prevent encapsulation of the implant that makes the inspection of the implant in the post-operative period difficult.

In one or more embodiments, the intraocular implant has a small diameter needle 630 (see FIG. 53) of 23 to 34 gauge with a capacitor sensor or a nanocomposite pressure sensor disposed in the inside thereof, positioned at a 90 degree angle relative to the body of the implant, and exposed to the aqueous fluid so as to measure the intraocular pressure (IOP) of the eye 610. The pressure sensor 618 of the intraocular implant is operatively connected to the processor of the implant, and to the antenna 622 and radio frequency (RF) generator 620 of the implant (see FIG. 51). The electrical energy for the radio frequency (RF) generator is provided by a small battery that can be charged from outside as it is done with inductive coupling using an electromagnetic field that transfers energy from a transmitter to a receiver, as known in the art. The needle 630 with the capacitor sensor inside it, penetrates the remaining corneal stroma located in the corneal periphery with minimal pressure, and is open to the inside of the anterior chamber 632 (see FIG. 53). In one or more embodiments, the needle 630 is less than 500 microns in length and less than 200 microns in diameter, and remains permanently in the anterior chamber 632 of the eye 610, without exciting a tissue response due to its cross-linked surface and its size, but can also be removed or replaced with ease. The intraocular pressure (IOP) values measured by the capacitor sensor are transmitted to a processor (e.g., a microprocessor), which is operatively coupled with the radio frequency (RF) generator 620, which transmits the information to remote devices by the means of the antenna 622. Because the wall of the corneal pocket 624 is cross-linked, it will not produce a scar around the implant and its sensor 618, radio frequency (RF) generator 620, and antenna 622, thus permitting direct visual inspection of the implant, which is capable of being removed and/or replaced if needed.

In one or more embodiments, the intraocular implant may be assembled during the surgery after the cross-linked pocket 624 is created. Initially, the antenna 622 is placed in the cross-linked pocket 624 that is disposed radially inward from the limbus 616 of the eye 610 (see FIG. 51), and then the sensor 618 and the radio frequency (RF) generator 620 are placed in the corneal pocket 624 and connected to the antenna 622 as a part of a minimally invasive surgery in the corneal periphery. The capacitor sensor is located inside the needle 630, and the tip of the needle 630 is pushed gently in the anterior chamber 632 of the eye 610 so as to measure the intraocular pressure (IOP) directly, continuously, and precisely from the inside of the eye 610. The sensor 618 with small needle 630 and the radio frequency (RF) generator 620 are located in the corneal periphery avoiding interfering with the patient's vision. In contrast to the other aforementioned conventional technologies, this implant does not need an intraocular surgery for its implantation and the natural crystalline lens 628 of the eye 610 does not need to be removed in order to obtain permanent intraocular pressure (IOP) information for the eye 610.

In one or more embodiments, prior to the insertion of the intracorneal implant into the pocket 624 of the eye 610, a predetermined amount of hyaluronic acid or a viscous biocompatible material is injected into the pocket 624 so as to simplify the insertion of the intracorneal implant in the cross-linked pocket 624.

In one or more embodiments, the pressure sensor and transmitter of the intraocular implant are located inside the peripheral cross-linked pocket 624 of the cornea 612 of the eye 610 that does not occupy the central corneal region 614 of the eye 610. Because the central corneal region 614 of the eye 610 remains open with the intracorneal implant, the intraocular pressure (IOP) may also be measured by a Goldmann applanation tonometer placed on the central part 614 of the cornea 612 that is exposed. Because the implant described herein is peripherally disposed, the central corneal region 614 of the eye 610 is not covered by a conventional contact lens pressure sensor, as described above. Therefore, the intraocular pressure (IOP) can be measured by an ophthalmologist in two ways using a Goldman applanation tonometer and by means of the pressure sensor of the intracorneal implant located in the anterior chamber 632 of the eye 610. Advantageously, the ability to take these dual intraocular pressure (IOP) measurements provides a means of comparison between the values obtained by the intraocular pressure sensor and the Goldmann applanation tonometer to correlate or properly adjust the values obtained from the corneal intraocular pressure (IOP) sensor so as to ensure that measurements by the corneal intraocular pressure (IOP) sensor represent the true intraocular pressure (IOP) of the eye 610, and so the corneal intraocular pressure (IOP) sensor is capable of being properly adjusted using the software of the processor of the corneal intraocular pressure (IOP) sensor. The information obtained with the corneal intraocular pressure (IOP) sensor is also capable of being transmitted remotely via the radio frequency (RF) generator 620, and recorded and forwarded to an ophthalmologist who, in turn, can control the intraocular pressure (IOP) by medication or surgery.

In one or more embodiments, the transmitter of the intracorneal implant may be implanted separately from the pressure sensor 618 during the surgery, but then reconnected during the implantation.

Advantageously, the surgical implantation method and the corneal intraocular pressure (IOP) sensor described herein is capable of measuring the intraocular pressure (IOP) all day and night for a long period of time (e.g., weeks, months, or years), and then recording the intraocular pressure data that is measured so that an ophthalmologist can control the intraocular pressure (IOP) of the patient's eye by medication or surgery.

Any of the procedures described herein can be used alone, or in conjunction with, simultaneously with, before or after any other procedure, method or device that would treat or monitor glaucoma, prevent capsular opacification and fibrosis after cataract extraction during cataract surgery and/or prevent fibrosis around a shunt or stent after glaucoma surgery.

Illustrative embodiments of a drug delivery implant and methods using the same will now be described hereinafter. In accordance with the various embodiments described herein, in order to provide the medication to the anterior and posterior part of the eye with a slow release drug system, it is required to create an immune privileged space inside the cornea to keep the cellular response away and prevent production of cytokine by them, and position the device outside the central visual axis so that the device would not interfere with the patient's vision.

In the embodiments described herein, the device is placed in the far corneal periphery so that it will not affect the vision or visual field of the patient, and so that it has created a so-called artificial "immune-privilege" which does not generate an immune response from the body while fluid, soluble medications or nano-particulates and micro-particulates can travel through it. See, for example, FIGS. 63A-70B.

Because of the location of the implant inside the cornea, the released medication bypasses the epithelial barrier of the cornea, while providing medication in a slow manner by diffusion to the anterior part of the cornea, to the sclera, to the conjunctival tissue, and to the posterior segment of the eye including the retina, choroid, and the optic nerve head. This technique can provide similar immune-privileged spaces in other part of the body so that devices implanted there are not encapsulated.

Figure 62:
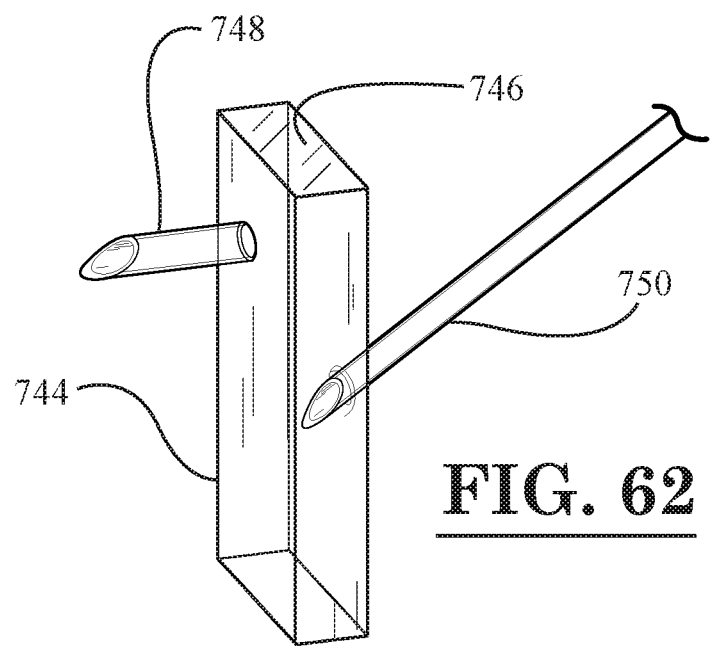
FIG. 62 illustrates yet another exemplary form of the drug delivery implant described herein, wherein the tubular implant comprises a needle for tissue penetration and the tubular implant is capable of being penetrating by a needle for taking liquid biopsies.

The drug delivery system of the embodiments described herein may be constructed so that it can have direct access to the anterior chamber, if needed, for both obtaining repeatedly a fluid biopsy from the eye or deliver medication(s) directly inside the eye in a fast or slow release manner, or for reducing the intraocular pressure of the eye by creating a minor flow through a porous implanted stent or tube through the corneal limbus without inducing a fibrous encapsulation of the stent. The stent can ameliorate also corneal dryness caused by dry eye syndrome. The stent can also be equipped with a pressure sensor indicating directly the intraocular pressure and communicating it with a radiofrequency device to outside the eye to a receiver or a processor. As one example, as shown in FIG. 62, the implant 744 may comprise a closed end 746 and a needle 748 for tissue penetration so that the implant 744 is capable of being used for taking liquid biopsies. In addition, stem cells or other cells can reside in, for example, a tubular implant, while having access to the oxygen and nutrients through the artificial barrier in an appropriately prepared corneal pocket. However the porous tubular implant permits these cells to migrate elsewhere in the eye or remain in place without being attacked by body's cellular response. Because the cellular body immune response is dependent on the production of the cells close to the implant or a foreign body to be taken up by the dendritic cells of the body at that location by creating a cell free space around the implant made of transparent amorphous cross-linked collagen. The invention of the embodiments described herein has eliminated the incentive for a Major Histocompatibility Complex (MHC) to occur. Because these MHC are present on the cell surface of the body cells to be activated in the production of an immune response. The release of theses cytokines activates the cellular immune system of the body to either eliminate the threat or isolate the device from the body completely by fibrocytes, thereby building a dense membrane (i.e., scar) around the implant. However, the cross-linked collagen permits the diffusion of water and small molecules permitting the needed growth factors from the incorporated stem cells placed inside the tubular implant needed for survival and the health of the cornea, retina etc.

Though this mechanism is very effective and useful, it affects the function of an implant that usually either releases a needed medication or measures or controls the release of a medication (e.g., measuring the blood glucose level and/or releasing insulin according to the glucose level found in the blood, etc.).

In order to isolate an implant in the body while preventing the immune cell to gain access to the device or build a membranous scar tissue around it, a method has been developed to isolate the implant in the body by killing all the cells adjacent to an implant, while maintaining a fluid-filled area around the implant or creating a barrier out of the surrounding tissue containing collagen and cross-linking the tissue in vivo. This barrier protects the implant from the antigen presenting dendritic cells in the tissue, while permitting the soluble medication or nano-sized particulate material to pass through the barrier so as to treat a pathological process in the body. One can also monitor the level of the analytes in the tissue fluid (e.g., aqueous fluid levels of glucose), which is a representative of the blood glucose level in the blood, from which it is originated. Aqueous level of most if not analytes found in the blood and could be used effectively to provide information on the health or disease processes affecting the eye or the body as a whole.

In the embodiments herein, implantation of a drug delivery device is described for the release or monitoring and controlling of a disease process in the eye, while crosslinking the tissue around the implant or implants (if more than one implant is provided). In any of the embodiments described herein, a plurality of drug delivery implants may be used (e.g., for delivering different medications), rather than a single drug delivery implant.

The technology described herein may be applied for any other device implantation in the body regardless of the location in the body. One of the benefits of the technology is that, if the device needs to be replaced, it can be done easily without dealing with the scar tissue formation that otherwise forms and makes the removal or replacement of the implant very complex because the tissue adhesions that usually forms between the tissue and the device.

One can use this concept described herein for diagnosis or therapy in diseases affecting the cornea, a metabolic disorder, genetic disorder, glaucoma, an infection affecting the eye or another portion of the body, a disease or disorder affecting the front or the back part of the eye or the conjunctiva or lens, an aging process, such as dry eye formation, retinal diseases including infective processes, genetic diseases requiring gene therapy (e.g., retinitis pigmentosa, etc. or metabolic disorders such as diabetes, etc.).

In one embodiment, if the media is clear, a two dimensional intrastromal corneal incision is created that is subsequently converted into a pocket in the corneal stroma using a femtosecond laser or a mechanical cutting system. The femtosecond laser passes through the clear media of the cornea. When the laser beam is focused inside the cornea, one can produce a two-dimensional cut or a three-dimensional cut around a thin part of the tissue that is removed to desired space, shape, depth, and location.

In another embodiment, in opaque elastic tissue (e.g., skin), one can use a knife or a syringe needle ending in a sharp cutting tip to cut a pocket in the tissue. If needed, the incision simultaneously involves removal of a three-dimensional tissue surrounding the surgical pocket to create some additional space for the implant using a similar cutting instrument, in the skin or soft tissue. In general, a cut creates a flexible three-dimensional space that can be filled with an implant. The implant is placed inside the needle and can be expelled from the needle by the syringe into the space created by knife.

In one or more embodiments, an injectable anesthetic (e.g., lidocaine or Bupivacaine) in a desired non-toxic preparation or concentration of 0.1-2% or more in a physiologic solution with, but preferably without, a preservatives, is injected in the corneal pocket to anesthetize the cornea postoperatively for a period up to 8-12 hours (e.g., if a PRK procedure is contemplated or after a corneal inlay implantation to prevent pain sensation completely in the postoperative period). This eliminates subjecting the entire corneal epithelium or the conjunctival epithelial cells to the damaging effect of topical anesthesia, which delays corneal re-epithelialization or conjunctival epithelial cells. Generally, the topical preservatives present in the topical anesthesia damages the cells that are bathed in them, and at times affects the regeneration of these cells (i.e., corneal epithelial or conjunctival cells) if applied frequently. Also, it may produce addiction to the topical anesthesia for eliminating the pain sensation caused by the loss of the corneal epithelial cells, whereas the injectable anesthetic does not damage the epithelial cells, including the nerve cells or their axons, except for blocking temporarily the neuronal transmission.

In one or more embodiments, the collagen cross-linker is mixed with the intracorneal locally injectable anesthetic, and injected simultaneously or sequentially in the corneal pocket.

In one or more embodiments, the pocket is filled with a biocompatible implant or implants (if more than one implant is provided) made of organic or non-organic material, or a mixture of it, and the implant is used for drug delivery. The implant may further be coated with a biocompatible material, such as collagen, elastin, polyethylene glycol, biotin and streptavidin, etc., as known in the art, or a composition thereof, to make the implant more biocompatible. The implant and/or the coating can be cross-linked with a cross-linker with the desired thickness and shape before or after implantation.

In one or more embodiments, the diameter of the corneal pocket can be 0.1 to 4 millimeters (mm), as needed. Only flat implants need a larger space with more than 0.2 mm. As shown in FIG. 63A-70B, the pocket can be circular, semi-circular, C-shaped, doughnut-shaped, rectangular, or any other shape.

In one or more embodiments, the implant or implants (if more than one implant is provided) can be located at a desired distance from the Bowman's membrane or from the corneal periphery, that is located away from the center of the visual axis (i.e., the implant may be off-centered, or ring-shaped in the peripheral cornea). See, for example, FIGS. 63A-70B.

In one or more embodiments, the implant or implants (if more than one implant is provided). is made to the desired shape, and size in diameter and length that fits with ease inside the corneal pocket without exerting pressure on the corneal tissue (i.e. without bulging it).

In one or more embodiments, a photosensitizer or cross-linker, such as riboflavin, is injected at the desired concentration in a biocompatible fluid or a viscous fluid prior to the implantation of the implant. However, it can be also administered simultaneously with the implant in the corneal pocket sufficiently to cover the internal wall of the pocket for a desired duration so that it penetrates at least 20 micron or wider, taking 5-30 seconds after injection prior to the cross-linking of the cornea, which prevents cell proliferation, encapsulation, or rejection of the implant while preserving an acellular barrier.

In one or more embodiments, ultraviolet (UV) radiation at the desired power (e.g., 1 to 4 mW/mm$^2$) and duration of 1-15 minutes, as needed, depending on the concentration of the photosensitizer or other radiation if another cross-linker is used (e.g., visible or infrared (IR) or another wave length) is applied externally to activate the photosensitizer in the corneal pocket, and to cross-link the collagen of the corneal stroma surrounding the corneal pocket, thereby killing only the cells located within the cross-linked cornea while preventing encapsulation of the drug implant while providing a physical stability to the cornea and preventing the wall of the pocket from adhering together or to the implant. This permits the implant to be replaced, if needed, with another implant with ease.

In one or more embodiments, the implant is coated with an organic material, such as collagen, dipped in a photosensitizer, or the implant can be coated with nanoparticles of the photosensitizer and implanted in the corneal pocket and ultraviolet (UV) radiation is applied with the desired power and duration using a painting technique using a small diameter fiber optic or other radiation with another wave length is applied if another cross-linker is used, externally or internally inside the pocket via a fiber optic to activate the photosensitizer in the corneal pocket and to cross-link the collagen of the corneal stroma surrounding the corneal pocket, thereby killing all cells located within the cross-linked cornea and cross-link the implant simultaneously. The corneal cross-linking prevents implant encapsulation with fibrous tissue, but provides a physical stability to the cornea without gluing the wall of the pocket together or to the implant.

In one or more embodiments, an injection of a small amount of hyaluronic acid in the pocket simplifies insertion of the drug implant in the corneal pocket.

In one or more embodiments, the drug implant has a tube-like structure with a size of 0.01 to 3 micron diameter holes in its wall, or having one micron or larger-sized holes for diffusion of fluid across it.

In one or more embodiments, the implant can be silicone, acrylic, methacrylate, hydroxyethyl methacrylate (HEMA), cross-linked organic or any other biocompatible transparent or non-transparent material, metallic or non-metallic, or a mixture thereof or coating other polymers, such as collagen or elastin with the desired thickness of 2 microns or more, as needed.

In one or more embodiments, the implant is made of various drug delivery polymers, such as polylactic acid or polyglycolic acid, or a combination thereof or polycaprolactone, or chitosan or other organic materials that can deliver the medication at a certain concentrations and dissolve within time ranging from 3-12 months or more.

In one or more embodiments, the biodegradable or non-biodegradable implant can be replaced with another one as before or a non-biodegradable material, but having biocompatible material or coating where the drug release occurs either through the small holes in the body of the implant at a certain rates depending on the size of the holes, or from one or both ends of the implant for drug delivery, as needed.

In one or more embodiments, the implant is a porous biodegradable polymer.

In one or more embodiments, the material inside the tubular implant is liquid, nanoparticles, suspension, powder, porous polymeric drug, etc.

In one or more embodiments, the implant is made using 3-D printing technology to the desired shape, size and/or coated with more biocompatible polymer(s) and cross-linked prior to the implantation, or it is implanted in a cross-linked pocket.

In one or more embodiments, the cross-linked corneal implant can be loaded with one or multiple medications needed for a short biocompatible drug delivery, or prophylactically to prevent an infection, or other used therapeutically medications to treat a disease process (e.g., inflammation, intraocular pressure (IOP), neovascularization, infection, or a cytokine, etc.).

In one or more embodiments, an organic cross-linked material can be used as above for a short term drug delivery of 1 to 4 weeks.

In one or more embodiments, an organic cross-linked material can be used as above for a short term drug delivery of 5 to 50 weeks or longer.

Figure 59:
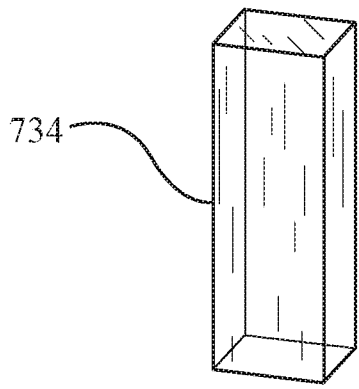
FIG. 59 illustrates still another exemplary form of the drug delivery implant described herein, wherein the implant is in the form of a rectangular flat tube.
Figure 63A:
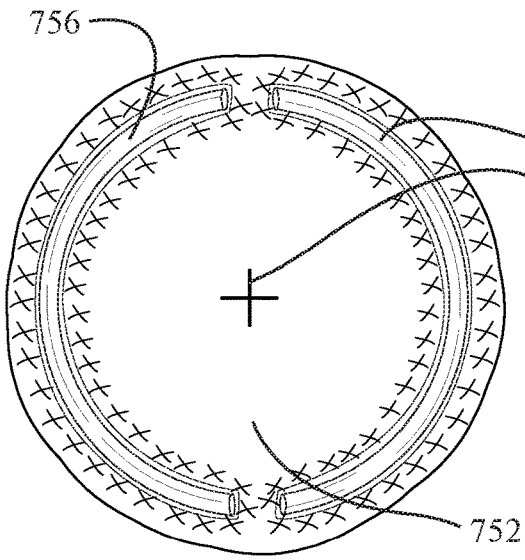
FIG. 63A is a front view of a cornea of an eye illustrating a two-part semi-circular drug delivery implant disposed in a cross-linked pocket in the peripheral portion of the cornea that is spaced apart from the central visual axis of the eye so as not to obstruct the central portion of the eye.
Figure 63B:
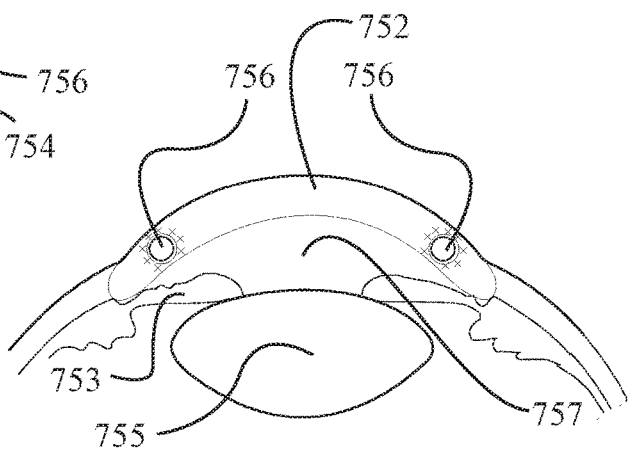
FIG. 63B is a partial side cross-sectional view of the eye of FIG. 63A illustrating the two-part semi-circular drug delivery implant disposed in the cross-linked pocket in the peripheral portion of the cornea.
Figure 64A:
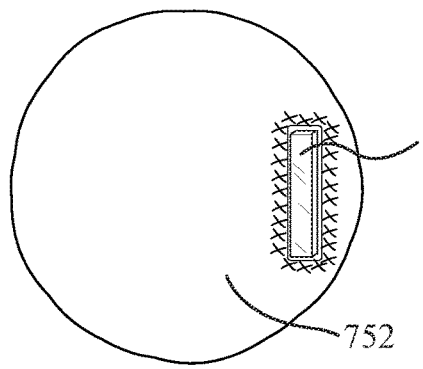
FIG. 64A is a front view of a cornea of an eye illustrating a generally linear drug delivery implant disposed in a cross-linked pocket in the peripheral portion of the cornea that is spaced apart from the central visual axis of the eye so as not to obstruct the central portion of the eye.
Figure 64B:
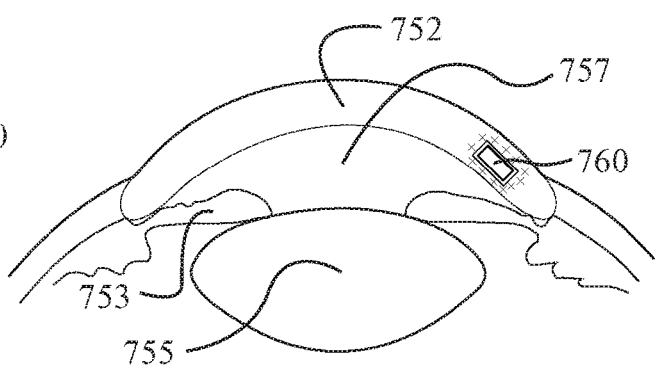
FIG. 64B is a partial side cross-sectional view of the eye of FIG. 64A illustrating the generally linear drug delivery implant disposed in the cross-linked pocket in the peripheral portion of the cornea.

In one or more embodiments, the implant is a C-shaped flexible or semi-flexible structure, and can be implanted in the prepared corneal pocket according to the size or the shape of the implant (e.g., centered around the visual axis having a string shape, rod-like shape, or flat shape), while removing a small 3-D tissue from the stroma for the pocket formation to provide space for the implant for drug delivery to the cornea or the anterior chamber, trabecular meshwork, conjunctiva, or diffusing toward the posterior segment, such as the retina, choroid or the optic nerve of the eye. As shown in FIGS. 54A-54D, the drug delivery implant may be rod-shaped 710, C-shaped 712, two-part semi-circular 714, or one-part semi-circular 716. Also, as illustrated in FIG. 59, the implant may also be in the form of a rectangular flat tube 734. In FIGS. 63A and 63B, a two-part semi-circular drug delivery implant 756 disposed in a cross-linked pocket in the peripheral portion of the cornea 752 that is spaced apart from the central visual axis 754 of the eye so as not to obstruct the central portion of the eye. As shown in FIG. 63B, the two-part semi-circular drug delivery implant 756 is disposed adjacent to the anterior chamber 757 of the eye, and anteriorly with respect to the iris 753 and lens 755 of the eye. In FIGS. 64A and 64B, a generally linear drug delivery implant 760 is disposed in a cross-linked pocket in the peripheral portion of the cornea 752.

Figure 66A:
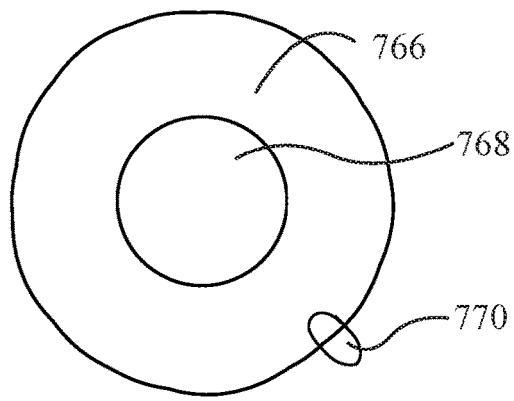
FIG. 66A is a front view of a cornea of an eye illustrating a pupil, cornea, sclera, and limbus of the eye.
Figure 66B:
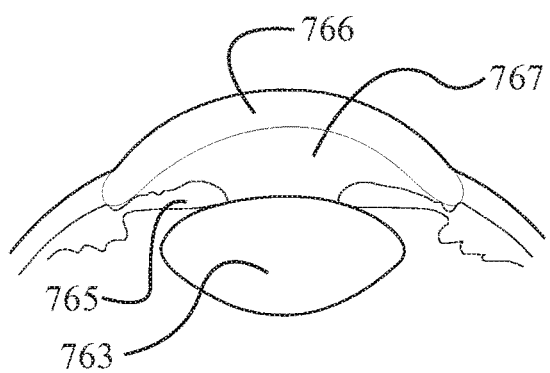
FIG. 66B is a partial side cross-sectional view of the eye of FIG. 66A illustrating an anterior chamber, iris, and lens of the eye.
Figure 67A:
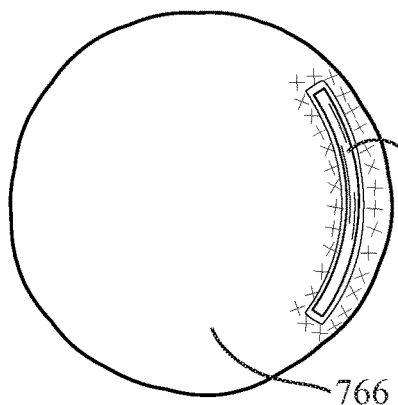
FIG. 67A is a front view of a cornea of an eye illustrating a one-part semi-circular drug delivery implant disposed in a cross-linked pocket in the peripheral portion of the cornea.
Figure 67B:
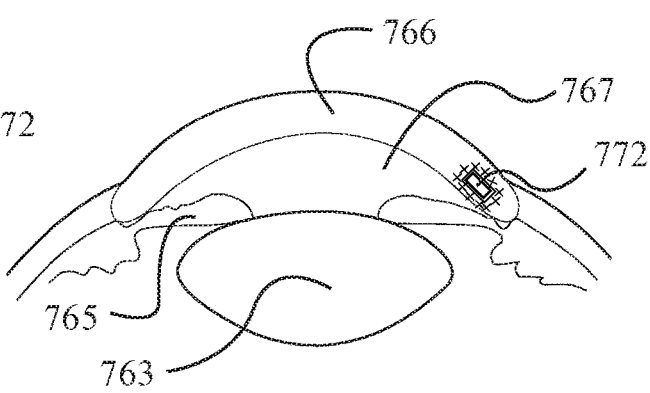
FIG. 67B is a partial side cross-sectional view of the eye of FIG. 67A illustrating the one-part semi-circular drug delivery implant disposed in the cross-linked pocket in the peripheral portion of the cornea.
Figure 68A:
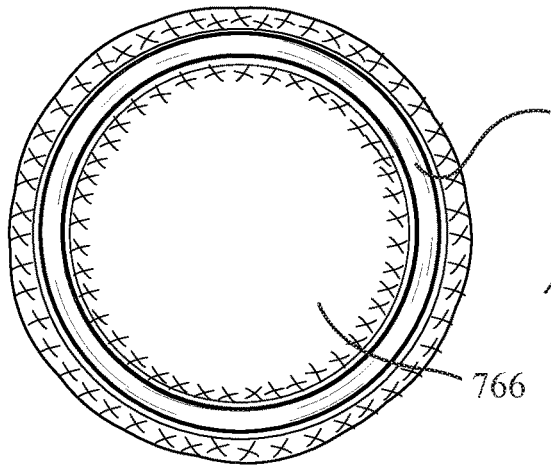
FIG. 68A is a front view of a cornea of an eye illustrating a doughnut-shaped drug delivery implant disposed in a cross-linked pocket in the peripheral portion of the cornea.
Figure 68B:
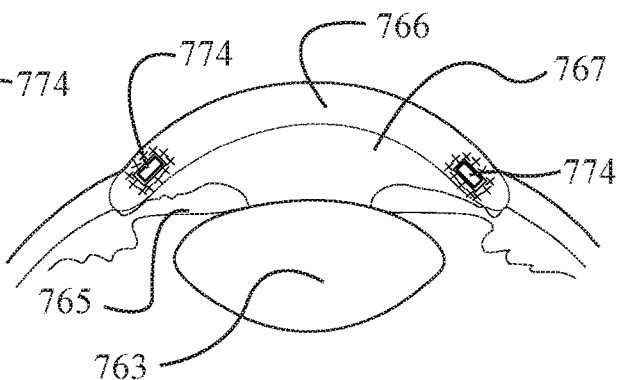
FIG. 68B is a partial side cross-sectional view of the eye of FIG. 68A illustrating the doughnut-shaped drug delivery implant disposed in the cross-linked pocket in the peripheral portion of the cornea.

Turning to FIGS. 66A and 66B, it can be seen that an eye generally includes a lens 763, an iris 765, cornea 766, an anterior chamber 767, a pupil 768, and a limbus 770. In FIGS. 67A and 67B, a one-part semi-circular drug delivery implant 772 is shown disposed in a cross-linked pocket in the peripheral portion of the cornea 766. In FIGS. 68A and 68B, a doughnut-shaped or ring-shaped drug delivery implant 774 is shown disposed in a cross-linked pocket in the peripheral portion of the cornea 766. In FIGS. 69A and 69B, a generally linear drug delivery implant 776 is shown disposed in a cross-linked pocket in the peripheral portion of the cornea 766.

In one or more embodiments, the implant is inserted in the corneal pocket through a small external incision made into the corneal pocket.

In one or more embodiments, the pocket itself can be filled with biodegradable nanoparticles for drug delivery to the entire ocular structures from the cornea to the optic nerve, and all tissues in between. The medication(s) can be anti-inflammatory, anti-infective, immune-suppressants, AntiVEGFs, biologics, Anti-PDGF, Anti IL-6, Rho kinase inhibitors, Wnt inhibitors, nerve growth factors, anti-glaucoma medications, gene(s) delivery in conjugation with viral or non-viral nanoparticles, such as nanoparticles, quantum dots, biodendrimers, etc. coated with polyethylene glycol (PEG) or cell penetrating agents along with an antibody to the specific tissue. This permits the genes or medications to be delivered after their migration out of the implant and the corneal pocket and to attach to the targeted cells in the cornea, conjunctiva, trabecular meshwork, retinal ganglion cells or photoreceptors, retinal and optic glial or nerve cells or their axons etc.

In one or more embodiments, the one or more medications in the drug implant may be anti-inflammatory agents, such as steroids, Dexamethasone, NSAIDS, Anti IL-17, Anti IL-6 and other Anti-ILs or antibiotics, fluoroquinolones, macrolides, cephalosporin A, vancomycin, aminoglycosides, penicillin and its derivatives or combination of antibiotics, etc., anti-virals, ganciclovir, valcyclovir, etc., anti-fungals, amphotericine B, etc., Anti-VEGFs, Avastin, lucentis, Aflilbercept, Anti-IL-6, anti-parasitic, etc., or other anti-inflammatory agents, such as NSAIDs or Rho kinase inhibitors, after any corneal surgery and act therapeutically to various diseases affecting the conjunctiva (e.g., dry eye), immune-suppressants, such as cyclosporine A, Mycophenolic acid, anti-proliferative agents, anti-metabolite agents, in uveitis, choroiditis or other medications, such as anti-glaucoma medication or combination of medications, gene delivery, DNA, RNA, siRNA etc. along with viral or non-viral delivery vehicles and CRISPR cas9 mediated homology-independent targeted integration (HITI) or homology directed repair (HDR) to modify the genetic components of various diseases of the eye.

In one or more embodiments, repeated crosslinking of the pocket can be performed as needed to prevent new cellular ingrowth and adhesion around the implant from the corneal tissue so that the implant's barrier is maintained, and the implant can be removed or replaced as needed (e.g., if the eye needs another or a combined medication to regulate disease process, such age related macular degeneration, glaucoma, uveitis, choroiditis or an infectious process of any origin).

In one or more embodiments, the peripheral cross-linked pocket is used to insert or inject medications needed to treat a corneal disease or glaucoma or a disease of the posterior segment. The medication can be in a form of nanoparticles, microspheres, lipid coating or PEG, streptavidin, biotin coating, etc., micelles, liposomes, thermosensitive chitosans, etc.

In one or more embodiments, one can inject or implant in the peripheral corneal pocket large-sized flexible, semi-solid or porous or solid rod, flat or tube or any shape and size polymeric material that can be absorbed with time and the medication is released slowly to the cornea or the anterior chamber of the eye or diffuses to the back of the choroid or retina and optic nerve.

In one or more embodiments, the diameter of these rod or flat-shaped shape implants can vary between 10 microns to 1 millimeter (mm) in diameter or larger with a length of 1 to 50 mm or longer.

Figure 61:
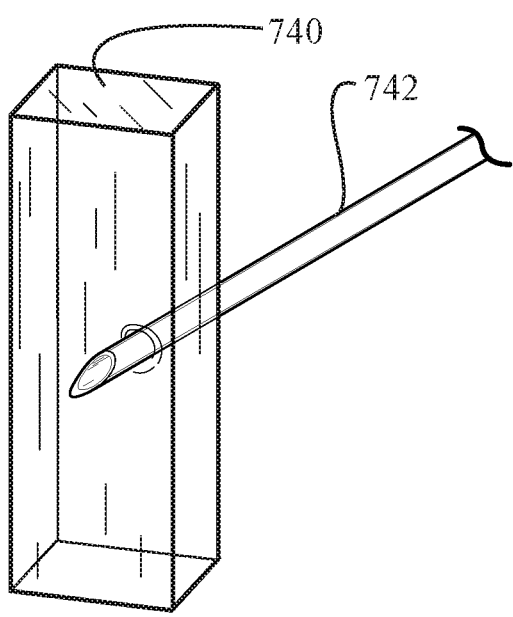
FIG. 61 illustrates still another exemplary form of the drug delivery implant described herein, wherein the implant is in the form of a rectangular tube that is refillable by injection.

In one or more embodiments, the porous tube can be made of semi-permeable non-biodegradable material that permits only the diffusion of the fluid/medication, etc. in and out of the tube, implanted in the peripheral cross-linked pocket. In these one or more embodiments, the tube can be refilled with medication as needed. For example, as shown in FIG. 61, the implant 740 in the form of a rectangular tube is refillable by injection with a needle 742.

In one or more embodiments, the drug implant tube contains stem cells, embryonic stem cells, ciliary hormone producing cells, or other hormone or factors producing stem cells, neuronal or glial stem cells, Mesnchymal stem cells, trabecular meshwork stem cells, limbal stem cells, modified skin stem cells, etc. in a biocompatible fluid that permits nutrition to reach the cells injected in the tube where the cells are immortalized to produce one or the other medication, growth factors, such as ciliary neurotrophic growth factor, RPE growth factor, nerve growth factors, anti-VEGFs, or other medications needed.

In one or more embodiments, the non-biodegradable tube with pores for drug and cell delivery is implanted in a cross-linked pocket with an implant in any part of the body for medication and cell delivery for various medications and functions.

Figure 57:
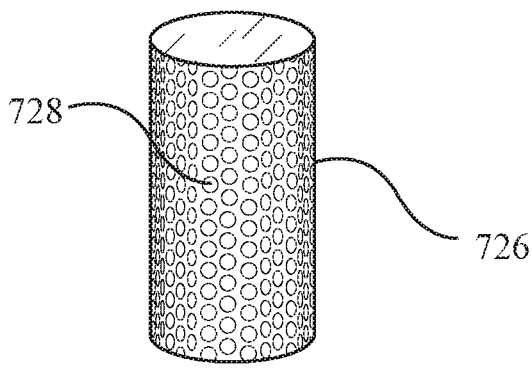
FIG. 57 illustrates another exemplary form of the drug delivery implant described herein, wherein the implant is tubular-shaped with holes formed in the side thereof.

In one or more embodiments, the implant is coated with biocompatible polymer(s) that is used for delivery of stem cells with medication in a corneal pocket. The implant has larger diameter holes of 5 microns and more in its wall permitting the cells to escape from the tubular implant into any tissue (e.g., corneal pocket containing stem cells, embryonic stem cells, ciliary body factor producing stem cells, neuronal or glial stem cells, Mesnchymal stem cells, trabecular meshwork stem cells, Limbal stem cells, modified skin stem cells, etc. in a biocompatible fluid) that permits nutrition to reach the cells injected in the tube where these cells can grow and pass through the holes of the implant and move toward a tissue. In FIG. 57, the tubular implant 726 has small holes 728 disposed in the circular peripheral side thereof, whereas the tubular implant 730 in FIG. 58 has large holes 732 disposed in the circular peripheral side thereof.

In one or more embodiments, the implant contains stem cells, embryonic stem cells, cilliary body hormone producing stem cells, neuronal or glial stem cells, Mesnchymal stem cells, trabecular meshwork stem cells, limbal stem cells, modified skin stem cells, etc. in a biocompatible fluid that permits nutrition to reach the cells injected in the tube along with Rho kinase inhibitors or Nerve growth factors to stimulate their regeneration and migration of theses cell and repair the pathology in the tissue.

In one or more embodiments, genetically modified cells are used to produce needed enzymes and medications. The combination of cross-linking of the cornea and killing the corneal cells and lack of vessels in the corneal makes it a suitable place for these cells in the tube implant to survive inside the tube without being attacked by the cellular body's response, thereby creating an immune privileged space for these cells to survive and produce medications needed locally or systemically (e.g. in many genetic diseases of the cornea such as Fuchs dystrophy, etc.).

In one or more embodiments, the pocket can be filled with a polymeric material that can become more semisolid, or becomes a gel, and contains medication for slow release of medication.

In one or more embodiments, the medication can be injected in the peripheral pocket along with corneal stem cells from the limbus or genetically modified skin stem cells, embryonic or pluripotential stem cells, or mesenchymal stem cells grown in the culture for implantation, in cases of cell loss of endothelium, or in genetically caused corneal opacification, such as macular dystrophy or trauma.

In one or more embodiments, the stem cells are mesenchymal stem cells injected in the corneal pocket along with ROCK inhibitors to replace or repair a cloudiness of the cornea.

In one or more embodiments, the stem cells are nerve cells to induce regeneration of the damaged corneal nerve (e.g., in diabetic patient) and after traumatic corneal injuries or after LASIK surgery.

In one or more embodiments, all tubular drug implants or devices are replaceable with ease.

In one or more embodiments, the tube can be refilled with medication to be used as slow release drug delivery that releases the drug in the cornea and anterior of the posterior segment of the eye.

In one or more embodiments, the tube is used for taking fluid samples from the eye.

In one or more embodiments, one creates an intrastromal corneal pocket in the peripheral cornea involving 2-4 mm 4-8 mm in width areas involving the cornea and the anterior sclera after bleaching out the peripheral conjunctival capillaries with a low dose of vasoconstrictive medication such as 0.5%4% phenylephrine applied locally with a Q-tipped applicator using a femtosecond laser.

In one or more embodiments, a small knife can be used to create a pocket in the cornea or elsewhere under the skin etc. if needed.

In one or more embodiments, the pocket width is more toward the corneal side than the scleral side or vice versa. The circumferential extent of the pocket can be 1 degree to 360 degrees of the corneal periphery (see FIGS. 63A, 63B, 67A, 67B, 68A, and 68B).

In one or more embodiments, using a small incision to access the intrastromal incision, one uses a curved probe to separate the corneal adhesion for injection of a photosensitizer cross-linker, such as riboflavin, at the desired concentration of 0.5%-4% in a biocompatible fluid, such as a physiological saline solution, etc. or suspension of particulates in a volume of 0.01 milliliters (ml) to 1 milliliter (mm) as needed only for the extent of the corneal pocket to cover the internal walls of the pocket for a desired duration that the photosensitizer penetrates at least 20 microns and beyond the corneal pocket in the corneal stroma to isolate that localized area of the cornea from the rest so that it does not respond with cell migration into the surrounding implant and so that it avoids tissue bounding together or to the implant.

In one or more embodiments, 0.01 ml to 0.1 ml of 0.02-2% lidocaine or bupivacaine solution can be injected alone or along with the photosensitizer in the corneal pocket to anesthetize the cornea for the next 1-15 hours, thereby eliminating pain sensation or discomfort of the surgery, and dry eye after surgery.

In one or more embodiments, the width of the corneal pocket can be 1-3 mm as needed. The peripheral corneal pocket can be circular, semi-circular, C-shaped, doughnut-shaped, straight, curved, or any other shape.

In one or more embodiments, the cross-linked pocket can be located at a desired distance from the Bowman's membrane in the corneal periphery.

In one or more embodiments, the ultraviolet (UV) radiation or other appropriate wave length of light at the desired power 0.5-50 mW/Cm2 and duration of 1-15 minutes, or other radiation with another wave length is applied externally in a stationary pattern or as a continuous painting/oscillatory technique with a focused small sized spot of 1-4 mm and a high energy to cover the width of the pocket, or on a painting oscillatory fashion entering the corneal pocket with a small diameter fiber optic and to activate the photosensitizer in the corneal pocket and crosslink the collagen of the corneal stroma surrounding the corneal pocket, and preventing the wall from adhering to itself or to a future implant, while providing a physical stability to the wall of the corneal pocket and preventing cell migration and rejection of an implant.

In one or more embodiments, ultraviolet (UV) radiation at the desired power in a stationary or focused light for a duration of 10 seconds to 15 minutes for the stationary radiation, or for a duration of 10 seconds to 20 minutes for the painting approach, depending on the power of the radiation and the length of the pocket used (or other radiation with another photosensitizer and wave length) is applied externally or via a fiber optic inserted inside the pocket to activate the photosensitizer and cross-link the collagen of the corneal stroma surrounding the corneal pocket while preventing cell migration, encapsulation, or rejection of the implant and protecting the anterior corneal stroma and the stem cells.

In one or more embodiments, the corneal pocket is three-dimensionally cut in order to remove a part of the stroma and create a space for the implant.

In one or more embodiments, the wall of the corneal pocket can absorb the photosensitizer from the implant after it is dipped in a photosensitizer solution or the implant is coated with nanoparticles of the cross-linker and placed in the corneal pocket to leak out, which is then followed by UV radiation at the desired power and duration or other radiation with another wave length applied externally or internally via a fiber optic to activate the photosensitizer in the corneal pocket and cross-link the collagen surrounding the implant. This technique provides a physical stability to the cornea preventing adhesion or gluing the implant to the surrounding tissue and preventing fibrous ingrowth or encapsulation or rejection of the implant, which can lead to implant rejection. This makes it possible to exchange the implant when needed without much trauma to the cornea surrounding the implant.

In one or more embodiments, the photosensitizer is conjugated to the surface of the implant having a polymeric coating, such as collagen, that releases the photosensitizer (e.g., riboflavin) from the implant once it is exposed to the water content of the tissue in the corneal pocket surrounding it. The riboflavin is released and stains the wall of the implant which is subsequently cross-linked with UV light. This prevents tissue adhesion between the implant and the corneal tissue and maintains a potential space between the corneal wall and the implant, thereby preventing activation of an immunologic response or neovascular tissue response by releasing from the tissue vascular endothelial cell factors (VEGF) in response to a foreign implant. The cross-linking process can be repeated as needed every 6 months to a year or more as needed. The cross-linking of the collagen protects the implant containing particulate medication(s), which releases the drug for a long time, and prevents the pocket from being invaded by the immune cellular elements and keeps the lumen of the tube shaped implant open.

In one or more embodiments, during the cross-linking, the corneal pocket remains pristine not allowing cell traffic or access to the pocket surrounded by the cross-linked amorphous collagen or other cross-linked tissues located in that area.

In one or more embodiments, the crosslinking can be repeated again in the postoperative period after implantation by injecting a cross-linker in the corneal pocket through a needle inside the wall of the pocket, which diffuses readily through the potential space around the implant and the wall of the pocket, and then is irradiated with UV light from the outside.

In one or more embodiments, the implant can be made of silicone, acrylic, methacrylate, HEMA, metallic or non-metallic, synthetic, organic, polymeric biodegradable, etc., coated with another or a biocompatible polymeric materials or a mixture thereof or coated with, for example, collagen or elastin, formed with a desired thickness of 2 microns to 100 microns, and conjugated with a cross-linker or the cross-linker is injected in the potential pocket space in the tissue and is cross-linked.

In one or more embodiments, the implant is made by the use of 3-D printing technology with the desired material, shape, size or thickness, transparent or non-transparent organic or non-organic or a mixture of them, a material such as collagen elastin, synthetic polymers can be coated again with riboflavin nanoparticles with one or more biocompatible polymer(s), and cross-linked with UV light prior to or preferably after implantation.

Figure 55:
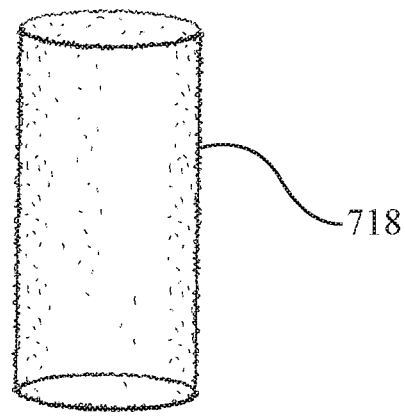
FIG. 55 illustrates an exemplary coated drug delivery implant, wherein the drug delivery implant is coated with a polymer and a photosensitizer.

In one or more embodiments, the implant is coated with a collagen polymer to a desired thickness or in combination with another polymer, such as polyvinyl alcohol, chitosan, polycaprolactone, etc., conjugated with riboflavin or another cross-linker and cross-linked before or after implantation in a preformed pocket with an appropriate wavelength of light or UV radiation to cross-link the polymeric coating inside the body allowing the cross-linker to be released in the tissue, and then cross-link the tissue surrounding the implant in order to, after implantation, release the incorporated medication from the implant slowly without inciting cellular attraction or encapsulation of the implant which inhibits a release of the medication(s) from the implant that is unpredictable. For example, as shown in FIG. 55, the implant 718 is coated with a polymer and/or a photosensitizer.

In one or more embodiments, the non-biodegradable flexible porous tube made of polymeric material or a non-organic compound in combination with cross-linked organic polymer coating is filled with microspheres, drug nanoparticles incorporated in a polymeric material, such as poly-lactic glycolic acid, chitosan, liposomes, polycaprolactone, or lipid-coated nanoparticles, etc. containing the medication so as to release the medication slowly from the tube implant.

In one or more embodiments, the implant can serve as a reservoir that releases the medications though the pores of 1 to 3 microns in diameter in its wall, and then can be refilled repeatedly by injecting in the tubular implant the medication through a 33-34 gauge needle through the cornea surrounding the tube.

In one or more embodiments, the implant releases immunosuppressive agents, such as cyclosporine, calcineurin inhibitors, mycophenolic acid, tacrolimus, siraliums, steroids, MPP inhibitors, NSAIDs, antimetabolytes, polyclonal antibodies, monocolonal antibodies, TNF inhibitors, Fingolimod, antibiotics, intraocular pressure (IOP) lowering agents, such as Rho kinase inhibitors, Fasudil, and other agents, pilocarpine, prostaglandin analogues, Brimonidine, etc., anti-virals, Anti-VEGFs, biologics, or neuroprotective releasing medication. The medications being released as needed at concentrations of nanograms or micrograms or mg/per hour depending on the polymeric material size of the holes, length of the polymer, etc.

In one or more embodiments, the implant can be positioned at any place in the body to control a function or release a medication without being encapsulated by the surrounding tissue, due to the cross-linking of the polymeric coating or the pocket being cross-linked prior to the implantation, while the medication can be an anti-VEGF, neuroprotective agents, such as nerve growth factors, Rho kinase inhibitor such as Fasudil, antibiotics, antiproliferative agents, anti-inflammatory agents, etc. at a non-toxic, beneficial concentration.

In one or more embodiments, the implant is made using 3-D printing technology to the desired shape, size or thickness from any material coated with collagen, elastin, or made of collagen, elastin, etc. or synthetic polymers which are further coated with more biocompatible polymer(s), such as acrylic, organic, etc., which are cross-linked prior to the implantation or coated with a cross-linker or the crosslinking nanoparticles are done subsequent to its release in the tissue prior to radiation with the UV light. In another embodiment, the implant is formed from glass using 3-D printing technology (i.e., the implant is 3-D printed glass).

In one or more embodiments, the implant is implanted in another part of the eye, such as under the conjunctiva, under the sclera, in the retina or sub-retinal space, under the skin using an implant containing medications such as Botox, or in other parts of the body using an implant which is coated with collagen to a desired thickness, dipped in a photosensitizer or has photosensitizer nanoparticles, such as riboflavin, etc. or the photosensitizer is injected surrounding the implant and implanted in desired location, such as under or over the sclera in the choroid, under the conjunctiva, etc. Then, ultraviolet (UV) radiation or another wavelength of light is used to cross-link the tissue at the desired power and duration depending on what technique is used. In these conditions, a focused UV or another wavelength of light is applied externally, in a painting oscillatory fashion only to the desired areas or internally through a fiber optic, etc. to activate the photosensitizer in the surrounding tissue where the implant is located. The cross-linked collagenous tissues surrounding the implant prevent creating an adhesion between the tissue and the implant or gluing the wall of the pocket together or to the implant. The cross-linked collagenous tissues surrounding the implant also have these additional benefits: (1) it is easier to replace the implant if needed, (2) fibrous ingrowth or encapsulation is prevented, (3) it permits injection of the cross-linker again to repeat the cross-linking process if needed, and (4) it prevents rejection of the implant and contributes to the slow release of the medication from the implant. Also, these implants can act as a shunt for glaucoma, or drainage shunt for cerebrospinal fluid, or other part of the body, such as a bladder neck for urine if the drainage system is provided with a unilateral valve that only opens when the bladder pressure increases to certain level, etc.

In one or more embodiments, the injection of a small amount of hyaluronic acid or other viscous fluid in the pocket simplifies the inserting of the implant in the peripheral corneal pocket or a pocket created in another tissue.

In one or more embodiments, the implant can be a biodegradable polymer carrying various medications and can be replaced.

In one or more embodiments, the implant is a tube-like structure having a thickness or diameter of 0.02 millimeters (mm) to 0.4 millimeters (mm) in one direction and up to 8 mm in another (flat) width, and being 1-60 mm long covering the entire corneal periphery without pressing the corneal tissue in any direction. The implant may be filled with a medication(s), a fluid, or a combination of them.

In one or more embodiments, the tube is not biodegradable having holes made in the wall of the tube with 0.2 to 3 microns in diameter, or 5 microns to 500 microns in diameter, to permit diffusion of the medications or cells placed in it to produce desired needed proteins, hormones, nerve growth factors, or other products needed for other body cell survival, such as cornea, retina, brain, etc.

In one or more embodiments, the tube has holes that are 5 to 15 microns in diameter so as to permit stem cells to exit the tube. The tube can be biodegradable implanted in a lightly cross-linked corneal pocket permitting, for example, stem cells to proliferate and/or migrate to the cornea. The stem cells can be obtained from limbal stem cells or mesenchymal stem or skin and cultured cells prior to the injection in the cornea or in another part of the body.

In one or more embodiments, the device is implanted in the wall of the vitreous cavity with one end closed and one end open to the vitreous cavity, or the implant can be under the retina or it can penetrate both the retina and the choroid and permit release of medication or the cells.

In one or more embodiments, the implant is implanted in the tissue surrounding the eye, on the face, etc. with one end closed and one end open to the tissue. The implant can be removed after the drug is released, and then replaced.

In one or more embodiments, the repeated crosslinking of the tissue surrounding the pocket can be performed as needed to prevent cellular ingrowth, and the implant can be removed and replaced as needed (e.g. in age related macular degeneration) to maintain delivery of the anti-glaucoma medication, anti-VEGFs, immunosuppressive or anti-inflammatory agents, or nerve growth factors, or Rho kinase inhibitors.

In one or more embodiments, the peripheral cross-linked pocket is used to insert or inject medications needed to treat a corneal disease, glaucoma, or a disease of the posterior segment. The medication can be in a form of nanoparticles, microparticles, micelles, liposomes, chitosans, polycaprolactone as nanoparticles, dendrimers, etc.

Figure 56A:
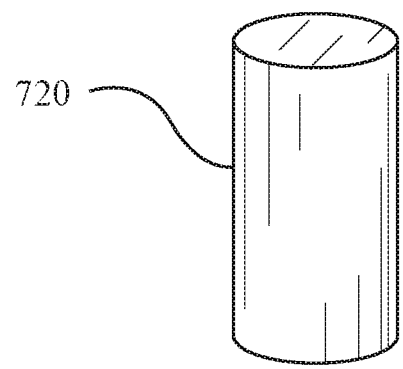
FIG. 56A illustrates a first exemplary form of the drug delivery implant described herein, which is in the form of a solid tubular implant.
Figure 56B:
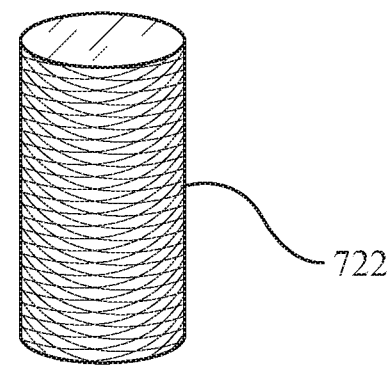
FIG. 56B illustrates a second exemplary form of the drug delivery implant described herein, which is in the form of a porous tubular implant.
Figure 56C:
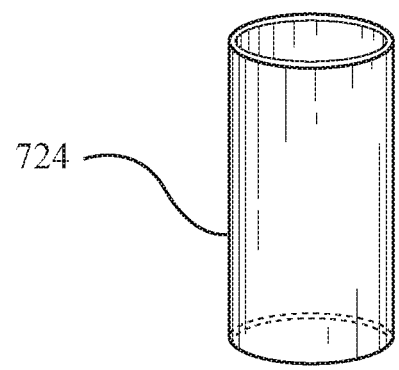
FIG. 56C illustrates a third exemplary form of the drug delivery implant described herein, which is in the form of a tubular implant with open ends.
Figure 60:
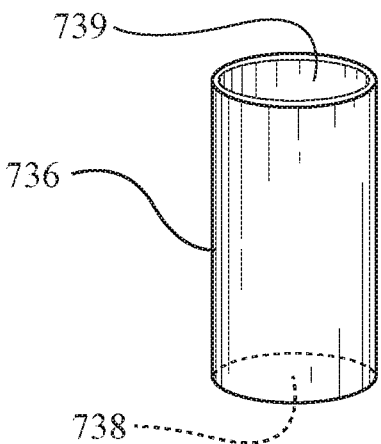
FIG. 60 illustrates yet another exemplary form of the drug delivery implant described herein, wherein the implant is in the form of a semi-solid or silicone tubular implant with one closed end and one open end.

In one or more embodiments, one can inject or insert an implant in the peripheral corneal pocket that is in the form of a large-sized flexible, semi-solid or solid, porous or solid rod-shaped implant, a flat implant, or tube-shaped implant that contains medication, or any shape and size polymeric material that can be absorbed with time and the medication is released slowly to the cornea or the anterior chamber of the eye or diffuses through the anterior chamber or through the sclera to the back of the eye, for treatment of the choroidal or retina and optic nerve diseases. As shown in FIGS. 56A-56C, the implant may be in the form of a solid implant 720, a porous implant 722, or a solid tubular implant 724 with an open end. Also, as shown in FIG. 60, the implant may be in the form of a semi-solid or silicone tubular implant 736 with one closed end 738 and one open end 739.

In one or more embodiments, the diameter of the rod or flat-shaped implant can have a length of 1 microns to a few millimeters (mm), or the length can be 1 to 40 millimeters (mm) or longer.

In one or more embodiments, the non-biodegradable tube is open-ended so that the medication exits only from one or both ends of the tube.

In one or more embodiments, the medication can be released for a duration of from 3 months to 3 or more years, such as when containing nanoparticles of fluoroquinolone dexamethasone, diclofenac, etc., and the implant can be replaced or removed if the desired effect has been achieved or reinjected in the corneal pocket.

In one or more embodiments, the tube is closed ended, but has pores for diffusion of the medication. For example, refer to the implants 726, 730 in FIGS. 57 and 58.

In one or more embodiments, the implant can be placed near any joint in the body and the cross-linking is done using ultraviolet (UV) radiation through the skin or through the fiber optic as described for localized drug delivery.

In one or more embodiments, the porous tube can be made of semipermeable non-biodegradable material that permits only the diffusion of fluid/medication, etc. in and out of the tube, and the tube is implanted in the peripheral cross-linked corneal pocket, wherein the tube can be refilled with medication as needed via an injection using a 33-34 gauge needle. For example, refer to FIG. 61.

In one or more embodiments, the tube contains cells in a biocompatible fluid that permits nutrition to reach the cells which are injected in the tube where the cells are immortalized to produce one or more medications, growth factors, such as a ciliary neurotrophic growth factor, RPE growth factor, nerve growth factors, anti-VEGFs, or other medications needed.

In one or more embodiments, the implant contains genetically modified cells producing other needed enzymes and medications. The combination of crosslinking of the cornea produces a wall of amorphous, acellular collagen and the corneal location that lacks vessels provides a suitable place for these cells in the tube implant to survive and produce medications as needed, which otherwise would have to be given repeatedly either locally or systemically, and in many genetic diseases of the cornea, such as Fuchs dystrophy, the cells have to be injected in the subconjunctival space where the cells could be attacked by the normal cellular body's immune response. The cross-linked pocket with the implant creates an immune-privileged space in the cornea or elsewhere for these cells to survive. For example, refer to FIGS. 63A-70B.

In one or more embodiments, the medication in the implant can be in any form or composition, such as antibiotics, anti-inflammatory, immune suppressants, anti-glaucoma medication, anti-vascular proliferation, stimulatory, such as Rho inhibitors. The polymers can be made of bio-degradable compounds, such as polylactic, polyglycolic acid or a combination of them, polycaprolactone, etc.

In one or more embodiments, the corneal cross-linked pocket contains a tubular implant filled with particulate immunosuppressive agents, such as cyclosporine etc., that release the medication at a constant, but low concentration of micrograms as needed. The medication diffuses in the cornea, sclera, and/or conjunctiva, thus eliminating the burning sensation of topical cyclosporine drops and the need for daily drop admiration in dry eye syndromes, or after refractive surgery or other diseases.

In one or more embodiments, the medication can be injected in the peripheral pocket along with corneal stem cells taken from the limbus or genetically modified stem cells and grown in the culture for implantation.

Figure 65A:
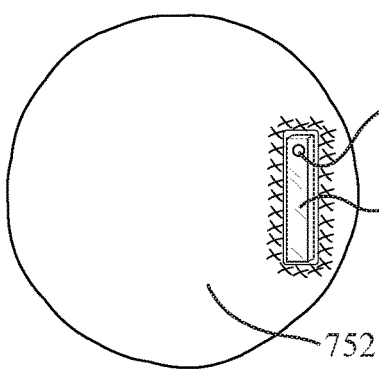
FIG. 65A is a front view of a cornea of an eye illustrating a tubular drug delivery implant disposed in a cross-linked pocket in the peripheral portion of the cornea, wherein the implant comprises a needle fluidly coupling the implant to the anterior chamber of the eye.
Figure 65B:
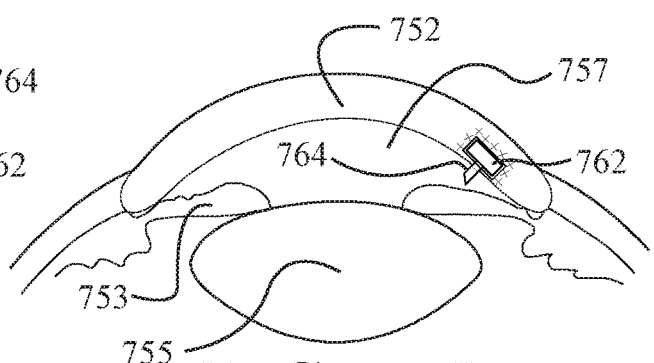
FIG. 65B is a partial side cross-sectional view of the eye of FIG. 65A illustrating the tubular drug delivery implant with the needle extending into the anterior chamber of the eye.

In one or more embodiments, as shown in FIGS. 65A and 65B, a non-biodegradable implant tube 762 as described herein is implanted in the cross-linked corneal pocket of the cornea 752 of the eye with iris 753 and lens 755, and the implant tube 757 is connected to the anterior chamber 762 with the aqueous fluid via a thin 23-34 gauge needle 764, where biomarkers such as VEGFs, glucose, and analytes, etc. are present both inside the aqueous and the tube system made of soft silicone. Similarly, as depicted in FIGS. 70A and 70B, an implant 778 is implanted in the cross-linked corneal pocket of the cornea 766 of the eye with iris 765, and the implant 778 is connected to the anterior chamber 767 with the aqueous fluid via a needle 780. The implants 762, 778 can be penetrated with a 30-34 gauge needle from outside and the aqueous can be aspirated in a volume of less than 0.50 microliters repeatedly over a long period of time without causing a collapse of the anterior chamber. The volume of the anterior chamber is 25 times more than the sample fluid taken. The minimal amount of aqueous fluid withdrawn will be replaced by the eye in less than 10 minutes. This provides a means of obtaining easily a fluid biopsy repeatedly from the eye without penetrating the entire cornea or the eye wall directly with the complication of iris or lens injury and retinal injury. The fluid sample can be examined in chronic disease processes, such as uveitis for biomarker of a disease, viral infection that persist in the eye long after the body has healed, such as Ebola, Zika, Herpes viruses or other viral diseases or non-viral infections that can be detected and treated appropriately. The biomarkers can be obtained from the implanted tube, and can provide valuable information on many metabolic diseases of the body or the eye, a systemic disease (e.g., Alzheimer disease), age related macular degeneration, glucose level, or other analytes (e.g., diabetes) in diabetic retinopathy and other slow progressive degenerative eye diseases, tumors, infection, uveitis, poisoning or drug overdose, etc.

In one or more embodiments, a plurality of implants are implanted in the cornea of the eye. In these one or more embodiments, each of the implants is used for a different purpose. For example, a first one of the implants may be in form of a corneal drug delivery implant used for delivering one or more medications to the eye, as described above. A second one of the implants may be used for taking liquid biopsies from a portion of the eye, as described herein (e.g., extracting a liquid biopsy of the aqueous fluid from the anterior chamber of the eye). A third one of the implants may be used for stem cell delivery and/or gene therapy in the manner described above. A fourth one of the implants may be used for measuring the intraocular pressure of the eye of the patient (e.g., intracorneal implant comprising a pressure sensor 618 illustrated in FIGS. 52 and 53). That is, the fourth implant may contain a pressure sensor configured to measure an intraocular pressure of an eye and to output a signal based on the measured intraocular pressure of the eye, the pressure sensor configured to be implanted in a cornea of the eye; a processor operatively coupled to the pressure sensor, the processor configured to generate intraocular pressure data based upon the signal outputted by the pressure sensor; and a transmitter device operatively coupled to the processor, the transmitter device configured to transmit the intraocular pressure data generated by the processor to a remote receiver located outside of the eye, the transmitter device configured to be implanted in the cornea of the eye. In addition to the pressure sensor, the third implant may further comprise a needle configured to penetrate a posterior portion of the cornea of the eye, the needle configured to open into the anterior chamber of the eye so as to measure the intraocular pressure of the eye without obstructing vision through the central cornea.

In one or more embodiments, one can measure the amount of VEGF present in the aqueous providing information on the disease progression requiring treatment (e.g., anti-VEGFs or no treatment). Anti-VEGFs or another medication can be administered directly in the tube to reach the posterior segment avoiding repeated intraocular injection through the sclera, without having the risk of retinal detachment or lens injury. As another example, liquid biopsy of aqueous in a patient with diabetic retinopathy, where the retina is in need of treatment with the laser coagulation, provides the information regarding whether the disease process is under the control or not.

In one or more embodiments, for the first time one can obtain from the aqueous biopsy, instant information needed for the doctor to diagnose a disease process at the bedside and be able to follow the process over a long period of time with ease.

In one or more embodiments, nanoparticles carrying other medications can be delivered as slow release nanoparticles from the tube in the anterior chamber to treat glaucoma for a long period of time, thereby eliminating the need for repeat therapy. These medications may include pilocarpine, prostaglandin analogues for treatment of glaucoma, Rho kinase inhibitors, or neuroprotective agents or Brimonidine, etc.

In one or more embodiments, the implanted tube is filled with desired medications, as described above, and is coated with collagen or albumin loaded with riboflavin particles that are diffused after implantation in the pocket. The ultraviolet (UV) radiation used for cross-linking permits the diffusing of the medication from the implant as a slow release device, and prevents vascular growth around the implant containing the medication.

In one or more embodiments, the implanted tube can be 100 microns to 1 millimeters (mm) in diameter and 4 mm to 40 mm long, or less than 100 micron in diameter and no longer than a few millimeters in length. The implanted tube maybe filled with any desired medication to be implanted in any tissue and cross-linked after implantation.

In yet one or more further embodiments, methods are disclosed herein which include administering Wnt inhibitors either alone, or in combination with Rho kinase inhibitors (i.e., Rock inhibitors), that are useful for alleviating the effects of conditions that are caused by acute or chronic inflammatory processes, such as chronic inflammatory dry eye disease, lichen planus, arthritis, psoriasis, plantar fasciitis, pars planitis, papillitis, optic nerve neuritis, scleritis, keratitis, chronic Meibomian gland inflammation, and uveitis.

In one embodiment, Wnt inhibitors or Rho kinase inhibitors are used as topical drops, ointment, gel, non-toxic injectable formulation to treat the dry eye syndrome or mucosal inflammatory diseases, such as lichen planus, chronic joint disease, arthritis, chronic choroiditis, plantar fasciitis, pars planitis, scleritis, iritis, scleritis gingivitis, pars planitis and uveitis.

A method of treating dry eye with deficiency or aqueous production which is associated often with the Meibomian gland disease, affecting about 7% to 34% of all Americans, pathophysiology of chronic dry eye disease including a cycle of inflammation involving both innate and adaptive immune responses is also disclosed herein.

In one embodiment, dry eye syndrome (DES) or keratoconjunctivitis sicca, a disease affecting tear production leading to damage to the corneal surface, associated often with disturbance of Meibomian gland, lachrymal gland, conjunctival goblet cells, nasolacrimal duct and pain sensation is treated by Wnt inhibitors or Rho kinase inhibitors used as topical drops, ointment, gel, non-toxic injectable formulation.

In one embodiment, the method used for treatment of the eye utilizes over the counter physiological saline solutions with some other components to affect the inflammatory component of the dry eye or improve on the composing of the tear film, such as tear film osmolarity, or adding lipids, mucin, etc. Other topical medications include TheraTears® (Advanced Vision Research), Refresh® and Celluvisce® (Allergan), Tears Natural® and Bion Tears® (Alcon), GenTeal® and HypoTears® (CIBA Vision), each of which contain electrolytes and has varying pH levels, osmolarities, Restasis® (0.05% cyclosporine, Allergan), and Xiidra® (5% lifitegrast, Shire), which attacks the inflammatory process by a different mechanism than cyclosporine. Most of these medications are applied as a drop to maintain the conjunctival wetness as needed usually 1-3 drop during the day or ointment at night most of these medications may be used in combination with Rock inhibitors such as Fasudil, or Wnt inhibitors such as sulforaphane and vitamin D, etc.

In one embodiment, the administration of Rock inhibitors not only reestablishes the tear production by reducing the conjunctival inflammatory cytokines and inflammatory response, but also enhances the nerve fibers to grow and reestablish the function of conjunctival goblet cells to produce mucin, which is essential for tear film lubrication. Rho-associated protein Kinase (Rock) is a kinase belonging to the family of serine-threonine Kinase involved in regulating the shape and the cytoskeleton of the cells, it is an important regulator of cell migration, stimulates PTEN phosphatase activity, leading to uncontrolled cell division in cancer. Rock is active in inflammatory processes, cancer, Parkinson's disease, diabetes, and many neurodegenerative diseases and produces and stiffens collagen in tumors, such as pancreatic cancer. Therefore, Rock inhibitors inhibit inflammatory processes, blocking cell migration.

In one embodiment, Rock inhibitors may be used in combination with functionalized nanoparticles of polycaprolactone, polylactic or polyglycolic acid, etc. to reduce the inflammation during immune therapy or thermoimmune therapy. In one embodiment, a potent ROCK inhibitor, orally bioavailable Fasudil hydrochloride, inhibitor of cyclic nucleotide dependent- and Rho-kinases GSK 269962 is used. In one embodiment, potent and selective ROCK inhibitor GSK 429286, Selective Rho-kinase (ROCK) inhibitor H1152 dihydrochloride, or Botox is used.

In one embodiment, selective Rho-kinase (ROCK) inhibitor Glycyl H 1152 dihydrochloride, or another selective Rho-kinase (ROCK) inhibitor is administered as topical ointment, drop, or gel. Also, a more selective analogue of H1152, that is cell-permeable, a selective Rho-kinase inhibitor OXA 06 dihydrochloride, a potent ROCK inhibitor PKI1447 dihydrochloride, potent and selective ROCK inhibitor antitumor SB 772077B, a potent Rho-kinase inhibitor, vasodilator SR 3677 dihydrochloride, a potent, selective Rho-kinase (ROCK) inhibitor TC-S7001, a potent and highly selective ROCK inhibitor, orally active Y-27632 dihydrochloride or Botox also may be administered.

In one embodiment, aqueous tear-deficient dry eye, occurring as a result of not enough tears being produced due to a dysfunction of the lacrimal glands, is treated with Wnt inhibitors or Rho kinase inhibitors as topical drops, ointment, gel, or a non-toxic injectable formulation.

In one embodiment, the Wnt inhibitors compound that is used includes FH535, IWP-2, PNU-74654, IWR-1endo, IWR-exo, demethoxycurcumin, sulforaphane and vitamin D, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, and akinumab.

In one embodiment, patients with moderate-to-severe dry eye having both elements of evaporative dry eye and aqueous tear-deficient dry eye, and that are on topical medications for other diseases, such as glaucoma, drops, or antibiotics containing preservative that over time damage the conjunctival goblet cells and other cells and induce dry eye syndrome, are treated with Wnt inhibitors or Rho kinase inhibitors as topical drops, ointment, gel, or a non-toxic injectable formulation.

In one embodiment, administration of Wnt inhibitors, such demethoxycurcumin, sulforaphane and vitamin D, or Rho kinase inhibitors, such as Fasudil derivatives, is done as topical drops, a gel, a non-toxic injectable formulation, or injectable Botox, 1-100 units as needed, administered locally at multiple locations or Rock inhibitors molecules at doses of 1 Pg-nanograms to a few micrograms as slow release delivery system.

In one embodiment, patients who are on topical medications for other diseases, such as glaucoma, drops or antibiotics containing preservatives and over time damage the conjunctival goblet cells and other cells and induce dry eye syndrome, or patients with dry eye and glaucoma are treated either by implanting matrices of polylactic acid or polyglycolic acid, polyanhydride, or chitosan polymers under the conjunctiva with slow release polymers containing either Wnt inhibitors or Rock inhibitors, such as Botox or Fasudil derivatives, releasing the medication over months or years locally at multiple locations to release the non-toxic doses of the medications from 1 picogram (pg) to 1 nanograms (ng) or more each day.

In one embodiment, patients who develop dry eye as a result of systemic medication, such as in cancer patients developing dry eye after administration of checkpoint inhibitors in cancer immune therapy, are treated either by Wnt inhibitors or Rock inhibitors with slow release polymers containing either Wnt inhibitors, such as demethoxycurcumin, CCTO36477, KY02111, WAY-316606, SFRP, IWP, LGK974, C59, Ant1.4Br/Ant 1.4C1, ivermectin, niclosamide, sulforaphane and vitamin D, or Rock inhibitors, such as Botox or Fasudil derivatives, etc., releasing the medication over months or years locally at multiple locations to release the non-toxic doses slow release medications from 1 pg to 10 ng each day or more.

In one embodiment, the Sjorgen syndrome is associated with low salivary flow, lymphocytic infiltration of the lacrimal gland and salivary gland auto antibodies in serum, rheumatoid factor, connective tissue diseases, such as Sjogren's syndrome, to the list of immune-related adverse events that can develop during cancer treatment with immune checkpoint inhibitors are treated with Rock inhibitors and Wnt inhibitors at non-toxic concentrations of sulforaphane and vitamin D, CCTO36477, KY02111, WAY-316606, SFRP, IWP, LGK974, C59, Ant1.4Br/Ant 1.4C1, ivermectin, niclosamide, or Rock inhibitors such as Botox or Fasudil etc., releasing the medication slowly over months or years locally at multiple locations to release the non-toxic doses slow release medications from 1 picogram (pg) to 10 nanogram (ng) each day locally.

In one embodiment, the patients being treated have a dry eye syndrome unassociated with Sjögren's syndrome (SS) (i.e., non-SS keratoconjunctivitis sicca (KCS)) with a sensation of foreign body in the eyes, photophobia, excessive tearing, ocular irritation and pain. Other symptoms are increased tear film osmolality, decrease in tear breakup time, increase in the conjunctival enzymes metalloproteinase 9 and 17, and changes in impression cytology of the conjunctival cells. These patients are treated with Rock inhibitors, such as injectable Botox, 1-10 units, or in combination with metalloproteinase inhibitors doxycycline, low molecular weight heparin, lovenox, and dexamethasone at concentration of 0.1%-5%.

In one embodiment, when inflammation is one of the mechanisms that causes damage to the ocular surface in dry eye disease seen in autoimmune diseases such as Sjögren's syndrome, and rheumatoid arthritis and neuropathic disorders, optic nerve neuritis, papillitis, scleritis, uveitis, inflammatory, infectious, chemical, traumatic diseases, etc., the patients are treated with injectable Rock inhibitors, such as Botox or Fasudil derivatives, conjugated with slow release polymers, etc. releasing the medication over months or years locally at multiple locations as the non-toxic doses release the medications slowly for months to a year at concentration of 1 pg to 10 ng each day.

In one embodiment, the pathological conditions resulting in dry eye include pemphigus and Sjogren's syndrome, which affect the eye by either damaging the conjunctival cells responsible for maintaining the wetness of the cornea and the conjunctiva, or by damaging the lacrimal glands of the eye and/or the meibomian glands of the eye lid or other pathological conditions resulting in dry eye include hypolacrimation, alacrima, Stevens-Johnson syndrome, marginal blepharitis pemphigus, ocular pemphigoid, scleritis, or diabetes are treated with the Rock inhibitor Fasudil, Botox, etc. at a picogram to nanogram concentration or in combination with metalloproteinase inhibitors, doxycycline 0.1%-5% solution, low molecular weight heparin 0.1%-5% solution, or dexamethasone 0.1-2% solution in combination with MTOR inhibitors at 0.1%-5% solution.

In one embodiment, the dry eye of patients occurring in post-corneal surgery (including but not limited to post-LASIK surgery) with surgical damage to the corneal nerves, other conditions resulting in dry eye including the aging process, environmental factors (e.g., dry home and/or work environments), and extended use of visual display terminals (e.g., employment, recreation) are treated with Rock inhibitors, or in combination with metalloproteinase inhibitors, low molecular with heparin, or Wnt inhibitors or Rock inhibitor, such as Botox, 1-100 units administered locally at multiple locations, small doses or Rock inhibitors molecule, Fasudil and its derivatives, etc., at doses of 1 nanogram (ng) to a few micrograms (µg) as a slow release polymer.

In one embodiment, the dry eye can also occur after cataract surgery and refractive surgery (i.e., the LASIK procedure) and photorefractive keratectomy, smile procedure, partial or complete corneal transplants, which are the majorities of present refractive surgery where these procedures are performed, but dry eye is more common with LASIK where the superficial nerves are cut, and where the eye dries out because the corneal reflex is affected and the eye subsequent to these surgeries becomes dry while many eyes experience regeneration of the nerves, but it takes about one year or more to achieve it all. Patients with these conditions are treated with Rock inhibitors, or in combination with metalloproteinase inhibitors, low molecular with heparin, or Wnt inhibitors or Rock inhibitors, such as Botox, 1-100 units administered locally over the cornea as drops 1-4 times daily or injectable preparation at multiple locations, small doses or Rock inhibitors molecule, such as Fasudil or its derivatives, etc., at doses of 1 nanogram or a few micrograms as a slow release non-toxic preparation.

In one embodiment, patients with paresis or paralysis of the fifth or seventh cranial nerves causing dry eye as a result of interfering with proper lid closure are treated with Rock inhibitors, such as Botox, 1-10 units administered topically over the cornea at multiple locations, and in small doses, or Rock inhibitors, such as the molecule Fasudil, or its derivatives, etc. at doses of 1 nanogram to a few micrograms as topical ointment, drop, gel, etc.

In one embodiment, the patient has lichen planus associated with a chronic inflammatory disease of the skin, mucous membranes, and nails presenting a burning sensation in the mouth, throat esophagus, vagina and the mucosa appears as a lattice-like network of white lines near sites of erosion. Lichen planus can also affect the skin accompanied with sensation of itching, reddish-purple polygon-shaped skin lesions on the lower back, wrists, and ankles. Lichen planus very rarely leads to oral cancer in about 5% of the patients. The cause of lichen planus is unknown, but it is thought to be the result of an autoimmune process with an unknown initial trigger. It is known that tobacco, alcohol, and stress aggravate the lesions. Thus far, there has not been a cure, but many different anti-inflammatory medications and procedures have been used in efforts to control at best the symptoms thereof. In one embodiment, the patients with lichen planus are treated either by Wnt inhibitors or Rock inhibitors as a topical solution drops, gel, non-toxic injectable formulation, ointment or oral, or if needed, systemic administration of these medications or Rock inhibitor, such as Botox, 1-100 units administered locally as ointment over the lesion or injectable preparation at multiple locations, small doses or Rock inhibitors as Botox or molecule Fasudil, and its derivatives etc. at doses of 1 nanogram to a few micrograms.

In one embodiment, the patients with lichen planus are treated locally, by topical or injection subcutaneously with either by Wnt inhibitors or Rock inhibitors, such as Botox, 10-100 units as needed administered locally at multiple locations or Rock inhibitors, such as Fasudil, etc. molecules at doses of 1 nanogram to a few micrograms.

In one embodiment, Wnt signaling is involved in the control of stem cell proliferation. Wnt mutation causes developmental defects in many disease processes including inflammation and cancer.

In one embodiment, the Wnt inhibitors compounds used are: FH535, IWP-2, PNU-74654, IWR-1endo. IWR-exo, demethoxycurcumin, sulforaphane and vitamin D, CCTO36477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, akinumab Wnt inhibitors.

In one embodiment, the oral doses for the Wnt inhibitor niclosamide is 1 to 2 gram tablet once, or to repeat in 7 days, if needed.

In one embodiment, the small molecule Fasudil, a rock inhibitor Fasudil (HA-1077), a selective RhoA/Rho kinase (ROCK) inhibitor, or Y-27632, small molecule inhibitor of ROCK1 and ROCK2, Botulinum toxin a is rock inhibitor marketed under the brand names Botox, Dysport Myobloc. Xeomin, etc. Botulinum toxin, all having good penetration into the cornea, and do not increase intraocular pressure or cause cataracts and may be dissolved in an organic solvent such as DMSO or alcohol or sterol, lanosterol, squalene, and/or squalamine, or containing a polyanhydride, poly (glycolic) acid, poly(lactic) acid, or polycaprolactone polymer for the treatment of the lid, conjunctiva, lacrimal gland corneal diseases and glaucoma.

In one embodiment, Fasudil is used as a single, oral 40-80 milligram (mg) dose orally as two 40 mg Fasudil tablets are administered.

In one embodiment, the methods include administering Wnt inhibitors, either alone or in combination with Rho kinase inhibitors, orally, locally by injection or drops, spray or ointment for alleviating the effects of conditions that result in lack of moisture or wetness in the eye.

In one embodiment, Rho kinase inhibitors, may be administered orally, locally by injection or drops, spray or ointment for alleviating the effects of conditions that result in lack of moisture or wetness in the eye, such as the inflammatory conditions resulting in dry eye including pemphigus and Sjogren's syndrome, which affect the eye by either damaging the conjunctival cells, or by damaging the lacrimal glands of the eye and/or the meibomian glands of the eye lid.

In one embodiment, the required treatment of Rho kinase inhibitors, such as Botox in 1-2 units, may be administered locally by injection or drops, spray or ointment for other inflammatory processes resulting in dry eye include hypolacrimation, alacrima, xerophthalmia, Stevens-Johnson syndrome, pemphigus, ocular pemphigoid, marginal blepharitis, nerve pain, diabetes, and/or post-corneal surgery after cutting the corneal nerves (including but not limited to post-LASIK surgery). Other conditions resulting in dry eye include the aging process, environmental factors (e.g., dry home and/or work environments), and extended use of visual display terminals (e.g., employment, recreation, etc.).

In one embodiment, inhibition of Wnt signaling or ABC transporters by RNA interference may be a valuable therapeutic strategy in dry eye including hypolacrimation, alacrima, xerophthalmia, and Stevens-Johnson syndrome.

In one embodiment, a number of Rock inhibitors are used in non-toxic doses in combination with functionalized nanoparticles, conjugated with polymeric coatings, such as chitosan, polyanhydride, cyclodextrin as a potent ROCK inhibitor; bioavailable Fasudil hydrochloride, inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor, more selective analogue of H1152, cell-permeable, selective Rho-kinase inhibitor OXA 06 dihydrochloride, potent ROCK inhibitor PKI1447 dihydrochloride, potent and selective ROCK inhibitor, antitumor SB 772077B, potent Rho-kinase inhibitor, vasodilator SR 3677 dihydrochloride, potent, selective Rho-kinase (ROCK) inhibitor TC-S7001, potent and highly selective ROCK inhibitor, orally active Y-27632 dihydrochloride and may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer to reduce the inflammation processes in the eye, sclera, lid, conjunctiva, or other mucosal diseases, mouth, throat, skin, etc.

In one embodiment, Wnt inhibitors, such as canakinumab, ivermectin, or niclosamide may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer prior to its application.

In one embodiment, small molecule Wnt inhibitor PKF118-310, the Wnt/β-catenin pathway inhibitor and Fasudil, a rock inhibitor Fasudil (HA-1077), a selective RhoA/Rho kinase (ROCK) inhibitor, or Y-27632, small molecule inhibitor of ROCK1 and ROCK2, etc. may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer to release non-toxic medication slowly at a desired concentration.

In one embodiment, early management includes the use of lubricants, artificial tear substitutes, ointment, gel, or emulsion. Topical anti-inflammatory agents, topical Rock inhibitors, anti-interleukin (IL1) TNF-alfa TNF-α, hyaluronic acid, low molecular heparin 0.1-5% solution alone, or in combination with metalloproteinase inhibitors doxycycline 0.1-5% solution immunosuppressive agent or inhibitor, e.g., mycophenolic acid, as local or systemic therapy.

In one embodiment, topical Rock inhibitors are applied to the cornea as drops or spray or subconjunctival injection as a slow release compound combined with chitosans in 0.1 microgram/ml to 40 microgram/ml or more for topical application.

In another embodiment, the Rock inhibitors are coated with the slow release polymers, such as lactic acid, glycolic acid, etc. at a concentration of 200 nanograms to 1 micrograms/ml or more and administered topically, subconjunctival, or inside the eye subcutaneously inside the plantar fascial.

In another embodiment, the Rock inhibitors are released from a polymeric explant or implant (e.g., an implant as depicted in FIGS. 54A-58) either placed over or under the conjunctiva and sutured to the sclera to release, e.g., Fasudil, etc. at concentrations of 0.01 micrograms/ml to 40.0 micrograms/ml or more per day.

In one embodiment, the Rock inhibitors release, after placement in the upper or lower cul-de-sack of the conjunctiva or as a slow release punctal plaque or implanted subconjunctivally, at a rate of 1 picogram to a 10 nanograms/day of the medication.

In one embodiment, the Rock inhibitors release, after placement in the suprachoroidal space, inside the eye, behind the eye, inside the gingiva, subcutaneously in plantar fascia, or as a slow release polymeric plaque or implanted to release medication at a rate of 1 picogram to a 10 nanograms/day of the non-toxic medication.

In another embodiment, the nanoparticles or dendrimers are conjugated with Rock inhibitors and chitosan delivered as a slow release system that can be released from a temperature sensitive polymer that melts at 42-43 degrees C. and is used with a warm compressor over or under the lid, or light thermal application, or the use of a compressive focused ultrasound applied to lid, conjunctiva, cornea, or the lid releasing 1 picogram to a 10 nanograms/day of the medication.

In one embodiment, the Rock inhibitors or Wnt inhibitors are delivered with simultaneous application of amniotic membrane and slow release nanoparticles applied post corneal surgery, such as LASIK, cataract corneal transplant, or any other corneal surgical intervention at 10 picograms to 20 nanograms of medication per day.

In one embodiment, the Rock inhibitors or Wnt inhibitors are delivered with simultaneous application of amniotic membrane and low molecular weight heparin slow release nanoparticles applied post corneal surgery, such as LASIK, cataract, corneal transplant uveitis scleritis or chemical injury to the cornea or conjunctiva at concentrations of 0.001 micrograms/ml to 40 micrograms/ml or more or topical or subconjunctival Botox, at 1-100 units or topical at 1-5 units or more in a physiological solution of Botox, or similar preparations.

In one embodiment, the Rock inhibitors or Wnt inhibitors are delivered with simultaneous application of low molecular weight heparin (levonox) with other medications, such as tetracycline, Doxycycline or metalloproteinase inhibitors, dexamethasone 0.1%-1% concentration as slow release polymeric nanoparticles or liposomes applied post corneal surgery such as LASIK, cataract, corneal transplant, uveitis, scleritis or thermal or chemical injury to the cornea or conjunctiva, e.g., Fasudil derivatives, etc., at 0.1 micrograms/ml to 40 micrograms/ml or more, or Botox at 1-3 units.

In one embodiment, after LASIK or any refractive surgery or cataract surgery, Rock inhibitors at doses of 0.1 micrograms/ml to 40 micrograms/ml or more for topical application or Wnt inhibitor can be injected in the anterior chamber, or applied as drops in the post-operative period to replace prednisolone or other steroids, or NASIDs, and encourage regrowth of the cut neurons in the cornea.

In one embodiment, after LASIK or any refractive surgery or cataract surgery, Wnt inhibitors, or Rock inhibitors, such as botulinum toxin (Botox) can be injected under the conjunctiva or applied as drops in the post-operative period to encourage regrowth of the cut neurons in the cornea after LASIK or other corneal surgery at doses of 1 to 10 units of Botox injected under the conjunctiva or 1-2 drops daily at concentration of 10 picograms to 500 picograms of Botox in physiological solution or topical as drops.

In one embodiment, in dry eye syndrome, Rock inhibitors or Wnt inhibitor, such as botulinum toxin (Botox) can be applied as drops or injected subconjunctivally to eliminate the inflammatory component of the dry eye at doses of 1-10 units once a month or once every 2 to 3 months with slow release nanoparticle conjugates in biodegradable polymers.

In one embodiment, in dry eye syndrome, Rock inhibitors, such as botulinum toxin (Botox), Fasudil, etc. or Wnt inhibitors, such as niclosamide, ivermectin, FH535, IWP-2, PNU-74654, IWR-1endo. IWR-exo, demethoxycurcumin, sulforaphane and vitamin D can be given orally at the tolerated dose or 40 mg Fasudil or 1 gram niclosamide or 10-100 units of Botox to eliminate the inflammatory component of dry eye, sulforaphane at 400 micrograms and Vitamin D 3000-5000 IU.

In one embodiment, the Rock inhibitors, such as Fasudil derivatives at concentrations or 10 picograms to 10 nanograms to 1 microgram per drop Botox solution of 0.1 units of Botox can be administered with small molecule Wnt inhibitors at a low concentration 1-10 microgram.

In one embodiment, a topical or subconjunctival or intraocular administration of the Rock inhibitors, such as Fasudil derivatives, etc., at concentrations or 10 picograms to 100 nanograms/0.25 ml or Botox solution of 0.1-1 units can be administered with small molecule Wnt inhibitors or a low concentration of sulforaphane and vitamin D to inhibit the inflammatory processes or auto-immune response.

In one embodiment, Rock inhibitors are administered with antibody coated nanoparticles conjugated with thermosensitive nanoparticles and Adalimumab, a humanized antibody administered topically or subcutaneously at a nontoxic dose.

In one embodiment, Rock inhibitors are administered with antibody coated nanoparticles, dendrimers, liposomes, etc. to the conjunctiva as liposomes or ointment in Meibomian gland inflammation to release medication at a concentration of 1 picogram to 100 units or more picograms/0.25 ml to 0.5 ml along with an antibiotic.

In one embodiment, Wnt inhibitors or Rock inhibitors, such as Fasudil derivatives, etc. are administered with nanoparticles, dendrimers, thermosensitive polymers conjugated with polylactic or polyglycolic acid or chitosan, microspheres, liposomes, dendrimers, and combinations thereof, and they are administered as drops, or injected in the conjunctival or lacrimal glands along with immunosuppressive agents, such as mycophenolic acid, etc.

Figure 58:
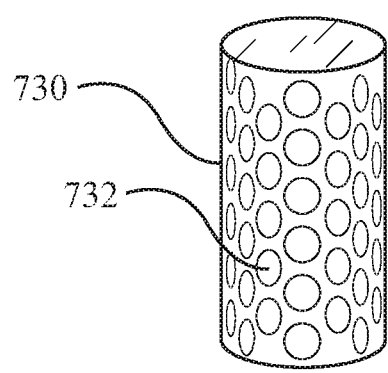
FIG. 58 illustrates yet another exemplary form of the drug delivery implant that is similar to that which is depicted in FIG. 57, except that the tubular-shaped implant of FIG. 58 has larger-sized holes formed in the side thereof.

In one embodiment, topical administrations, subconjunctival injections, sub-tenon injections, suprachoroidal injections, intravitreal injections can be combined with small molecule Wnt inhibitors or standard anti-inflammatory agents (e.g., steroids, dexamethasone, etc.), nanoparticle implants, biodegradable or non-biodegradable polymers, NASIDs, immunotherapy immunosuppressants, etc. to treat inflammatory processes of the lid conjunctiva or the cornea and the lid or throughout the day. For injection, a dose of about 50 picograms/ml to about 200 micrograms/ml may be used, or a surgical implant may be used, for example, in a diffusible walled reservoir (e.g., as shown in FIGS. 56B, 57, and 58) sutured to the wall of the sclera, or may be contained within an inert carrier, such as microspheres, dendrimers, or liposomes to provide a slow-release drug delivery system.

In one embodiment, a formulation of Wnt or Rock inhibitors is used from the group consisting of topical administration at a concentration of about 50 picograms/ml to less than 1 micrograms/ml, subconjunctival injection at a dose in the range of about 1 picogram/ml to about 200 micrograms/ml, intravitreal injection at a dose in the range of about 0.1 picogram/ml to about 20 micrograms/ml, or retrobulbar injection at a dose in the range of about 2 micrograms/ml to about 200 micrograms/ml in slow release microspheres or dendrimers. In one embodiment, a formulation of Wnt or Rock inhibitors is used comprising intraocularly administering to a patient after corneal surgery at picogram to nanogram concentrations.

In one embodiment, a formulation of Wnt or Rock inhibitors is used as a composition consisting essentially of Rock inhibitors in a pharmaceutically acceptable formulation and in an amount effective to enhance post-surgical to enhance ocular moisture, nerve regeneration in the patient wherein the composition is administered at a concentrations up to about 10 micrograms/ml by at least one of slow release polycaprolactone, polylactic, or polyglycolic acid, etc. over many months, intraocular administration of the composition, or is administered topically at a concentration in the range between about 10 picograms/ml to less than 1 microgram/ml depending on the composition of the medication.

In one embodiment, wherein the polymeric composition is administered by subconjunctival injection at a dose in the range of about 1 picogram/ml to about 20 micrograms/ml, intravitreal injection at a dose in the range of about 1 picogram/0.1 ml to about 20 nanograms/ml, or retrobulbar injection at a dose in the range of about 20 nanograms/ml to about 2 micrograms/ml.

In one embodiment, a formulation of Wnt or Rock inhibitors is used to enhance post-surgical ocular moisture or in papilitis, optic nerve neuritis, uveitis or scleritis in the patient wherein the composition is administered at a concentration up to about 50 picograms/ml by at least one of intraocular injection, or the composition is administered topically at a concentration in the range between about 50 picograms/ml to less than 1 micrograms/ml.

In one embodiment, a formulation of Wnt or Rock inhibitors is used wherein the composition is administered by subconjunctival injection at a dose in the range of about 1 picograms/ml to about 2 micrograms/ml, intravitreal injection at a dose in the range of about 1 nanogram/0.1 ml to about 20 nanograms/ml, or retrobulbar injection at a dose in the range of about 200 nanograms/ml to about 2 micrograms/ml.

In one embodiment, a method to treat an ocular condition in a patient comprises intraocularly administering to the patient a pharmaceutically acceptable formulation of a drug selected from the group consisting of Rock inhibitors, such as Fasudil or derivatives in nanogram to microgram concentrations in microspheres, dendrimers, physiological solution, botulinum toxin in picogram concentrations in polymeric microspheres or 0.3-5 units injectable, or Wnt inhibitors, such as niclosamide, ivermectin, nanogram to microgram concentration in microspheres, dendrimers, suspension or another polymer, sulforaphane 10-400 nanograms in microspheres, dendrimers, or another polymer and Vitamin D taken orally in 1000-5000 IU etc., Fasudil derivatives taken orally 1-40 mg, niclosamide orally in 10-500 mg tablets, sulforaphane in capsule 10-40 mg or more ivermectin taken orally 1-400 mg or more and topical formulation as drops, ointment, or gel in a non-toxic formulation for the patient undergo surgery in the eye for refractive errors, diabetic retinopathy, retinal detachment, or after cataract surgery or refractive surgery for the duration until the eye is free of inflammation and has recovered from the surgery.

In one embodiment, non-toxic doses of Rock inhibitors in an amount up to about 1-200 micrograms/ml effective to treat dry eye or another ocular condition selected from diabetic retinopathy, retinitis pigmentosa, or age related macular degeneration without substantial toxicity and at least one Wnt inhibitor or Rock inhibitor, wherein the composition is administered by at least one of intraocular injection at a concentration up to about 2 picograms/ml, or the composition is administered topically at a concentration in the range between about 1 picograms/ml to less than 10 nanograms/ml.

In one embodiment, a formulation of Wnt or Rock inhibitors is used as topical administration at a concentration between about 50 picograms/ml to 200 nanograms/ml, subconjunctival injection at a dose in the range of about 1 picograms/ml to about 20 micrograms/ml in a slow release polymer, intravitreal injection at a dose in the range of about 1 picogram/0.1 ml to about 2 micrograms/ml, or retrobulbar injection at a dose in the range of about 1 picograms/ml to about 200 nanograms/ml suspension in a slow release polymer depending on the composition of the medication.

In one embodiment, a method to treat an ocular condition in a patient by intraocularly administering a pharmaceutically acceptable formulation of Wnt inhibitors or rock inhibitors in an amount effective to treat the condition. The method provides treatment while avoiding systemic administration of systemic medication. In one embodiment, a sustained release pharmaceutically acceptable formulation is implanted intraocularly in a polymeric slow release compound having about 20 nanograms to 1 microgram or more of Fasudil to about 0.1 micrograms to 40 micrograms or 1 milligram of Fasudil or other Rock inhibitors implanted in or on the eye and may continuously deliver Fasudil for five or more years.

In another embodiment, a concentration up to about 10 or more micrograms of Rock inhibitors is administered intraocularly without substantial toxicity.

In another embodiment, Fasudil derivatives are taken orally 1-40 mg, niclosamide is taken orally in 10-500 mg tablets, sulforaphane is taken orally in capsule 10-40 mg or more, ivermectin is taken orally 1-400 mg or more, and topical formulations may be administered as drops, ointment, or gel in a non-toxic formulation.

In another embodiment, Rock inhibitors at a concentration in the range of about 1 picogram/ml (0.0000000001%) to less than 0.1 micrograms/ml (less than 0.001%) is administered topically. In other embodiments, Fasudil or another Rock inhibitor at a concentration in the range of about 1 nanogram/ml to about 200 micrograms/ml is injected under the conjunctiva, or a concentration in the range of about 1 picogram/0.1 ml to about 200 micrograms/ml is injected in the vitreous, or a concentration in the range of about 20 picograms/ml to about 200 nanograms/ml is injected behind the eyeball.

In one embodiment, the Rock inhibitors, such as Fasudil, etc., or Wnt inhibitors, such as niclosamide, are administered as topical or a spray at non-toxic concentrations of 1 picogram/ml to 20 nanograms/ml in a physiological pH balanced, with osmolarity of 310 to prevent and treat, decrease the time of onset, or lessen the severity of a wide variety of diseases such as lichen planus, ocular conditions, such as retinitis pigmentosa, ocular irritation following corneal surgery (e.g., LASIK surgery), age related macular degeneration, diabetic retinopathy, dry eye disease, scleritis, papillitis, and uveitis, scleritis pars planatis, vogt-koyanagii syndrome, psoriasis, Lichen Planus, etc.

In one embodiment, the Rock inhibitors, such as Fasudil, etc., or Wnt inhibitors, such as niclosamide, are administered as topical or a spray at non-toxic concentrations of 1 picogram/ml to 20 nanograms/m, or in an ointment or cream, or suspension of microspheres and dendrimers in meibomian gland disease.

In one embodiment, the Rock inhibitors, such as Botulinum toxins are administered as topical or a spray at non-toxic concentrations of 1 picogram/ml to 1 nanograms in a cream, ointment, suspension of microspheres or dendrimers, etc. for topical application in lichen planus, nerve damage after LASIK or refractive surgery procedures, or diabetes or wrinkle treatment.

In one embodiment, the Rock inhibitors, such as Fasudil 40-80 mg/kg, etc., or Wnt inhibitors, such as niclosamide, 100-500 mg or ivermectin, 250 mg to 2000 mg are administered orally to prevent and treat, decrease the time of onset, or lessen the severity of a wide variety of diseases, such as optic nerve neuritis, papillitis, variety of idiopathic uveitis, scleritis, or ocular conditions, such as retinitis pigmentosa, ocular irritation following corneal surgery (e.g., LASIK surgery), age related macular degeneration, diabetic retinopathy, dry eye disease, papillitis, uveitis, and lichen planus.

In one embodiment, the Rock inhibitors or Wnt inhibitors are administered as topical or a spray at non-toxic concentrations of 1 picogram/ml to 20 nanograms/ml in a physiological pH balanced solution with osmolality of 310 to treat the corneal nerve cuts after LASIK surgery to decrease inflammatory process and encourage fast regrowth of neurons from the cut end of the corneal nerves and enhance corneal sensation recovery time and prevent dry eye formation.

In one embodiment, the Rock inhibitors (40-80 mg/kg) or Wnt inhibitors are administered orally after LASIK surgery to decrease inflammatory process and to encourage fast regrowth of neurons from the cut end of the corneal nerves and enhance corneal sensation recovery time and prevent dry eye formation.

Another embodiment of the invention is a method to treat ocular conditions including ocular irritation following corneal surgery, conjunctivitis, canaliculitis or Schlemm's canal of the eye, iritis, lacrimal and Meibomian glands are treated with Rock inhibitors, such as Fasudil or its derivatives in nanogram to microgram concentrations in microspheres, dendrimers, physiological solution, Botulinum toxin in picogram concentrations in polymeric microspheres dendrimers, or 0.3-5 units injectable, or Wnt inhibitors, such as niclosamide, ivermectin, nanogram to microgram concentration in microspheres suspension or another polymer, sulforaphane 10-400 nanogram in microspheres, dendrimers, or another polymer and Vitamin D taken orally in 1000-5000 IU, etc.

In one embodiment, a sustained release pharmaceutically acceptable formulation is implanted intraocularly (e.g., using an implant as depicted in FIGS. 54A-58). For example, a matrix containing in the range of between about 0.4 to 1 mg Fasudil can last for ten or more years. In another embodiment, a concentration up to about 1 microgram Fasudil or others, or Rock inhibitors, is administered intraocularly, inside the joint in arthritis, or subcutaneously or subgingival injection in lichen planus without substantial toxicity.

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 microgram/ml is injected under the conjunctiva, or a concentration in the range of about 1 nanogram/0.1 ml to about 200 micrograms/ml is injected in the vitreous, or a concentration in the range of about 20 nanograms/ml to about 20 micrograms/ml is injected in a slow release polymer, such as polycaprolactone or polylactic or glycolic, in the vitreous cavity or behind the eyeball or other part of the body as needed.

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 micrograms/ml is injected under the conjunctiva, or a concentration in the range of about 1 nanogram/0.1 ml to about 200 micrograms/ml is injected in the vitreous, or a concentration in the range of about 20 nanograms/ml to about 20 micrograms/ml is injected in a slow release polymer, such as polycaprolactone or polylactic or glycolic, in the vitreous cavity or behind the eyeball in subconjunctival space, or subcutaneously as needed.

In another embodiment, a composition is formulated for intraocular administration and dosing with Fasudil derivatives in a pharmaceutically acceptable formulation (e.g., in a physiologically acceptable solvent, such as sterol, lanosterol, squalene, and/or squalamine, buffered to a physiological pH, etc.). The composition may be in a solution, a suspension, an emulsion, etc., and it may be administered in the form of eye drops, a cream, an ointment, a gel, an injectable, etc., to the eye and/or the eye lid. The composition contains niclosamide or Fasudil in an amount effective to treat an ocular condition without substantial toxicity or mucosal or joint inflammatory diseases.

In one embodiment, the non-toxic doses of Wnt inhibitors, Rock inhibitors, or Botox, act as an anti-inflammatory agent. The botulinum toxin or botox preparation may be administered topically to the eye or eye lid, forehead skin at 1 pictogram to 1 nanogram concentrations, 1 pictogram to 5 nanogram concentrations, for example, using drops, an ointment, a cream, a gel, a suspension of microspheres, dendrimers, etc. The agent(s) may be formulated with excipients such as methylcellulose, hydroxypropyl methylcellulose, hydroxypropyl cellulose, the LD50s of any naturally occurring botulinum toxin protein is at 1.3 nanograms per kilogram (abbreviated ng/kg). In a 75 kg (165 lbs.) subjects, the LD50 for botulinum toxin would be 97.5 nanograms if injected directly into a vein or artery. 100 unit vials contains 0.75 nanograms=750 picograms of botulinum toxin A in the entire vial.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, the concentrations 1-20 picograms of Botox in a physiological solution, or up to 30 picograms conjugated with antibody coated nanoparticles would be non-toxic to the body or when conjugated with thermosensitive polymeric coating of the nanoparticles in a physiologic solution or used as drops or injectable.

In one embodiment, the Wnt inhibitors or Rock inhibitors may be injected into the eye, for example, injection under the conjunctiva or tenon capsule, intravitreal injection, or retrobulbar injection. The agent(s) may be administered with a slow release drug delivery system, such as polymers, matrices, microcapsules, or other delivery systems formulated from, for example, glycolic acid, lactic acid, combinations of glycolic and lactic acid, liposomes, silicone, polyanhydride polyvinyl acetate alone or in combination with polyethylene glycol, etc. The delivery device can be implanted intraocularly, for example, implanted under the conjunctiva, implanted in the wall of the eye, sutured to the sclera, for long-term drug delivery or injected in the vitreous cavity (e.g., using an implant as depicted in FIGS. 54A-58).

In one embodiment, one uses a composition containing Rock inhibitors, such as Fasudil etc., at a concentration in the range of about 50 picogram/ml (0.000000005%) to about 50 micrograms/ml (0.005%), niclosamide at a concentration in the range of about 50 picograms/ml to about 50 micrograms/ml, or a combination of Fasudil or an immune suppressive agent, such as mycophenolic acid, to achieve a total concentration of both agents of about 50 picogram/ml to about 50 microgram/mw. Within this range, the agent(s) has wide safety and efficacy, permitting specific doses or administration protocols to be formulated for specific applications. For example, some patients may prefer once a day administration compared to administration more than once a day, so a higher concentration of agent(s) may be used for these patients.

In another embodiment, Rock inhibitors, such as Fasudil, may also be administered by injection. Intraocular injection may be desirable or necessary, for example, for conditions in which topical administration is either not advised or is inadequate, for patients who have difficulty self-administering medications, etc. In one embodiment, the volume injected is less than 0.3 ml. In another embodiment, the volume injected is in the range of about 0.01 ml to about 0.3 ml. For intravitreal administration (injection into the vitreous), Rock inhibitor concentrations in the range of about 1 nanogram/0.1 ml to about 20 microgram/ml (0.002%) may be used without toxicity or adverse side effects.

In another embodiment, niclosamide used in amounts ranging from about 1 nanogram to about 10 micrograms is contained in an aqueous-based cream excipient. In another embodiment, the amount of Fasudil, etc., or other Rock inhibitors ranges from about 1 nanogram to about 10 micrograms, and is contained in an aqueous-based cream excipient. In another embodiment, Fasudil and niclosamide or mycophenolic acid are present in an aqueous-based cream excipient in various proportions. In another embodiment, to achieve a total amount of combined agents of about 1 nanogram to about 10 micrograms, the drug(s) may be incorporated directly into the cream in solution, or may be contained in liposomes or microspheres, dendrimers, either in solution or in an anhydrous form. The cream formulation is usually applied to the eye at bedtime, but it may be applied any time throughout the day if the cream does not cause blurred vision. In another embodiment, the agent(s) is formulated as a solution or suspension and is applied topically in the form of eye drops.

In another embodiment, for long term delivery of a Rock inhibitor or a Wnt inhibitor, either alone or in combination, and/or for sustained release, a matrix housing containing the agent(s) may be implanted into the eye. For example, a reservoir containing in the range of about 1 milligram to about 5 milligrams of agent(s) is estimated to be able to release about 1 microgram agent(s) per day. At such a release rate, continuous, sustained dosing may occur over 1000 to 5000 days. If less than 1 microgram of agent(s) per day is released, sustained dosing may last up to or more than a decade. In one embodiment, less than 50 micrograms/day of agent(s) is released from the matrix. In another embodiment, agent(s) is released form the matrix at a rate in the range of about 50 picograms/day to about 50 micrograms/day. In another embodiment, agent(s) is released from the matrix at a rate in the range of about 1 microgram/day to about 5 micrograms/day.

In another embodiment, a surgically implanted intraocular device or matrix may be provided with a reservoir container (e.g., as shown in FIGS. 56B, 57, and 58) having a diffusible wall of polyvinyl alcohol or polyvinyl acetate or polycaprolactone and containing milligram quantities of a Rock inhibitor or Wnt inhibitor, or a combination of them may be implanted in the sclera. As another example, milligram quantities of agent(s) may be incorporated into a polymeric matrix having dimensions of about 1 millimeter (mm) by 2 millimeter (mm), and made of a polymer such as polycaprolactone, poly(glycolic) acid, poly(lactic) acid, or a polyanhydride, or a lipid such as sebacic acid, and may be implanted on the sclera or in the eye.

In another embodiment, as one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. The agent(s), in amounts ranging from picogram to microgram quantities, is added to a solution of egg PC, and the lipophilic drug binds to the liposome.

In another embodiment, the implantable formation may be in the form of a capsule of any of the polymers previously disclosed (e.g., polycaprolactone, polyglycolic acid (PGA), polylactic acid (PLA), polyanhydride) or lipids that may be formulated as microspheres or dendrimers. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be injected intraocularly. In a formulation for topical application, the drug is slowly released over time as the liposome capsule degrades due to wear and tear from the eye surface. In a formulation for intraocular injection, the liposome capsule degrades due to cellular digestion, other slow release polymers, such as PLA, PGA, polycaprolactone, microspheres, dendrimers are also utilized.

In another embodiment, the time-release administration, however, is formulated so that the concentration released at any period of time does not exceed a toxic amount. This is accomplished, for example, through various formulations of the vehicle (coated or uncoated microspheres, coated or uncoated capsule, lipid, dendrimers, or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formation and loading of microspheres, dendrimers, microcapsules, liposomes, etc. and their ocular implantation are standard techniques known by one skilled in the art.

In another embodiment, a combination of Rock inhibitors or Wnt inhibitors may be dissolved in an organic solvent, such as DMSO or alcohol or sterol, lanosterol, squalene, and/or squalamine, or containing a polyanhydride, poly(glycolic) acid, poly(lactic) acid, or polycaprolactone polymer.

In one embodiment, Rock inhibitors, such as Fasudil or Botox, etc. or Wnt inhibitors, such as niclosamide, alone or in combination with low molecular weight heparin and metalloproteinase inhibitors, such as doxycycline, tetracycline, etc. can be used at non-toxic concentrations with or without dexamethasone, for dry eye or lichen planus lesions of the mucosa, or skin or other inflammatory diseases of the retina, cornea, conjunctival sclera or optic nerve neuritis, scleritis, uveitis in an appropriate physiological solution or ointment, etc.

In one embodiment, the intravenous solution form of Rock inhibitors or Wnt inhibitors may be diluted to achieve the indicated concentration using 0.9% NaCl or 5% dextrose, or an organic solvent such as dimethyl sulfoxide (DMSO) or sterol, lanosterol, squalene, and/or squalamine. Intraocular administration may be any of the routes and formulations previously described. For injection, either a solution, emulsion, suspension of a liquid, capsular formulation of microspheres, dendrimers, or liposomes, etc. may be used.

In one embodiment, Rock inhibitors or Wnt inhibitors or Botox may be injected subconjunctivally to treat uveitis at a dose in the range of about 1 picogram/ml to about 200 picograms/ml, or intravitreally at a dose of about 1 gram/0.1 ml to about 200 picograms/ml. In one embodiment, the dose is about 50 picograms/0.1 ml. To treat scleritis involving the anterior sclera, Rock inhibitors or Wnt inhibitors or Botox may be administered topically.

In one embodiment, Rock inhibitors or Wnt inhibitors or Botox may be injected to treat scleritis involving the posterior sclera, may be administered by retrobulbar injection at a dose in the range of about 20 picograms/ml to about 800 picograms/ml or more and dissolved in DMSO or a very low concentration of alcohol or sterol, lanosterol, squalene, and/or squalamine.

In one embodiment, to treat neuritis or papillitis, Rock inhibitors may be administered by retrobulbar injection at a dose in the range of about 200 picograms/ml to about 800 nanograms/ml of Fasudil and its derivatives, etc.

In one embodiment, to treat neuritis or papillitis, Rock inhibitors (e.g., Fasudil) may be administered orally at a dose in the range of about 40-80 milligrams of Fasudil tablets, etc. or one time niclosamide 1-2 grams orally.

In one embodiment, the ocular solutions contain at least one Rock inhibitor or Wnt inhibitor such as sulforaphane and provide anti-inflammatory, anti-cell proliferation, anti-cell migration effects if given orally with Vitamin D, topically as dendrimer or microsphere delivery or an injectable non-toxic preparation.

In one embodiment, the solution is administered intraocularly after cataract surgery before insertion of a replacement intraocular lens, resulting in reduced post-operative inflammation, which may eliminate the need for a steroid therapy.

In one embodiment, the solution may be one that is invasively administered, for example, an irrigation or volume replacement solution containing at least one Rock inhibitor, such as Botox, or Wnt inhibitor.

In one embodiment, the solution may be one that is non-invasively or topically administered in the form of drops, ointments, gels, creams, etc. and may include eye lubricants and contact lens solutions. The solution may contain a supratherapeutic concentration of agent(s), such as 40 micrograms/ml or to 80 micrograms/ml or more for topical application ranges, 40 nanograms/ml to 4 micrograms/ml Fasudil and its derivatives, etc. so that a therapeutic concentration of a topically administered solution accumulates in a diseased ocular structure sufficient to treat the disease.

In one embodiment, medications are administered with antibody coated nanoparticles, dendrimers, thermosensitive polymers, nanoparticles, dendrimers, lactic or glycolic acid, chitosan or combinations, etc. Immunosuppressives are all conjugated with the antibody coated nanoparticles for slow release as topical drops or an injectable preparation for dry eye after LASIK, meibomian gland inflammation, optic nerve neuritis, uveitis, scleritis, etc.

In one embodiment, Rock inhibitors or Wnt inhibitors are administered by topical drops, spray, subconjunctival injection, sub-tenon injection, suprachoroidal injection, intravitreal injection in combination with standard anti-inflammatory agents, etc. and steroids, dexamethasone, etc. as a nanoparticle implant formed from biodegradable or non-biodegradable polymers.

In one embodiment, a method of using Rock inhibitors or Wnt inhibitors is disclosed where Rock inhibitors or Wnt inhibitors are administered at non-toxic doses to lichen planus of the skin or mucosa. Lichen which is associated with is a chronic inflammatory disease of the skin, mucous membranes and nails, presents a burning sensation in the mouth, throat esophagus, vagina, pharynx, stomach, anus, bladder, conjunctiva, and the mucosa appears as a lattice-like network of white lines near sites of erosion can also affect the skin accompanied with sensation of itching, reddish-purple polygon-shaped skin lesions on the lower back, wrists, and ankle thought to be the result of an autoimmune process with an unknown initial trigger.

In one embodiment, a formulation of Wnt or Rock inhibitors is used to treat the lesion of Lichen planus conditions using Rock inhibitors and Wnt inhibitors as topical drop spray application or injection into the subcutaneous tissue around or inside the lesion, or implantation in multiple sites close to the lesion releasing, e.g., Fasudil, etc., at doses or 1-500 picograms or injection of Botox around the lesion or inside the lesion at 10-100 units once a month or once every 2-3 months.

In one embodiment, a formulation of Wnt and/or Rock inhibitors is used to treat the lesion of lichen planus conditions using Rock inhibitors and/or Wnt inhibitors used as topical or drop spray application, mouth wash preparation of Fasudil derivatives at 1 nanogram to 1 microgram or more preparation or Wnt inhibitors, such as niclosamide, ivermectin, nanogram to microgram concentration in microspheres, dendrimer suspension or, sulforaphane 10-400 nanograms in microspheres, dendrimers, or in another polymer in addition to Vitamin D taken orally in 1000-5000 IU, etc. or injection into the subcutaneous tissue around or inside the lesion, or implantation in in multiple sites close to the lesion releasing, e.g., Fasudil, etc., at doses or 1-500 picograms or injection of Botox around the lesion or inside the lesion at 10-100 units once a month, or once every 2-3 months.

In one embodiment, in treating lichen planus, for example, a topical administration may contain between about 10 picograms/ml drug to about 50 micrograms/ml of Fasudil, etc. or other Rock inhibitors in a formulation which may be applied at bedtime or throughout the day or as an injection, a dose of about 50 picograms/ml to about 200 micrograms/ml around or inside the lesion. In one embodiment, the medication may be used as a surgical implant, for example, in a diffusible walled reservoir (e.g., as shown in FIGS. 56B, 57, and 58) sutured to the surrounding tissue, or may be contained within an inert carrier, such as microspheres, dendrimers, or liposomes, to provide a slow-release drug delivery system to release the medication at 1 picogram to 100 picograms (e.g., Fasudil, etc.) per day.

In one embodiment, a formulation of Wnt or Rock inhibitors is used to treat ocular conditions, such as dry eye disease, as well as other conditions, is disclosed. Rock inhibitors and Wnt inhibitors are used as s topical drop spray application or injection into the eye, or implantation in or on the eye (e.g., using an implant as depicted in FIGS. 54A-58). For example, a topical administration may contain between about 10 picograms/ml drug to about 50 micrograms/ml drug in a formulation which may be applied at bedtime.

In one embodiment, the patient is administered with Rock inhibitors or Wnt inhibitors alone or in combination with NSAIDs or to treat plantar fasciitis associated with chronic pain in the bottom of the foot and heal it, which is caused by being overweight, with more less inflammatory processes as seen also in other conditions such as osteoarthritis, spondylitis, reactive arthritis due to over use of immune response.

In one embodiment, non-toxic doses of Rock inhibitors, such as Fasudil, etc., 200 picograms to 2 nanograms or as Botox (10-100 units) is administered locally at multiple locations in treatment of plantar fasciitis or diabetic neuronal pain.

In one further embodiment, the pathway of inflammation and scarring in the cornea after refractive surgery is blocked by inactivation of Rho Kinase, GSK and Wnt pathway by using either a polymeric implant, or biodegradable polymeric nanoparticles or microparticles that release Rock inhibitors, such as fasudil, netarsudil, or a Wnt combination with Rock inhibitors, such as fasudil, netarsudil, botox, SAR407899, etc. and/or Wnt inhibitors, such as FH535, IWP-2, PNU-74654, IWR-1endo, IWR-exo, or GSK inhibitors SB-216763 without having the side effects of steroid in the eye that can produce an increased intraocular pressure or can reduce the immune defense activation that combats infection.

In one embodiment, after refractive surgery or cataract surgery, the corneal nerves are cut or ablated by administration of a laser, thus producing loss of corneal sensitivity, epithelial erosion and inflammation/infection, due to the loss of the corneal reflex and lid reflex that normally keeps the corneal surface moist and prevents dry eye formation. These complications can be prevented by topical application of Rock inhibitors, Wnt inhibitors, integrin inhibitors, or GSK inhibitors to encourage the nerve growth while inhibiting TGF beta production and scarring.

Example 1

A 26 year old patient had undergone a LASIK procedure for a −5.00 D correction of myopia 3 month ago. The patient developed a dry eye condition with loss of cornel reflex and low tear film production as measured with Schirmer's test and slightly reduced visual acuity. The ocular examination demonstrated loss of corneal sensation and reduced tear film production and presence of debris in the conjunctiva and the lid margin with a mild inflammation of the conjunctiva. The patient was treated with topical application of a Rock inhibitor, such as rhopressa solution applied one or twice daily in a physiological solution. The patient felt relieved of the discomfort within two (2) weeks, and the tear production increased from the previous exam. In three months, the patient was symptom free, the visual acuity improved, and the treatment was reduced to once a day drops.

In one embodiment, one uses Rock inhibitor alone or in combination with GSK 3 inhibitors SB-216763, etc. to encourage the corneal nerve growth and faster recovery of the corneal sensation and rehydration that maintains the health of the mucin producing cells of the conjunctiva and meibomian gland.

In one embodiment, a topical application or polymeric slow release delivery of Rock inhibitors, Wnt inhibitors, integrin inhibitors, or GSK inhibitors are used to treat dry eye.

The following anti-inflammatory Rock inhibitors are administered to the external adnexa and conjunctiva as drops in the form of polymeric nanoparticles or microparticles, or are implanted under the conjunctiva or skin affecting the inflammatory cell pathway, and are readily available. The Rock inhibitors are administered at non-toxic concentrations of 0.01 ng to 30 ng or more microgram/ml release for a short time or a long duration. The Rock inhibitors may be potent ROCK inhibitors, such as Ropresa, netarsudil, Fasudil hydrochloride, inhibitor of cyclic nucleotide dependent- and Rho-kinases GSK 269962, Potent and selective ROCK inhibitors GSK 429286, Selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor or Botulinum toxin, such as Botox in 1-100 international units or very slow release with porous silicon implant; orally active Y-27632 dihydrochloride and SAR407899 as a topical solution, polymeric nanoparticles or microparticles with or without cell penetrating peptides or implant.

In one embodiment, after corneal surgery or cataract extraction, a preparation of Rock inhibitors, Wnt inhibitors, integrin inhibitors, or GSK-3 inhibitors alone, or in combination can be used to reduce the inflammatory side effects of inflammation and scarring or loss of corneal sensation.

In one embodiment, one uses a bioerodible implant comprising a non-anti-inflammatory agent acting on cell pathways of inflammation including Wnt inhibitors, Rho inhibitors, integrin inhibitors, GSK inhibitors SB-216763, or lithium chloride at micro to millimolar (mM) concentrations or in combinations, wherein the inflammation is mediated by various conditions.

Example 2

A 67-year female patient with a history of dry eye and cataract extraction in both eyes is complaining of discomfort, with the sensation of foreign body and dryness, hyperemia, mucoid discharge photophobia, and reduced visual acuity, which is not relieved by over-the-counter eye drops. The patient had typical symptoms of dry eye disease with meibomian gland dysfunction, with reduced Schirmer's test results for tear film production, blepharitis, and redness of the lid margins and crusting of the lashes. The patient was initially treated with over-the-counter artificial tear preparation, hyaluronic acid and gel, and ointment at night, and absorbable punctal plug, which did not improve the symptoms significantly, and subsequently topical anti-inflammatory topical agent, such as a steroid and cyclosporine that moderately improved the condition. Since her inflammation was not significantly reduced, she was treated with an off label use of a Rock inhibitor at concentration of 2 micrograms/ml twice daily drops combined with topical tetracycline along with application, low molecular weight heparin, 1% solution (Lovenox), a light shampooing of the lashes at night, and an ointment at night. The symptoms were relieved significantly after a month of therapy.

In one embodiment, after laser surgery, a preparation of a bioerodible implant comprising of Rock inhibitors, Wnt inhibitors, or integrin inhibitors alone or in combination can be used to reduce the inflammatory and side effects, such as scarring on the external eye or inside the eye, or on the skin or mucosa.

In one embodiment, after refractive surgery, and/or in a case of dry eye, integrin inhibitors, are administered with cell penetrating peptides (CPP) or activatable cell penetrating peptide (ACPP) coated dendrimers or nanoparticles or macrolides, such as cyclosporine A, mycophenolic acid, tacrolimus or ascomycin as nanoparticles or conjugated with the dendrimers, or in a preparation in the early stage of glaucoma as a topical medication at concentrations of Rock inhibitors of 1-5 microgram/ml once or twice per day and macrolides at concentrations of 0.000000001% to 1% in a physiological solution.

In one embodiment, lasers are used to cut and/or coagulate the tissue (e.g., exam or infrared (IR) lasers). In this embodiment, lasers may be used for refractive surgery, cosmetic surgery, excision, or ablation of the tumors, etc.

In one embodiment, after refractive surgery or cataract extraction, one administers a polymeric implant or nanoparticles of dendrimers containing inhibitors of the Glycogen Synthase Kinase-3 (GSK-3) which is a serine/threonine protein kinase that plays a key role in Wnt/β-catenin signaling during embryonic development, inflammation, and cancer. Inhibition of GSK-3 by SB-216763 inhibits the Wnt pathway in inflammation and cell proliferation and encourages the nerve growth.

Other lasers are used to treat diabetic retinopathy, macular edema, etc. to reduce the ischemic retina and VEGF production or externally, such as skin or mucosa. However any laser application, including when used as cosmetic skin or mucosal resurfacing and skin tightening, is associated with minor or major thermal release with damage to the cells exposed to it and causes cytokine release, activation of inflammatory cell pathways with leakage of the fluid from the capillaries. In one or more embodiments, Rock inhibitors, Wnt inhibitors, integrin inhibitors and/or inhibition of GSK-3 by SB-216368 are applied to the laser treated areas, before or after treatment, thereby reducing the unwanted side effects of laser application, such as inflammation and activation of TGF-beta and scarring.

In one embodiment, the Rock inhibitors, Wnt inhibitors, integrin inhibitors, and GSK-3 inhibitors are used in combination with cosmetic fillers as slow release polymeric implants, or nano- or micro-particulates or liposomes or micelles to reduce the inflammatory process, the available fillers include Juvederm and Juvederm Voluma (hyaluronic acid filler, Allergan); Belotero (hyaluronic acid, Merz Pharmaceuticals); Sculptra (poly-L-lactic acid, Sanofi); and Artefill/Bellafill (polymethylmethacrylate, Suneva).

In one embodiment, Rock inhibitors, Wnt inhibitors, GSK-3 inhibitors, and/or Integrin inhibitors can be added to any solution, ointment, cream with antibiotics, antifungals, antivirals after cosmetic laser application or after the application of focused ultrasound for tissue tightening.

In one embodiment, in laser cosmetic resurfacing, e.g., application of laser, visible or infrared, $CO_2$, or Erbium laser or radiofrequency or focused ultrasound can be associated with excessive inflammation, fluid release from the skin and subdermal tissue, or from the mucosal tissue in mouth or after vaginal laser resurfacing causing pain and unforeseen scaring. The use of Rock inhibitors, e.g., netarsudil, Fasudil hydrochloride, or topical solution, inhibitor of cyclic nucleotide dependent- and Rho-kinases GSK 269962, potent and selective Rock inhibitor GSK 429286, or Lithium chloride selective Rho-kinase (ROCK) inhibitor H1152 dihydrochloride, at non-toxic concentration when released alone, or with integrin inhibitors, or Wnt inhibitors alone or in combination with a preparation of lanosterol, squalene or squalamine as a topical preparation, or polymeric slow release nano-micro particles reduces the inflammatory process and enhances the healing process, while squalamine has the advantage of acting as anti-bacterial, anti-fungi, antiviral etc., thus preventing infection of the superficial wound created after laser surgery of the skin or mucosa. The anti-inflammatory agents such as squalene, lanosterol or squalamine can contribute to the health of these cells and assist in dissolving the debris from the skin or mucosa, and in combination, e.g. rock inhibitors act as anti-inflammatory without producing side effects of steroids or NSAIDs, such as coronary disease, gastric ulcer, infection, bacterial, fungi or viral infection.

Example 3

A fifty year old female patient had undergone a $CO_2$ laser facial resurfacing for skin rejuvenation for photo-damaged skin, rhytides, and wrinkles. The per pulse power used for the laser ablation had been below that which is normal, and the beam had reached deeper tissue rather than causing superficial skin surface evaporation. She developed an excessive erythema, swelling of the treated area which was initially treated with complete closed dressing, and application of antibiotic Bactroban ointment and later the face was treated with Cetaphil, which did not decrease the inflammatory response. Topical steroidal ointment was avoided out of fear of infection, since the edema swelling lasted more than ten days the patient was, in addition to the standard therapy, administered a physiological solution having 1 microgram/ml Rock inhibitor and at night with a cream having similar concentration of Rock inhibitor. The patient was advised to return if the swelling did not decrease and increased exudate was noted. Seven days after final examination the erythema and swelling was reduced and the face regained its normal appearance.

The cosmetic facial or mucosa surgery utilizes laser thermal energy to damage superficial skin or mucosal layer end encourage their rejuvenation. The depth of and size of the laser application is decided upon by the need of the condition. The pulsed carbon dioxide ($CO_2$) and erbium: yttrium-aluminum-garnet (Er:YAG) or other infrared lasers are the most common laser used in skin/mucosal resurfacing though radio frequency wave and focused ultrasound also are used for one or the other indication. The absorption of (Er:YAG) laser is more by subcutaneous tissue whereas the ($CO_2$) is by the water molecules producing deeper skin lesion of 50-100 μm, creating a thermal necrosis. In general, skin evaporation requires a fluence about 5-7 $J/cm^2$, whereas the Er:YAG laser requires fluence of 0.5 and 1.7 $J/cm^2$.

The advantage of the Er:YAG laser is reduction of leakage of fluid from the tissue; however, the applications of these lasers depend on the location and degree of tissue tightening that is needed. The contra indications are active inflammatory lesions of the skin, or viral, bacterial, fungal infections, etc.

Though erythema after laser skin or mucosa resurfacing takes about 5-7 days to heal. During which time, the skin and mucosa are vulnerable to infection, continuation or excessive inflammation, and the use of steroids, etc.

In general, the skin is treated postoperatively with topically applied anti-bacterial ointment, cream such as mupirocin 2% (Bactroban), or other antibiotics or antiviral medications such as valcyclovir taken orally and skin treatment with topical Silver sulfadiazine. The complications are sever erythema, edema that might last for weeks that requires application of steroidal cream with hydrocortisone 2.5% cream etc. addition to Retin-A 0.05% that might lead to dermatitis or in combination with hydroquinone 5%, for a month or more. Hyperpigmentation is also another side effect of the laser surgery that might require micropeels with 30-50% glycolic acid, etc.

The major complication of the procedure is infection caused by bacteria, viruses or fungi, often associated with the use of steroids in the cream.

In one embodiment, after cosmetic skin or mucosal laser surgery, one uses Rock inhibitors, Wnt inhibitors, integrin inhibitors and/or GSK inhibitors, such as SB-216763 in a physiological solution, cream or polymeric slow release nano- or micro-particles, liposomes or micelles to reduce the inflammatory process without being in need of steroidal medications.

In one embodiment, after cosmetic skin or mucosal laser surgery, one uses Rock inhibitors, Wnt inhibitors, integrin inhibitors, and/or GSK inhibitors or lithium chloride at a non-toxic concentrations, to reduce the inflammatory process without being in need of steroidal medications, but in the presence of the bacteria, viruses, or fungi infection, one can add anti-bacterial medication of anti-viral or anti-fungal medication as known in the art to the above mentioned cell pathway inhibitors without having the side effects of the steroid that is known to encourage the growth of bacteria, viral, and specifically fungal infections.

Example 4

A 55-year patient underwent a routine $CO_2$ laser facial resurfacing and was treated initially with the routine postoperative therapy including complete closed dressing, and application of antibiotic Bactroban ointment and skin treatment with topical Silversulfadiazine and later the patient's face was washed with Cetaphil, in addition to application of steroidal ointment, to reduce postoperative inflammation and systemic ciprofloxacin to prevent infection. Two days post-operative, the patient noticed pain and sever exudation from the treated areas with associated red exudate. The patient was given additional antibiotics to cover *Pseudomonas* infection, but because of the worsening of the condition, the patient was given systemic penecilin and carbapenem to treat a potential *Propionibacterium* infection. A laboratory examination revealed presence of therapy resistant *Propionibacterium* which cannot respond to the standard medication, because of the side effects of systemic clindamycin, the wound area was treated with a 1% riboflavin solution for a period or ten minutes, then radiated with UV radiation of 10 miliW/cm2 as a oscillatory or painting technique for 30 minutes to cover the entire wound area and kill the bacteria. Subsequently the laser-treated area was cleansed and washed with a physiological solution having 500 microg clindamycin/ml and 1 microgram Rock inhibitor per day and dressed with a cream containing the same medications without riboflavin daily. The systemic medication was continued with carbapenem, the healing process continued for another week as gradually the wound healing took place in an additional 10 days and the skin gradually gained its normal appearance.

In one embodiment, after cosmetic surgical resurfacing, the infection might be caused by antibiotic resistant bacteria, one can administer a solution of riboflavin at concentrations of 0.1-4% or more and followed with the UV radiation to the exposed surfaces without producing any skin burn but crosslinking the proteins of the bacteria, viruses, or fungi, and oozing vessel along with antibiotic antibody-coated nanoparticles with cell penetrating peptides (CPP) or ACPP, to enhance penetration of the medication inside the pathogens and damage them while combining the medications with non-toxic does of Rock inhibitors, Wnt inhibitors, integrin inhibitors and/or GSK inhibitors SB-216368 to reduce post-surgical inflammation, prevent release of TGF beta and other cytokines to prevent sever scarring, the treatment can be repeated daily as needed until a complete wound healing is achieved. In one embodiment, one can administer any other photosensitizer with a different wavelength of light to initiate a photodynamic effect in the skin and treat the skin as described above subsequently.

In another embodiment, the disease is Acne vulgaris, one of the most common skin diseases in the United States characterized by chronic skin disease of the hair follicles and their accompanying sebaceous gland. The disease initiates without inflammation in the mild early stages but it is accompanied by inflammatory processes associated with infection caused by the *Propionibacterium acnes*, an anaerobic bacteria leading to severe nodulocystic acne.

At present, the blockages of the glands were treated by mechanical extraction, injection of steroid in the lesion, or light or laser application to the lesion.

In one embodiment, Acne vulgaris is treated initially with topical tretinoin, clindamycin and benzoyl peroxide, isotretinoin topical Retinoi; however, retinoid can induce dermatitis, and should be used with topical and systemic antibiotics, such as doxycycline, tetracycline, minocycline, in combination with topical or intradermal injection of Rock inhibitors, Wnt inhibitors, integrin inhibitors, GSK inhibitors and/or oral medication, such as a combination of ethinyl estradiol, drospirenone.

In one embodiment, one administers the Rock inhibitors and Wnt inhibitors, integrin inhibitors, and/or GSK-3 inhibitors, such as SB-216368, at non-toxic doses to reduce the vascular leakage after laser surgery for acne or debridement in this disease process and eliminate the side effects of infection or delayed wound healing specifically in diabetic patients.

In one embodiment, in patients having facial acne, the Retinoids are comedolytic and reduces desquamation when given along with antibacterial benzoyl peroxide applied topically twice daily. However, the patients can develop dermatitis after application within 2 weeks.

In one embodiment, in patients with acne one administers Rock inhibitors, Wnt inhibitors, GSK-3 inhibitors and/or integrin inhibitors, as a solution at a non-toxic dose of nanograms to micrograms/ml administered for skin debridement or as ointment, cream or polymeric slow release nanoparticles, microparticles, liposomes, micelles, etc. with squalene or squalamine, or lanosterol, and its derivatives used to reduce the inflammatory processes while eliminating the need for steroid therapy, thereby eliminating steroid associated complications, such bacterial or viral infections, or often fungal infections.

The frequent use of topical and oral antibiotics to treat *C. acne* bacteria or other bacteria produces often antibiotic resistance bacterial infection.

In one embodiment, one administers a combination topically or by injection of riboflavin at 0.1-2% or more concentrations in combinations with Rock inhibitors as a topical or injectable preparation to crosslink the collagen of the subdermal or submucosal tissue using the UV laser radiation at 360-400 nm wavelength or another wavelength with another photosensitizer and 1 milliwatt to 10 milliwatt or more of power as needed along with anti-bacterial, antifungal, antivirals, etc. to damage the bacteria, fungi, viruses, or parasitic infections.

Example 5

An 18 year male patient was referred because of prior therapy of an acne infection. The patient was initially treated with by mechanical extraction, injection of steroid in the lesion and light application to the area. Despite the therapy with topical tretinoin, and benzoyl peroxide, isotretinoin and topical Retinoid and clindamycin, the bacterium found by laboratory examination revealed to be *Propionibacterium* resistant to the antibiotics including clindamycin. The clinical examination showed about 10 mm swollen lesion with deep red hollow around a central exudate. The lesion was treated administration of a 2% solution of riboflavin containing 20 microgram/ml Rock inhibitor Fasudil nanoparticles conjugated with CPP in addition GSK inhibitor SB-216368 in millimolar concentrations for 1-2 hours, followed by UV radiation of 5 mW/cm2 for a period of ten minutes, followed by daily administration of a cream dressing having squalamine in addition to polymeric nanoparticles of Rock inhibitors and GSK inhibitors for daily application, and oral carbapenem. The lesion gradually decreased indicating that the local therapy of antibiotic resistant bacteria is possible with the riboflavin crosslinking combined with an antibiotic to which a bacterium might be resistant.

In one embodiment, any therapy resistant acne is treated with application of solution or mixture of riboflavin, antibody-coated nanoparticles in addition to Rock inhibitors, conjugated with cell penetrating agents (CPP) to penetrate the skin and attached to the *C. acne* bacteria, and they are damaged by UV radiation which crosslinks the protein of the bacteria and the collagenous tissue around the gland and also simultaneously damages the comedone producing cells of the gland and reduce inflammation.

In one embodiment, the polymeric implant or polymeric nano- or micro-particles with CPP can be combined with antibiotics, antifungals, antivirals, antineoplastic, macrolides, etc. as needed.

In one embodiment, the biodegradable polymeric compositions orthoesters, anhydrides, amides, calcium alginate polysaccharides functionalized celluloses, carboxymethylcellulose polycaprolactone copolymers of glycolic and lactic acid, polymers of D-lactic acid, L-lactic acid, racemic lactic acid, glycolic acid, preferably about 2-150 micrometers in diameter and 20 microns to 4 mm in length, porous silicon implant or nano- or micro-particles are used to deliver the Rock inhibitors, Wnt inhibitors, GSK inhibitors, and integrin inhibitors.

In one embodiment, after crosslinking, the skin glands of the skin are treated with a solution of viscous gel, or ointment containing Rock inhibitors, Wnt inhibitors, integrin inhibitors and/or GSK-3 inhibitors at non-toxic doses to inhibit inflammatory response in the tissue.

One procedure involves topical administration of a 1-10% or more solution of riboflavin in a physiological solution having the osmolarity of 200-400 or more mOSm and the pH of 5-8, with or without low molecular weight heparin in 0.1-1% or combined with cell penetrating peptides (CPP) or activatable cell penetrating peptides (ACPP) for enhance cell penetration, with or without dextran, or cyclodexterin or metallic nanoparticle or organic nanoparticles conjugated with riboflavin that are also UV light absorbing to simultaneously heat up the nanoparticle and damage the cell wall of the bacteria, fungi, or the viral proteins, and the prions.

In one embodiment, the crosslinking solution also contains an antibiotic to which the C. acne is generally sensitive, such as doxycycline tetracycline, minocycline, and/or clindamycin, and is used with Rock inhibitors, Wnt inhibitors, integrin inhibitors, and/or GSK-3 inhibitors individually or in combination.

In one embodiment, the crosslinking solution can contain riboflavin and/or retinoids along with another medication and riboflavin, and Rock inhibitors, Wnt inhibitors, integrin inhibitors and/or GSK-3 inhibitors, where the UV radiation does not affect these medications except for activating the photosensitizer riboflavin, which after UV exposure, creates singlet oxygen and reactive spices that crosslinks the protein, damaging or killing the bacteria, fungi, or viruses including prions and comedone producing sebaceous glands or sweat glands or the skin debris preventing recurrent of infection in these areas or undesirable odor.

In one embodiment, one uses the riboflavin alone or in combination with Rock inhibitors, for topical application, or if needed micro-puncture with radiofrequency needle of the area, and crosslinking the superficial skin glands with UV radiation and eliminating the sweat glands and sebaceous glands in the areas needed to eliminate undesirable odor from the secretion of these glands along with microbiota the accumulate and grow in that area.

In one embodiment, the crosslinking solution can contain squalamine, squalene or lanosterol to encourage with or without CPP or ACPP for dissolving the comedone and debris that accumulate in the outflow channels and seal and sebaceous gland, or along with another medication, such as riboflavin or psoralens, in nanoparticles or microparticles or in combination of both, with UV radiation by two different mechanisms, riboflavin crosslinks the proteins of the bacteria, while psoralens damages their DNA.

In one embodiment, the UV radiation can be applied with 1-30 mW or more for a short period of 1 minute to 60 minutes depending on the surface areas that are treated to eliminate the bacteria, microbiota, and eliminate the sebaceous glands and sweat glands, or the infected skin areas as needed.

In one embodiment, the crosslinking solution, in addition to riboflavin has a Rock inhibitor, such as Fasudil and its derivatives, netarsudil or SAR407899, and is coated with slow release polymers, such as lactic acid and/or glycolic acid at a concentration of 200 nanograms to 1 micrograms/ml or more and is administered topically, or subcutaneously inside the acne lesion using nano- or microparticles with (alpha)-cyclodextrin, or (beta)-cyclodextrin, or (gamma)-cyclodextrin, hydroxypropyl-b-cyclodextrin (bHPCD) for slow release and tissue penetration with or without cell penetrating agents.

In one embodiment, Botulinum toxin botox can be used as a Rock inhibitor in solution, or in polymeric nanoparticles, to release the medication at a slow rate of 1 picogram or more a day to 1 nanogram or 1-100 international units along with a cream with or without squalene in addition, or as solution with polymeric nanoparticles for administration on the skin, mucosa, or cornea as solution of suspension, etc.

In one embodiment, one implants or injects bioerodible polymeric nano- or microparticles for slow release having Wnt inhibitors or Rock inhibitors, integrin inhibitors, or GSK-3 inhibitors alone or in combination with or without ACPP, whereby an agent is released from the polymeric component, such as PLA, PGLA, or combination thereof by erosion of the polymer, and the medication is delivered topically or injected in the subdermal tissue at a release rate of 0.01 nanograms to 1 microgram/ml or more to achieve a constant release concentration of 1 nanogram or more a day for 3 weeks to 6 month or more than a year after laser surgical procedure.

In one embodiment, in patient with acne, Rock inhibitors, such as Fasudil derivatives, Netarsudil C28H27N3O3 (Rhopressa), or SAR407899, netarsudil etc. at concentrations of 10 picograms to 100 micrograms/0.25 ml or Botox solution of 0.1-1 to 25-100 international units can be administered as a slow release implant or injectable as nano- or microparticles with CPP or (alpha)-cyclodextrin, or (beta)-cyclodextrin, or (gamma)-cyclodextrin, hydroxypropyl-b-cyclodextrin (bHPCD) in the dermis or subdermal tissue or inside the acne lesion as a slow release polymeric plaque or implanted to release medication at a rate of 1 picogram to 10 nanograms/day or more of the non-toxic medication along with a nontoxic dose of a macrolide such as cyclosporine, mycophenolic acid, tacrolimus, or ascomycin etc. at concentrations of 0 00000001-1% w.v or applied to the skin or conjunctiva or mucosa of the mouth or genitalia as non-toxic doses to treat inflammatory diseases of the eye, skin, or mucosa.

In one embodiment, the nanoparticles or dendrimers are conjugated with Rock inhibitors, CPP and integrin inhibitors such as abciximab, Eptifibatide, Tirofiban, αIIbβ3 antagonists, Natalizumab, 3 mg to ±52 μg/mL, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, or risuteganib, Volociximab, JSM6427, or GSK inhibitors and chitosan or PEG delivered as a slow release system that can be released as a temperature sensitive polymer that melts at 42-43 degrees C. using a warm compressor over or under the lid, or thermal application with light, low level laser light, or the use of a compressive focused ultrasound applied to lid, conjunctiva or cornea or the lid releasing 1 picogram to 10 nanograms/day or more of the medication.

In one embodiment, Rock inhibitors or integrin inhibitors are injected after crosslinking in the acne lesion at non-toxic concentrations in the lesion to reduce inflammatory processes and reduce cellular proliferation, blocking TGF beta, and scar formation.

In one embodiment, the Rock inhibitors, such as Fasudil derivatives at concentrations or 10 picograms to 10 nanograms to 1 microgram per drop Botox solution of 0.1 units of Botox can be administered with small molecule Wnt inhibitors, such as FH535, IWP-2, PNU-74654, IWR-1endo, IWR-exo, Demethoxycurcumin, CCTO36477, KY02111, WAY-316606, SFRP or integrin inhibitors, such as abegrin cilengitide, abciximab, tirofiban, natalizumab eptifibatide or at a low concentration of 1 microgram to 10 micrograms as a solution, or in an ointment containing squalene or lanosterol or squalamine to combat bacterial, viral, and fungal infections, while reducing simultaneously the inflammatory processes without steroidal medication that creates the side effect of encouraging bacterial, viral, or fungal infections or parasitic infection of a lesion.

In one embodiment, before or after crosslinking of the acne using topical riboflavin or Psoralens in nano- or microparticles with or without CPP or ACPP solution and UV radiation, one can apply topically an ointment or cream containing squalene, lanosterol, or squalamine to dissolve the comedone of the acne alone or in combination with Rock inhibitors, such as fasudil netarsudil, botox, SAR407899, etc. and/or Wnt inhibitors, such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide.

In one embodiment, the Rock inhibitors are selected from the group consisting of Fasudil, Ripasudil, RKI-1447, Y-27632, GSK429286A, Y-30141, Botox and combinations thereof where the device such as porous silicon or polylactic acid or polycaprolactone releases the Rock inhibitor for 1 year to 3 years at a rate of about 1 micrograms/day to 5 micrograms/day, and botox as a concentration of 1-100 international unit or more released at 1 units or more per day.

In one embodiment, one administers to the eye surface or under the conjunctiva, in the choroid, in the anterior chamber, or in the vitreous cavity, the Rock inhibitor for reducing TGF-β production after therapy and the subsequent scar formation in form of drops or combined with polymeric nanoparticles for slow release delivery after any ocular surgery such as retinal detachment, or complicated retinal detachment traumatic retinal detachment, as proliferative vitreoretinopathy, vitrectomy with or without air or silicone oil tamponade, refractive surgery LASIK, smile surgery, or intracorneal implantion or corneal crosslinking, small molecule PRK or transepithelial PRK, smile procedure, corneal inlay, etc., glaucoma surgery, trans-scleral laser application, for glaucoma, or retinal tear, or application to the ciliary body or from inside the eye to the ciliary processes in glaucoma, cataract surgery laser trabeculoplasty, as polymeric, dendrimers, PGA, PLA or combination or polycaprolactone or chitosan or as liposomal or micelle form.

In one embodiment, Rock inhibitors, such as Fasudil (HA-1077 a selective RhoA/Rho kinase (ROCK) inhibitor), Y-27632, small molecule inhibitor of ROCK1 and ROCK2 which acts as an anti-inflammatory agent and Ripasudil, netarsudil etc. in form of drops or combined with polymeric nanoparticles or implants for slow release delivery are administered at non-toxic concentrations for daily use or slow release after laser cosmetic, ocular, laser facial, mucosal resurfacing, or after transurethral resection of benign prostate, vaginal laser resurfacing, the ablation of cervical localized tumors or precancerous lesions on the skin or mucosa.

in one embodiment, Wnt inhibitors are compounds, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1 or oral ivermectin, niclosamide, or apicularen and bafilomycin, XAV939, XAV939, G007-LK and G244-LM, NSC668036, SB-216763, gemtuzumab, etc. are used in form of drops at pico and nM concentrations, or integrin inhibitors, as solution, or combined with polymeric nanoparticles for slow release delivery of polymeric implants or injectable, or as an ointment.

The conventional signaling receptors and integrins serves as linkers between the actin cytoskeleton and extracellular intracellular signaling matrix, stimulating the cell survival, growth, and cell proliferation.

In one embodiment, the anti-integrins are used as a solution of polymeric erodible nanoparticles, microparticles, and are administered to inhibit cell proliferation and migration and scar formation where the integrin inhibitors are selected from the group consisting of abegrin cilengitide, abciximab, tirofiban, natalizumab, and eptifibatide, and the drug delivery system includes dendrimers, PGLA, PLA or combination of them to treat skin or mucosal inflammation after surgical laser surgery, or in acne vulgaris, etc.

In one embodiment, the cell penetrating peptides extend the agent penetration to at least one of the posterior segment of the eye or anterior segment of the eye or from the cornea to the retina using Rock inhibitors.

In one embodiment, the mucophilic preparation comprises a compound selected from the group consisting of chitosan, a dendrimer, cell penetrating peptide (CPP), activatable cell penetrating peptide (ACPP), hyaluronic acid, low molecular weight heparin, squalene and its derivatives and combinations thereof.

In one embodiment, the Rock inhibitors are administered with macrolides, such as cyclosporine A, mycophenolic acid, tacrolimus, or ascomycin in the early stages of glaucoma as a topical medication at concentrations of Rock inhibitors 1-5 micrograms/ml once or twice per day and macrolides at concentrations of 0.000000001% to 1% in a physiological solution. In one embodiment, to reduce inflammatory processes, one administers polymeric nanoparticles or dendrimers of Wnt inhibitors compounds, such as FH535, IWP-2, PNU-74654, IWR-1endo, IWR-exo, Demethoxycurcumin.

In one embodiment, Rock is active in inflammatory processes, and activates TGF-β formation, that creates scar formation specifically after any surgery, such as skin, intraocular surgery such as retinal detachment, vitrectomy with or without air or silicone oil, tamponade, leading to cell proliferation and redetachment of the retina and Rock inhibitors prevent side effects of excessive scar formation, such as proliferative retinopathy and keloids in cosmetic surgery.

In another embodiment, Rock and other enzymes are activated by inflammatory processes that can be prevented prophylactically before or after the surgery, to reduce TGF-β formation, that creates undesirable scar formation specifically after any surgery, such as skin, mucosa, intraocular surgery such as retinal detachment, vitrectomy with or without air or silicone oil, tamponade, leading to cell proliferation and re-detachment of the retina and Rock inhibitors prevent side effects of excessive scar formation such as proliferative retinopathy and keloids in cosmetic surgery or laser surgery for acne and/or in psoriasis using Rock inhibitors, such as fasudil, rhopressa, netarsudil, and in nano- to microgram concentrations in 1 ml or more or Botulinum toxin as Botox etc. at 1-100 international units depending on the location of application and if used in a slow release filler's absorbable polymers, such as lactic acid or hyaluronic acid or in slow absorbable implant, such as porous silicon, or one administers Wnt inhibitors, such as FH535, IWP-2, PNU-74654, IWR-1endo, IWR-exo, Demethoxycurcumin, CCTO36477, KY02111, WAY-316606, SFRP or integrin inhibitor such as abegrin, cilengitide, abciximab, tirofiban, natalizumab, eptifibatide, GSK inhibitors or integrin inhibitors at non-toxic doses and applied in a physiological solution or as slow release polymeric nanoparticles, microparticles, or as biodegradable implant or inside the space provided in a non-biodegradable implant that can be removed and replaced as needed.

In one embodiment, rock inhibitors are used in hair transplantation to reduce inflammatory responses of the transplanted cells at concentrations of 1 nanogram to 30 microgram/ml.

In one embodiment, Rock inhibitors with GSK inhibitors are used after corneal transplantation to reduce corneal transplant rejection as polymeric nano- or microparticles, etc.

In one embodiment, the Rock inhibitor in tissue or hair transplantation is Botox used at picogram concentrations or as international units 1/0.1 ml to 20 IU or more/0.1 ml in the post-operative period to prevent rejection and inflammation.

In another embodiment, the Botox or similar compound, such as Fasudil, botulinum toxin, (Botox), rhopressa, netasudil, etc. or Wnt inhibitor such as FH535, IWP-2, or integrin inhibitors, are used with squalamine to prevent inflammation and rejection after tissue transplantation.

In one embodiment, Rock inhibitors are used with GSK inhibitors and/or integrin inhibitors in sub-chronic inflammation of hair follicles leading to hair loss, the preparation can be used as a solution, polymeric nanoparticles or microparticles for slow release of picogram release/day.

In one embodiment, Rock inhibitors and a macrolide, such as cyclosporine, mycophenolic acid, or tacrolimus, etc. is used with Rock inhibitors as in a solution, cream, ointment or slow release polymeric nanoparticles or microparticles with biodegradable polymers for treatment of chronic inflammatory processes, such as glaucoma, male hair loss, or alopecia areata, acne vulgaris, in the form of a solution, cream etc. to slow down the loss of hair or prevent it, or in psoriasis to reduce the inflammatory component of the disease without the use of steroidal ointment, or after cosmetic surgery to reduce thermal damage and inflammation.

One of the most common causes of hair loss is male alopecia, which is hormonal and genetic. It occurs during the puberty and continues thereafter. This process though is not considered inflammatory, it is hard to not expect that a very slow progressive inflammation might cause the apoptotic loss of hair stem cells and the hair bulb. However inflammatory processes cause more rapid loss of the hair, such as alopecia areata, psoriasis, or other skin diseases.

The standard therapy for the hair loss is the use of topical minoxidil a blood pressure lowering medication applied twice daily. Minoxidil (Rogaine) is available at 2% to 5% concentrations preparations where it slows down the loss of hair, the mechanism of its action are local vasodilatation and/or nonspecific replacement of dihydrotestosterone (DHT)-binding sites in the hair bulb and nonspecific occupation of dihydrotestosterone (DHT)-binding sites in the hair. The alternative medication is finistride, a 5-alpha reductase inhibitor that blocks conversion of testosterone to DHT. Finasteride is taken orally and is more effective than minoxidil. The other method that may help with the maintaining the hairs longer in women's hair loss, and potentially in men, is the use of laser light radiation to heat up the skin and potentially open the skin capillaries. In progressed stages at present the only manner to cover the loss of hair is by transplantation of some of the remaining hair to new area. The surgical techniques is done as strip transplantation or mini-grafts and micrografts. Minigrafts and micrografts are removed with the size of 1-3 mm in diameter using a knife and a fine forceps or trephine and implanting them in the slit or holes in the recipient skull. Postoperatively, the skin is treated locally with oral prednisone to reduce the swelling of the tissue, and the pain is controlled with ibuprofen, acetaminophen, or codeine etc.

The postoperative side effects are bleeding, tissue swelling, edema, potentially infection, scar or keloid as a result of cytokine release activation of Wnt pathway rho enzymes producing TGF beta that induces excessive scar and keloids.

In one embodiment, after hair transplantation, one administers the standard medication, such as anti-infective solution and dressing to the area to prevent infection with simultaneous administration of oral proscar (finastride) and topical Rock inhibitors, Wnt inhibitors, and/or GSK-3 inhibitors or integrin inhibitors as slow release polymeric nanoparticles or microparticles with or without CPP or ACPP to inhibit the inflammatory component of hair transplantation after the surgery, or in combination with other anti-inflammatory medications, such as squalamine or lanosterols to combat infection as a solution or cream.

In one embodiment of early stage of male alopecia, or alopecia areata that is localized to one or more areas of the skull, one may administer a therapy, such as oral finasteride or topical application of a solution or cream having Rock inhibitors, such as fasudil, Netarsudi, or SAR407899 as a lotion with or without polymeric slow release nanoparticles or microparticles with or without CPP or ACPP, with or without squalamine to inhibit the inflammatory component at non-toxic concentrations or picogram to 100 nanograms or more, or in case of Botulinum toxin at 1-10 international units or more per milliliter applied using a Q-tipped applicator followed with femtosecond, nanosecond, micropulses, millipuses or pulses of less than one second to two second duration or more of laser with wavelength of green to infrared, preferably yellow or red wavelength with an energy length that does not produce any injury or scratches to the skin, but has the effect of tissue rejuvenation and stimulating the stem cells of the hair follicles using a thin laser probe with transparent smooth surface with no sharp edges that can pass through the hair to reach the skull directly, running it over the skull's skin covering all areas to be treated with one or multiple fibers optics ending at the probe's end can fire simultaneously or individually and the power supply has a battery or the hand piece can be disposable.

In one embodiment, the Rock inhibitor is one of Botulinum toxin at 1-10 international units or more per milliliter applied to the skin of the scalp with a Q-tipped applicator as polymeric nanoparticles or microparticles of polylactic or glycolic acid or orthoesters with or without CPP or ACPP, with or without squalamine to release the medication slowly over time to prevent inflammatory processes of the hair bulbs.

Example 6

A 24 year old male patient having symptoms of male inherited androgenic pattern baldness which started 2 years earlier with the loss of hair and thinning of the central and the top of the skull, had used the usual medication to reduce the testosterone hormone, but has not been effective in preventing the hair loss. He chose to be treated with the standard oral finistride medication and laser pulses to the skull treated with topical Rock inhibitors in polymeric nanoparticles or microparticles releasing the medication at concentrations of 100-1000 nanograms/ml applied daily with a Q-tipped applicator daily and the laser pulses once to three times per week to rejuvenate the hair cells and stimulate the stem cells to multiply by laser pulses, 1-3 times a week; the patient returned for the follow-up of 2 month and felt that the hair loss has been diminished by the daily use of the topical application of Rock inhibitors and the laser application sessions.

In one embodiment of early stage male alopecia, or alopecia areata that is localized to one or more areas of the skull, one can administer oral finasteride or topical application of a solution having Rock inhibitors, such as fasudil, Netarsudi, or SAR 407899 as a solution with or without polymeric slow release nanoparticles or microparticles with or without CPP or ACPP but no Botox to inhibit inflammatory component at non-toxic concentrations or picogram to 100 nanogram concentrations applied using a Q-tipped applicator followed with femtosecond, nanosecond micropulses or millipulses or pulses of less than one second to two second pulse duration or more of a laser with the wavelength of green to infrared preferably yellow or red wavelength with an energy length that produces no or minimal injury or scratches to the skin to stimulate the stem cells of the hair follicles, using a thin laser probe with a transparent smooth surface and no sharp edges that can pass through the hair to reach the skull directly, rubbing it over the skull's skin covering all areas to be treated without stopping in one place to prevent excessive injury to the skin having one or multiple fibers optics ending at the probe's end that is connected to a diode laser and can fire individually or multiple pulses as the probe moves over the skin and the power supply has a battery or the hand piece can be disposable.

In one embodiment, after cosmetic surgery, the topical administration of Rock inhibitors, anti-integrin inhibitors or other anti-inflammatory medications, such as squalamine or lanosterols alone or in combination with a macrolide as drops, polymeric nanoparticles or implants for slow release over a long period of time to reduce the inflammation and scarring.

Psoriasis is a genetic disease associate with an autoimmune response with elevated tumor necrosis factor (TNF), release of cytokines, interleukin IL-12, IL17, IL 23 inflammation and cell proliferation and manifested as plaques demonstrating dry, itchy, swollen, scaly areas of the skin found around the joints (e.g., elbow and knee) with or without joint involvement, and the skin around the plaques are red and inflamed. The lesions may affect any part of the body and may be associated with exfoliation and inflammation which is in general treated with systemic and, in addition to phototherapy, systemic cyclosporine, injectable secukinumab, Adalimumab, etanercept, with their systemic side effects including lymphoma and topical application cooking oil, sea salt, topical steroids and Vitamin D as Calcipotriol with some limited beneficial effect.

In one embodiment, a patient suffering from skin psoriasis which is treated with the standard topical medications and steroid, causes thinning of the skin, bruising and bleeding.

In one embodiment, the psoriasis lesions of a patient are treated with a combination of Rock inhibitors such as Fasudil, botulinum toxin, (Botox), rhopressa, netasudil, etc. and/or Wnt inhibitor compounds, such as FH535, IWP-2, PNU-74654, IWR-1endo, IWR-exo, Demethoxycurcumin, CCTO36477, KY02111, WAY-316606, SFRP or integrin inhibitor such as abegrin cilengitide, abciximab, tirofiban, natalizumab eptifibatide, risuteganib alone or in combination locally used in non-toxic concentrations or picogram to 1-30 or more micrograms as nanoparticles or dendrimers with ACPP or CPP for better tissue penetration, microparticles, PLA, PGLA, or combination, or polycaprolactone, or as liposomes, or micelles to reduce the inflammation processes locally alone or in combination with systemic immune therapy.

In another embodiment psoriasis lesions of a patient are treated with a combination of Rock inhibitors such as Fasudil, botulinum toxin, (Botox), rhopressa, netasudil, etc. or Wnt inhibitor compounds, such as FH535, IWP-2, PNU-74654, IWR-1endo, IWR-exo, Demethoxycurcumin, CCTO36477, KY02111, WAY-316606, SFRP or integrin inhibitors such as abegrin, cilengitide, or Wnt inhibitor with ACPP or CPP for better tissue penetration or integrin inhibitors alone or in combination locally used in non-toxic concentrations or picogram to 1-30 or more micrograms as nanoparticles or dendrimers in combination with Calcipotriol in treatment of psoriasis as lotion, ointment, or cream with 0.001-0.008% of calcipotriol to reduce the inflammatory response.

Example 7

A 15 year old female patient was suffering from early stage psoriasis around the elbows and neck that did not improve despite the topical therapy, steroids, Vitamin D analogues, Calcipotriene (Dovonex calcineurin inhibitors, Salicylic acid, topical retinoids, coal tar and moisturizers in an ointment, light and UVB radiation, the patient refused to have systemic immune suppressants such as methotrexate, cyclosporine or biologics such as secukinumab (Cosentyx) and ixekizumab (Taltz)etanercept (Enbrel), infliximab (Remicade), adalimumab (Humira), ustekinumab (Stelara), golimumab (Simponi), apremilast (Otezla), the patient was treated with therapies without steroids but administering Rock inhibitors, such as nanoparticles, or microparticles conjugated with CPPs or slow release implant of Fasudil etc. or Wnt inhibitors or integrin inhibitors alone or in combination with other topical therapies such as squalene as ointment or cream which improved her condition without having the side effects of steroids, biologics.

In one embodiment, the psoriasis lesions of a patient are treated with a combination of Rock inhibitors such as Fasudil, botulinum toxin, (Botox), rhopressa, netasudil, etc. or Wnt inhibitors such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide, risuteganib alone or in combination locally used in non-toxic concentrations of picogram to 1-3 or more micrograms as nanoparticles, dendrimers, microparticles, PLA, PGLA, or combination or polycaprolactone or as liposomes, or micelles or implantable along with fillers such as Juvederm and Juvederm Voluma (hyaluronic acid filler; Allergan), Belotero (hyaluronic acid; Merz Pharmaceuticals), Sculptra (poly-L-lactic acid), Sanofi or combination or as porous implantable porous silicon injected under the skin to release the medication over 1-3 years, and gradually reduce the inflammation processes locally alone or in combination with systemic immune therapy.

In one embodiment, the joint psoriasis is treated with injection inside the joint of preparation of Rock inhibitors such as Fasudil, botulinum toxin, (Botox), rhopressa, netasudil, etc. or Wnt inhibitors such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide alone or in combination locally used in non-toxic concentrations or picogram to 1-3 or more micrograms as nanoparticles dendrimers, microparticles, PLA, PGLA, or combination or polycaprolactone or as liposomes, or micelles or implantable erodible polymers with the size of 0.1-3 mm and diameter of 10-100 or more microns.

In one embodiment, one administers the combination of Rock inhibitors in nano and picogram concentrations such as fasudil, Netarsudil and macrolides such as cyclosporine, mycophenolic acid, tacrolimus, or ascomycin etc. at concentrations of 0 00000001-1% w.v or applied as non-toxic doses in the treatment of open angle glaucoma or in conjunction with alpha adrenergic anti-glaucoma medications as topical drops or polymeric nanoparticles or implants under the conjunctiva, to the cornea, and Rho-kinases GSK 269962, potent and selective Rock inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent Rock inhibitor PKI1447 dihydrochloride, potent and selective Rock inhibitor; antitumor SB 772077B, potent Rho-kinase inhibitor; vasodilator SR 3677 dihydrochloride, potent, selective Rho-kinase (ROCK) inhibitor TC-S7001, potent and highly selective Rock inhibitor; orally active Y-27632 dihydrochloride or SAR407899.

In one embodiment, the integrins are transmembrane receptors that act as mechanosensors and signal transduction platforms, adhesion molecules in many diseases processes, and their inhibition can prevent or treat the development of the inflammatory diseases and their sequelae.

In one embodiment, one administers polymeric nanoparticles or dendrimers with the anti-integrins such as Risuteganib, vedolizumab, integrin-targeted therapeutics, abegrin cilengitide, abciximab, tirofiban, natalizumab eptifibatide are used alone or in combination with Rho-kinase inhibitors or Wnt inhibitors among others, or anti-VEGFs, GSK-3 inhibitors, or GSK 429286 to reduce the inflammation and reduce cell proliferation, and can be used simultaneously for drug delivery purposes in cutaneous inflammatory diseases.

In one embodiment, one administers polymeric nanoparticles or dendrimers with Rock inhibitors, Wnt inhibitors, integrin inhibitors, or GSK inhibitors that are used in a slow release form as polymeric nanoparticles such as biodegradable polylactic acid, polyglycolic acid, (PLGA) copolymer, PLGA copolymer, about 10% to 90% by weight of the implant, or a 50/50 PLGA copolymer for about 3-months to a year, or in porous silicon for 1-3 years in concentrations of 0.01 microgram/day to 5 micrograms/day as needed.

In one embodiment, the GSK-3 inhibitor lithium chloride at mM concentrations or SB-216763, a GSK-3β cell-permeable inhibitor can be added to the solution of Rock inhibitors or the ointments to interrupt the Wnt pathway and reduce localized skin inflammation and enhance the nerve growth after the skin surgery or inflammatory skin or mucosa diseases preventing severe fibrosis of the tissue.

In one embodiment, the Rock inhibitors, Wnt inhibitors, integrin inhibitors, or GSK inhibitors are used along with antiproliferative medications after removal of cutaneous precancerous lesion or after skin or tumor resection or with antibiotics in infection caused by bacteria using nanoparticles, dendrimers, and microparticles of PLA, PGLA, with crosslinking the tissue using riboflavin and UV radiation.

In one embodiment, the Rock inhibitors, Wnt inhibitors, integrin inhibitors, Fasudil, botulinum toxin, (Botox), rhopressa, netasudil, etc. or Wnt inhibitors such as FH535, IWP-2, or GSK inhibitors are used along with macrolides, anti-infective medication with or without squalamine are administered in a physiological preparation with polymeric nanoparticles, microparticles, or cream for surface application after thermal or chemical burns of the skin or mucosa such as conjunctiva, mouth, accidental ingestion of hot fluid or chemical, etc. face, hand, legs or skull etc. as a solution, cream, etc. to reduce inflammation and scarring.

In one embodiment, nanoparticles deliver Rock inhibitors, Wnt inhibitors, integrin inhibitors, Fasudil, rhopressa, netasudil, etc. or Wnt inhibitors such as FH535, IWP-2, or GSK inhibitors are used along with macrolides, anti-infective medication with or without squalamine are administered in a physiological preparation with polymeric nanoparticles, microparticles, or cream with or without squalamine/antibiotics or with semifluorinated alkane/siloxane for surface application after thermal or chemical burns of the skin or mucosa such as conjunctiva, mouth, accidental ingestion of hot fluid or chemical etc. face, hand, legs or skull etc. as solution, cream, etc. to reduce activation of TGF-beta and scarring.

In one embodiment, nanoparticles deliver rock inhibitors, Wnt inhibitors, integrin inhibitors, Fasudil, rhopressa, netasudil, etc. or Wnt inhibitors such as FH535, IWP-2, or GSK inhibitors are used along with macrolides, anti-infective medication with polymeric nanoparticles, microparticles, surface application after thermal or chemical burns of the skin or mucosa such as conjunctiva, mouth, accidental ingestion of hot fluid or chemical etc. face, hand, legs or skull to the respiratory tract to reduce activation of TGF-beta and scarring, and fibrosis after inflammatory diseases of the lung.

Inhalation has been used for long time for delivery of medication not only to the lung but also for systemic therapy bypassing intravenous administration. However, it seems to be most attractive for the diseases affecting the lungs and the cardiovascular system which is closely related to the arterial oxygenated blood returning to the heart, left ventricle, aorta and coronary arteries etc.

The distribution of the medication through inhalation is fast and can be also localized to specific lobes of the lung if delivered through a nasal tube under bronchoscopy visualization of the catheter or a tube, after local spray anesthesia of the surfaces of the nasal, throat and trachea. The respiratory tract include nose pharynx followed by trachea, bronchi and lung alveoli. The right lung has three lobes whereas the left lung has two lobes. Both have alveoli, blood that are covered with a layer of mucin and fluid and function as gas exchange, in addition to its vessels and lymph nodes. The clearance of the medication from the lung occurs mostly by systemic absorption, mucociliary or macrophage enzymatic activity.

Liquid nebulizers or pressure metered doses are used to deliver aerosolized medications in the respiratory system, however, the use of standard methodology has suffered from short half life time necessitating repeated applications.

Small lipophilic and hydrophobic drugs are comprehensively absorbed within 1-2 minutes from the lung into the systemic circulation via passive diffusion, while small hydrophilic drugs are absorbed within 65 minutes, factors that contribute to enhance drug bioavailability are slowing down the enzymatic degradation, targeting the site of the lung, or the diseases process, reduce the frequency of the application of the medication and reducing local or systemic side effects. Among these factors are the size of the particles delivered.

In general, the particles of 2-3 microns are deposited in the upper respiratory tract, whereas the smaller than 2 micron particles reach the lung alveoli and the particles smaller than 0.5 micron can also be exhaled. Therefore, the size of the particles determines where the particles travel and also the length of the duration of the drug delivery. The majority of deposited particles are cleared by mucociliary clearance that is increased by inflammatory diseases of the lung. The aerosolized particles have a size of 0.001 to about 100 microns. One successful example of particulate-based drug delivery system includes the use of large porous microparticles (LPPs) with size greater than 5 μm, but with a density of less than 0.1 g/L or less. The LPPs showed an appealing ability to escape macrophage uptake and deposit homogeneously in the lung.

In one embodiment, the nanoparticles or microparticles can be can be the size of 0.1-5 microns, can be swellable after administration, crosslinked or noncrosslinked chitosan, or pegulated poly chitosans, micelles, hyaluronic acid, HA-conjugated medication, PEG-microspheres of lactic acid or glycolic acid or combination liposomes filled with medication, solid lipid nanoparticles or PEG-SLN, chitosan, poly (lactic-co-glycolic) acid, poly(lactic) acid, poly(butylcyanoacrylate), and poly(lactic-co-lysine, poly butylcyanoacrylate (PCL) or Polymeric micelles, amphiphilic macromolecules self-assemble to core-shell nanostructure or Cyclodextrins (CDs) are cyclic polymers of α-D-glycopyranose composed of cyclic oligosaccharides, CDs; α-, β- and γ-CDs, etc.

In one embodiment, the antibody-coated polymeric nanoparticles can carry antibiotics, antifungals, antiviral medication, macrolides, antiproliferative agents in addition to Rock inhibitors, or Wnt inhibitors or GSK inhibitors or integrin inhibitors to reduce inflammatory components of the lung disease, prevent pulmonary fibrosis, in patients with tumors of the lung along with antiproliferative agents, multiple checkpoint inhibitors, or immune stimulators such as IL-2, Tumor Necrotic Factors, Toll-like receptors, etc.

In one embodiment, the antibody coated polymeric nanoparticles are delivered with nebulizers, or pressure metered dose devices.

In one embodiment, the antibodies are coated to deliver the medications etc.

In one embodiment, the nanoparticles are delivered locally in the lung under the control of a bronchoscope in aerosolized polymeric nanoparticles.

In one embodiment, the polymeric nano- or microparticles are delivered in semifluorinated alkane that evaporates fast while leaving the medication at the desired location locally or diffusely in the lung carrying Rock inhibitors, or Wnt inhibitors, or GSK inhibitors or anti-integrins in conjunction with antibiotics, antifungal, antivirals, anti-neoplastic medication to control the inflammatory process in the lung and eliminating the side effects of steroids or NSAIDS.

In one embodiment, the polymeric nano or microparticles are delivered in semifluorinated alkane that evaporates fast while leaving the medication at the desired location locally or diffusely in the lung carrying Rock inhibitors, or Wnt inhibitors, or GSK inhibitors or ant-integrins in conjunction with medications that stabilize heart rhythm, or treat atherosclerotic disease of the coronary vessels, aorta, lung vessels or acrotic artery and the entire circulatory diseases.

Although semifluorinated alkane (SFA) compounds have been described for the transport of various medications, and to deliver various medications, the maximal expected duration of medication after the SFA evaporation is about 4-6 hours. They have not been described to transport slow release medications from polymeric compounds such as polymeric compositions orthoesters, Anhydrides, amides, calcium alginate polysaccharides functionalized celluloses, carboxymethylcellulose, polycaprolactone, copolymers of glycolic and lactic acid, polymers of D-lactic acid, L-lactic acid, racemic lactic acid, glycolic acid, or porous silicon (not silicone oil), etc. The SAF delivery of medication using nanoparticles of 1-100 nm limits the duration of the medication release, which occurs fast. However, polymeric nanoparticles can be made from preferably about 1 nm-150 micron in diameter and 20 micron-1 mm or more in length depending if it is used for inhalation or on the surface of the skin or mucosa and use the SAF for their carrier while the polymeric compound remains on or inside the tissue for days or even months if desired for the release of the medication depending on the percentage of the drug per volume of the polymer such as 10% w/v to 50% w/v or more is selected and the polymeric compound. This combination of SAF with polymeric slow release compound(s) delivers the medication longer than described previously for the semifluorinated alkane/medication alone and eliminates the need for daily multiple applications. One can also choose the previously described composition of SFA with a straight chain or branched perfluoro alkyl group or a composition depending on the number of carbon molecules, etc. that can evaporate faster or slower at room temperature or when it reaches 37C, or the body temperature. The active component of the SFA/Polymer for use in the present preparation are compounds that inhibit or stimulate one or the other cellular activity such as Wnt inhibitors, Rock inhibitors, GSK inhibitors, or integrin inhibitors; though practically any other medications can be delivered with this system such as antibacterials, antifungals, anti-virals anti-parasitics, anti-inflammatory agents, including prostaglandin analogues, antihistaminic, growth hormones, or biologics, anti-VEGFs, macrolides, anti-proliferative, vasoconstrictive or vasodilatators.

In one embodiment, perfluorocarbon liquids or semifluorinated alkane such as F4H5, F4H6, F4H8, F6H6 F6H8 etc. alone or in combination with one siloxane can be used as a carrier formulation to carry slow release polymeric nano- to microparticles of polylactic, micelles, or polycaprolactone, copolymers of glycolic and lactic acid of Rock inhibitors, such as fasudil netarsudil, SAR407899, etc. and/or Wnt inhibitors such as FH535, IWP-2, PNU-74654, IWR-1endo, IWR-exo, or GSK inhibitors SB-216763 etc. at non-toxic concentrations releasing 1 picogram to nanogram/ml or higher concentrations or integrin inhibitors such as abciximab, Eptifibatide, Tirofiban, αIIbβ3 antagonists, Natalizumab, 3 microgam/ml as topical applications after refractive surgery of the cornea, cataract, LASIK or smile procedure or glaucoma surgery or glaucoma laser surgery or after cosmetic facial laser surgery or skin resurfacing, or after laser surgery, etc. for laser and non-laser treatment of acne vulgaris or as topical application, lotion, cream in dry eye, psoriasis, skin or mucosa burn, or after laser surgery for hair regrowth or hair transplantation along with an antibiotic to prevent infection while discouraging keloid formation, in oral, nasal, or respiratory system diseases, for asthma, pulmonary hypertension, or in treatment of pneumonia to inhibit TGF-beta activation and to prevent pulmonary fibrosis.

Example 8

A 40 year old patient had undergone a LASIK procedure one month ago for a −7.00 D correction of myopia developed reduced visual acuity in an irritated eye with presence of debris at the lid margin and low tear film production. The corneal sensation was reduced as measured with Cochet Bonnet aesthesiometer, loss of cornel reflex, the conjunctiva and the lid margin were inflamed. The patient was treated with topical application of a Rock inhibitor as polymeric PGLA nanoparticle and in semifluorinated alkane and polymeric PGLA nanoparticle of cyclosporine, once a day for one week then as needed once or twice a week. The treatment was continued for another three months, the discomfort disappeared and tear production increased and visual acuity returned to normal.

In one embodiment, perfluorocarbon liquids or semifluorinated alkane such as F4H5, F4H6, F4H8, F6H6 F6H8 etc. alone with or without siloxane with polymeric slow release nano-microparticles of polylactic, polyglycolic acid, or polycaprolactone or porous silicon dispersed in the semifluorinated alkane formulation, conjugated with or without an additional amphiphilic cationic polymer such as such as CPP or ACPP, poly{N—[N-(2-aminoethyl)-2-aminoethyl] aspartamide} (PEG-pAsp(DET)/semifluorinated alkane complex etc. as a lotion or suspension, cream to carry Rock inhibitors such as fasudil, netarsudil, SAR407899, etc. and/or Wnt inhibitors such as FH535, IWP-2, PNU-74654, IWR-1endo, IWR-exo, etc. or integrin inhibitors such as abciximab, Eptifibatide, Tirofiban, αIIbβ3 antagonists, Natalizumab, 3 microgam/ml or GSK inhibitors at non-toxic concentrations of 1 picogram to nanograms or more daily release from the nanoparticles at a concentration as needed with or without squalamine, lanosterol, squalene preparation for topical application after refractive surgery of the cornea, cataract, LASIK or smile procedure or glaucoma surgery or after cosmetic facial laser surgery or skin resurfacing, vaginal laser surgery, or after acne laser surgery or without surgery etc. to prevent cellular proliferation, scar formation and keloid and for treatment of acne vulgaris encouraging wound healing, without the use of steroid and NSAIDs or as topical application or injected under the skin in psoriasis, or after laser surgery for hair regrowth with or without laser application or hair transplantation to encourage hair growth and prevent keloid formation.

Intraocular inflammation affects the trabecular meshwork of the eye, blocking the outflow channel of the intraocular fluid. In addition, inflammation incites production of cell adhesion molecules, cell adhesion, cell proliferation, cell migration and production of the fibrous membrane leading to damage to the trabecular meshwork and outflow channels of the aqueous.

Rock inhibitors block the activity of the Rho enzyme which is a part of the serine-threonine family that acts when the Wnt signaling is activated during the inflammation and cell proliferation, and scar formation. Its inhibition reduces the inflammation and cell proliferation, and in addition, it enhances the vascular blood flow and prevents vasoconstriction and ischemia. Polymeric delivery of Rock inhibitors for a long therapeutic effect after ocular surgery that prevents inflammation and scarring of the tissue specifically where the clear media is important, such as the cornea, has not been reported.

In one embodiment, an exemplary dosing of netarsudil 0.02% (0.2 mg per ml)=200 microgram/ml or 20 microgram/ 0.1 ml.

In one embodiment, one administers topically, at doses of 1-200-microgram per milliliter or more, or injects intraocularly, subconjunctivally, in the choroid, or the vitreous at doses of 1-20 micrograms per 0.1 milliliter or more, as implants a bio-erodible implant or polymeric nanoparticle or microparticles to release the medication at a non-toxic dose of nanogram to microgram concentrations or more per day for a long time at 1-6 or 12 months comprising an anti-inflammatory agent acting on cell pathways of inflammation including Wnt inhibitors, Rho inhibitors such as fasudil, netasudil, or ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, botulinum toxin (Botox)potent, selective Rho-kinase (ROCK) inhibitorTC-57001, potent and highly selective ROCK inhibitor; orally active Y-27632 dihydrochloride, where the inflammation is mediated by various conditions of the eye, such as post ocular surgery procedures such as refractive surgery, LASIK, smile, PRK, trauma, cataract surgery, glaucoma surgery, complicated or recurrent vitreoretinal surgery, and/or laser surgery.

In one embodiment, one administers the Rock inhibitors with a slow release drug delivery system, such as polymers, matrices, microcapsules, nanoparticles or microspheres, microparticles of porous silicon or other delivery systems formulated from, polyglycolic acid, lactic acid, combinations of glycolic and lactic acid, liposomes, silicon, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of the polymeric implant for slow release of medication such as porous silicon implant, polycaprolactone can be implanted intraocularly where the inflammation is mediated by various conditions of the eye such as post ocular surgery procedures such as refractive surgery, such as LASIK, smile procedure, trauma, cataract surgery, glaucoma surgery, or glaucoma selective laser trabeculoplast (SLT) for glaucoma, vitreoretinal surgery, vitrectomy, sub-retinal surgery, recurrence of retinal detachment, and laser surgery of the retina in diabetic retinopathy or diabetic macular edema.

Integrins are transmembrane proteins which are active in cell proliferation and cell-to-cell adhesion in many disease processes and scarring.

In one embodiment, one administers integrin inhibitors as a slow release drug delivery system, such as polymers, matrices, microcapsules, nanoparticles or microspheres, microparticles of porous silicon or other delivery systems formulated from polyglycolic acid, lactic acid, combinations of glycolic and lactic acid, liposomes, silicone, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of polymeric implant for slow release of medication such as porous silicon implant, polycaprolactone can be implanted intraocularly such as abegrin cilengitide, abciximab, tirofiban, natalizumab eptifibatide or a low concentration 1 micrograms to 10 micrograms as a solution or polymeric nano- or microparticles or suspension, topically, at doses of 1-200-micrograms per milliliter or more or injecting intraocularly, subconjunctivally, in the choroid, or the vitreous at doses of 1-20 micrograms per 0.1 milliliter or more, or as implants as a bio-erodible implant or polymeric nanoparticles or microparticles to release the medication at a non-toxic dose of a nanogram to microgram concentration or more per day for a long time at 1-6 or 12 or more months comprising integrin inhibitors or in combination with GSK inhibitors, wherein the chronic inflammation-mediated by various conditions of the eye such as in diabetes retinopathy, immune response, optic neuritis, retinitis, uveitis, or caused by pathogens or post-ocular surgery procedures such as refractive surgery, trauma, cataract surgery, glaucoma surgery, vitreoretinal surgery, laser surgery regenerative procedures such as stem cell transplantation and gene therapy, clinically the inflammatory process is associated with low grade to frank serum leakage from the vascular structure of the retina or the choroid causing bleeding, damage to the vascular endothelial cell, vascular occlusion and ischemia, or macular edema.

Wnt signaling pathways are activated by the cell surface receptors initiating cell division, cell proliferation, and inflammation and cancer cell metastatic process.

In one embodiment, the Wnt inhibitors such as Dickkopf (Dkk) proteins, Wnt Inhibitory Factor-1 (WIF-1) in a non-toxic nano- to microgram concentration, Rock inhibitors or integrin inhibitors such as abegrin cilengitide, abciximab, tirofiban, natalizumab eptifibatide or a low concentration 1 microgram to 10 micrograms as a solution or GSK-3 inhibitors with or without ACPP may be injected into the eye, for example, injection under the conjunctiva or tenon capsule, intravitreal injection, or retrobulbar injection as a slow release nanoparticle. The agent(s) may be administered with a slow release drug delivery system, such as polymers, matrices, microcapsules, nanoparticles or microspheres, microparticles of porous silicon or other delivery systems formulated from, polyglycolic acid, lactic acid, combinations of glycolic and lactic acid, liposomes, porous silicon, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of a polymeric implant for slow release of medication such as porous silicon implant, polycaprolactone can be implanted intraocularly, in the peripheral lens capsule after cataract surgery, as a circle, C-shaped, rod, wire or nanoparticle, over the lens in the choroid for example, implanted under the conjunctiva, implanted in the wall of the eye, sutured to the sclera, for long-term drug delivery or injected in the vitreous cavity for a short term drug administration where the inflammation is mediated by various conditions of the eye such as post ocular surgery procedures such as corneal refractive surgery, LASIK, smile, photorefractive keratectomy, trauma, cataract surgery, glaucoma surgery, vitreoretinal surgery, laser surgery, or infection.

In one embodiment, the topical application of Rock inhibitors, integrin inhibitors, GSK-3 inhibitors, Wnt inhibitors are applied to the cornea and conjunctiva as a solution or polymeric nanoparticles or an implant under the conjunctiva to release medication for 3-6 months delivering nanogram to microgram concentrations or in case of Botulinum toxin (Botox) <1-10 international unit as an injection in 0.1-3 milliliters or topical application or spray or evaporative solution or in a evaporative semifluorinated alkane to enhance corneal nerve growth and corneal sensation to prevent dry eye or pain and scarring after the corneal surgery including corneal transplant, and cataract extraction.

In one embodiment, biodegradable polymeric compositions are orthoesters, anhydrides, amides, calcium alginate, polysaccharides, functionalized celluloses, carboxymethylcellulose, polycaprolactone, copolymers of glycolic and lactic acid, polymers of D-lactic acid, L-lactic acid, racemic lactic acid, glycolic acid, porous silicon implant or nano- or microparticles. The polymer can be of any size, but preferably for injectable compounds, it can be about 2-150 micrometers or larger in diameter and 20 microns to 4 millimeters in length or longer.

In one embodiment, the polymeric implant or nano- or microparticles can be combined with antibiotics, antifungals, antivirals, antineoplastic macrolides, etc. as needed.

In one embodiment, the device contains a ROCK inhibitor such as Fasudil, netarsudil, etc. or ROCK inhibitor selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride.

In one embodiment, the device may also contain at least one of an anti-vascular endothelial growth factor (VEGF), such as avastin, ranizumab, afibercept, an anti-platelet derived growth factor (PDGF), an integrin inhibitor such as abegrin cilengitide, abciximab, tirofiban, natalizumab eptifibatide or a low concentration 1 microgram to 10 micrograms as a solution, a beta-blocker, an adrenergic agonist, a carbonic anhydrase inhibitor, a cholinergic agent, a prostaglandin analog, a derivative of cannabinoid receptors, and combinations thereof working synergistically as needed or GSK inhibitor 429286.

In another embodiment, Rock inhibitors or integrin inhibitors such as abciximab, Eptifibatide, Tirofiban, αIIbβ3 antagonists, Natalizumab, 3 mg to ±52 μg/mL, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427, are administered intraocularly or topically to a patient suffering from ocular inflammatory processes caused by viral or non-viral infection or after eye surgery, such as glaucoma, retinal detachment, or cataract extraction at a concentration in the range of about 1 nanogram/ml (0.0000001%) to less than 1 microgram/ml (less than 0.0001%).

In one embodiment, injectable or polymeric nanoparticle or microparticles of the Wnt inhibitors such as FH535, IWP-2, PNU-74654, IWR-1endo, IWR-exo, niclosamide or Rock inhibitors or integrin inhibitor such as abegrin cilengitide, abciximab, tirofiban, natalizumab eptifibatide or a low concentration 1 microgram to 10 micrograms as a solution or polymeric nanoparticles, GSK-3 inhibitors 429286, alone or in combination with or without ACPP may be injected into the vitreous cavity as an implant or nano- or microparticles at concentration of 1 nanogram to few microgram release per day for 1-6 months in chronic inflammatory diseases, such as diabetic retinopathy, uveitis, macular edema, dry and wet macular degeneration, with or without anti VEGFs, retinal detachment, ocular tumors, multifocal choroiditis, uveitis, proliferative vitreoretinopathy (PVR), fungal or viral infections, sympathetic opthalmia, histoplasmosis, and uveal diffusion.

In another preferred embodiment, proliferative vitreoretinopathy (PVR) caused by recurrent retinal detachment and formation of traction bands and membrane over and under the retina, nanoparticles, e.g., dendrimer or microparticles of the Wnt inhibitors such as FH535, IWP-2, PNU-74654, IWR-1endo, IWR-exo, niclosamide or Rock inhibitors or integrin inhibitors such as abegrin cilengitide, abciximab, tirofiban, natalizumab eptifibatide or a low concentration 1 microgram to 10 micrograms as a solution or polymeric nanoparticles with CPP, or GSK-3 inhibitor 429286, alone or in combination with or without ACPP may be injected in the vitreous cavity, subconjunctivally, or inside the choroid to prevent the side effects of the surgery.

Laser trabeculoplasty is a procedure in which argon laser is applied to the trabecular meshwork of the eyes outflow channels. ALT is applied to reduce the intraocular pressure in about 20-30% of cases after the one year. The disadvantages have been potential scar formation in the trabecular meshwork. Subsequent studies using selected laser trabeculoplasy (SLT) demonstrated that the thermal or coagulative energy may not have been needed for many of the patients.

Though various laser pulses have been used for SLT, no report describes the use of femtosecond to nanosecond pulses.

In one embodiment, SLT laser application using femtosecond, nanopulse or micropulse application encourages the renewal of the remaining cells, and to treat glaucoma. In one embodiment, therefore it would be desirable to eliminate the inflammatory process using Rock inhibitors such as fasudil hydrochloride (inhibitor of cyclic nucleotide dependent- and rho kinases); netarsudil rhpressa, GSK 429286 (a selective ROCK inhibitors); H 1152 dihydrochloride (a selective ROCK inhibitor); glycyl-H 1152 dihydrochloride (a more selective analog of H 1152 dihydrochloride); HA 1100 hydrochloride (a cell-permeable, selective ROCK inhibitor); SR 3677 hydrochloride (a potent, selective ROCK inhibitor); Y 39983 dihydrochloride (a selective ROCK inhibitor); and Y 27632 dihydrochloride a selective p160 ROCK inhibitor or Wnt inhibitors, such as FH535, IWP-2, PNU-74654, IWR-1endo, IWR-exo, niclosamide or integrin inhibitor such as abegrin cilengitide, abciximab, tirofiban, natalizumab, eptifibatide or a low concentration 1 micrograms to 10 micrograms as a solution or polymeric nanoparticles with CPP or GSK3 inhibitors 429286 have a beneficial effect and assists in reduction of the intraocular inflammation at the trabecular meshwork, thus reducing the intraocular pressure while increasing the inflow and outflow of the aqueous and simultaneously having a neuroprotective effect on the retinal ganglion cells.

In one embodiment, in addition to abegrin cilengitide, abciximab, tirofiban, natalizumab, or eptifibatide, the integrin inhibitor may also be in the form of R-G-Cysteic Acid (i.e., linear form of R-G-NH—CH(CH.sub.2-SO.sub.3H) COOH or cyclic form of R-G-NH—CH(CH.sub.2-SO.sub.3H)COOH) and their a derivatives as a solution or slow release compound such as PLGA or micelles or other polymeric nanoparticle.

In one embodiment, one implants or injects a bioerodible polymer having a Wnt inhibitor such as FH535, IWP-2, PNU-74654, IWR-1endo, IWR-exo, niclosamide inhibitors or Rock inhibitors or integrin inhibitor or GSK-3 inhibitors 429286, alone or in combination with or without ACPP, whereby an agent is released from the polymeric body by erosion of the polymer, and the medication is delivered in the vitreous cavity or in the anterior chamber at the rate of 0.1 nanograms to 1 micrograms per milliliter or more to achieve a constant concentration of 1 nanogram to microgram or more per day for 3 weeks to 6 months after SLT or any other surgical procedure.

The increased intraocular pressure over time damages the retinal ganglion cells through various pathways, specifically activation of transient receptor potential vanillod isoform4 (TRPV4) ion channels, pannexin-1 (Panx1), and p2x7 receptors that ultimately lead to the retinal ganglion cell degeneration. In one embodiment, with the rise in the intraocular pressure, Rock inhibitors are administered simultaneously with probenecid to inhibit pannexin-1 (Panx1), and p2x7 receptors.

In one embodiment, one uses Rock inhibitors, with Wnt inhibitors or Anti-integrins or GSK inhibitors given topically subconjunctivally or intravitreally as a slow release polymer that reduces the signal for cellular adhesion and proliferation to eliminate the side effects of the rise in the intraocular pressure and damage to the retinal ganglion cells.

In one embodiment, the Wnt inhibitors or Rock inhibitors or integrin inhibitors such as abegrin cilengitide, abciximab, tirofiban, natalizumab eptifibatide or a low concentration 1 microgram to 10 micrograms as a solution or polymeric nanoparticles or GSK inhibitors 429286 can be in polymeric nanoparticles, micelles, solution as a topical application, delivering the medication from one nanogram to one microgram to 20 micrograms per day or more. The medication can be implanted or injected in the eye as an implant in a micro-nanoparticle format in dendrimers, or polylactic or polyglycolic acid or a combination or as slow drug delivery polymers using chitosan or polycaprolactone, porous silicon or coated with CPP or ACPP to reduce the inflammatory process, etc.

In one embodiment, small molecule Wnt inhibitor PKF118-310, the Wnt/β-catenin pathway inhibitor and Fasudil, a Rock inhibitor Fasudil (HA-1077), a selective RhoA/Rho kinase (ROCK) inhibitor, or Y-27632, small molecule inhibitor of ROCK1 and ROCK2, with CPP or ACPP, etc. may be dissolved in an organic solvent such as DMSO or alcohol or sterol, lanosterol, squalene, and/or squalamine, with CPP or ACCPP or containing a polyanhydride, poly(glycolic) acid, poly(lactic) acid, or as nano- or microparticles with (alpha)-cyclodextrin, or (beta)-cyclodextrin, or (gamma)-cyclodextrin, hydroxypropyl-b-cyclodextrin (bHPCD) or polycaprolactone polymer or dendrimers to release a non-toxic dose of medication slowly at desired concentration to the external or internal eye at a non-toxic concentration or along with a macrolide, cyclosporine A, mycophenolic acid, ascomycin, tacrolimus or anti-integrin or GSK-3 inhibitors 429286, or such as a topical lithium or zinc preparation, bis-indole, indirubin, aminopyrimidines, arylindolemaleimides SB-216763, Paullones, pyrazolo [3,4-b] quinoxalines, human kinome, tideglusib, β-carboline alkaloids β-carboline alkaloids Palinurin and tricantin, peptide L803-mts, Axin GID-25 residues, NP-Tideglusib (Noscira).

Other lasers are used to treat diabetic retinopathy, macular edema, to reduce the ischemic retina and VEGF production. However, any laser application, including when used to treat the retinal tear, or open a hole in the iris for passage of aqueous, is associated with minor or major thermal release and damage to the cells exposed to it and causes activation of inflammatory cell pathways leakage of the fluid from the capillaries and cytokine release. The Rock inhibitors, Wnt inhibitor and integrin inhibitors or GSK inhibitors 429286, application to the laser treated areas reduces the unwanted side effects of laser application such as inflammation, cell migration and severe scar formation.

In one embodiment, after laser surgery, a preparation of Rock inhibitors, Wnt inhibitors, or integrin inhibitors alone or in combination can be used to reduce the inflammatory side effects and severe scar formation.

In one embodiment, the Rock inhibitor is used to reduce TGF-β production after therapy and the subsequent scar formation in form of drops or combined with polymeric nanoparticles for slow release delivery after any ocular surgery such as retinal detachment, vitrectomy, retinotomy, glaucoma surgery, cataract surgery, laser trabeculoplasty by intraocular injection or as slow release nanoparticles, dendrimers, polyglycolic acid (PGA) or polylactic acid PLA or a combination or polycaprolactone or chitosan or as liposomal preparation or micelles.

In one embodiment, the Rock inhibitors are selected from the group consisting of Fasudil, Ripasudil, RKI-1447, Y-27632, GSK429286A, Y-30141, and combinations thereof where the device releases the ROCK inhibitor for 3 months to 3 years.

In one embodiment, the Rock inhibitors are selected from the group consisting of Fasudil (HA-1077 a selective RhoA/Rho kinase (ROCK) inhibitor), Y-27632, small molecule inhibitor of ROCK1 and ROCK2 which act as an anti-inflammatory agent and Ripasudil, Netarsudil etc.

In one embodiment, the Rock inhibitors, such as Fasudil (HA-1077 a selective RhoA/Rho kinase (ROCK) inhibitor), Y-27632, small molecule inhibitor of ROCK1 and ROCK2 which acts as an anti-inflammatory agent and Ripasudi, netarsudil, etc. in form of drops or combined with polymeric nanoparticles, dendrimers, or microparticles for slow release delivery after any ocular surgery such as retinal detachment, glaucoma, cataract and after trauma.

In one embodiment, the Rock inhibitor Fasudil (HA-1077) a selective RhoA/Rho kinase (ROCK) inhibitor), a selective ROCK inhibitor such as SAR407899, Y-27632, small molecule inhibitor of ROCK1 and ROCK2 or Ripasudi, netarsudil are administered and released at nanogram to microgram concentrations in a polymeric drug delivery or Botulinum toxin such as Botox as picogram to nanogram concentrations or 1-10 units or more concentration per day which act as an TGF beta inhibitor and as anti-inflammatory agent after retinal surgery, glaucoma surgery preventing cell proliferation and adhesion.

The conventional signaling receptors and integrins serve as linkers between the actin cytoskeleton and extracellular intracellular signaling matrix, stimulating the cell survival, growth, and cell proliferation.

In one embodiment, the anti-integrin are used to inhibit cell proliferation and migration and scar formation in microgram concentrations, e.g., in retinal detachment surgery, vitrectomy to prevent development of proliferative vitreoretinopthy that leads to fixed fold and re-detachment of the retina or after cataract surgery or laser surgery of the retina and trabecular meshwork or laser surgery of the iris or ciliary body or laser of ciliary processes to reduce the intraocular pressure where the integrin inhibitors are selected from the group abegrin, cilengitide, abciximab, tirofiban, natalizumab eptifibatide at non-toxic doses of nanogram to microgram concentrations per milliliter or more.

In one embodiment, the Rock inhibitors such as fasudil, netarsudil, etc. or anti-integrins such as abciximab, Eptifibatide, Tirofiban, αIIbβ3 antagonists, Natalizumab at microgram per milliliter, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427, can be administered as prophylaxis of scar formation after laser surgery, in refractive surgery, post cataract complication or macular edema, or post glaucoma surgery to prevent encapsulating of a stent or closing the drainage channel by a scar, or after retinal surgery or vitrectomy to prevent postoperative cell proliferation in the vitreous cavity over and under the retina and inhibiting cell proliferative vitroretinopathy, or after refractive surgery.

In one embodiment, the non-toxic doses of Wnt inhibitors, integrin inhibitors and/or Rock inhibitors, or Botox, act as an anti-inflammatory agent. The botulinum toxin or botox preparation may be administered topically to the eye or eye lid, forehead skin at1 picogram to 1 nanogram concentrations, 1 pictogram to 5 nanogram or higher concentrations of microgram concentrations, for example, using drops, an ointment, a cream, a gel, a suspension of microspheres, dendrimers, micelles, etc. The agent(s) may be formulated with excipients such as methylcellulose, hydroxypropyl methylcellulose, hydroxypropyl cellulose, the LD50s of any naturally occurring botulinum toxin protein is at 1.3 nanograms per kilogram (abbreviated ng/kg). In a 75 kg (165 lbs.) subjects, the LD50 for botulinum toxin would be 97.5 nanograms if injected directly into a vein or artery. 100 unit vials contains 0.75 nanograms=750 picograms of botulinum toxin A in the entire vial and the amount of non-toxic doses are 1-50 or more international units.

In one embodiment, one administers polymeric nanoparticles or dendrimers to inhibit the Glycogen Synthase Kinase-3 (GSK-3) which is a serine/threonine protein kinase, and plays a key role in Wnt/β-catenin.

In one embodiment, the (GSK-3) inhibitor 269962, is administered in a slow release polymeric form or lithium or zinc preparation, bis-indole indirubin, aminopyrimidines, arylindolemaleimides SB-216763, Paullones, pyrazolo [3,4-b] quinoxalines, human kinome, tideglusib, β-carboline alkaloids β-carboline alkaloids Palinurin and tricantin, peptide L803-mts, Axin GID-25 residues, NP-12/Tideglusib at non-toxic concentrations.

In one embodiment, when nanoparticles are coated with cell penetrating peptides (CPPs), the agent penetration is extended to at least one of the posterior segment of the eye or anterior segment of the eye or from the cornea to the retina.

In one embodiment, a mucophilic preparation such as chitosan or micelles, of Rock inhibitors, integrin inhibitors, or Wnt inhibitors is administered comprising a compound selected from the group consisting of chitosan, dendrimer, coated or linked with cell penetrating peptides (CPPs), activated cell penetrating peptides (ACPPs), hyaluronic acid, and combinations thereof.

In one embodiment, the integrin inhibitors are administered with cell penetrating peptide or ACPP coated dendrimers or nanoparticles, macrolides such as cyclosporine A, mycophenolic acid, tactolimus or ascomycin as nanoparticles or conjugated with the dendrimers or in a solution in the early stage of glaucoma as a topical medication at a concentration of Rock inhibitors of 1-5 micrograms per milliliter once or twice per day and macrolides at concentration of 0.000000001% to 0.1% in a physiological solution.

In one embodiment, a porous tubular implant further contains stem cells, or genetically modified stem cells, for slow release where the stem cells are selected from the group consisting of cultured stem cells, genetically modified stem cells, embryonic stem cells, mesenchymal stem cells, neuronal stem cells, pluripotent stem cells, glial stem cells, stem cells or genetically modified stem cells having complement receptor 35, and combinations thereof to treat loss of cells in the retina, retinal pigment epithelium, corneal genetic diseases or loss of ganglion cells or choroid or cells in trabecular meshwork.

In one embodiment, the Rock inhibitors are administered with macrolides such as cyclosporine A, mycophenolic acid, tacrolimus or ascomycin in the early stage of glaucoma as topical medication at a concentration of Rock inhibitors 1-5 microgram/ml once or twice per day and macrolides at concentration of 0.000000001% to 0.1% in a physiological solution for topical application or injection in the eye.

In one embodiment, the slow release preparation of Rock inhibitors or integrin inhibitors or combination thereof are administered inside the eye as a polymeric implant in the lens capsule after cataract surgery, or implanted in the vitreous or in the anterior chamber or in the suprachoroidal space or under the conjunctiva to deliver medication for 3-6 months to release medication at microgram concentrations in a non-toxic dose daily after cataract surgery, glaucoma surgery, to prevent encapsulation of a glaucoma stent or bleb scarring or membrane formation after retinal surgery, or cell proliferation after retinal surgery, or retinal laser surgery.

In an embodiment, where a patient's eye shows increased intraocular pressure or glaucoma, activation of transient receptor potential vanillod isoform4 (TRPV4) ion channels, pannexin-1 (Panx1), and p2x7 receptors are activated leading to glial cell activation and inflammatory response involving Toll-like receptors, complement molecules, tumor necrosis factor-a (TNFa), and interleukin-1.beta. leading to degeneration of the ganglion cells, retina, systemic or topical or local administration of probenecid, nanoparticle-coated probenecid, mefloquine, alone or preferably with ROCK inhibitors inhibit the panx1 pathway preventing release of ATP and ganglion cell degeneration.

In one embodiment, one uses laser pulses to heat up the tissue and create a scar around a retinal tear preventing a retinal detachment or cryosurgery by freezing the retinal tissue around the retinal tear that is not seldom is associated with heavy scars and traction formation. The laser surgery is also often associated with inflammation that causes cell proliferation on the retina, producing traction on the retina or pre-retinal and sub-retinal scar formation, inducing re-detachment of the retina due to cell proliferation in proliferative vitreoretinopathy. In one embodiment, one administers a slow release preparation of Rock inhibitors or integrin inhibitors or combination thereof inside the eye as a polymeric implant, or nano- or microparticles in the lens capsule after cataract extraction, or after laser or retinal surgery, or the polymeric implant placed as described in U.S. application Ser. No. 15/269,444, which is expressly incorporated by reference herein in its entirety, in the vitreous or in the anterior chamber or in the suprachoroidal space or under the conjunctiva to deliver medication for 3-6 months and release medication at microgram concentrations in a non-toxic dose daily and prevent the side effects of the surgery.

In one embodiment, one administers polymeric nanoparticles or dendrimers to inhibit the Glycogen Synthase Kinase-3 (GSK-3) which is a serine/threonine protein kinase, and plays a key role in Wnt/β-catenin pathway.

In one embodiment, the GSK-3 inhibitor such as 429286, are administered with cell penetrating peptides ((CPP) or ACPP coated-dendrimers or nanoparticles, or macrolides such as cyclosporine A, mycophenolic acid, tacrolimus or ascomycin as nanoparticles or conjugated with the dendrimers or in a solution in the early stage of glaucoma as a topical medication at concentration of Rock inhibitors of 1-5 micrograms per milliliter once or twice per day and macrolides at concentration of 0.000000001% to 0.1% or more in a physiological solution.

In one embodiment, in a dry form of age related macular degeneration, one administers laser applications around the degenerative areas to induce a minor inflammation that acts as a beacon for the stem cells and simultaneously one injects 1000-100,000 genetically modified stem cells along with Rock inhibitors to induce retinal pigment growth within the areas where these cells are lost and to enhance regeneration of the sensory retina.

In one embodiment, in a dry form of age related macular degeneration, one administers laser spots around the degenerative areas to induce a minor inflammation that acts as a beacon for the stem cells or genetically modified stem cells and simultaneously injects 1000-100,000 modified stem cells along with Rock inhibitors under the retina close to the degenerative areas to stimulate regrowth and survival or the survival of the stem cells, while the slow release polymer releases Rock inhibitors in the vitreous cavity for 1-3 years using porous silicon implant, polylactic acid or injectable porous nano- or microparticles carrying Rock inhibitors with GSK-3 inhibitors.

In one embodiment, when the stem cells of a patient also carry the genetic defect that they have inherited, the stems cells of the patient are modified in cell culture prior to the administration to the eye. The stem cells may be cultured stem cells, genetically modified stem cells, embryonic stem cells, mesenchymal stem cells, neuronal stem cells, pluripotent stem cells, glial stem cells, etc. These stem cells can be genetically modified using the technology known as non-homologous end joining (NHEJ) or homologous directed repair (HDR) in which the gene modification is done along with CRISPR cas9 or Cpf1 using nanoparticles as a vector to deliver the gene(s) inside the cells, or to cut out the mutated gene, eliminating the side effects of immune activation, as observed with the viral vector gene delivery. The functionality of this technology is described in the U.S. Pat. No. 10,022,457, which is expressly incorporated by reference herein in its entirety.

In one embodiment, for gene transfer, one uses CRISPR-conjugated to the desired nanoparticles via thiol to create a strong electrostatic bound. CRISPR-NP are then conjugated with Cas 9 and gRNA to be used in non-homologous end joining NHEJ or the NP-DNA conjugate is hybridized with the donor DNA, thus creating NP-donor DNA suspended in sodium silicate, generating NP-Donor-Cas9 RNP-silicate, which is re-suspended in a cationic polymer such as cyclodextrin or calixarene-based polycationic amphiphiles polymer as gene delivery systems or PAsp(DET) to be used in Homology Directed repair (HDR) after administration to the stem cells with appropriate gene(s).

In one embodiment, the nanoparticles, can be metallic, such as gold or ferric oxide, combination of silica/gold, QDs, polymeric organic, cationic polymeric NP, PAsp(DET), piezoelectric, such as perovskites, quartz, or other vectors such as Naked DNA, etc. with the size of 5-50 nanometers.

In one embodiment, the nanoparticle is gold or ferromagnetic covered with gold before conjugated with the CRISPR 'gRNA-cationic polymer and or gold NP-Donor DNA and suspended in silicate and a cationic polymer.

In one embodiment, one can attach multiple genes to the nanoparticles via thiol or amine, amide, before suspending in silicate and cationic polymer to encourage cell penetration and escape from the endosome after their administration to the tissue culture.

In one embodiment, the nanoparticle is PAsp(DET) or gold to which CRISPR or donor DNA is attached via thiol, before suspending the complex in sodium silicate to be followed by another cationic polymer to enhance cell penetration and endosomal escape and gene(s) delivery to the nucleus after their administration to the stem cell culture.

In one embodiment, the device further contains stem cells, where the stem cells are selected from the group consisting of cultured stem cells or modified genetically modified stem cells, genetically modified stem cells, embryonic stem cells, or modified genetically modified embryonic stem cells, mesenchymal stem cells, or genetically modified mesenchymal stem cells, neuronal stem cells, or genetically modified stem cells, neuronal pluripotent stem cells, glial stem cells, or genetically modified stem cells, neuronal stem cells having complement receptor 35, and combinations thereof.

In one embodiment, the method comprising injecting stem cells or genetically modified stem cells to replace the loss of endothelial cells and normalize the function of the perifoveal capillaries in patients with diabetic macular edema associated with vascular leakage, demonstrable deep retinal vascular deformation or loss, age related macular degeneration, glaucoma, and retinal ischemia either centrally or peripherally.

In one embodiment, the stem cells or genetically modified stem cell are administered at a concentration of about 5,000 to 100,000 stem cells or genetically modified stem cells having complement receptor 35 (CD 35) in combination with ROCK inhibitors.

In one embodiment, the method comprising injecting stem cells or genetically modified stem cells to replace the loss of endothelial cells and normalize the function of the perifoveal capillaries in patients with diabetic macular edema associated with vascular leakage, demonstrable deep retinal vascular deformation or loss, age related macular degeneration, glaucoma, and retinal ischemia either centrally or peripherally.

In one embodiment, the stem cells or genetically modified stem cell are administered at a concentration of about 5,000 to 100,000 stem cells or genetically modified stem cells having complement receptor 35 (CD 35) in combination with Rock inhibitors.

In another further embodiment, the treatment does not apply any means that provides 100% oxygen to the patient, since 100% oxygen is toxic to the tissue and increases the inflammatory response that is not desirable in patients with COVID-19.

In one embodiment, the amount of oxygen for inhalation is 20-30% or 30-40% or 40-50% or 50-80% best with standard C-Pap used for sleep apnea coupled with an oxygen tube supplying a certain amount of oxygen to the air through the nose or mask.

In one embodiment, the treatment is divided into two or three stages, depending on the severity of the lung inflammation, at least one or two antivirals, one to two Rock inhibitors or one to two Wnt inhibitors, one or two GSK inhibitors, or one or two integrin inhibitors, at least one or two protease inhibitors alone or at least one or two IL-1 or IL inhibitors or one to two known antivirals, such as amantadine, nucleoside analogs such as AZT, aciclovir, ganciclovir, and vidarabine in combinations are used as inhalation where the medication is dissolved in semifluorinated alkanes or combined as polymeric release nanoparticles or one to two known antivirals such as amantadine, nucleoside analogs such as AZT, aciclovir, ganciclovir, and vidarabine such as, or again depending on the severity of the disease, e.g., in end-stage disease, one can administer these combination of medications, orally, intravenously, semifluorinated alkanes with alkyl chains are harmless in the examined range from $C_6$ to $C_{10}$ but preferably $C_6$, in addition to inhalation with simultaneous administration of macrolide immune-suppressants, such as cyclosporine, mycophenolic acid and with heparin or low molecular weight heparin or Coumadin, prevent overactive immune response and blood clot formation to prevent vascular infarct, a side effect of the COVID-19 infection. Furthermore plasmapheresis, kidney dialysis can be done to remove cytokines with or without extra-corporal oxygenation if blood oxygenation remains low with the ventilator, etc.

In the abovedescribed treatment with two or three stages, the antiviral agents prevent either the attachment of viruses to the cell wall or block their cell penetration or inhibit the virus replication by damaging the nucleic acid (DNA or RNA) of the virus, etc. The anti-inflammatory compound affects the cell pathway of cell inflammation in response to various agents affecting the cells in a tissue or in an organ. Among the most important anti-inflammatory compounds are Wnt inhibitors that prevent early stage inflammation, Rock inhibitors that prevent rock proteins activation, which blocks TGF beta that stimulates scar formation after the inflammation is controlled. Similarly integrin inhibitors contribute to healing of the inflamed tissue preventing it from becoming overactive producing over active scarring, and GSK-3 are active in intracellular signaling pathways, involved in cellular proliferation, migration, and apoptosis. Inhibition of GSK-3 contributes to the healing process. GSK-3 inhibitors increases the CD8(+) OT-I CTL function and the clearance of viral infections. Interleukins (ILs) are a group of cytokines produced by cells and participate in a number of inflammatory processes. There are a number of interleukins from IL-1 to IL-17, inhibition of these cytokines significantly reduces an inflammatory response in the tissue produced after an number of diseases, such as bacterial and viral infections, etc. Azidothymidine (AZT) or Zidovudine (ZDV) is an antiretroviral used to prevent and treat HIV/AIDS infection along with Acyclovir, ganciclovir and Vidarabine are active against a broad spectrum of viral infection in patients with AIDS or acquired immunodeficiency syndrome, etc. Semifluorinated alkanes are non-toxic and do not cause irritation, and can carry oxygen used previously as a blood substitute. However, no one has used this characteristic to deliver simultaneously oxygen in the lung simultaneously with other medications by loading them also with oxygen prior or as aerosolized nanodrops or microdrops in the spay system. Semifluorinated alkanes dissolve numerous hydrophilic or hydrophobic compounds. Their temperature transition from liquid to vapor is low, so they can evaporate easily. They can be formed as a liquid compound or can be aerosolized for inhalation through the nose or mouth along with various medications. Their applications are best for surfaces of the skin or mucosa or aerosolized for inhalation to reach the alveoli of the lung, etc. They may not be approved yet for intravenous application. For the latter application, one can use a physiologic solution with a pH of 7-7.5 and osmolality of about 300 mosmol to administer the medications intravenously or as spray for inhalation. The anti-inflammatory agents described above, including the anti-virals can be taken orally, such as Zidovudine and Acyclovir, ganciclovir and Vidarabine etc. However, a formulation of these and others antivirals can be given intravenously or intramuscularly in solution or can be dissolved in semifluorinated alkanes for inhalation.

In one embodiment, a method of drug delivery is described for treatment of respiratory tract inflammatory diseases caused by various viruses, such as influenza, parainfluenza, SAR or coronaviruses, COVID-2 or COVID-19, etc., EBV, Herpes virus, etc., or a bacterial infection, etc. where the anti-viral medications are administered along with cell pathway inhibitors to block an inflammatory response of the tissue which does not inhibit an immune response, such as a Rock inhibitor, Wnt inhibitor, GSK inhibitor, integrin inhibitors, or in combination, dissolved in a non-toxic or non-irritative semifluorinated alkanes liquid, or other liquids, which are amphiphilic liquids dissolving both hydrophilic and hydrophobic drugs, or maintaining polymeric slow release nanoparticles carrying the medication applied as a spray or evaporative solution or in a evaporative aerosolized drops during the inhalation passing through the nose or mouth to reach the lung alveoli, while on the way the nano- or micro-droplets attach to the mucosa, epithelia or endothelial cells of the nose pharynx, larynx, epiglottis trachea, bronchi and lung alveoli. The semifluorinated alkanes rapidly evaporates at body temperature leaving the medication(s) or slow release nanoparticle on the surface of the tissue, thus releasing the medication over a time period of one day to one week to 3 weeks or months depending on the composite of the polymer.

In one embodiment, a method of drug delivery is described for treatment of respiratory tract inflammatory diseases caused by various viruses, such as influenza, parainfluenza, SAR or coronaviruses, COVID-2 or COVID-19, etc., EBV, Herpes virus, etc., or bacterial infections, etc. where the anti-viral medication is administered along with cell pathway inhibitors to block an inflammatory response of the tissue which does not inhibit immune response, such as Rock inhibitors such as Fasudil hydrochloride, or ROCK2, Fasudill-(5-Isoquinolinesulfonyl)-2 Methylpiperazine Calcium Channel Blockers, or as SAR407899, or Inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin in conjunction with at least two antivirals, such as Glidesivir, Favipiravir, Remdesivir, nanoviricides, Oyal, umifenovir, tamivir ribavirin dissolved in a liquid semifluorinated alkanes, or other liquids, or as polymeric slow release nanoparticles applied as drops or spray or evaporative solution or in a evaporative aerosolized nano- to micro-drops that travels through the nasal mucosa to reach the lung alveoli, while on the way, attaches to the mucosa, epithelia or endothelial cells or nose pharynx, larynx, epiglottis traches, bronchi and lung alveoli. The semifluorinated alkanes rapidly evaporate at body temperature leaving the medication(s) or slow release nanoparticles of polylactic, polyglycolic acid or combination thereof, or combination of polycaprolactone, anhydrides, porous silicone, micelles, and/or liposomes on the surface of the tissue or slow release nanoparticle on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, etc., EBV, Herpes virus, etc., or bacterial infections, etc. where the anti-viral medications are administered with a cell pathway inhibitor to block an inflammatory response of the tissue which does not inhibit an immune response, such as in a physiologic pH adjusted to 7-7.5 pH and osmolarity of 280-300 mOsm or slow release polymeric nanoparticles from the Wnt compound, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, etc., small molecule Wnt inhibitor PKF118-310, the Wnt/β-catenin pathway inhibitor dissolved in a liquid semifluorinated alkane, or other liquids, or as polymeric slow release nanoparticles applied as a spray or evaporative solution or in evaporative aerosolized drops that travel through the nasal mucosa to reach the lung alveoli while on the way attaches to the mucosal, epithelial, or endothelial cells of nose pharynx, larynx, epiglottis traches, bronchi and lung alveoli. The semifluorinated alkane rapidly evaporates at body temperature, thereby leaving the medication(s) or slow release nanoparticles on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, etc. EBV, Herpes virus, etc., or bacterial infections, etc. where the anti-viral medication is administered with a cell pathway inhibitor to block an inflammatory response of the tissue which does not inhibit an immune response like steroids, the cell pathway inhibitor being, for example, a GSK 269962 inhibitor or GSK inhibitors, such as synthetic small-molecule ATP-competitive inhibitors, and substrate-competitive inhibitors, non-ATP-competitive inhibitors, where FRAT/GBP competes with Axin inhibiting GSK-3 activity or anti-integrins such as Risuteganib, vedolizumab, anti-integrins, such as abciximab, Eptifibatide, Tirofiban, $\alpha IIb\beta 3$ antagonists, Natalizumab, 3 mg to ±52 μg/mL, MLN-00002, Firategrast, IVL745, antagonists of $\alpha v\beta 3$ and/or $\alpha v\beta 5$ integrins, LM609, Vitaxin, Abegrin, CNTO95, Cilengitide. MLD-based disintegrins, L000845704, SB273005, Volociximab, JSM6427 or dissolved in a liquid semifluorinated alkanes or other liquids with other medications or as polymeric slow release nanoparticles applied as a spray or evaporative solution or in evaporative aerosolized drops that travels through the nasal mucosa to reach the lung alveoli while on the way attaching to the mucosal, epithelial or endothelial cells or nose pharynx, larynx, epiglottis traches, bronchi and lung alveoli where the semifluorinated alkane/medication(s) rapidly evaporates leaving the medication(s) or slow release nanoparticles on the surface of these organs after inhaling one time to 10 times as needed, thereby releasing the medication over a time from one day to 2 weeks or more. However, the dose applied through this methodology is <30 times in concentration compared to systemic medication given intravenously, etc. and it is more effective locally, to combat the viruses and their complications.

In one embodiment, a method of drug delivery described for treatment of respiratory tract inflammatory diseases caused by various viruses, such as influenza, parainfluenza, SAR or coronaviruses, COVID-2 or COVID-19 etc. EBV, Herpes virus, etc., or bacterial infections, etc. where the anti-viral medications are administered with IL-1 and or IL-6 inhibitors, such as Kevzara (sarilumab) or in combination with Rock inhibitors, etc. to block inflammatory response IL-6 of the tissue which does not inhibit immune response (as steroids do), dissolved in liquid semifluorinated alkanes or other liquids with other medications or as polymeric slow release nanoparticles applied as a spray or an evaporative solution or in evaporative aerosolized drops that travel through the nasal mucosa to reach the lung alveoli while on the way attaching to the mucosal, epithelial or endothelial cells or nose pharynx, larynx, epiglottis traches, bronchi and lung alveoli where dissolved medication in the semifluorinated alkanes rapidly evaporates from the lung leaving the medication(s) and/or slow release nanoparticles on the surface of these organs after inhaling, one time to 10 times or more as needed releasing the medication over a time period from one day to 2 weeks or more.

In one embodiment, a method of drug delivery described for treatment of respiratory tract inflammatory diseases caused by various viruses, such as influenza, parainfluenza, SAR or coronaviruses, COVID-2 or COVID-19, etc. EBV, Herpes virus, etc., or bacterial infections, etc. where the anti-viral medication is administered with a protease inhibitor, such as Ebselen, an inhibitor to target COVID-19, Mpro or Ganovo to block the entry of the virus in the cell dissolved in a liquid semifluorinated alkane or other liquids which does not cause irritation, with other medications, or as polymeric slow release nanoparticles applied as a spray or evaporative solution or in a evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where the semifluorinated alkane rapidly evaporates leaving the medication(s) or slow release nanoparticles on the surface of these organs after inhaling one time to 10 times as needed, thereby releasing the medication over a time from one day to 2 weeks to months or years.

In one embodiment, a method of drug delivery described for treatment of respiratory tract inflammatory diseases caused by various viruses, such as influenza, parainfluenza, SAR or coronaviruses, COVID-2 or COVID-19, etc., EBV, Herpes virus etc., or bacterial infections, etc. where the anti-viral medication such as Lopinavir, or linebacker and equivir, or HIV protease inhibitor darunavir, is administered with a protease inhibitor such as Ganovo or INO-4800 to block the entry of the virus into the cell and APNO1 an angiotensin converting enzyme 2 to block the virus adhesion to the cells, or in combination with a Rock inhibitor, Wnt inhibitor, GSK inhibitor, or integrin inhibitor or IL-1 or IL-6 inhibitor Kevzara dissolved in a liquid semifluorinated alkane or other liquids with other medications as a nanoparticle compound or as polymeric slow release nanoparticles applied as spray or evaporative solution or in evaporative aerosolized drops that travel through the nasal mucosa to reach the lung alveoli while on the way attaching to the mucosal, epithelial or endothelial cells or nose pharynx, larynx, epiglottis traches, bronchi and lung alveoli where the semifluorinated alkane rapidly evaporates because of high body temperature, leaving the medication(s) or slow release nanoparticles on the surface of these organs after inhaling one time to 10 times or more as needed, releasing the medication over a time from one day to 2 weeks to months or years in the chronic disease of the lung.

In one embodiment, a method of drug delivery described for treatment of respiratory tract inflammatory diseases caused by various viruses, such as influenza, parainfluenza, SAR or coronaviruses, COVID-2 or COVID-19, etc., EBV, Herpes virus, etc., or bacterial or fungal infections, etc. where the anti-viral medication such as Lopinavir, or linebacker and equivir, Arbidol, NanoViricide and/or an HIV protease inhibitor darunavir, is administered with a protease inhibitor such as Ganovo or INO-4800 to block the entry of the virus to the cell and APNO1 an angiotensin converting enzyme 2 to block the virus adhesion to the cells, or in combination with PolyTop mAb therapy or cocktail of antibody therapy by regeneron Velochimmune or Vir's antibody platform or VAAST platform human monoclonal antibody or TZLS-501 an IL 6 inhibitor or Kevzara or Actems Tocilizumab with Rock inhibitors, Wnt inhibitors, GSK inhibitors or integrin inhibitors or anti-bacteria or antifungal or IL-1 inhibitors dissolved in a liquid semifluorinated alkane or other liquids and other medications and polymeric slow release nanoparticles are applied as a spray or evaporative solution or in evaporative aerosolized drops that travel through the nasal mucosa or mouth to reach the lung alveoli while on the way attaching to the mucosal, epithelial or endothelial cells or nose pharynx, larynx, epiglottis traches, bronchi and lung alveoli where the semifluorinated alkane/medication(s) rapidly evaporates leaving the medication(s) or slow release nanoparticles on the surface of these organs after inhaling one time to 10 times or more as needed releasing the medication over a time from one day to 2 weeks, months, or years.

In one embodiment, after inhalation or systemic treatment of viral inflammation with antivirals, a severe inflammatory response is treated with Rock, Wnt, GSK, or integrin inhibitors alone or in conjunction with other therapeutic immunosuppressant agents dissolved in the semifluorinated alkanes or other liquids with other medications, such as a macrolide cyclosporine, mycophenolic acid, ascomycin Immunomycin, FR-900520, FK520, is an ethyl analog of tacrolimus (FK506) for inhalation, can reduce the overt inflammatory response of the disease process; although, in a later stage of the disease, steroids can be used even though steroids have their unwanted side effects and also can be replaced with NSAIDs that are more desirable, however, inhalation would be preferable to systemic therapy, except in desperate end stage cases where systemic steroids might be useful in combination with antivirals.

In one embodiment, in an immunosuppressed individual after organ transplantation, in addition to inhalation therapy, systemic administration of natural killer cells or modified killer T-cells systemically along with Wnt, Rock, GSK inhibitors and integrin inhibitors, antibiotics or antifungals, both as inhalation dissolved in semifluorinated alkanes or other liquids, or systemically can be given to combat an inflammation or any superinfection with bacteria and fungi which require additional antibacterial and/or antifungal medications can be administered both systemically or by inhalation dissolved in semifluorinated alkanes or other liquids as needed.

In one embodiment, a method of drug delivery described for treatment of respiratory tract inflammatory diseases caused by various viruses, such as influenza, parainfluenza, SAR or coronaviruses, COVID-2 or COVID-19, etc., EBV, Herpes virus, etc., or bacterial infections, etc. where the anti-viral medication such as Lopinavir, or linebacker and equivir, unifenovir and a vaccine, such as encapsulated mRNA 1273, COVI-19 S-Timer, or ASRS-cov-2 viral-like particles (VLP) or Li-key vaccine etc. with a Rock inhibitor, Wnt inhibitor, GSK inhibitor, or integrin inhibitor or IL-1 dissolved in a liquid semifluorinated alkane or other liquids with other medications or as polymeric slow release nanoparticles applied as a spray or evaporative solution or in evaporative aerosolized drops that travel through the nasal mucosa to reach the lung alveoli while on the way attaching to the mucosal, epithelial, or endothelial cells or nose, pharynx, larynx, epiglottis, trachea, bronchi and lung alveoli where the semifluorinated alkane rapidly evaporates leaving the medication(s) or slow release nanoparticles on the surface of these organs after one or more times of inhalation as needed.

In one embodiment, a vaccine is administered to a patient every 3-6 months to prevent re-infection by a coronavirus that causes COVID-19.

In one embodiment, the described medication can be supported by oral administration of flavonoid compound found in the vegetable, fruits or coco, sulforaphane, vitamin D and high doses of vitamin C. or quercetin etc.

Example 9

The patient was a 60 year old female patient with no history of heart disease, and had a running nose and cough of 2 days duration, fever and chills, and a productive cough. The patient was somewhat weak and had loss of appetite and sense of the smell recently, no history of heart disease or smoking. Her EKG was normal, the COVID-19 culture became positive and she was treated with a combination of remdesivir, a Wnt inhibitor, and a protease inhibitor dissolved in a semifluorinated alkane or other liquids used for inhalation 4 times along with supportive therapy for 3 weeks through which she gradually recovered.

In one embodiment, in early coronavirus infection, it is treated with a combination of an antiviral medication such as Remdesivir, oseltamivir ribavirin at non-toxic concentrations or Rock inhibitor or Wnt inhibitor, or GSK inhibitor or integrin inhibitor at non-toxic concentrations in a liquid of semifluorinated alkanes or other liquids which does not cause irritation, sprayed in the nose or through the mouth or nebulized for deep breathing through the mouth 1-10 times or more as needed.

Example 10

A 50 year-old man felt that he might have come in contact with someone who had been sneezing in the bus on his was to home 3 days ago. He complained of cold-like symptoms, but had a significant elevated temperature of 101 degrees F. and muscle weakness, sore throat, some coughing, the chest x-ray showed normal lung image with no difficulty in breathing. His COVID-19 virus test became positive. He was treated with a combination of fasudil, a Rock inhibitor and oseltamivir (Tamiflu) in a semifluorinated alkane for inhalation 4 times daily dissolved in semifluorinated alkane or other liquids and oral Tylenol, and baby aspirin 2-3 times daily as needed, his symptoms improved gradually within 3 days while he was on therapy and followed for 5 weeks when the symptoms completely recovered and he returned to work.

In one embodiment, in early coronavirus infection without history of hypertension or known cardiac disease, QTC prolongation or failure, stent or infarct, it is treated with a combination of an antiviral medication such as Remdesivir, tamivir, ribavirin at non-toxic concentrations and/or Rock inhibitor or Wnt inhibitor, or GSK inhibitor or integrin inhibitor, or in combinations, at non-toxic low concentration of Hydroxychloroquine/chloroquine which has shown some efficacy against viruses such as HIV, Zika virus, even SARS-CoV, by oral administration high doses of 400 mg to 600 mg with the side effect of heart and kidney disease, but low concentrations of 6 mg or less were used in a liquid semifluorinated alkane which does not cause irritation, sprayed in the nose, or through the mouth, or nebulized for inhalation, deep breathing through the mouth 1-4 times or more as needed to block intracellular penetration of the virus. Of note is that previously high oral doses of 600 mg Hydroxychloroquine/chloroquine had been given orally and not by inhalation at 1/100 of the oral dose. The oral daily administration can have serious systemic complications.

In one embodiment, antivirals alone or combined with protease inhibitors, or with convalescent plasma, antibody against COVID-19, Baricitinib, etc. can be administered when dissolved in semifluorinated alkanes or other liquids which does not cause irritation, sprayed in the nose or through the mouth or nebulized for inhalation, with C-Puff for deep breathing through the mouth 1-4 times daily or as slow release polymeric nanoparticles once for prophylactic viral upper respiratory tract prior to the start of the infection or in situations that one suspects that he or she might come or have come in contact with a person carrying viral diseases wherein the antiviral can be chosen depending on the expectation of specific viruses and the treatment can continue for a period of time until the danger passes, e.g., in traveling by plane to certain areas with reported cases.

Example 11

A 44 year-old male executive had to travel to Italy by plane to an area which was considered a hot zone for coronavirus. The person was not complaining or having any symptoms of COVID-19, his blood pressure was normal, no fever or running nose, etc. His temperature was 97 degrees F. and his examination was otherwise normal. He was advised of the option of doing nothing or not traveling or treating himself prophylactically with daily application of combination therapy with oseltamivir (Tamiflu) and Baricitinib, and a GSK inhibitor, and COVID-19 S-Timer intranasally followed with deep breathing 3-4 times daily in a semifluorinated alkane for 3 days until he returned, he was then examined for signs of COVID-19 disease. He felt that the medication was well tolerated and no side effects were produced, his repeat examination showed he was normal with no fever, cough, or running nose, etc.

In one embodiment, a method of drug delivery described for treatment of respiratory tract inflammatory diseases caused by various viruses, bacteria, etc. or chronic smoking or exposure to toxic aerosolized nanoparticles and air pollution or asthma and allergens and pathogens, where the inflammation or its consequences are treated with an inflammatory cell pathway inhibitor to block the inflammatory response of the tissue while it does not inhibit an immune response, such as a Rock inhibitor, Wnt inhibitor, GSK inhibitor, or integrin inhibitors IL-1 and IL-6 inhibitors dissolved in liquid semifluorinated alkanes or other liquids as the drug, or in polymeric slow release nanoparticles applied locally as a spray or evaporative solution or in evaporative aerosolized drops that travels through the nasal cavity or mouth to reach the lung alveoli and while on the way attaching to the mucosa, epithelial or endothelial cells of the mouth, nose throat, pharynx, larynx, epiglottis, trachea, bronchi and lung alveoli where the semifluorinated alkanes which is non-toxic or causes irritation to the tissue, rapidly evaporates leaving the medication(s) or slow release nanoparticles, such as polymeric lactic, glycolic acid, or in combination, or porous silicon or polycaprolactone, etc. as known in the art on the surface of these tissues, releasing the medications over a time of daily inhalation, daily for one week to 3 weeks, then the release of the medication from the nanoparticles continues for months or years to inhibit chronic inflammatory lung diseases.

In one embodiment, the disease process affects many other organs and creates an inflammatory response that can damage these organs, such as in bacterial or viral infections or immune or autoimmune response, chronic inflammation of the prostate, gastro-intestinal tract, joints, one applies a similar strategy for treatment combining anti-bacterial and antiviral with Rock inhibitors, Wnt inhibitors, GSK inhibitors, and integrin inhibitors, IL-6 inhibitors, in a known non-toxic dose administered locally, systematically, or orally either with semifluorinated alkane or the standard way in a physiological solution, or in the form of polymeric functionalized nanoparticles for slow release of the medication.

In one embodiment, the patient having a cytokine storm as a result of a viral infection and body's cellular immune/humoral response receiving the inventive therapy, undergoes plasmapheresis to remove, e.g., such cytokines, enzymes, dead cells, etc. from the circulation. Plasmapheresis is a known method to remove unwanted toxic components from blood plasma. Because the patient's plasma is treated extracorporeal, then reinfused, in contrast to reinfusing only cellular components of the patient's blood, plasmapheresis also beneficially detoxifies the patient's plasma without compromising blood volume and with minimal or no fluid loss. This technique avoids the serious complications and side effects of simply returning the cellular components of the blood to the patient. Additionally, all precautions are observed to avoid hypotension and loss of calcium ions in the process of citrate anticoagulation that this procedure requires. The patient can be treated initially with presently available anticoagulants such as heparin, or low molecular weight heparin, coumadin, etc., which can be immediately neutralized post-procedure. Neutralization uses standard techniques known in the art, such as calcium, etc. Hemofiltration treatment is performed with activated carbon, treatment on non-ionic exchange resins, etc. for removing free toxins and also toxin bound with plasma proteins, etc. as in renal dialysis methods. The process may be instituted or repeated as needed. The addition of Rock inhibitors or Wnt inhibitors, GSK inhibitors, integrin inhibitors, IL-1 inhibitors, or IL-6 inhibitors along with other therapeutic agents, such as disulfiram, anakinra, or macrolide immune suppressants such as cyclosporine, mycophenolic acid, Ascomycin Immunomycin, FR-900520, FK520, is an ethyl analog of tacrolimus (FK506) which can be administered systemically or for inhalation dissolved in semifluorinated alkanes or other liquids can reduce the overt inflammatory response seen in immune therapy or an autoimmune disease. In some cases with kidney involvement or its protection, kidney dialysis, hemodialysis and or serum electrophoresis is done to remove unwanted toxins and creatinine, etc.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of treating, reducing, or alleviating a medical condition in a patient, the method comprising:

administering to a patient in need thereof a biocompatible drug comprising one or more antiviral medications together with one or more cell pathway inhibitors, the biocompatible drug conjugated with slow release polymeric nanoparticles and dissolved in a non-toxic semifluorinated alkane, the slow release polymeric nanoparticles being selected from the group consisting of polylactic acid, polyglycolic acid, polycaprolactone, porous silicon, and combinations thereof, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to deposit the slow release polymeric nanoparticles with the biocompatible drug on one or more surfaces of respiratory tract tissue at a desired treatment location such that the biocompatible drug is delivered to the respiratory tract tissue being treated over an extended period of time, the one or more surfaces of respiratory tract tissue on which the slow release polymeric nanoparticles are deposited in the patient being selected from the group consisting of one or more surfaces within the mouth, one or more surfaces within the nose, one or more surfaces within the throat, one or more surfaces of the pharynx, one or more surfaces of the larynx, one or more surfaces of the epiglottis, one or more surfaces of the trachea, one or more surfaces of the bronchi, one or more surfaces of the lung alveoli, and combinations thereof;

wherein the administration of the biocompatible drug to the patient treats the one or more respiratory tract inflammatory diseases, reduces the symptoms associated with the one or more respiratory tract inflammatory diseases, and/or alleviates one or more respiratory tract inflammatory diseases.

2. The method according to claim 1, wherein the one or more respiratory tract inflammatory diseases are selected from the group consisting of influenza, parainfluenza, severe acute respiratory syndrome, a coronavirus disease, an Epstein-bar virus disease, a herpes virus disease, a bacterial infection, and combinations thereof.

3. The method according to claim 1, wherein the one or more respiratory tract inflammatory diseases comprise a coronavirus disease, the coronavirus disease selected from the group consisting of COVID-2, COVID-19, and combinations thereof.

4. The method according to claim 1, wherein the slow release polymeric nanoparticles are used as a carrier of the biocompatible drug; and
wherein the biocompatible drug with the semifluorinated alkane and the slow release polymeric nanoparticles is administered by inhalation to the patient to treat one or more respiratory tract inflammatory diseases.

5. The method according to claim 4,
wherein the semifluorinated alkane is used to transport the biocompatible drug with the slow release polymeric nanoparticles.

6. The method according to claim 1, wherein the one or more antiviral medications are selected from the group consisting of amantadine, Lopinavir, linebacker and equivir, Arbidol, a nanoviricide, remdesivir, favipiravir, oseltamivir ribavirin, and combinations thereof.

7. The method according to claim 1, wherein the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

8. The method according to claim 1, wherein the biocompatible drug further comprises one or more protease inhibitors and an antibody cocktail therapy in combination with the one or more antiviral medications and the one or more cell pathway inhibitors.

9. The method according to claim 1, wherein the method further comprises the step of:
after treatment with the biocompatible drug, removing cytokines, enzymes, and/or dead cells, from the circulation of the patient by plasmapheresis so to prevent a cytokine storm.

10. The method according to claim 1, wherein the biocompatible drug is administered to the patient by inhalation, orally, nasally, or combinations thereof.

11. A method of treating, reducing, or alleviating a medical condition in a patient, the method comprising:
administering to a patient in need thereof a biocompatible drug comprising one or more antiviral medications together with one or more cell pathway inhibitors dissolved in a non-toxic aerosolized compound and conjugated with slow release polymeric nanoparticles, the slow release polymeric nanoparticles being selected from the group consisting of polylactic acid, polyglycolic acid, polycaprolactone, porous silicon, and combinations thereof, the patient having one or more respiratory tract inflammatory diseases, the one or more antiviral medications preventing an attachment of viruses to cell walls, blocking a penetration of the viruses into cells, and/or inhibiting virus replication by damaging nucleic acids of the viruses, the one or more cell pathway inhibitors blocking an inflammatory response of inflamed tissue without inhibiting an immune response of the patient, and the non-toxic aerosolized compound evaporating quickly upon administration to the patient so as to deposit the slow release polymeric nanoparticles with the biocompatible drug on one or more surfaces of respiratory tract tissue at a desired treatment location such that the biocompatible drug is delivered to the respiratory tract tissue being treated over an extended period of time, the one or more surfaces of respiratory tract tissue on which the slow release polymeric nanoparticles are deposited in the patient being selected from the group consisting of one or more surfaces within the mouth, one or more surfaces within the nose, one or more surfaces within the throat, one or more surfaces of the pharynx, one or more surfaces of the larynx, one or more surfaces of the epiglottis, one or more surfaces of the trachea, one or more surfaces of the bronchi, one or more surfaces of the lung alveoli, and combinations thereof;
wherein the administration of the biocompatible drug to the patient treats the one or more respiratory tract inflammatory diseases, reduces the symptoms associated with the one or more respiratory tract inflammatory diseases, and/or alleviates one or more respiratory tract inflammatory diseases.

12. The method according to claim 11, wherein the one or more respiratory tract inflammatory diseases are selected from the group consisting of influenza, parainfluenza, severe acute respiratory syndrome, a coronavirus disease, an Epstein-bar virus disease, a herpes virus disease, a bacterial infection, and combinations thereof.

13. The method according to claim 11, wherein the one or more respiratory tract inflammatory diseases comprise a coronavirus disease, the coronavirus disease selected from the group consisting of COVID-2, COVID-19, and combinations thereof.

14. The method according to claim 11, wherein the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

15. The method according to claim 11, wherein the biocompatible drug further comprises one or more protease inhibitors in combination with the one or more antiviral medications and the one or more cell pathway inhibitors.

16. The method according to claim 11, wherein the one or more antiviral medications are selected from the group consisting of amantadine, azidothymidine, aciclovir, ganciclovir, vidarabine, and combinations thereof.

17. The method according to claim 11, wherein the method further comprises the step of:
administering one or more immunosuppressants and at least one of heparin, low molecular weight heparin, and Coumadin to prevent an overactive immune response and blood clot formation so as to prevent vascular infarct, the one or more immunosuppressants being selected from the group consisting of a macrolide, cyclosporine, mycophenolic acid, Baricitinib, and combinations thereof.

18. The method according to claim 11, wherein, after treatment with the biocompatible drug, the method further comprises the steps of:
removing cytokines, enzymes, and/or dead cells from the circulation of the patient by plasmapheresis and kidney dialysis so to prevent a cytokine storm; and/or
delivery of oxygen to the patient by extracorporeal membrane oxygenation when the blood oxygenation level of the patient is low.

19. The method according to claim 11, wherein the biocompatible drug further comprises one or more protease inhibitors in combination with the one or more antiviral medications and the one or more cell pathway inhibitors; the one or more protease inhibitors are selected from the group consisting of darunavir, Ganovo, and combinations thereof; and the one or more antiviral medications are selected from the group consisting of remdesivir, favipiravir, and combinations thereof.

20. The method according to claim 11, wherein the one or more antiviral medications are selected from the group consisting of equivir, Arbidol, a nanoviricide, remdesivir, favipiravir, and combinations thereof; and the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

21. The method according to claim 1, wherein the extended period of time during which the biocompatible drug is delivered to the respiratory tract tissue is at least two weeks.

22. The method according to claim 1, wherein the biocompatible drug further comprises micelles or liposomes used as a carrier of the biocompatible drug; and
wherein the biocompatible drug with the semifluorinated alkane and the micelles or liposomes are administered by inhalation to the patient to treat one or more respiratory tract inflammatory diseases.

23. A method of prophylactically treating a medical condition in a patient, the method comprising:
administering to a patient in need thereof a biocompatible drug comprising one or more antiviral medications together with one or more cell pathway inhibitors, the patient prophylactically treating one or more respiratory tract inflammatory diseases, the one or more antiviral medications preventing an attachment of viruses to cell walls, blocking a penetration of the viruses into cells, and/or inhibiting virus replication by damaging nucleic acids of the viruses, and the one or more cell pathway inhibitors blocking an inflammatory response of inflamed tissue without inhibiting an immune response of the patient;
wherein the administration of the biocompatible drug to the patient prophylactically treats the one or more respiratory tract inflammatory diseases.

24. The method according to claim 23, wherein the biocompatible drug is administered to the patient by inhalation, orally, nasally, topically, intravenously, intramuscularly, inside a body cavity, or combinations thereof.

* * * * *